United States Patent
Kita et al.

(10) Patent No.: US 9,737,504 B2
(45) Date of Patent: *Aug. 22, 2017

(54) DIHYDROOROTIC AND ACID DEHYDROGENASE INHIBITOR

(71) Applicant: NAI INC.

(72) Inventors: Kiyoshi Kita, Tokyo (JP); Ken Daniel Inaoka, Tokyo (JP); Hiroyuki Saimoto, Tottori (JP); Masaichi Yamamoto, Tokyo (JP)

(73) Assignee: INSTITUTE OF MITOCHONDRIA SCIENCE, INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/181,458

(22) Filed: Jun. 14, 2016

(65) Prior Publication Data

US 2016/0296494 A1 Oct. 13, 2016

Related U.S. Application Data

(63) Continuation of application No. 14/404,252, filed as application No. PCT/JP2013/064806 on May 28, 2013, now abandoned.

(30) Foreign Application Priority Data

May 29, 2012 (JP) .................................. 2012-122221

(51) Int. Cl.
| | | |
|---|---|---|
| A61K 31/341 | (2006.01) | |
| A61K 31/216 | (2006.01) | |
| A61K 31/11 | (2006.01) | |
| A61K 31/336 | (2006.01) | |
| C07D 309/12 | (2006.01) | |
| C07C 69/738 | (2006.01) | |
| C07C 47/56 | (2006.01) | |

(Continued)

(52) U.S. Cl.
CPC .......... *A61K 31/341* (2013.01); *A61K 9/0019* (2013.01); *A61K 9/1623* (2013.01); *A61K 9/2018* (2013.01); *A61K 9/2027* (2013.01); *A61K 9/2054* (2013.01); *A61K 9/2059* (2013.01); *A61K 9/4866* (2013.01); *A61K 31/11* (2013.01); *A61K 31/121* (2013.01); *A61K 31/216* (2013.01); *A61K 31/222* (2013.01); *A61K 31/336* (2013.01); *A61K 31/351* (2013.01); *A61K 31/357* (2013.01); *A61K 47/02* (2013.01); *A61K 47/12* (2013.01); *A61K 47/34* (2013.01); *C07C 47/56* (2013.01); *C07C 47/565* (2013.01); *C07C 47/575* (2013.01); *C07C 49/248* (2013.01); *C07C 49/255* (2013.01); *C07C 49/258* (2013.01); *C07C 69/63* (2013.01); *C07C 69/738* (2013.01); *C07D 303/14* (2013.01); *C07D 303/32* (2013.01); *C07D 307/20* (2013.01); *C07D 309/12* (2013.01)

(58) Field of Classification Search
IPC .................. A61K 31/341,31/216, 31/11, 31/336
See application file for complete search history.

(56) References Cited

U.S. PATENT DOCUMENTS 3,546,073 A 12/1970 Evans, Jr.
6,605,639 B1 8/2003 Tamura et al.
(Continued)

FOREIGN PATENT DOCUMENTS

EP 1176134 1/2002
JP 56025310 6/1981
(Continued)

OTHER PUBLICATIONS

Arteaga et al., Phase I Clinical and Pharmacokinetic Trial of Brequinar Sodium (DUP 785; NSC 368390), Cancer Res., 49(16):4648-4653 (1989).
(Continued)

*Primary Examiner* — Shirley V Gembeh
(74) *Attorney, Agent, or Firm* — Sughrue Mion, PLLC

(57) ABSTRACT

The present invention provides a novel dihydroorotic acid dehydrogenase inhibitor which is applicable to various diseases. When used as an active ingredient, a compound represented by formula (I):

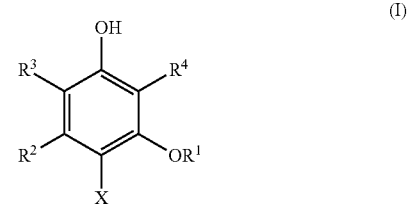

(wherein
X represents a halogen atom,
$R^1$ represents a hydrogen atom,
$R^2$ represents an alkyl group containing 1 to 7 carbon atoms,
$R^3$ represents —CHO, and
$R^4$ represents —$CH_2$—CH=C($CH_3$)—$R^0$ (wherein $R^0$ represents an alkyl group containing 1 to 12 carbon atoms which may have a substituent on the terminal carbon and/or on a non-terminal carbon, etc.)),
an optical isomer thereof or a pharmaceutically acceptable salt thereof has a high inhibitory effect on dihydroorotic acid dehydrogenase and can be used as an immunosuppressive agent, a therapeutic agent for rheumatism, an anticancer agent, a therapeutic agent for graft rejection, an antiviral agent, an anti-*H. pylori* agent, a therapeutic agent for diabetes or the like.

4 Claims, 3 Drawing Sheets

(51) Int. Cl.

| | | |
|---|---|---|
| C07C 47/565 | (2006.01) | |
| C07C 47/575 | (2006.01) | |
| C07C 49/258 | (2006.01) | |
| C07D 303/14 | (2006.01) | |
| C07D 307/20 | (2006.01) | |
| A61K 9/00 | (2006.01) | |
| A61K 9/20 | (2006.01) | |
| A61K 9/48 | (2006.01) | |
| C07C 69/63 | (2006.01) | |
| A61K 31/121 | (2006.01) | |
| A61K 31/222 | (2006.01) | |
| A61K 31/351 | (2006.01) | |
| A61K 31/357 | (2006.01) | |
| C07C 49/248 | (2006.01) | |
| C07C 49/255 | (2006.01) | |
| C07D 303/32 | (2006.01) | |
| A61K 47/02 | (2006.01) | |
| A61K 47/12 | (2006.01) | |
| A61K 47/34 | (2017.01) | |
| A61K 9/16 | (2006.01) | |

(56) References Cited

U.S. PATENT DOCUMENTS

| | | |
|---|---|---|
| 2005/0153870 A1 | 7/2005 | Ando et al. |
| 2013/0296422 A1 | 11/2013 | Saimoto et al. |

FOREIGN PATENT DOCUMENTS

| | | |
|---|---|---|
| JP | 7278041 | 10/1995 |
| JP | 2005126343 | 5/2005 |
| JP | 2006213644 | 8/2006 |
| WO | 0035867 | 6/2000 |
| WO | 0053563 | 9/2000 |
| WO | 03063849 | 8/2003 |
| WO | 2012060387 | 5/2012 |

OTHER PUBLICATIONS

Baldwin et al., "High-throughput Screening for Potent and Selective Inhibitors of *Plasmodium falciparum* Dihydroorotate Dehydrogenase", J. Biol. Chem., 280(23):21847-21853 (2005).
Cleaveland et al., "Identification of a Novel Inhibitor (NSC 665564) of Dihydroorotate Dehydrogenase with a Potency Equivalent to Brequinar", Biochem. Biophys. Res. Commun., 223(3):654-659 (1996).
Copeland et al., "Helicobacter pylori-selective Antibacterials Based on Inhibition of Pyrimidine Biosynthesis", J. Biol. Chem., 275(43):33373-33378 (2000).
Dexter et al., "NSC 368390 [6-Fluoro-2-(2'-fluoro-1,1'-biphenyl-4-yl)-3-methyl-4-quinolinecarboxylic Acid Sodium Salt], against Experimental Tumors", Cancer Res., 45:5563-5568 (1985).
Evers et al., Inhibition of human cytomegalovirus signaling and replication by the immunosuppressant FK778, Science Direct, Antiviral Research, 65:1-12 (2005).
Zameitat et al., "Biochemical characterization of recombinant dihydroorotate dehydrogenase from the opportunistic pathogenic yeast *Candida albicans*", FEBS J., 273(14):3183-3191 (2006).
Forrest et al., "Novel Mechanisms of Brequinar Sodium Immunosuppression on T Cell Activation1, Transplantation", 58(8):920-926 (1994).
Gustafson et al., "Identification of a new antifungal target site through a dual biochemical and molecular-genetics approach", Curr. Genet., 30(2):159-165 (1996).
Hoffmann et al., "Broad-spectrum antiviral that interferes with de novo pyrimidine biosynthesis", Proc. Natl. Acad .Sci., USA, 108(14):5777-5782 (2011) (Mar. 21, 2011 [Epub ahead of print]).
Haque et al., "Parallel Synthesis of Potent, Pyrazole-Based Inhibitors of *Helicobacter pylori* Dihydroorotate Dehydrogenase", J. Med. Chem., 45(21):4669-4678 (2002).
International Search Report for PCT/JP2013/064806 dated Jul. 2, 2013.
Ittarat et al., "Effects of Atovaquone and Other Inhibitors on *Pneumocystis carinii* Dihydroorotate Dehydrogenase", Antimicrob. Agents Chemother., 39(2):325-328 (1995).
Davis et al., The Immunosuppressive Metabolite of Leflunomide Is a Potent Inhibitor of Human Dihydroorotate Dehydrogenase, Biochemistry, 35:1270-1273 (1996).
Min Qing et al., "Characterization of Dengue Virus Resistance to Brequinar in Cell Culture", Antimicrob. Agents Chemother., 54(9):3686-3695 (2010).
Papageorgiou et al., "Pyrazole Bioisosteres of Leflunomide as B-Cell Immunosuppressants for Xenotransplantation and Chronic Rejection: Scope and Limitations", J. Med. Chem., 41(18):3530-3538 (1998).
Phillips et al., "Triazolopyrimidine-Based Dihydroorotate Dehydrogenase Inhibitors with Potent and Selective Activity against the Malaria Parasite *Plasmodium falciparum*", J. Med. Chem., 51(12):3649-3653 (2008).
Schwartsmann et al., "Phase I study of Brequinar sodium (NSC 368390) in patients with solid Malignancies", Cancer Chemother. Pharmacol., 25(5):345-351 (1990).
Chen et al., "Mechanism of Action of the Novel Anticancer Agent 6-Fluoro-2-(2'-fluoro-I,I'-biphenyl-4-yl)-3-methyl-4-quinolinecarboxylic Acid Sodium Salt (NSC 368390): Inhibition of *de Novo* Pyrimidine Nucleotide Biosynthesis", Cancer Res., 46(10):5014-5019 (1986).
Stosic-Grujicic et al., "Leflunomide protects mice from multiple low dose streptozotocin (MLD-SZ)-induced insulitis and diabetes", Clin. Exp. Immunol., 117(1):44-50 (1999).
Williamson et al., "Dihydroorotate Dehydrogenase is a high affinity binding protein for A77 1726 and mediator of a range of biological effects of the immunomodulatory Compound", J. Biol. Chem., 270(38):22467-22472 (1995).
Zhang et al., "Anti-inflammatory sesquiterpenoids from a sponge-derived fungus *Acremonium* sp.", Journal of Natural Products, 72(2):270-275 (2009).
Qi, Qiaojuan et al., "F01WB-1315 A and B, two dihydroorotate dehydrogenase inhibitors from microbial metabolites", Acta Microbiologica Sinica, Apr. 4, 2009, vol. 49, No. 4, pp. 485-491 (total 9 pages).

DIHYDROOROTIC AND ACID DEHYDROGENASE INHIBITOR

CROSS REFERENCE TO RELATED APPLICATIONS

This application Continuation of U.S. application Ser. No. 14/404,252, filed Nov. 26, 2014, is a 371 National Stage of International Application No. PCT/JP2013/064806, filed on May 28, 2013; which claims priority from Japanese Patent Application No. 2012-122221, filed on May 29, 2012; the contents of each of which are incorporated herein by reference in their entirety.

TECHNICAL FIELD

The present invention relates to an inhibitor of dihydroorotic acid dehydrogenase (hereinafter abbreviated as "DHOD"), which comprises a halogen-containing dihydroxybenzene derivative with an alkyl side chain as an active ingredient. The present invention also relates to an immunosuppressive agent, a therapeutic agent for rheumatism, an anticancer agent, a therapeutic agent for graft rejection, a therapeutic agent for diabetes, an antiviral agent and an anti-*Helicobacter pylori* agent ("*Helicobacter pylori*" is expressed hereinafter as "*H. pylori*"), each of which comprises a novel halogen-containing dihydroxybenzene derivative with an alkyl side chain as an active ingredient.

BACKGROUND ART

The first inhibitor of human DHOD was reported in 1985, and NSC368390 (renamed later as Brequinar) caused 90% or more inhibition of the growth of human MX-1 breast, LX-1 lung, BL/STX-1 stomach and CX-1 colon carcinomas in nude mice at a dose of 20 to 40 mg/kg/day, and was also effective against HCT-15, clone A and DLD-2 tumors, particularly its growth inhibition of DLD-2 colon cancer was as high as 98% (Non-patent Document 1). In the next year, UMP levels in NSC368390-treated cells were found to be reduced by 50% after treatment with 25 μM NSC368390, and isotope-labeled substrates were used to measure the activity of all enzymes responsible for the pyrimidine de novo synthetic pathway, indicating that the fourth enzyme DHOD was strongly inhibited (Ki=23.5 nM) (Non-patent Document 2). In 1989 (USA) and in 1990 (Netherlands), Phase I clinical trials were initiated, and 45 and 43 solid tumor patients, respectively, were administered one after another. The results obtained are reported in Non-patent Document 3 and Non-patent Document 4. In the same year. Brequinar was reported to be more effective than five drugs used for treatment of head and neck squamous cell carcinomas.

In 1993, experiments in mice showed that allograft rejection was caused later by Brequinar derivatives, suggesting that DHOD inhibitors have an immunosuppressive effect. In 1994. Brequinar was reported to suppress the growth of lymphocytes and was also reported to inhibit cell cycle transition from the G0/G1 phase to the S and G2+M phases (Non-patent Document 5). In 1995, there was a report showing that the target of Leflunomide used for treatment of rheumatoid arthritis was human dihydroorotic acid dehydrogenase (hereinafter abbreviated as HsDHOD); and hence DHOD was confirmed again to be promising as a target for anticancer and immunosuppressive purposes, as in the case of Brequinar. DHOD purified from mouse spleens was identified to bind to A771726 (Leflunomide metabolite) with high affinity, thus indicating that Leflunomide is metabolized in vivo into A771726, and this A771726, but not Leflunomide, has an immunosuppressive effect (Non-patent Document 6, Non-patent Document 7). It should be noted that A771726 binds to the ubiquinone-binding site in known HsDHOD inhibitors. In 1996, NSC 665564 was reported to inhibit HsDHOD at the same level as Brequinar and thereby suppress the growth of various cancer cells (Non-patent Document 8). In 1998, Leflunomide was reported to arrest the growth of T-lymphocytes in the G1 phase. In the same year, esters of Leflunomide were found to suppress the growth of B-lymphocytes and hence were proposed as therapeutic agents for graft rejection in organ transplantation.

In 2000, A771726 suppressed diabetic symptoms in a concentration-dependent manner in the NOD (non-obese diabetic) mouse model of diabetes, and hence inhibitors of human DHOD were found to be effective in T cell triggered disease, i.e., insulin-dependent diabetes mellitus (IDDM).

The following reports have been issued for DHOD in non-human organisms. Membrane-bound DHOD is used as a drug target for malaria (Non-patent Document 9, Non-patent Document 10) and also for *Helicobacter pylori* (Non-patent Document 11, Non-patent Document 12) and *Candida albicans* (Non-patent Document 13, Non-patent Document 14).

In addition, an analog (FK778) of Leflunomide has already been reported to suppress the growth of human cytomegalovirus (Non-patent Document 15). Moreover, Brequinar has been reported to suppress the growth of flaviviruses (dengue virus, West Nile virus, yellow fever virus, and Powassan virus), plus-strand RNA alphavirus (Western equine encephalitis virus) and negative-strand RNA rhabdovirus (vesicular stomatitis virus) (Non-patent Document 16). At last, in March 2011, it was reported in PNAS (Proc Natl Acad Sci USA) that a compound (Compound A3) suppressing the growth of a wide range of viruses [negative-sense RNA viruses (influenza viruses A and B, Newcastle disease virus, and vesicular stomatitis virus), positive-sense RNA viruses (Sindbis virus, hepatitis C virus, West Nile virus, and dengue virus), DNA viruses (vaccinia virus and human adenovirus) and retroviruses (HIV)] was found through HTS (high-throughput screening) (Non-patent Document 17). The inhibitory effect of this compound on virus growth was suppressed by orotic acid, but not suppressed by dihydroorotic acid which is a substrate of DHOD, thus indicating that the target of Compound A3 inhibits dihydroorotic acid dehydrogenase present in human mitochondria and thereby exerts an inhibitory effect on virus growth (Non-patent Document 17). Further, as a result of analyzing their toxicity on human cells, these compounds were found to show 1500-fold to 2400-fold or more selectivity between cytotoxicity ($CC_{50}$) and virus growth inhibition ($IC_{50}$) depending on the type of cells. The reason that these compounds have an inhibitory effect on virus growth has been confirmed to be because viral RNA-DNA synthesis is stopped upon reduction of the pyrimidine pool in the infected cells (Non-patent Documents 19 to 21).

As described above, in humans. DHOD inhibitors have been known to be promising as anticancer agents or immunosuppressive agents since 1980s, and studies are also actively proceeding now. As a mechanism for immunosuppression, DHOD inhibitors suppress the growth of activated T-lymphocytes and B-lymphocytes. The pyrimidine pool in normal cells is mediated by uracil transport, salvage pathway and de novo synthesis. However, activated lymphocytes and cancer cells depend on de novo synthesis. Since 1990s, it has been reported that upon inhibition of DHOD, normal cells can survive due to the uracil transport and salvage pathway, whereas lymphocytes and cancer cells cannot grow.

Moreover, DHOD inhibitors are suggested as drug targets for T-lymphocyte-mediated diabetes.

In the other organisms, membrane-bound DHOD is known as a drug target in malaria and *H. pylori*, and many articles have been reported for drug design using DHOD as a target. On the other hand, DHOD inhibitors are known to be imperative for candidiasis because they exert growth inhibition.

CITATION LIST

Non-Patent Documents

Non-patent Document 1: Daniel L. Dexter, David P. Hesson, Robert J. Ardecky, Ganti V. Rao, Davette L. Tippett, Betsy A. Dusak, Kenneth D. Paull, Jacqueline Plowman, Barbara M. DeLarco, V. L. Narayanan, and Martin Forbes. Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors. *Cance Res*. (1985) 45: 5563-5568

Non-patent Document 2: Shih-Fong Chen, Regina L. Ruben and Daniel L. Dexter Mechanism of action of the novel anticancer agent 6-fluoro-2-(2'-fluoro-1,1'-biphenyl-4-yl)-3-methyl-4-quinolinecarboxylic acid sodium salt (NSC 368390): inhibition of de novo pyrimidine nucleotide biosynthesis. *Cance Res*. (1986) 46(10):5014-5019

Non-patent Document 3: Arteaga C L. Brown T D, Kuhn J G, Shen H S. O'Rourke T J, Beougher K, Brentzel H J, Von Hoff D D, Weiss G R. Phase I Clinical and Pharmacokinetic Trial of Brequinar Sodium. *Cancer Res*. (1989) 49(16): 4648-4653

Non-patent Document 4: Schwartsmann G, Dodion P, Vermorken J B, ten Bokkel Huinink W W, Joggi J, Winograd B, Gall H, Simonetti G, van der Vijgh W J, van Hennik M B. et al. Phase I study of Brequinar sodium (NSC 368390) in patients with solid malignancies. *Cancer Chemother Pharmacol*. (1990) 25(5): 345-351.

Non-patent Document 5: Forrest T L, Ware R E, Howard T, Jaffee B D, Denning S M. Novel mechanisms of brequinar sodium immunosuppression on T cell activation. *Transplantation*. (1994) 58(8): 920-926.

Non-patent Document 6: Williamson R A, Yea C M, Robson P A, Curnock A P, Gadher S, Hambleton A B, Woodward K, Bruneau J M, Hambleton P, Moss D, Thomson T A, Spinella-Jaegle S, Morand P, Courtin O, Sautés C, Westwood R, Hercend T, Kuo E A, Ruuth E. Dihydroorotate dehydrogenase is a high affinity binding protein for A77 1726 and mediator of a range of biological effects of the immunomodulatory compound. *J Biol Chem*. (1995) 270 (38): 22467-22472.

Non-patent Document 7: Davis J P, Cain G A, Pitts W J, Magolda R L, Copeland R A. The immunosuppressant leflunomide inhibits lymphocyte proliferation by inhibiting pyrimidine biosynthesis. *Biochemistry*. (1996) 35(4): 1270-1273.

Non-patent Document 8: Cleaveland E S, Zaharevitz D W, Kelley J A, Paull K, Cooney D A, Ford H Jr. Identification of a novel inhibitor (NSC 665564) of dihydroorotate dehydrogenase with a potency equivalent to brequinar. Biochem Biophys Res Commun. (1996) 223(3): 654-659.

Non-patent Document 9: Baldwin J, Michnoff C H, Malmquist N A, White J, Roth M G, Rathod P K, Phillips M A. High-throughput Screening for Potent and Selective Inhibitors of *Plasmodium falciparum* Dihydroorotate Dehydrogenase. *J Biol Chem*. (2005) 280(23): 21847-21853

Non-patent Document 10: Phillips M A, Gujjar R. Malmquist N A, White J, El Mazouni F, Baldwin J, Rathod P K. Triazolopyrimidine-based dihydroorotate dehydrogenase inhibitors with potent and selective activity against the malaria parasite *Plasmodium falciparum*. *J Med Chem*. (2008) 51(12): 3649-3653.

Non-patent Document 11: Copeland R A, Marcinkeviciene J, Haque T S, Kopcho L M, Jiang W, Wang K, Ecret L D, Sizemore C, Amsler K A, Foster L, Tadesse S, Combs A P, Stem A M, Trainor G L, Slee A, Rogers M J, Hobbs F. *Helicobacter pylori*-selective Antibacterials Based on Inhibition of pyrimidine biosynthesis. *J Biol Chem*. (2000) 275(43): 33373-33378.

Non-patent Document 12: Haque T S, Tadesse S, Marcinkeviciene J, Rogers M J, Sizemore C. Kopcho L M, Amsler K, Ecret L D, Zhan D L, Hobbs F, Slee A, Trainor G L, Stem A M, Copeland R A, Combs A P. Parallel synthesis of potent, pyrazole-based inhibitors of *Helicobacter pylori* dihydroorotate dehydrogenase. *J Med Chem*. (2002) 45(21): 4669-4678.

Non-patent Document 13: Elke Zameitat, Zoran Gojkovic, Wolfgang Knecht, Jure Piskur and Monika Lo'ffler. Biochemical characterization of recombinant dihydroorotate dehydrogenase from the opportunistic pathogenic yeast *Candida albicans*. *FEBS J*. (2006); 273(14): 3183-3191.

Non-patent Document 14: Gustafson G, Davis G, Waldron C, Smith A, Henry M. Identification of a new antifungal target site through a dual biochemical and molecular-genetics approach. Curr Genet. (1996) 30(2): 159-165.

Non-patent Document 15: David L. Evers; Xin Wang, Shu-Mei Huong, Kenneth A. Andreoni, Eng-Shang Huang. Inhibition of human cytomegalovirus signaling and replication by the immunosuppressant FK778.

Non-patent Document 16: Min Qing, Gang Zou, Qing-Yin Wang, Hao Ying Xu, Hongping Dong, Zhiming Yuan and Pei-Yong Shi. Characterization of Dengue Virus Resistance to Brequinar in Cell Culture. Antimicrob Agents Chemother, (2010) 54(9): 3686-3695.

Non-patent Document 17: Hans-Heinrich Hoffmann, Andrea Kunza, Viviana A. Simona, Peter Palesea, and Megan L. Shawa. Broad-spectrum antiviral that interferes with de novo pyrimidine biosynthesis. Proc Natl Aced Sci USA. 2011 Mar. 21. [Epub ahead of print].

Non-patent Document 18: June P. Davis, Gary A. Cain, William J. Pitts, Ronald L. Magolda, and Robert A. Copeland. The Immunosuppressive Metabolite of Leflunomide Is a Potent Inhibitor of Human Dihydroorotate Dehydrogenase. *Biochemistry* (1996) 35: 1270-1273.

Non-patent Document 19: Papageorgiou C, Albert R, Floersheim P, Lemaire M, Bitch F, Weber H P, Andersen E, Hungerford V, Schreier M H. Pyrazole bioisosteres of leflunomide as B-cell immunosuppressants for xenotransplantation and chronic rejection: scope and limitations. *J Med Chem*. (1998) 41(18): 3530-3538.

Non-patent Document 20: Stosic-Grujicic S. Dimitrijevic M, Bartlett R. Leflunomide protects mice from multiple low dose streptozotocin (MLD-SZ)-induced insulitis and diabetes. *Clin Exp Immunol*. (1999) 117(1): 44-50.

Non-patent Document 21: Ittarat I, Asawamahasakda W, Bartlett M S, Smith J W, Meshnick S R. Effects of atovaquone and other inhibitors on *Pneumocystis carinii* dihydroorotate dehydrogenase. *Antmicrob Agents Chemother.* (1995) 39(2): 325-358.

SUMMARY OF THE INVENTION

Problem to be Solved by the Invention

The problem of the present invention is to provide a novel DHOD inhibitor which is applicable to various diseases.

Means to Solve the Problem

As a result of extensive and intensive efforts and studies repeated to solve the problem stated above, the inventors of the present invention have found that dihydroxybenzene derivatives having a certain type of side chain have a high DHOD inhibitory effect. The present invention has been completed on the basis of this finding.

The present invention provides a DHOD inhibitor comprising, as an active ingredient(s), one or two or more of compounds represented by formula (I):

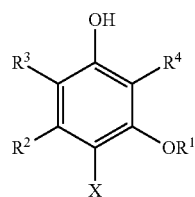

(wherein
X represents a halogen atom,
$R^1$ represents a hydrogen atom,
$R^2$ represents an alkyl group containing 1 to 7 carbon atoms.
$R^3$ represents —CHO, and
$R^4$ represents —CH$_2$—CH=C(CH$_3$)—$R^0$ (wherein $R^0$ represents an alkyl group containing 1 to 12 carbon atoms which may have a substituent on the terminal carbon and/or on a non-terminal carbon, an alkenyl group containing 2 to 12 carbon atoms which may have a substituent on the terminal carbon and/or on a non-terminal carbon, or an alkynyl group containing 2 to 12 carbon atoms which may have a substituent on the terminal carbon and/or on a non-terminal carbon)), optical isomers thereof and pharmaceutically acceptable salts thereof, as well as a pharmaceutically acceptable carrier.

The present invention also provides an immunosuppressive agent, a therapeutic agent for rheumatism, an anticancer agent, a therapeutic agent for graft rejection, an antiviral agent, an anti-*H. pylori* agent and a therapeutic agent for diabetes, each comprising one or two or more of compounds represented by formula (I), optical isomers thereof and pharmaceutically acceptable salts thereof, as well as a pharmaceutically acceptable carrier.

The present invention further provides a kit comprising one or two or more of compounds represented by formula (I), optical isomers thereof and pharmaceutically acceptable salts thereof, as well as instructions for use.

Advantageous Effects of the Invention

Because of having high DHOD inhibitory activity, the above compounds represented by formula (I) are extremely useful as DHOD inhibitors for use in therapeutic agents for various DHOD-related diseases, such as various types of cancers, rheumatism, graft rejection in organ transplantation, viral diseases, *H. pylori*-induced diseases, diabetes and so on.

DESCRIPTION OF EMBODIMENTS

Figure 1:
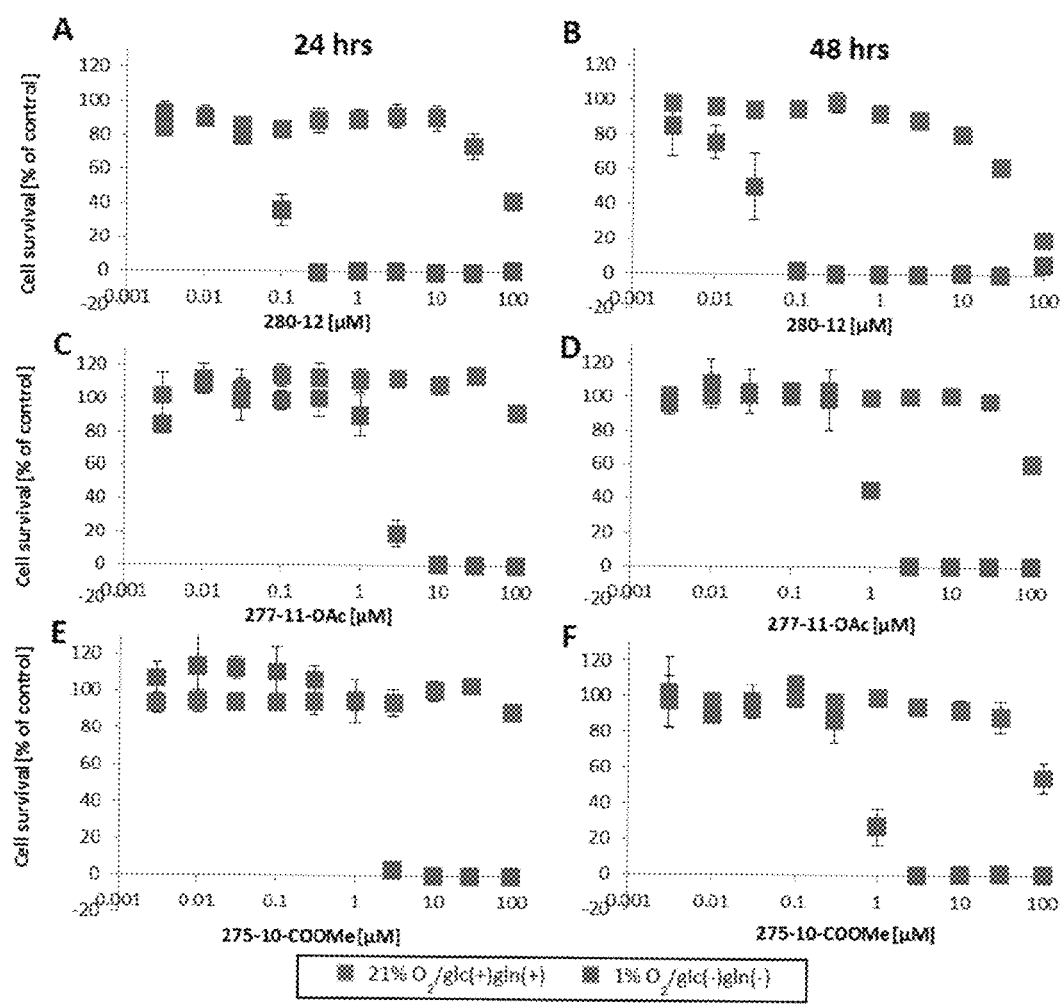
FIG. 1 shows graphs indicating the growth inhibitory effect on colorectal cancer cells (DLD-1 cells) provided by the compounds of the present invention.

The present invention will be described in more detail below.

In the compounds to be used in the present invention, a halogen atom refers to any of a fluorine atom, a chlorine atom, a bromine atom and an iodine atom.

In the compounds to be used in the present invention, an alkyl group containing 1 to 7 carbon atoms refers a linear or branched alkyl group containing 1 to 7 carbon atoms, as exemplified by a methyl group, an ethyl group, a n-propyl group, an i-propyl group, a n-butyl group, an i-butyl group, a s-butyl group, a t-butyl group, a n-pentyl group, a n-hexyl group, a n-heptyl group and so on.

In the compounds to be used in the present invention, an alkyl group containing 1 to 16 carbon atoms refers to a linear or branched alkyl group containing 1 to 16 carbon atoms, as exemplified by a methyl group, an ethyl group, a n-propyl group, an i-propyl group, a n-butyl group, an i-butyl group, a s-butyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group and so on.

In the compounds to be used in the present invention, an alkenyl group containing 2 to 16 carbon atoms refers to a linear or branched group containing 2 to 16 carbon atoms, which has one or more double bonds, as exemplified by a vinyl group, —CH$_2$—CH=C(CH$_3$)—(CH$_2$)$_2$—CH=C(CH$_3$)$_2$, —CH$_2$—CH=C(CH$_3$)—(CH$_2$)$_2$—CH=C(CH$_3$)—(CH$_2$)$_2$—CH=C(CH$_3$)$_2$, —CH=C—CH$_2$CH$_2$)n-(CH$_2$)$_2$—CH$_3$ (where n is an integer of 1 to 3) and so on.

In the compounds to be used in the present invention, an alkynyl group containing 2 to 16 carbon atoms refers to a linear or branched group containing 2 to 16 carbon atoms, which has one or more triple bonds or which has one triple bond and one double bond, as exemplified by an ethynyl group, a 2-pentynyl group, a 2-hexynyl group, a 2-octynyl group, a 7-methyl-6-octen-2-ynyl group and so on.

In the compounds to be used in the present invention, an alkyl group containing 1 to 16 carbon atoms, which has any type of substituent on the terminal carbon, refers to a linear or branched alkyl group containing 1 to 16 carbon atoms, which has a substituent(s) on the carbon atom located at the most distant position from the carbon atom in the alkyl group attached to a carbon atom of the benzene ring in the compound of formula (I). Examples of any type of substituent include —COOH, —COORa (where Ra means an alkyl group containing 1 to 7 carbon atoms), —CHO, —COOCH$_2$CH(OH)CH$_2$OH, —COO—CH$_2$—Rb (where Rb means a group obtained by removing one of the hydrogen atoms on the carbons of an aromatic hydrocarbon such as benzene, naphthalene, anthracene or the like), —O—CO-Rc (where Rc means an alkyl group containing 1 to 7 carbon atoms), —OH, —O-Rd (where Rd means an alkyl group containing 1 to 7 carbon atoms), —O—CH$_2$—O—CH$_3$, -HET (where HET means a group obtained by removing one hydrogen atom from the carbon or nitrogen atom(s) of a heterocyclic compound (e.g., pyridine, furan, thiophene, furanone, pyran, pyranone, imidazole, 1,3-dioxolane, oxirane, 3,3-dimethyloxirane)), —O-HET (where HET has the same meaning as defined above) and so on.

In the compounds to be used in the present invention, an alkyl group containing 1 to 16 carbon atoms, which has any type of substituent on a non-terminal carbon, refers to a linear or branched alkyl group containing 1 to 16 carbon atoms, which has a substituent(s) on a carbon atom(s) other than the carbon atom located at the most distant position from the carbon atom in the alkyl group attached to a carbon atom of the benzene ring in the compound of formula (I). Examples of any type of substituent include —COOH, —COORa (where Ra means an alkyl group containing 1 to 7 carbon atoms), —CHO, —COOCH$_2$CH(OH)CH$_2$OH, —COO—CH$_2$—Rb (where Rb means a group obtained by removing one of the hydrogen atoms on the carbons of an aromatic hydrocarbon such as benzene, naphthalene, anthracene or the like), —O—CO-Rc (where Rc means an alkyl group containing 1 to 7 carbon atoms), —OH, —O-Rd (where Rd means an alkyl group containing 1 to 7 carbon atoms), —O—CH$_2$—O—CH$_3$, -HET (where HET means a group obtained by removing one hydrogen atom from the carbon or nitrogen atom(s) of a heterocyclic compound (e.g., pyridine, furan, thiophene, furanone, pyran, pyranone, imidazole, 1,3-dioxolane, oxirane, 3,3-dimethyloxirane)). —O-HET (where HET has the same meaning as defined above) and so on.

In the compounds to be used in the present invention, an alkenyl group containing 2 to 16 carbon atoms, which has any type of substituent on the terminal carbon, refers to a linear or branched alkenyl group containing 2 to 16 carbon atoms, which has a substituent(s) on the carbon atom located at the most distant position from the carbon atom in the alkenyl group attached to a carbon atom of the benzene ring in the compound of formula (I). It should be noted that the term "alkenyl" used herein also includes those having two or more double bonds. Examples of any type of substituent include —COOH, —COORa (where Ra means an alkyl group containing 1 to 7 carbon atoms), —CHO, —COOCH$_2$CH(OH)CH$_2$OH, —COO—CH$_2$—Rb (where Rb means a group obtained by removing one of the hydrogen atoms on the carbons of an aromatic hydrocarbon such as benzene, naphthalene, anthracene or the like), —O—CO-Rc (where Rc means an alkyl group containing 1 to 7 carbon atoms), —OH, —O-Rd (where Rd means an alkyl group containing 1 to 7 carbon atoms), —O—CH$_2$—O—CH$_3$, -HET (where HET means a group obtained by removing one hydrogen atom from the carbon or nitrogen atom(s) of a heterocyclic compound (e.g., pyridine, furan, thiophene, furanone, pyran, pyranone, imidazole, 1,3-dioxolane, oxirane, 3,3-dimethyloxirane)), —O-HET (where HET has the same meaning as defined above) and so on.

In the compounds to be used in the present invention, an alkenyl group containing 2 to 16 carbon atoms, which has any type of substituent on a non-terminal carbon, refers to a linear or branched alkenyl group containing 2 to 16 carbon atoms, which has a substituent(s) on a carbon atom(s) other than the carbon atom located at the most distant position from the carbon atom in the alkenyl group attached to a carbon atom of the benzene ring in the compound of formula (I). It should be noted that the term "alkenyl" used herein also includes those having two or more double bonds. Examples of any type of substituent include —COOH, —COORa (where Ra means an alkyl group containing 1 to 7 carbon atoms), —CHO, —COOCH$_2$CH(OH)CH$_2$OH, —COO—CH$_2$—Rb (where Rb means a group obtained by removing one of the hydrogen atoms on the carbons of an aromatic hydrocarbon such as benzene, naphthalene, anthracene or the like), —O—CO-Rc (where Rc means an alkyl group containing 1 to 7 carbon atoms), —OH, —O-Rd (where Rd means an alkyl group containing 1 to 7 carbon atoms), —O—CH$_2$—O—CH$_3$, -HET (where HET means a group obtained by removing one hydrogen atom from the carbon or nitrogen atom(s) of a heterocyclic compound (e.g., pyridine, furan, thiophene, furanone, pyran, pyranone, imidazole, 1,3-dioxolane, oxirane, 3,3-dimethyloxirane)), —O-HET (where HET has the same meaning as defined above) and so on.

In the compounds to be used in the present invention, an alkynyl group containing 2 to 16 carbon atoms, which has any type of substituent on the terminal carbon, refers to a linear or branched alkynyl group containing 2 to 16 carbon atoms, which has a substituent(s) on the carbon atom located at the most distant position from the carbon atom in the alkynyl group attached to a carbon atom of the benzene ring in the compound of formula (I). It should be noted that the term "alkynyl" used herein also includes those having two or more triple bonds. Examples of any type of substituent include —COOH, —COORa (where Ra means an alkyl group containing 1 to 7 carbon atoms), —CHO, —COOCH$_2$CH(OH)CH$_2$OH, —COO—CH$_2$—Rb (where Rb means a group obtained by removing one of the hydrogen atoms on the carbons of an aromatic hydrocarbon such as benzene, naphthalene, anthracene or the like), —O—CO-Rc (where Rc means an alkyl group containing 1 to 7 carbon atoms), —OH, —O-Rd (where Rd means an alkyl group containing 1 to 7 carbon atoms), —O—CH$_2$—O—CH$_3$, -HET (where HET means a group obtained by removing one hydrogen atom from the carbon or nitrogen atom(s) of a heterocyclic compound (e.g., pyridine, furan, thiophene, furanone, pyran, pyranone, imidazole, 1,3-dioxolane, oxirane, 3,3-dimethyloxirane)), —O-HET (where HET has the same meaning as defined above) and so on.

In the compounds to be used in the present invention, an alkynyl group containing 2 to 16 carbon atoms, which has any type of substituent on a non-terminal carbon, refers to a linear or branched alkynyl group containing 2 to 16 carbon atoms, which has a substituent(s) on a carbon atom(s) other than the carbon atom located at the most distant position from the carbon atom in the alkynyl group attached to a carbon atom of the benzene ring in the compound of formula (I). It should be noted that the term "alkynyl" used herein also includes those having two or more triple bonds. Examples of any type of substituent include —COOH, —COORa (where Ra means an alkyl group containing 1 to 7 carbon atoms), —CHO, —COOCH$_2$CH(OH)CH$_2$OH, —COO—CH$_2$—Rb (where Rb means a group obtained by removing one of the hydrogen atoms on the carbons of an aromatic hydrocarbon such as benzene, naphthalene, anthracene or the like), —O—CO-Rc (where Rc means an alkyl group containing 1 to 7 carbon atoms), —OH, —O-Rd (where Rd means an alkyl group containing 1 to 7 carbon atoms), —O—CH$_2$—O—CH$_3$, -HET (where HET means a group obtained by removing one hydrogen atom from the carbon or nitrogen atom(s) of a heterocyclic compound (e.g., pyridine, furan, thiophene, furanone, pyran, pyranone, imidazole, 1,3-dioxolane, oxirane, 3,3-dimethyloxirane)), —O—HET (where HET has the same meaning as defined above) and so on.

Among the compounds to be used in the present invention, some compounds have optical isomers. The respective optical isomers and mixtures thereof are all included in the present invention. Either a racemic mixture or an optical isomer may be used as the DHOD inhibitor of the present invention. It should be noted that optical isomers may be obtained by resolving their racemic mixture in a well-known manner (e.g., preferential crystallization, column chromatography with an optically active stationary phase, techniques used to obtain diastereomers).

Examples of pharmaceutically acceptable salts of the compounds to be used in the present invention or optical isomers thereof include the following salts.

When a salt is formed with OH of the phenol, examples include a Na salt, a K salt, a Li salt, an ammonium salt, etc.

When X in formula (I) is COOH, examples include a Na salt, a K salt, a Li salt, an ammonium salt, etc.

The compounds to be used in the dihydroorotic acid dehydrogenase inhibitor of the present invention may be specifically exemplified by a dihydroorotic acid dehydrogenase inhibitor comprising one or two or more of compounds represented by formula (I):

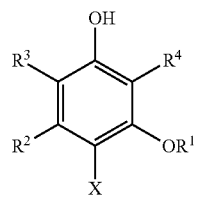

wherein

X represents a chlorine atom,

R$^1$ represents a hydrogen atom,

R$^2$ represents a methyl group,

R$^3$ represents —CHO, and

R$^4$ represents —CH$_2$—CH=C(CH$_3$)—R$^0$ (wherein R$^0$ represents an alkyl group containing 1 to 12 carbon atoms which may have a substituent on the terminal carbon and/or on a non-terminal carbon, or an alkenyl group containing 2 to 12 carbon atoms which may have a substituent on the terminal carbon and/or on a non-terminal carbon), provided that when R$^0$ has a substituent, the substituent is selected from the group consisting of —O—CO—C(CH$_3$)$_3$, —O—CO—CH(CH$_3$)$_2$, —C(CH$_3$)$_2$—O—CH$_3$, —O-(2-furyl), —OH, —CH(OCH$_3$)—CH$_2$—CO—C(CH$_3$)$_3$, —CHO, —CO—O—CH$_3$, —CO—CH$_3$, —O—CO—CH$_3$ and —CO—C(CH$_3$)$_3$, optical isomers thereof and pharmaceutically acceptable salts thereof, as well as a pharmaceutically acceptable carrier.

Further, the compounds to be used in the dihydroorotic acid dehydrogenase inhibitor of the present invention may be specifically exemplified by a dihydroorotic acid dehydrogenase inhibitor comprising one or two or more of the above compounds represented by formula (I), which are selected from the group consisting of:

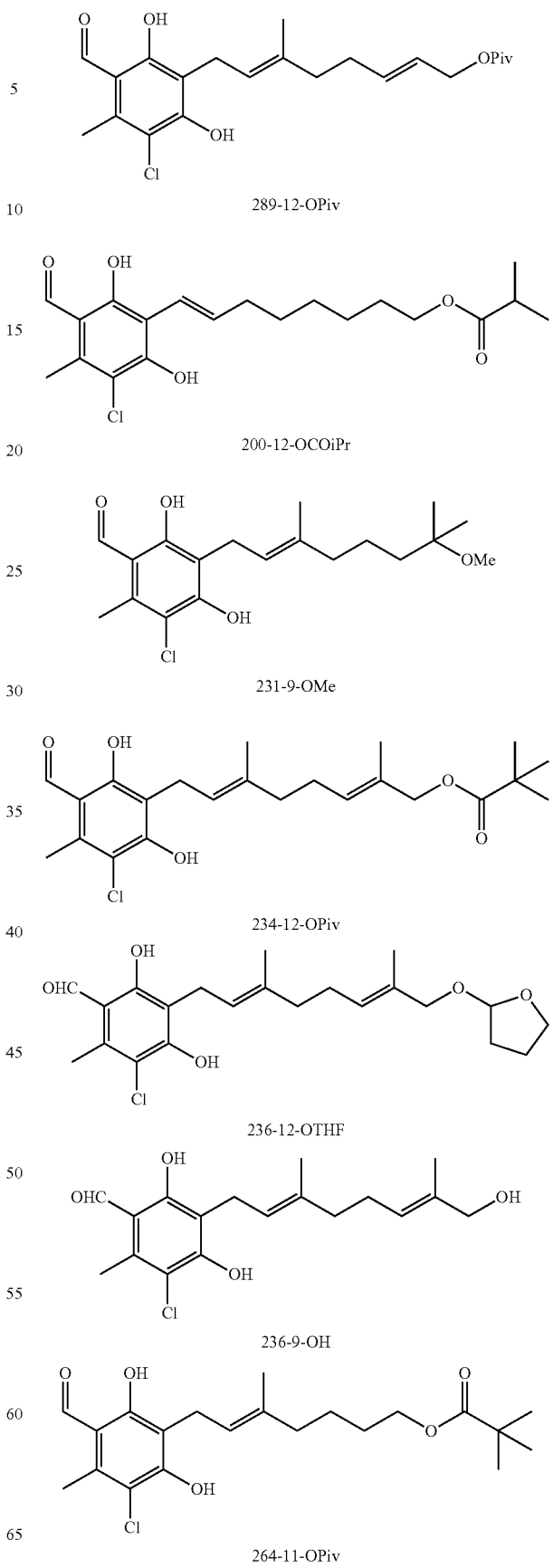

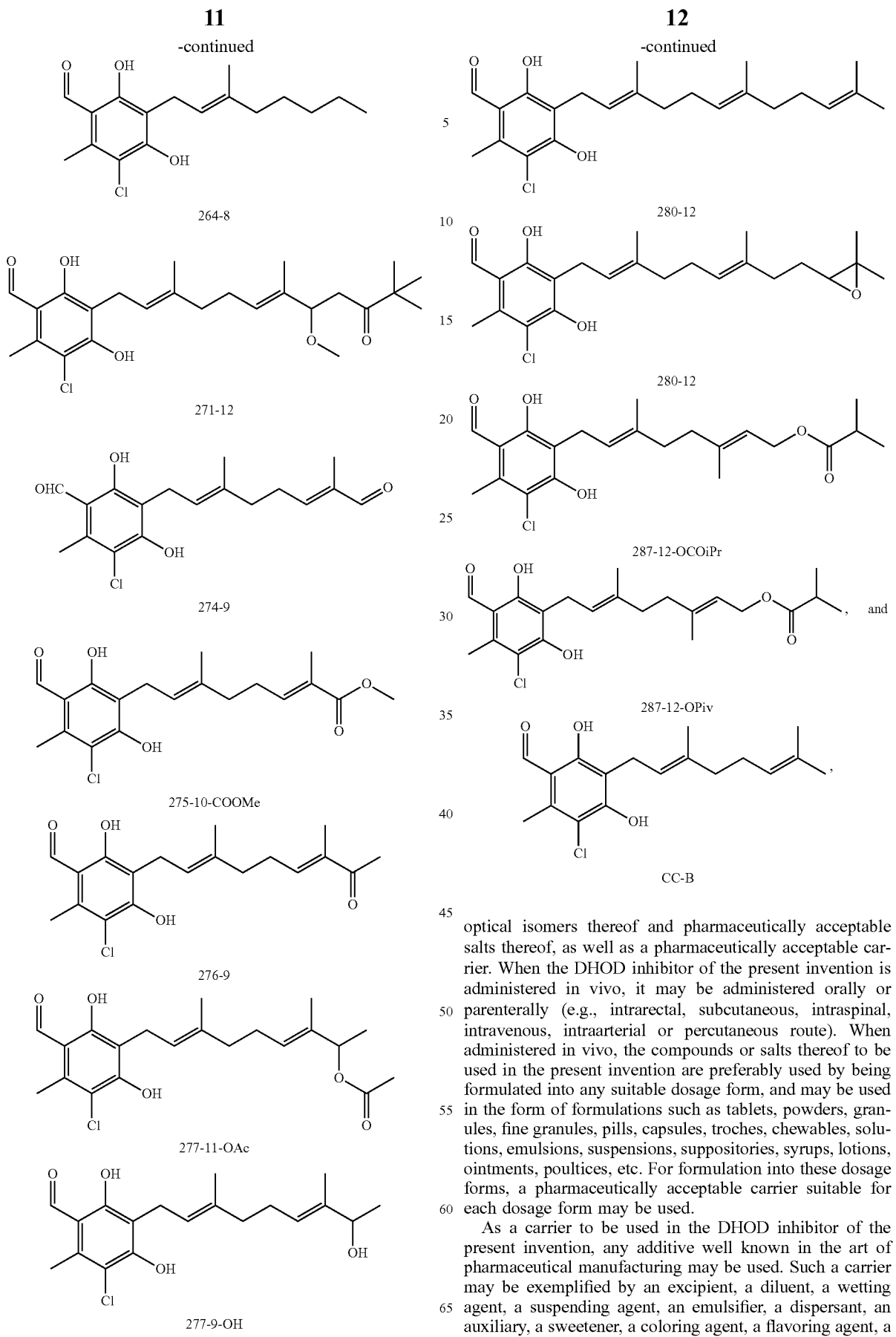

optical isomers thereof and pharmaceutically acceptable salts thereof, as well as a pharmaceutically acceptable carrier. When the DHOD inhibitor of the present invention is administered in vivo, it may be administered orally or parenterally (e.g., intrarectal, subcutaneous, intraspinal, intravenous, intraarterial or percutaneous route). When administered in vivo, the compounds or salts thereof to be used in the present invention are preferably used by being formulated into any suitable dosage form, and may be used in the form of formulations such as tablets, powders, granules, fine granules, pills, capsules, troches, chewables, solutions, emulsions, suspensions, suppositories, syrups, lotions, ointments, poultices, etc. For formulation into these dosage forms, a pharmaceutically acceptable carrier suitable for each dosage form may be used.

As a carrier to be used in the DHOD inhibitor of the present invention, any additive well known in the art of pharmaceutical manufacturing may be used. Such a carrier may be exemplified by an excipient, a diluent, a wetting agent, a suspending agent, an emulsifier, a dispersant, an auxiliary, a sweetener, a coloring agent, a flavoring agent, a buffering agent, an antiseptic, a preservative, a buffering agent, a binder, a stabilizing agent and so on. From among well-known and commonly-used carriers, those required for the intended dosage form may be selected. It should be noted that examples of an excipient or an auxiliary include lactose, various starches (e.g., corn starch), chitin, chitosan, glucose, sucrose, cellulose, methylcellulose, carboxymethyl cellulose, magnesium stearate, lauryl sulfate, talc, vegetable oils (e.g., soybean oil, peanut oil, olive oil), lecithin and so on.

It should be noted that the DHOD inhibitor of the present invention may comprise glycerol. The amount of glycerol to be added is not limited in any way and may be adjusted as appropriate if necessary.

When the DHOD inhibitor of the present invention is administered by the intravenous or intraspinal route, preferred dosage forms are solutions. For preparation of solutions, they may be prepared, for example, by using purified water, physiological saline, an alcohol (e.g., ethanol, propylene glycol, glycerine, polyethylene glycol), a solvent (e.g., triacetin), etc. The thus prepared solutions may be used by being diluted with, for example, lactated Ringer's solution, maintenance solution, a solution for postoperative recovery, a replenisher for dehydration, physiological saline for drip infusion, etc. Such formulations may further comprise auxiliaries such as an antiseptic, a wetting agent, an emulsifier, a dispersant and a stabilizer. Moreover, administration in the form of suspensions can also be regarded as one of the preferred dosage forms.

Likewise, for preparation of solid formulations including tablets, pills, powders, granules, fine granules, troches, chewables and so on, they may be prepared in a standard manner, for example, by adding a carrier (e.g., sodium bicarbonate, calcium carbonate, starch, sucrose, mannitol, carboxymethyl cellulose) and additives (e.g., calcium stearate, magnesium stearate, glycerine). Moreover, they may be formulated as enteric-coated formulations by being provided with an enteric coating by spraying a solution of an enteric material (e.g., cellulose acetate phthalate, hydroxypropyl methylcellulose phthalate, polyvinyl alcohol phthalate, a styrene-maleic anhydride copolymer, a methacrylic acid-methyl methacrylate copolymer) in an organic solvent or in water. Such a pharmaceutically acceptable carrier generally further comprises an auxiliary, an aromatic, a stabilizer or an antiseptic, each being used when needed.

The dose of the compounds to be used in the present invention, optical isomers thereof or pharmaceutically acceptable salts thereof may be selected as appropriate on the basis of the state, physique, diathesis, age and sex of a patient to be applied, as well as the intended route of administration, the intended dosage form, etc. In general, a dose of 10 to 1000 mg per kg body weight is sufficient to achieve the object. The DHOD inhibitor of the present invention is desirably formulated into tablets or capsules, and any other dosage form suitable for oral administration by being neutralized with an alkali and then dissolved in water or by being mixed with a suspending agent, an excipient or auxiliaries thereof, by way of example. More specifically, the DHOD inhibitor of the present invention is desirably formulated into enteric-coated tablets which prevent the compounds from being digested in the stomach and thereby allow the compounds to reach the intestinal tract without being digested. As an excipient or auxiliaries thereof, lactose, various starches, glucose, fructose, cellulose, methylcellulose, carboxymethyl cellulose, magnesium stearate, lauryl sulfate, talc, vegetable oils, lecithin or the like may be used for preparation. Moreover, the concentration of an active ingredient(s) in the formulation is generally 0.0001% to 100% by weight, preferably 0.001% to 10% by weight, when expressed as a concentration in the formulation.

A kit for the DHOD inhibitor comprises one or two or more of the above compounds represented by formula (I), optical isomers thereof and pharmaceutically acceptable salts thereof, as well as instructions for use.

The compounds of the present invention have a very wide range of members, and accordingly there are many various synthesis procedures. By way of example, the compounds of the present invention may be prepared as shown below.

PREPARATION EXAMPLES

The compounds to be used in the present invention will be further described in more detail by way of the following illustrative examples. It should be noted that these examples are not intended to limit the scope of the present invention.

1. Derivatives 215-15-COOEt, 215-15-COO$^i$Pr and 215-13-COOH

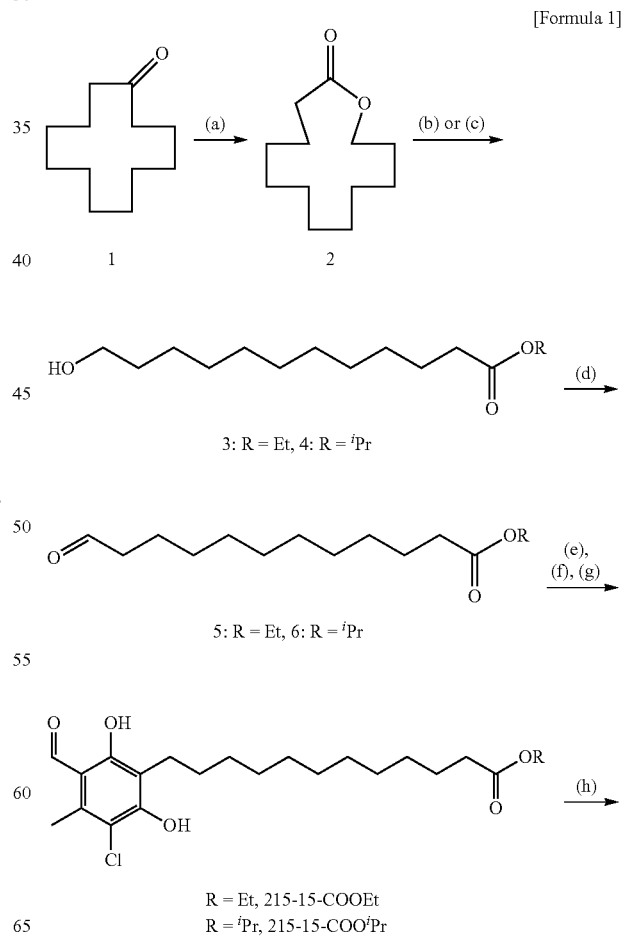

Scheme 1.

[Formula 1]

3: R = Et, 4: R = $^i$Pr

5: R = Et, 6: R = $^i$Pr

R = Et, 215-15-COOEt
R = $^i$Pr, 215-15-COO$^i$Pr

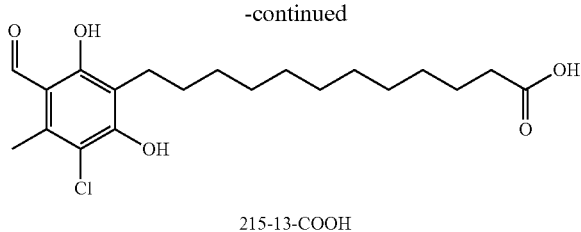

215-13-COOH

Reagents:
(a) H$_2$O$_2$, maleic anhydride, Ac$_2$O, CHCl$_3$,
(b) EtOH, H$_2$SO$_4$,
(c) i) KOH, MeOH ii) $^i$PrOH, H$_2$SO$_4$,
(d) DMSO, (COCl)$_2$, Et$_3$N, CHCl$_3$,
(e) 112, KOH, CaCl$_2$, MeOH,
(f) H$_3$PO$_4$, AcOH,
(g) H$_2$, Pd—C, EtOAC,
(h) NaOH, acetone/H$_2$O.

Ethyl 12-(3-chloro-5-formyl-2,6-dihydroxy-4-methylphenyl)dodecanate (215-15-COOEt)

To a solution of acetic anhydride (12.5 ml, 132 mmol) in CHCl$_3$ (16 ml), 30% aqueous hydrogen peroxide (10 ml, 98 mmol) was added at 0° C. and stirred at the same temperature for 1 hour. Then, maleic anhydride (10.0 g, 102 mmol) in solid state was added, followed by stirring for 2 hours while gradually returning to room temperature. Upon confirmation of heat generation in the reaction mixture, cyclododecanone (compound 1, 2.52 g, 13.8 mmol) in solid state was added thereto and stirred at 35° C. for 16 hours. After returning to room temperature, the reaction mixture was further cooled to 0° C. and filtered to remove the precipitated maleic acid. The filtrate was washed with H$_2$O and further washed with an aqueous solution prepared to contain 10% KOH and 10% Na$_2$SO$_3$ and with saturated aqueous sodium chloride, and then dried over Na$_2$SO$_4$. After the solvent was distilled off, the residue was loaded onto silica gel column chromatography (hexane:EtOAc=1:1) to give compound 2 as a crude product. The resulting product was used for the subsequent reaction without further purification.

To a solution of the resulting compound 2 (crude 2.70 g) in EtOH (100 ml), sulfuric acid (0.5 ml) was added at room temperature, followed by heating and stirring at 70° C. for 17 hours. After the solvent was almost completely distilled off, the residue was extracted with EtOAc. The organic layer was washed with aqueous solutions of sat. NaHCO$_3$ and sat. NaCl, and then dried over Na$_2$SO$_4$. After the solvent was distilled off the residue was purified by silica gel column chromatography (hexane:EtOAc=7:1→3:1) to give the corresponding ethyl ester (compound 3) (1.85 g, 55% for 2 steps).

$^1$H-NMR (400 MHz, CDCl$_3$) δ 4.14 (2H, q, J=7.3 Hz, CO$_2$CH$_2$CH$_3$), 3.64 (2H, t, J=6.4 Hz, CH$_2$OH), 2.26 (2H, t, J=7.5 Hz, CH$_2$CO$_2$Et), 1.71 (1H, br, OH, 1.68-1.53 (4H, m, CH$_2$CH$_2$OH & CH$_2$CH$_2$CO$_2$Et), 1.28 {14H, m, (CH$_2$)$_7$}, 1.26 (3H, t, J=7.3 Hz, CO$_2$CH$_2$CH$_3$).

Under an argon stream, CHCl$_3$ (30 ml) was mixed with oxalyl chloride (1.16 ml, 13.5 mmol) at room temperature and then cooled to −55° C. After DMSO (1.90 ml, 26.8 mmol) was added dropwise and stirred for 15 minutes, a solution of compound 3 (1.63 g, 6.67 mmol) in CHCl$_3$ (15 ml) was added dropwise thereto and further stirred for 3 hours. After addition of Et$_3$N (5.6 ml, 40 mmol), the reaction mixture was stirred for 45 minutes while elevating the temperature to 0° C., and H$_2$O was added to stop the reaction. After the organic layer was separated and collected, the aqueous layer was extracted with EtOAc. The combined organic layers were washed with aqueous solutions of sat. NH$_4$Cl and sat. (saturated) NaCl, and then dried over Na$_2$SO$_4$. After the solvent was distilled off, the residue was purified by silica gel column chromatography (hexane:EtOAc=5:1) and the resulting solid was further purified by recrystallization (hexane:EtOAc=10:1) to give an aldehyde (compound 5) (1.53 g, 95%). Mp. 60-61° C.

$^1$H-NMR (500 MHz, CDCl$_3$) δ 9.77 (1H, t, J=1.8 Hz, CHO), 4.12 (2H, q, J=7.1 Hz, CO$_2$CH$_2$CH$_3$), 2.42 (2H, dt, J=1.8, 7.3 Hz, CH$_2$CH$_2$CHO), 2.28 (2H, t, J=7.6 Hz, CH$_2$CO$_2$Et), 1.65-1.58 (4H, m, CH$_2$CH$_2$CHO and CH$_2$CH$_2$CO$_2$Et), 1.28 {12H, br, (CH$_2$)$_6$}, 1.25 (3H, t, J=7.1 Hz, CO$_2$CH$_2$CH$_3$).

To a solution of 3-chloro-4,6-dihydroxy-2-methylbenzaldehyde (hereinafter abbreviated as compound 112, 0.285 g, 1.527 mmol) in MeOH (1.0 ml), CaCl$_2$.2H$_2$O (0.200 g, 1.360 mmol) was added and then cooled to 0° C. To this mixture, KOH (1.1 M in MeOH, 2.3 ml, 2.5 mmol) was added and stirred for 5 minutes, and a solution of compound 5 (0.447 g, 1.844 mmol) in MeOH (1.0 ml) was further added dropwise thereto and stirred for 16 hours while gradually returning to room temperature. After addition of a 0.1 M aqueous KOH solution (10 ml), the reaction mixture was extracted three times with EtOAc. The combined organic layers were washed with an aqueous solution of sat. NaCl and dried over Na$_2$SO$_4$. After the solvent was distilled off, the residue was purified by silica gel column chromatography (hexane:EtOAc=3:1) to give the corresponding aldol adduct (0.145 g, 22%).

To a solution of the resulting secondary alcohol (0.075 g, 0.175 mmol) in AcOH (1.5 ml), H$_3$PO$_4$ (0.06 ml) was added and stirred at 70° C. for 6 hours. After returning to room temperature, the reaction mixture was diluted with H$_2$O and EtOA. After the organic layer was separated and collected, the aqueous layer was extracted twice with EtOAc. The combined organic layers were washed with aqueous solutions of sat. NaHCO$_3$ and sat. NaCl, and then dried over Na$_2$SO$_4$. After the solvent was distilled off, the residue was purified by silica gel column chromatography (hexane:EtOAc=5:1) and the resulting solid was further purified by recrystallization (hexane:EtOAc=10:1) to give the corresponding olefin (0.048 g, 67%).

The resulting olefin (42 mg, 0.10 mmol) was dissolved in EtOAc (5 ml) and cooled to 0° C., followed by addition of a catalytic amount of Pd—C. This mixture was stirred for 2 hours under a hydrogen atmosphere. After Pd—C was filtered off, the solvent was distilled off and the residue was purified by silica gel column chromatography (hexane:EtOAc=4:1). The resulting solid was further recrystallized from hexane to give the desired product (19.5 mg, 47%). Mp. 59-60° C.

$^1$H-NMR (400 MHz, CDCl$_3$) δ 12.65 (1H, s, Ar—OH), 10.14 (1H, s, Ar—CHO), 6.33 (1H, s, Ar—OH), 4.12 (2H, q, J=7.2 Hz, CO$_2$CH$_2$CH$_3$), 2.66 (2H, t, J=7.7 Hz, ArCH$_2$), 2.61 (3H, s, Ar—CH$_3$), 2.28 (2H, t, J=7.3 Hz, CH$_2$CO$_2$Et), 1.63-1.56 (2H, m, CH$_2$), 1.54-1.49 (2H, m, CH$_2$), 1.38-1.24 {17H, m, (CH$_2$)$_8$ & CO$_2$CH$_2$CH$_3$)}. IR (KBr) 3348, 2930, 2853, 1736, 1610, 1452, 1416, 1377, 1327, 1279, 1240, 1167, 1128, 1020, 916, 860, 785, 708, 590 cm$^{-1}$. HRMS (EI) calcd. For C$_{22}$H$_{33}$ClO$_5$: 412.2018. found 412.2032.

Isopropyl 12-(3-chloro-5-formyl-2,6-dihydroxy-4-methylphenyl)dodecanate (215-15-COO$^i$Pr)

Compound 2 (crude, 5.418 g) was refluxed in KOH (1.5 M in MeOH, 40 ml, 60 mmol) for 3 hours. After returning to room temperature, the reaction mixture was poured into H$_2$O and washed twice with EtOAc, and the aqueous layer was then acidified with 2 M HCl and extracted twice with EtOAc. The combined organic layers were washed with sat. aq. NaCl and dried over Na$_2$SO$_4$. After the solvent was distilled off, the precipitated crude crystals were recrystallized from a mixed solvent of acetone:hexane=1:5 to give the corresponding carboxylic acid (4.326 g, 72% for 2 steps). Mp. 82-83° C.

$^1$H-NMR (400 MHz, CDCl$_3$) δ 3.65 (2H, t, J=6.6 Hz, CH$_2$OH), 2.35 (2H, t, J=7.5 Hz, CH$_2$CO$_2$H), 1.67-1.53 (4H, m, CH$_2$CH$_2$OH and CH$_2$CH$_2$CO$_2$Et), 1.28 {16H, br, CH$_2$OH, COOH & (CH$_2$)$_7$}.

To a solution of this carboxylic acid (0.803 g, 3.71 mmol) in $^i$PrOH (50 ml), H$_2$SO$_4$ (0.5 ml) was added at room temperature and stirred at 70° C. for 20 hours. After returning to room temperature, the reaction mixture was evaporated to distill off about half of the solvent, and then poured into H$_2$O. This mixture was extracted twice with EtOAc, and the combined organic layers were washed with sat. aq. NaCO$_3$ and sat. aq. NaCl, and then dried over Na$_2$SO$_4$. After the solvent was distilled off, the residue was purified by silica gel column chromatography (hexane:EtOAc=4:1→1:1) to prepare the corresponding isopropyl ester (compound 4) (0.680 g, 71%).

$^1$H-NMR (400 MHz, CDCl$_3$) δ 5.00 {2H, sep, J=6.2 Hz, OCH(CH$_3$)$_2$}, 3.64 (2H, t, J=5.9 Hz, CH$_2$OH), 2.29 (2H, t, J=7.5 Hz, CH$_2$CO$_2$Et), 1.68-1.53 (4H, m, CH$_2$CH$_2$OH and CH$_2$CH$_2$CO$_2$Et), 1.42 (1H, br, OH), 1.27 {14H, m, (CH$_2$)$_7$}, 1.22 {6H, d, J=6.2 Hz, OCH(CH$_3$)$_2$}.

The same steps were then repeated to give the desired product (3% yield from compound 4). Mp. 56° C.

$^1$H-NMR (400 MHz, CDCl$_3$) δ 12.66 (1H, s, Ar—OH), 10.14 (1H, s, Ar—CHO), 6.33 (1H, s, Ar—OH), 5.00 {1H, m, CO$_2$CH(CH$_3$)$_2$}, 2.66 (2H, t, J=7.7 Hz, Ar—CH$_2$), 2.61 (3H, s, Ar—CH$_3$), 2.25 {2H, t, J=7.5 Hz, CH$_2$CO$_2$ $^i$Pr}, 1.65-1.57 (2H, m, CH$_2$), 1.54-1.48 (2H, m, CH$_2$), 1.26 {14H, br, (CH$_2$)$_7$}, 1.22 {6H, d, J=6.2 Hz, CH(CH$_3$)$_2$}. IR (KBr) 3287, 2922, 2845, 1703, 1616, 1456, 1421, 1377, 1279, 1248, 1196, 1105, 836, 631, 590 cm$^{-1}$. HRMS (EI) Found: 426.2186. Calcd. for C$_{23}$H$_{35}$ClO$_5$: 426.2173.

12-(3-Chloro-5-formyl-2,6-dihydroxy-4-methylphenyl)dodecanoic acid (215-13-COOH)

To a solution of 215-15-COOEt (101 mg, 0.246 mmol) in a mixture of acetone (1.3 ml)/H$_2$O (0.7 ml), NaOH (21 mg, 0.48 mmol) was added at room temperature and stirred for 12 hours. The reaction mixture was diluted with EtOAc and then acidified with a 1 M aqueous HCl solution, followed by addition of sat. aq. NaCl to separate and collect the organic layer. Then, the aqueous layer was extracted twice with EtOAc, and the combined organic layers were dried over Na$_2$SO$_4$. After the solvent was distilled off, the residue was purified by silica gel column chromatography (hexane:EtOAc=2:1) to give the desired product. Mp. 130-131° C.

$^1$H-NMR (400 MHz, CDCl$_3$) δ 12.66 (1H, s, Ar—OH), 10.14 (1H, s, Ar—CHO), 6.34 (1H, br, Ar—OH), 2.66 (2H, t, J=7.7 Hz, Ar—CH$_2$), 2.61 (3H, s, Ar—CH$_3$), 2.35 (2H, t, J=7.3 Hz, CH$_2$COOH), 1.65-1.46 (4H, m, CH$_2$CH$_2$COOH & ArCH$_2$CH$_2$), 1.35 {14H, br, (CH$_2$)$_7$}. IR (KBr) 3360, 2920, 2855, 1715, 1612, 1472, 1420, 1283, 1246, 1180, 1126, 937, 853, 785, 588 cm$^{-1}$. HRMS (EI) Found: 384.1712. Calcd. for C$_{20}$H$_{29}$ClO$_5$: 384.1704.

2. Compound 215-13-COOEt

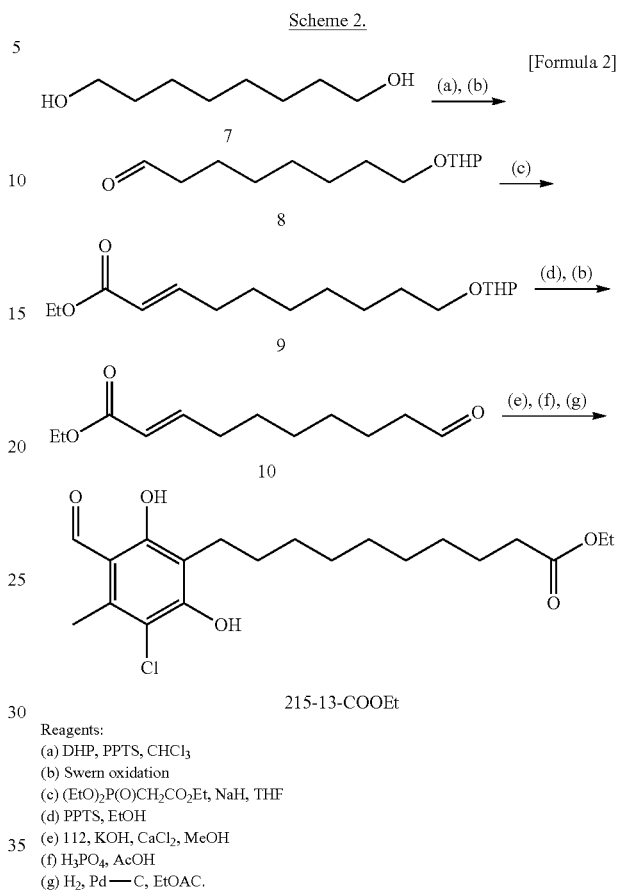

Scheme 2.

[Formula 2]

Reagents:
(a) DHP, PPTS, CHCl$_3$
(b) Swern oxidation
(c) (EtO)$_2$P(O)CH$_2$CO$_2$Et, NaH, THF
(d) PPTS, EtOH
(e) 112, KOH, CaCl$_2$, MeOH
(f) H$_3$PO$_4$, AcOH
(g) H$_2$, Pd—C, EtOAC.

Ethyl 10-(3-chloro-5-formyl-2,6-dihydroxy-4-methylphenyl)decanate (215-13-COOEt)

To a solution of 1,8-octanediol (compound 7, 5.85 g, 40.0 mmol) in CHCl$_3$ (100 ml), DHP (3.46 ml, 37.9 mmol) and a catalytic amount of PPTS were added at room temperature under an argon stream and then stirred for 16 hours. After the reaction mixture was diluted with H$_2$O and stirred for 5 minutes, the organic layer was separated and collected, and the aqueous layer was extracted with EtOAc. The combined organic layers were washed with aqueous solutions of sat. NaHCO$_3$ and sat. NaCl, and then dried over Na$_2$SO$_4$. After the solvent was distilled off, the residue was purified by silica gel column chromatography (hexane:EtOAc=3:1→2:1) to give the corresponding THP ether (4.95 g, 54%).

To a solution of oxalyl chloride (2.0 ml, 23 mmol) in CHCl$_3$ (50 ml), DMSO (2.8 ml, 40 mmol) was added dropwise at −55° C. After 15 minutes, a solution of the primary alcohol (2.18 g, 9.46 mmol) in CHCl$_3$ (20 ml) was added dropwise and stirred for 2 hours. To this mixture, Et$_3$N (8.0 ml, 58 mmol) was added dropwise and then stirred for 45 minutes while elevating the temperature to 0° C. The reaction mixture was diluted with H$_2$O to separate and collect the organic layer, and the aqueous layer was then extracted with EtOAc. The combined organic layers were washed with sat. aq. NaCl and dried over Na$_2$SO$_4$. After the solvent was distilled off, the residue was purified by silica gel column chromatography (hexane:EtOAc=5:1) to give an aldehyde (compound 8) (1.95 g, 90%).

¹H-NMR (400 MHz, CDCl₃) δ 9.77 (1H, t, J=1.8 Hz, CHO), 4.57 (1H, dd, J=2.6, 4.8 Hz, OCHO), 3.90-3.84 (1H, m, CH₂O), 3.73 (1H, td, J=6.8, 9.6 Hz, CH₂O), 3.53-3.48 (1H, m, CH₂O), 3.38 (1H, td, J=6.6, 9.5 Hz, CH₂O), 2.42 (2H, dt, J=1.8, 7.5 Hz, CH₂CHO), 1.87-1.78 (1H, m, OCHCH₂), 1.75-1.68 (1H, m, OCHCH₂), 1.67-1.49 (8H, m, 4×CH₂), 1.43-1.28 (6H, m, 3×CH₂).

Then, to a suspension of NaH (50% purity, 0.378 g, 7.88 mmol) in THF (50 ml), diethyl phosphonoacetic acid diethyl ether (1.45 ml, 7.25 mmol) was added at 0° C. under an argon stream and stirred for 1.5 hours. After this reaction mixture was cooled to −60° C. a solution of 8 (1.44 g, 6.31 mmol) in THF (15 ml) was added dropwise thereto. The reaction mixture was stirred at the same temperature for 30 minutes and then returned to room temperature, followed by stirring for 18 hours. This mixture was cooled again to 0° C. and H₂O was then added thereto in small portions to decompose excess NaH. After H₂O was further added, the mixture was extracted twice with Et₂O. The combined organic layers were washed with sat. aq. NaCl and dried over Na₂SO₄. After the solvent was distilled off, the residue was purified by silica gel column chromatography (hexane:EtOAc=7:1) to give the corresponding ethyl ester (compound 9) (1.62 g, 86%).

To a solution of the ester (compound 9) (1.15 g, 3.85 mmol) in EtOH (30 ml), a catalytic amount of PPTS was added at room temperature, followed by heating and stirring at 60° C. for 2.5 hours. After the solvent was almost completely distilled off, the residue was dissolved in EtOAc, and this solution was washed sequentially with H₂O, sat. aq. NaHCO₃ and sat. aq. NaCl, and then dried over Na₂SO₄. After the solvent was distilled off, the residue was purified by silica gel column chromatography (hexane:EtOAc=7:1) to give the corresponding primary alcohol (0.63 g, 76%).

¹H-NMR (500 MHz, CDCl₃) δ 6.96 (1H, dt, J=7.0, 15.6 Hz, CH═CHCO₂Et), 5.81 (1H, dt, J=1.5, 15.6 Hz, CH═CHCO₂Et), 4.18 (2H, q, J=7.1 Hz, CO₂CH₂CH₃), 3.64 (2H, t, J=6.5 Hz, CH₂CH₂OH), 2.19 (2H, ddt, J=1.4, 7.1, 7.6 Hz, CH₂CH═CH), 1.56 (2H, m, CH₂CH₂OH), 1.46 (2H, m, CH₂CH₂CH═CH), 1.37-1.31 {7H, m, (CH₂)₃ & OH}, 1.29 (3H, t, J=7.1 Hz, CO₂CH₂CH₃).

Subsequently, the resulting primary alcohol was converted by Swern oxidation into the corresponding aldehyde (10) (0.45 g, 72%).

¹H-NMR (400 MHz, CDCl₃) δ 9.77 (1H, s, CHO), 6.95 (1H, dt, J=7.0, 15.8 Hz, CH═CHCO₂Et), 5.81 (1H, dt, J=1.4, 15.8 Hz, CH═CHCO₂Et), 4.19 (2H, q, 0.1=7.2 Hz, CO₂CH₂CH₃), 2.43 (2H, dt, J=1.8, 7.3 Hz, CH₂CHO), 2.20 (2H, ddt, J=1.4, 7.0, 7.3 Hz, CH₂CH═CH), 1.66-1.60 (2H, m, CH₂CH₂CHO), 1.49-1.42 (2H, m CH₂CH₂CH═CH), 1.36-1.32 {4H, m (CH₂)₂}, 1.29 (3H, t, J=7.2 Hz, CO₂CH₂CH₃).

The same procedures as described above were then used to give the desired product (2% for 3 steps). Mp. 45-46° C.

¹H-NMR (400 MHz, CDCl₃) δ 12.67 (1H, s, Ar—OH), 10.14 (1H, s, Ar—CHO), 6.39 (1H, s, Ar—OH), 4.12 (2H, q, J=7.3 Hz, CO₂CH₂CH₃), 2.66 (2H, t, J=7.7 Hz, ArCH₂), 2.60 (3H, s, Ar—CH₃), 2.28 (2H, t, J=7.3 Hz, CH₂CO₂Et), 1.63-1.56 (2H, m, CH₂), 1.54-1.48 (2H, m, CH₂), 1.31-1.23 {13H, m, (CH₂)₅ and CO₂CH₂CH₃}. IR (KBr) 3452, 2922, 2853, 1736, 1637, 1468, 1421, 1377, 1327, 1286, 1248, 1175, 1119, 1084, 1018, 920, 843, 802, 726, 586 cm⁻¹. HRMS (EI) calcd. For C₂₀H₂₉Cl O₅: 384.1704. found 384.1687.

3. Compounds 200-12-COOMe, 215-12-COOMe, 215-13-COOⁱPr and 215-11-COOH

Scheme 3.

[Formula 3]

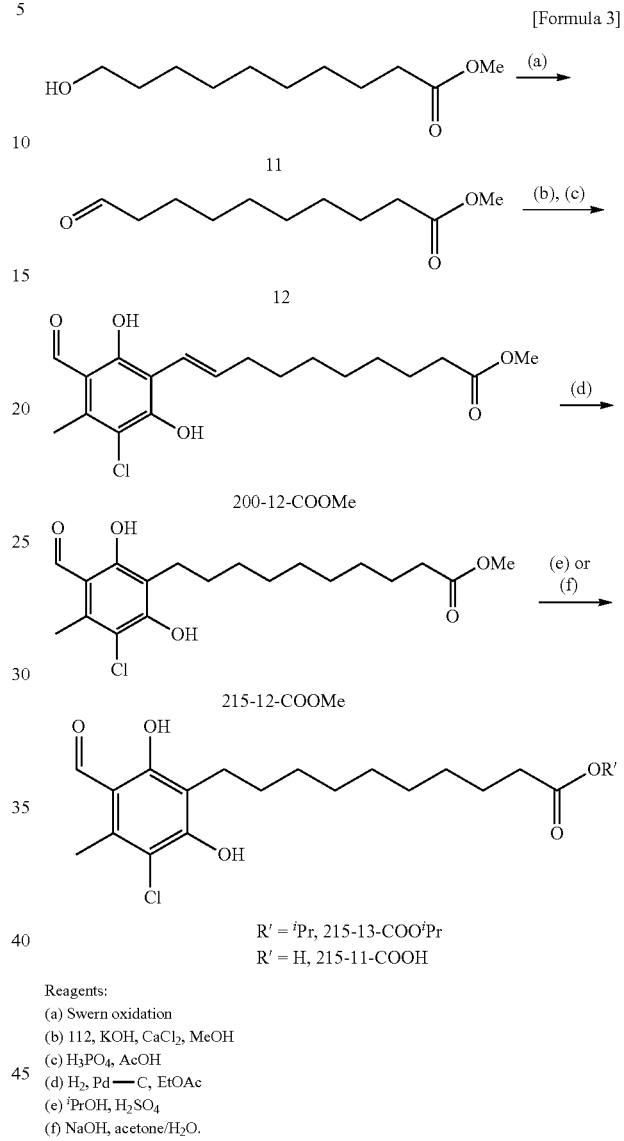

R' = ⁱPr, 215-13-COOⁱPr
R' = H, 215-11-COOH

Reagents:
(a) Swern oxidation
(b) 112, KOH, CaCl₂, MeOH
(c) H₃PO₄, AcOH
(d) H₂, Pd—C, EtOAc
(e) ⁱPrOH, H₂SO₄
(f) NaOH, acetone/H₂O.

(E)-Methyl 10-(3-chloro-5-formyl-2,6-dihydroxy-4-methylphenyl)-10-decenoate (200-12-COOMe)

Commercially available methyl 10-hydroxydecanoate (compound 11) was subjected to Swern oxidation to give an aldehyde (compound 12) (59% yield).

¹H-NMR (400 MHz, CDCl₃) δ 9.76 (1H, t, J=1.8 Hz, CHO), 3.67 (3H, s, CO₂CH₃), 2.42 (2H, dt, J=1.8, 7.3 Hz, CH₂CHO), 2.30 (2H, t, J=7.5 Hz, CH₂CO₂CH₃), 1.67-1.57 (4H, m, CH₂CH₂CHO & CH₂CH₂CO₂CH₃), 1.31 {8H, br, (CH₂)₄}).

This compound 11 was also subjected to aldol reaction with compound 112 and further dehydrated under acidic conditions to give the desired product (36% for 2 steps). Mp. 71-72° C.

¹H-NMR (400 MHz, CDCl₃) δ 13.05 (1H, s, Ar—OH, 10.14 (1H, s, Ar—CHO), 6.65 (1H, dt, J=6.8, 16.2 Hz, ArCH═CH), 6.63 (1H, s, Ar—OH), 6.50 (1H, d, J=16.2 Hz,

ArCH=CH), 3.67 (3H, s, COOCH$_3$), 2.61 (3H, s, Ar—CH$_3$), 2.33-2.23 (4H, m, CH=CHCH$_2$ & CH$_2$COOMe), 1.67-1.59 (2H, m, CH$_2$), 1.50-1.45 (2H, m, CH$_2$), 1.34 {6H, br (CH$_2$)$_3$}. IR (KBr) 3375, 2928, 2853, 1728, 1605, 1452, 1408, 1366, 1315, 1286, 1232, 1136, 1107, 980, 845, 802, 615, 592 cm$^{-1}$. HRMS (EI) Found: 368.1377. Calcd. for C$_{19}$H$_2$O$_5$Cl: (M$^+$), 368.1391. Anal. Found: C, 61.97; H, 6.86; Cl, 9.37%. Calcd. for C$_{19}$H$_{25}$O$_5$Cl: C, 61.87; H, 6.83; Cl, 9.61%.

Methyl 10-(3-chloro-5-formyl-2,6-dihydroxy-4-methylphenyl)decanate (215-12-COOMe)

The compound 200-12-COOEt was catalytically reduced to give the desired product (79% yield). Mp. 87-88° C.

$^1$H-NMR (400 MHz, CDCl$_3$) δ 12.65 (1H, s, Ar—OH), 10.14 (1H, s, Ar—CHO), 6.37 (1H, br, Ar—OH), 3.67 (3H, s, COOCH$_3$), 2.66 (2H, t, J=8.0 Hz, ArCH$_2$), 2.60 (3H, s, Ar—CH$_3$), 2.30 (2H, t, J=7.7 Hz, CH$_2$COOCH$_3$), 1.65-1.57 (2H, m, CH$_2$), 1.57-1.47 (2H, m, CH$_2$), 1.28 {10H, br, (CH$_2$)$_5$}. IR (KBr) 3358, 2928, 2853, 1736, 1611, 1421, 1250, 1171, 1132, 777, 590 cm$^{-1}$. HRMS (EI) Found: 370.1533. Calcd. for C$_{19}$H$_{27}$ClO$_5$: 370.1547. Anal. Found: C, 61.41; H, 7.32; Cl, 9.43%. Calcd. for C, 61.53; H, 7.34; Cl, 9.67%.

Isopropyl 10-(3-chloro-2,6-dihydroxy-5-formyl-4-methylphenyl)decanate (215-13-COO$^i$Pr)

To a solution of the compound 215-12-COOMe (114 mg, 0.307 mmol) in 2-propanol (25 ml), H$_2$SO$_4$ (0.25 ml) was added and refluxed for 18 hours. After returning to room temperature, the reaction mixture was evaporated to distill off the solvent, and the residue was extracted twice with EtOA. The combined organic layers were washed with sat. aq. NaHCO$_3$ and sat. aq. NaCl, and then dried over anhydrous Na$_2$SO$_4$. After the solvent was distilled off, the residue was purified by being subjected to silica gel column chromatography (hexane:EtOAc=7:1) and then recrystallization (hexane:EtOAc=9:1) to give the desired product. In addition, the mother liquor was concentrated, and the residue was purified by silica gel column chromatography (hexane:EtOAc=5:1) to further give the desired product (combined yield (83 mg, 68%)). Mp. 49° C.

$^1$H-NMR (400 MHz, CDCl$_3$) δ 12.66 (1H, s, Ar—OH), 10.14 (1H, s, Ar—CHO), 6.37 (1H, s, Ar—OH), 5.00 {1H, septet, J=6.2 Hz, CO$_2$CH(CH$_3$)$_2$}, 2.66 (2H, t, J=7.7 Hz, Ar—CH$_2$), 2.60 (3H, s, Ar—CH$_3$), 2.25 {2H, t, J=7.5 Hz, CH$_2$CO$_2$ $^i$Pr}, 1.64-1.57 (2H, m, CH$_2$), 1.54-1.48 (2H, m, CH$_2$), 1.28 {10H, br, (CH$_2$)$_5$}, 1.23 {6H, d, J=6.2 Hz, CH(CH$_3$)$_2$}. IR (KBr) 3271, 2916, 2845, 1703, 1610, 1468, 1412, 1366, 1325, 1286, 1251, 1217, 1109, 826, 631, 590 cm$^{-1}$. HRMS (EI) Found: 398.1841. Calcd. for C$_{21}$H$_{31}$ClO$_5$: 398.1860.

10-(3-Chloro-5-formyl-2,6-dihydroxy-4-methylphenyl)decanoic acid (215-11-COOH)

The compound 215-12-COOMe was hydrolyzed in the same manner as described above to give the desired product (89% yield). Mp. 154-156° C.

$^1$H-NMR (400 MHz, CDCl$_3$) δ 12.66 (1H, s, Ar—OH), 10.14 (1H, s, Ar—CHO), 6.34 (1H, br, Ar—OH), 2.66 (2H, t, J=7.7 Hz, ArCH$_2$), 2.61 (3H, s, Ar—CH$_3$), 2.35 (2H, t, J=7.5 Hz, CH$_2$COOH), 1.67-1.47 (4H, m, CH$_2$CH$_2$COOH & ArCH$_2$CH$_2$), 1.35 {10H, br, (CH$_2$)$_5$}. IR (KBr) 3360, 2920, 2853, 1715, 1614, 1470, 1418, 1371, 1236, 1184, 1126, 934, 847, 773, 588 cm$^{-1}$. HRMS (EI) Found: 356.1408. Calcd. for C$_{19}$H$_{25}$ClO$_5$: 356.1391.

4. Compounds 215-13-COOtBu, 501-16-G, 502-16-G and 500-15-G

Scheme 4.

[Formula 4]

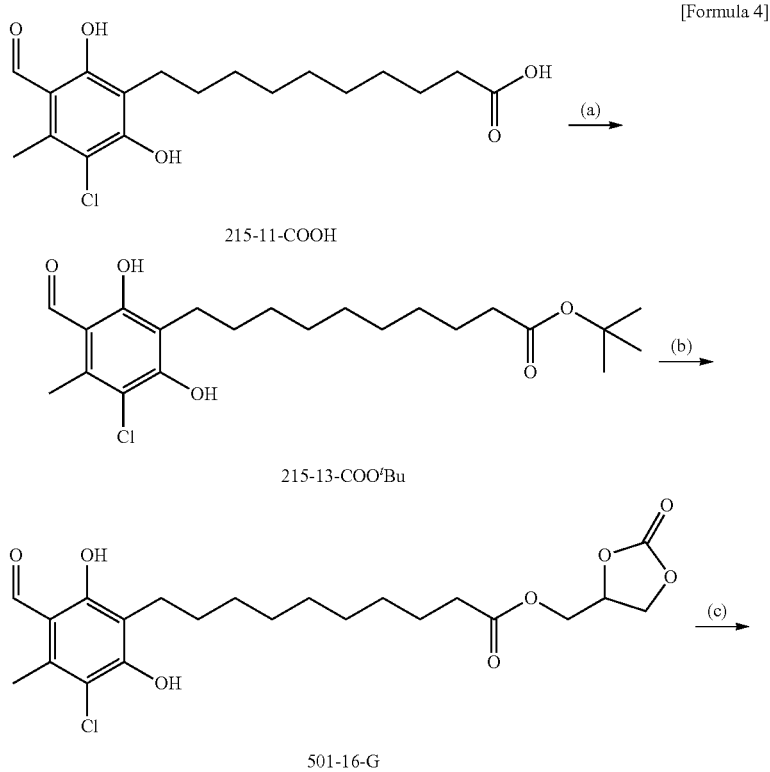

215-11-COOH 215-13-COO$^t$Bu 501-16-G

-continued

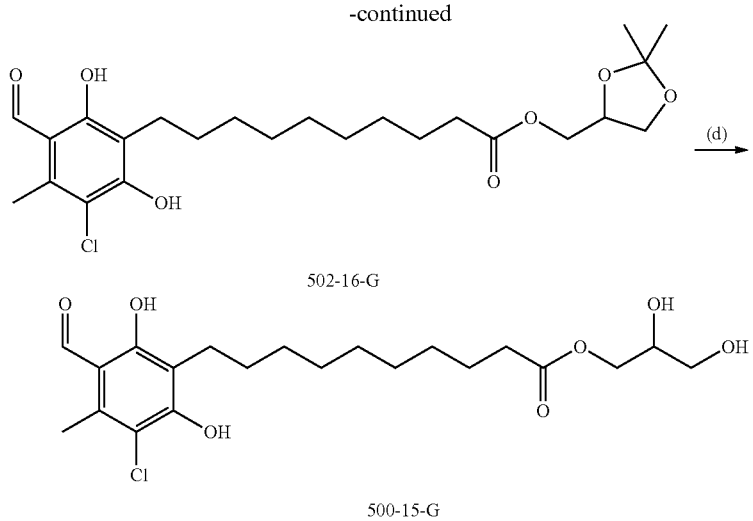

502-16-G 500-15-G

Reagents and conditions:
(a) tBuOH, TFAA, toluene
(b) 2,2-Dimethyl-1,3-dioxolane-4-methanol, DCC, DMAP, THF
(c) Glycerol 1,2-carbonate, DCC, DMAP, THF
(d) PPTS, MeOH.

tert-Butyl 10-(3-chloro-2,6-dihydroxy-5-formyl-4-methylphenyl)decanate (215-13-COOtBu)

To a suspension of the compound 215-11-COOH (144 mg, 0.403 mmol) in toluene (5 ml), TFAA (0.20 ml, 1.4 mmol) was added at 0° C. and stirred for 30 minutes while returning to room temperature. After the starting material was confirmed to be completely dissolved, the solution was cooled again to 0° C., mixed with $^t$BuOH (0.40 ml, 4.2 mmol) and stirred for 15 hours while returning to room temperature. The reaction mixture was diluted with sat. aq. NaHCO$_3$, stirred for 5 minutes and then extracted twice with EtOAc. The combined organic layers were washed with sat. aq. NaCl and dried over anhydrous Na$_2$SO$_4$. After the solvent was distilled off, the residue was purified by silica gel column chromatography (hexane:EtOAc=7:1→4:1) and further purified by PTLC (hexane:EtOAc=7:1) to give the desired product (28 mg, 17%).

$^1$H-NMR (400 MHz, CDCl$_3$) δ 12.65 (1H, s, Ar—OH), 10.14 (1H, s, Ar—CHO), 6.40 (1H, br, Ar—OH), 2.66 (2H, t, J=7.5 Hz, Ar—CH$_2$), 2.60 (3H, s, Ar—CH$_3$), 2.20 {2H, t, J=7.5 Hz, CH$_2$CO$_2^t$Bu}, 1.62-1.48 (4H, m, CH$_2$CH$_2$CO$_2^t$Bu & ArCH$_2$CH$_2$), 1.44 {9H, s, (CH$_3$)$_3$}, 1.29 {10H, br, (CH$_2$)$_5$}. IR (KBr) 3287, 2922, 2845, 1732, 1616, 1452, 1425, 1366, 1290, 1248, 1213, 1161, 1126, 934, 795, 716, 630, 590, 530 cm$^{-1}$.

1,3-Dioxolane-2-oxo-4-methyl 10-(3-chloro-5-formyl-2,6-dihydroxy-4-methylphenyl)decanate (501-16-G)

To a solution of the compound 215-11-COOH (184 mg, 0.516 mmol) in THF (30 ml), 2,2-dimethyl-1,3-dioxolane-4-methanol (98% purity, 0.25 ml, 2.0 mmol), DMAP (62 mg, 0.51 mmol) and DCC (130 mg, 0.630 mmol) were added at room temperature and stirred for 7 hours. After being diluted with phosphate buffer (pH 6.98) and EtOAc, the reaction mixture was filtered through celite, and the organic layer of the filtrate was separated and collected. After the aqueous layer was extracted twice with EtOAc, the combined organic layers were washed with sat. aq. NaCl and dried over anhydrous Na$_2$SO$_4$. After the solvent was distilled off, the residue was subjected to silica gel column chromatography (hexane:EtOAc=2:1→1:1) and further purified by PTLC (toluene:EtOAc=9:1). After the solvent was distilled off, the resulting crude product was purified again by silica gel column chromatography (hexane:EtOAc=2:1→3:2) to give the desired product (78 mg, 33%). Mp. 70-72° C.

$^1$H-NMR (400 MHz, CDCl$_3$) δ 12.65 (1H, s, Ar—OH), 10.13 (1H, s, Ar—CHO), 6.49 (1H, br, Ar—OH), 4.93 {1 H, m, CO$_2$CH$_2$CHOC(O)OCH$_2$}, 4.56 {1 H, dd, J=8.4, 8.8 Hz, CO$_2$CH$_2$CHOC(O)OCH$_2$}, 4.37 {1H, dd, J=3.3, 12.6 Hz, CO$_2$CH$_2$CHOC(O)OCH$_2$}, 4.31 {1H, dd, J=5.8, 8.8 Hz, CO$_2$CH$_2$CHOC(O)OCH$_2$ }, 4.26 {1H, dd, J=4.2, 12.6 Hz, CO$_2$CH$_2$CHOC(O)OCH$_2$}, 2.66 (2H, t, J=7.7 Hz, Ar—CH$_2$), 2.60 (3H, s, Ar—CH$_3$), 2.37 {2H, t, J=7.5 Hz, CH$_2$CH$_2$C(O)O}, 1.65-1.58 (2H, m, CH$_2$), 1.55-1.48 (2H, m, CH$_2$), 1.29 {10H, br, (CH$_2$)$_5$}. $^{13}$C-NMR (100 MHz, CDCl$_3$) δ 193.24, 173.27, 162.37, 156.26, 154.36, 137.27, 115.68, 113.41, 113.06, 73.75, 66.96, 62.78, 33.83, 29.41, 29.23, 29.18, 29.05, 28.94, 28.25, 24.66, 22.77, 14.40. IR (KBr) 3362, 2922, 2853, 1788, 1736, 1620, 1599, 1468, 1416, 1398, 1283, 1248, 1165, 1136, 1092, 1040, 878, 752, 586 cm$^{-1}$. HRMS (EI) Found: 456.1546. Calcd. for C$_{22}$H$_{29}$ClO$_8$: 456.1551.

2,2-Dimethyl-1,3-dioxolane-4-methyl 10-(3-chloro-5-formyl-2,6-dihydroxy-4-methylphenyl)decanate (502-16-G)

Esterification was conducted in the same manner to give the desired product (28% yield). Mp. 55-56° C.

$^1$H-NMR (400 MHz, CDCl$_3$) δ 12.65 (1H, s, Ar—OH), 10.14 (1H, s, Ar—CHO), 6.38 (1H, br, Ar—OH), 4.32 {1H, m, CHOC(CH$_3$)$_2$OCH$_2$—}, 4.17 {1H, dd, J=4.8, 11.7 Hz, C(O)OCH$_2$CH}, 4.11-4.06 {2H, m, CHOC(CH$_3$)$_2$OCH$_2$— & C(O)OCH$_2$CH}, 3.74 {1H, dd, J=6.2, 8.4 Hz, CHOC (CH$_3$)$_2$OCH$_2$}, 2.66 (2H, t, J=7.7 Hz, Ar—CH$_2$), 2.60 (3H, s, Ar—CH$_3$), 2.33 {2H, t, J=7.7 Hz, CH$_2$CH$_2$C(O)O}, 1.65-1.58 (2H, m, CH$_2$), 1.54-1.48 (2H, m, CH$_2$), 1.43 (3H, s, CH$_3$), 1.39 (3H, s, CH$_3$), 1.28 {10H, br, (CH$_2$)$_5$}. $^{13}$C-NMR (100 MHz, CDCl$_3$) δ 193.26, 173.69, 162.42, 156.20, 137.24, 115.74, 113.47, 113.04, 109.81, 73.60, 66.35, 64.50, 34.10, 29.47, 29.27, 29.25, 29.14, 29.03, 28.29, 26.67, 25.38, 24.82, 22.82, 14.44. IR (KBr) 3265, 2922, 2853, 1745, 1620, 1526, 1460, 1425, 1369, 1331, 1244, 1219, 1171, 1132, 1092, 1045, 1007, 980, 932, 851, 795, 712, 625, 596, 534 cm$^{-1}$. HRMS (EI) Found: 470.2047. Calcd. for C$_{24}$H$_{35}$ClO$_7$: 470.2071.

1-Glyceryl 10-(3-chloro-2,6-dihydroxy-5-formyl-4-methylphenyl)decanate (500-15-0)

To a solution of the compound 502-16-G (77 mg, 0.16 mmol) in MeOH (5 ml), PPTS (10 mg, 40 µmol) was added at room temperature and stirred at 50° C. for 20 hours. After returning to room temperature, the reaction mixture was evaporated to distill off the solvent and the residue was purified by silica gel column chromatography (hexane:EtOAc=2:1→EtOAc only) to give the desired product (11 mg, 16%). It should be noted that its methyl ester (compound 215-12-CO$_2$Me) was also obtained as a by-product in an amount of 10 mg (17%).

$^1$H-NMR (400 MHz, CDCl$_3$) δ 12.64 (1H, s, Ar—OH), 10.13 (1H, s, Ar—CHO), 6.62 (1H, br, Ar—OH), 4.21 {1H, dd, J=4.8, 11.7 Hz, C(O)OCH$_2$CH(OH)CH$_2$OH}, 4.15 {1H, dd, J=6.2, 11.7 Hz, C(O)OCH$_2$CH(OH)CH$_2$OH}, 3.94 {(1H, m, C(O)OCH$_2$CH(OH)CH$_2$OH}, 3.71 {1H, dd, J=3.6, 11.4 Hz, C(O)OCH$_2$CH(OH)CH$_2$OH), 3.61 (1H, dd, J=5.9, 11.4 Hz, C(O)OCH$_2$CH(OH)CH$_2$OH}, 2.98 (1H, br, OH), 2.65 (2H, t, J=7.5 Hz, Ar—CH$_2$), 2.60 (3H, s, Ar—CH$_3$), 2.35 {2H, t, J=7.7 Hz, CH$_2$CH$_2$C(O)O—}, 2.07 (1H, br, O$_H$), 1.66-1.58 (2H, m, CH$_2$), 1.55-1.49 (2H, m, CH$_2$), 1.28 {10H, br, (CH$_2$)$_5$}. IR (KBr) 3314, 2930, 2853, 1740, 1599, 1558, 1468, 1425, 1383, 1335, 1279, 1252, 1182, 1126, 1057, 928, 795, 743, 712, 625, 592, 534 cm$^{-1}$. HRMS (EI) Found: 430.1783. Calcd. for C$_{21}$H$_{31}$ClO$_7$: 430.1758.

5. Compounds 215-11-COOEt, 215-9-COOH and 215-18-Anthra

Scheme 5.

[Formula 5]

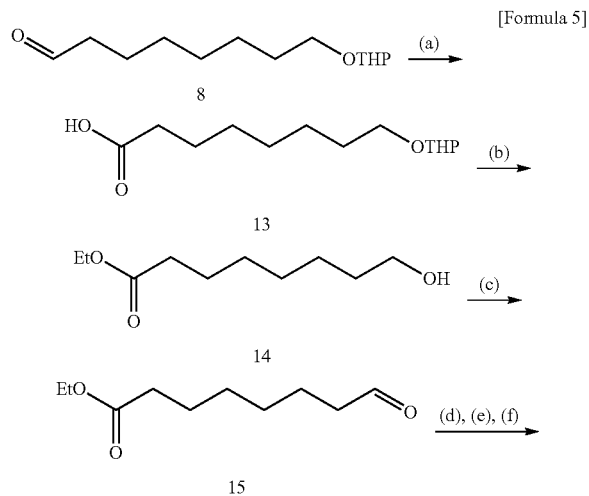

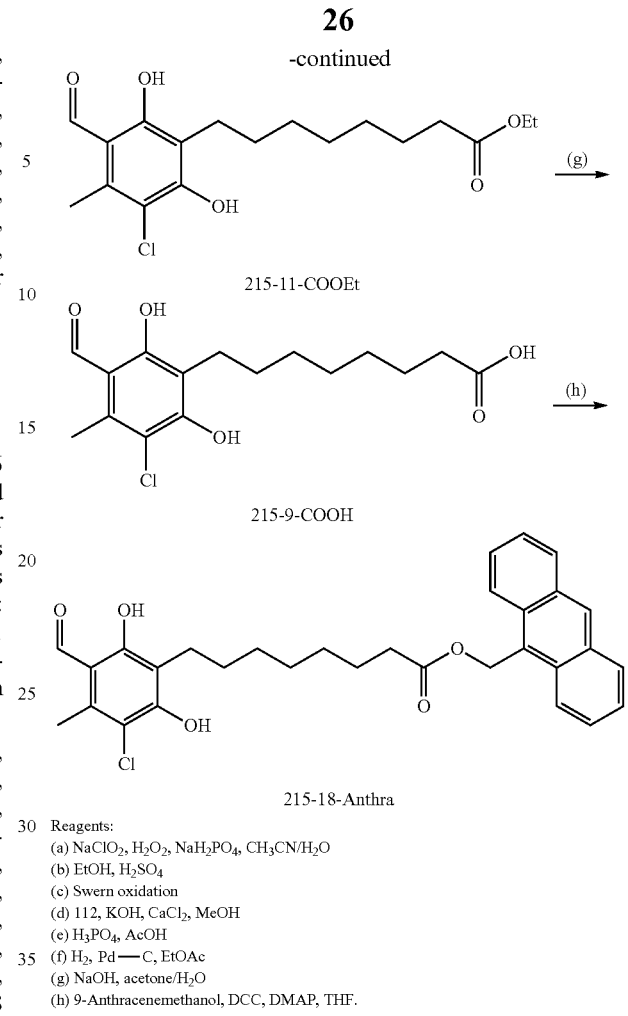

Reagents:
(a) NaClO$_2$, H$_2$O$_2$, NaH$_2$PO$_4$, CH$_3$CN/H$_2$O
(b) EtOH, H$_2$SO$_4$
(c) Swern oxidation
(d) 112, KOH, CaCl$_2$, MeOH
(e) H$_3$PO$_4$, AcOH
(f) H$_2$, Pd—C, EtOAc
(g) NaOH, acetone/H$_2$O
(h) 9-Anthracenemethanol, DCC, DMAP, THF.

Ethyl 8-(3-chloro-5-formyl-2,6-dihydroxy-4-methylphenyl)octanoate (215-11-COOEt)

To a solution of the aldehyde (compound 8, 1.950 g, 8.541 mmol) in MeCN (40 ml), a solution of NaH$_2$PO$_4$.2H$_2$O (3.312 g, 21.23 mmol) in H$_2$O (10 ml) was added at −15° C. and stirred for 10 minutes. This mixture was mixed with H$_2$O$_2$ (30% in H$_2$O, 7.8 ml, 76 mmol) and, after 5 minutes, with NaClO$_2$ (79%6 purity, 1.311 g, 11.45 mmol), and then further stirred for 1 hour. The reaction mixture was diluted with a 20% aqueous Na$_2$SO$_3$ solution, stirred for 10 minutes and then poured into 1 M HCl. This mixture was extracted three times with EtOAc, and the combined organic layers were washed with sat. aq. NaCl and dried over Na$_2$SO$_4$. After the solvent was distilled off, the residue was purified by silica gel column chromatography (hexane:EtOAc=4:1→2:1) to give a carboxylic acid (compound 13) (0.850 g, 41%).

To a solution of this compound 13 (0.453 g, 1.984 mmol) in EtOH (20 ml), H$_2$SO$_4$ (0.5 ml) wad added and stirred at 60° C. for 15 hours. After the solvent was distilled off, the residue was diluted with EtOAc. This dilution was washed with sat. aq. NaHCO$_3$ and sat. aq. NaCl, and then dried over Na$_2$SO$_4$. After the solvent was distilled off, the residue was purified by silica gel column chromatography (hexane:EtOAc=2:1) to give the corresponding ethyl ester (compound 14) (0.224 g, 60%).

$^1$H-NMR (400 MHz, CDCl$_3$) δ 4.12 (2H, q, J=7.0 Hz, OCH$_2$CH$_3$), 3.64 (2H, dd, J=6.6, 7.3 Hz, CH$_2$OH), 2.29 (2H, t, J=7.7 Hz, CH$_2$CO$_2$Et), 1.66-1.53 (5H, m, CH$_2$CH$_2$OH, CH$_2$CH$_2$CO$_2$Et, and OH), 1.34 {6H, m, (CH$_2$)$_3$}, 1.26 (3H, t, J=7.0 Hz, OCH$_2$CH$_3$).

The same procedures as described above were then used to synthesize the desired product. 2% yield from compound 14. Mp 54-55° C.

$^1$H-NMR (400 MHz, CDCl$_3$) δ 12.66 (1H, s, Ar—OH), 10.14 (1H, s, Ar—CHO), 6.34 (1H, s, Ar—OH), 4.11 (2H, q, J=7.3 Hz, CO$_2$CH$_2$CH$_3$), 2.66 (2H, t, J=7.5 Hz, Ar—CH$_2$), 2.61 (3H, s, Ar—CH$_3$), 2.28 (2H, t, J=7.3 Hz, CH$_2$CO$_2$Et) 1.65-1.49 (4H, m, ArCH$_2$CH$_2$ & CH$_2$CH$_2$CO$_2$Et), 1.34 {6H, br, (H$_2$)$_3$} 1.26 (3H, t, J=7.3 Hz, CO$_2$CH$_2$CH$_2$). IR (KBr) 3321, 2930, 2847, 1728, 1612, 1421, 1285, 1244, 1140, 783, 590 cm$^{-1}$. HRMS (EI) Found: 356.1381. Calcd. for C$_{18}$H$_{25}$ClO$_5$: 356.1391.

8-(3-Chloro-5-formyl-2,6-dihydroxy-4-methylphenyl)octanoic acid (215-9-COOH)

The compound 215-11-COOEt was hydrolyzed in the same manner as described above to give the desired product (66% yield). Mp. 149-150° C.

$^1$H-NMR (400 MHz, CDCl$_3$) δ 12.66 (1H, s, Ar—OH), 10.14 (1H, s, Ar—CHO), 6.33 (1H, br, Ar—OH), 2.66 (2H, t, J=7.7 Hz, ArCH$_2$), 2.61 (3H, s, Ar—CH$_3$), 2.35 (2H, t, J=7.7 Hz, CH$_2$COOH), 1.68-1.48 (4H, m, CH$_2$CH$_2$COOH & ArCH$_2$CH$_2$), 1.35 {6H, br, (H$_2$)$_3$}. IR (KBr) 3350, 2930, 2850, 1710, 1620, 1420, 1370, 1280, 1245, 1135, 1120, 940, 775, 590 cm$^{-1}$. HRMS (EI) Found: 328.1057. Calcd. for C$_{16}$H$_{21}$ClO$_5$: 328.1078.

9-Anthryl 8-(3-chloro-5-formyl-2,6-dihydroxy-4-methylphenyl)octanoate (215-18-Anthra)

215-9-COOH was esterified in the same manner as described above to give the desired product (53% yield). Mp. 150-151° C.

$^1$H-NMR (400 MHz, CDCl$_3$) δ 12.64 (1H, s, Ar—OH), 10.13 (1H, s, Ar—CHO), 8.51 (1H, s, Ar—H), 8.33 (2H, d, J=8.8 Hz, Ar—H), 8.03 (2H, d, J=8.4 Hz, Ar—H), 7.57 (2H, t, J=7.7 Hz, Ar—H), 7.49 (2H, t, J=7.4 Hz, Ar—H), 6.29 (1H, s, Ar—OH), 6.15 (2H, s, CO$_2$CH$_2$Ar), 2.62 (2H, t, J=7.3 Hz, Ar—CH$_2$), 2.60 (3H, s, Ar—CH$_3$), 2.32 {2H, t, J=7.5 Hz, CH$_2$CO$_2$CH$_2$Ar}, 1.62-1.55 (2H, m, CH$_2$), 1.50-1.42 (2H, m, CH$_2$), 1.27 {6H, br, (CH$_2$)$_3$}. IR (KBr) 3356, 2916, 2853, 1717, 1634, 1468, 1421, 1391, 1373, 1296, 1252, 1182, 1126, 1094, 949, 889, 795, 733, 638, 590 cm$^{-1}$. HRMS (EI) Found: 518.1859. Calcd. for C$_{31}$H$_{31}$ClO$_5$: 518.1860.

6. Compounds 217 and 224, known naturally occurring Colletorin B (compound 216), known naturally occurring Colletochlorin B, and known naturally occurring LL-Z1272α (compound 280-12)

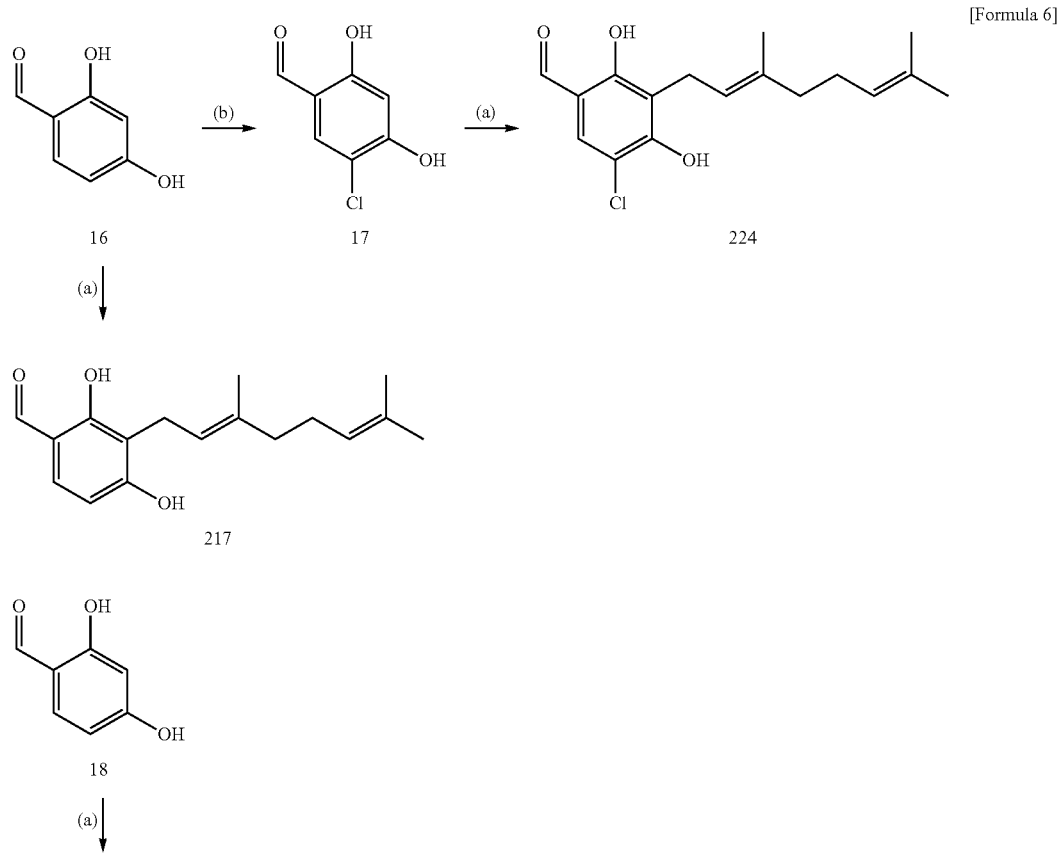

Scheme 6.

[Formula 6]

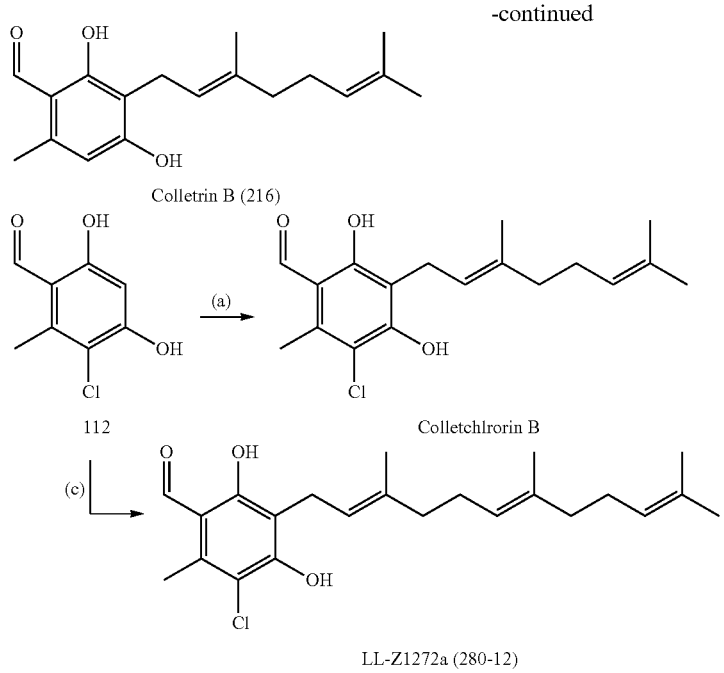

Reagents:
(a) Geranyl bromide, KOH, CaCl$_2$, MeOH,
(b) NCS, AcOH
(c) Farnesyl bromide, KOH, CaCl$_2$, MeOH Typical Experimental Procedures for Introduction of an Allyl-Based Side Chain into an Aromatic Ring Moiety To a solution of a resorcinol derivative (1.0 eq.) in KOH (1.0 M in MeOH. 1.5 eq.), a MeOH solution of the corresponding side chain bromide (1.2 eq) and CaCl$_2$.2H$_2$O (0.75 eq.) were added and stirred (8 to 24 hours) under cooling (−40° C. to 0° C.). The reaction mixture was diluted with EtOAc and filtered through celite. The filtrate was then poured into a 0.1 M aqueous KOH solution to separate and collect the organic layer. After the aqueous layer was further extracted twice with EtOAc, the combined organic layers were washed with sat. aq. NaCl and dried over Na$_2$SO$_4$. After the solvent was distilled off, the residue was purified by silica gel column chromatography or recrystallization to give the corresponding alkylated product. It should be noted that the aqueous layer was acidified with 2 M aq. HCl and then extracted twice with EtOAc to collect the unreacted resorcinol derivative.

Typical Experimental Procedures for Chlorination of an Aromatic Ring Moiety

To an acetic acid solution of a resorcinol derivative (1.0 eq.), NCS (1.1 eq) was added at room temperature, followed by heating (80° C. to 100° C.) and stirring (14 to 24 hours). After returning to room temperature, the reaction mixture was poured into H$_2$O and extracted with EtOAc. After the aqueous layer was further extracted with EtOAc, the combined organic layers were washed three times with sat. aq. NaHCO$_3$ and once with sat. aq. NaCl, and then dried over Na$_2$SO$_4$. After the solvent was distilled off, the residue was purified by silica gel column chromatography or recrystallization to give the corresponding chlorine-substituted product.

(E)-2,4-Dihydroxy-3-(3,7-dimethyl-2,6-octadienyl)benzaldehyde (compound 217)

Mp 85° C. $^1$H-NMR (400 MHz, CDCl$_3$) δ 11.79 (1H, s, Ar—O$\underline{H}$), 9.69 (1H, s, Ar—C$\underline{H}$O), 7.32 (1H, d, J=8.6 Hz, Ar—$\underline{H}$), 6.48 (1H, d, J=8.6 Hz, Ar—$\underline{H}$), 6.21 (1H, s, Ar—O$\underline{H}$), 5.27 (1H, t, J=7.0 Hz, ArCH$_2$C$\underline{H}$=C), 5.05 {1H, m, C$\underline{H}$=C(CH$_3$)$_2$}, 3.45 (2H, d, J=7.0 Hz, ArC$\underline{H}_2$), 2.16-2.05 (4H, m, C$\underline{H}_2$C$\underline{H}_2$), 1.82 (3H, s C$\underline{H}_3$), 1.68 (3H, s C$\underline{H}_3$). IR (KBr) 3145, 2922, 1620, 1487, 1443, 1383, 1313, 1248, 1213, 1150, 1059, 787, 718, 642, 530 cm$^{-1}$. Anal. Found: C, 74.41; H, 8.14%. Calcd for C$_{17}$H$_{22}$O$_3$: C, 74.42; H, 8.08%.

(E)-5-Chloro-2,4-dihydroxy-3-(3,7-dimethyl-2,6-octadienyl)benzaldehyde (compound 224)

Mp 94-95° C. $^1$H-NMR (500 MHz, CDCl$_3$) δ 11.53 (1H, s, Ar—O$\underline{H}$), 9.67 (1H, s, Ar—C$\underline{H}$O), 7.40 (1H, s, Ar—$\underline{H}$), 6.33 (1H, s, Ar—O$\underline{H}$), 5.23 {1H, t, J=7.3 Hz, ArCH$_2$C$\underline{H}$=C}, 5.05 {1H, t, J=7.0 Hz, C$\underline{H}$=C(CH$_3$)$_2$}, 3.44 (2H, d, J=7.3 Hz, ArC$\underline{H}_2$CH), 2.10-2.04 (2H, m, C$\underline{H}_2$), 2.02-1.98 (2H, m, C$\underline{H}_2$), 1.80 (3H, s, C$\underline{H}_3$), 1.65 (3H, s, CH$_3$), 1.57 (3H, s, C$\underline{H}_3$). IR (KBr) 3231, 2916, 1628, 1576, 1464, 1425, 1387, 1331, 1275, 1240, 1202, 1157, 1088, 912, 876, 750, 715, 604 cm$^{-1}$. HRMS (MI) Found: 308.1173. Calcd for C$_{17}$H$_{21}$O$_3$Cl: 308.1179.

(E)-2,4-Dihydroxy-3-(3,7-dimethyl-2,6-octadienyl)-6-methylbenzaldehyde (compound 216, known naturally occurring Colletorin B)

Mp 120-121° C. $^1$H-NMR (500 MHz, CDCl$_3$) δ 12.78 (1H, s, Ar—O$\underline{H}$), 10.08 (1H, s, Ar—C$\underline{H}$O), 6.21 (1H, s, Ar—$\underline{H}$), 6.15 (1H, s, Ar—O$\underline{H}$), 5.26 (1H, t, J=7.1 Hz, ArC$\underline{H}_2$CH=C), 5.04 {(1H, t, J=6.8 Hz, C$\underline{H}$=C(CH$_3$)$_2$}, 3.41

(2H, d, H=7.1 Hz, ArCH₂CH), 2.50 (3H, s, Ar—CH₃), 2.14-2.05 (4H, m, CH₂CH₂), 1.81 (3H, s, CH₃), 1.68 (3H, s, CH₃), 1.59 (3H, s, CH₃). IR (KBr) 3132, 2908, 1610, 1491, 1435, 1327, 1254, 1217, 1171, 1101, 1003, 829, 750, 644, 569 cm⁻¹.

(E)-3-Chloro-4,6-dihydroxy-5-(3,7-dimethyl-2,6-octadienyl)-2-methylbenzaldehyde (known naturally occurring Colletochlorin B)

44% yield. $^1$H-NMR (500 MHz, CDCl₃) δ 12.70 (1H, s, Ar—OH), 10.14 (1H, s, Ar—CHO), 6.42 (1H, s, Ar—OH), 5.22 (1H, t, J=6.9 Hz, ArCH₂CH=C), 5.06 {1H, t, J=6.6 Hz, CH=C(CH₃)₂}, 3.40 (2H, d, J=6.9 Hz, ArCH₂CH), 2.61 (3H, s, Ar—CH₃), 2.08-2.03 (2H, m, CH₂), 2.01-1.96 (2H, m, CH₂), 1.78 (3H, s, CH₃), 1.64 (3H, s, CH₃), 1.56 (3H, s, CH₃).

(E,E)-3-Chloro-4,6-dihydroxy-5-(3,7,11-trimethyl-2,6,10-dodecatienyl)-2-methylbenzaldehyde (compound 280-12, known naturally occurring LL-Z1272α)

Mp 72-73° C. $^1$H-NMR (400 MHz, CDCl₃) δ12.69 (1H, s, Ar—OH), 10.14 (1H, s, Ar—CHO), 6.41 (1H, s, Ar—OH), 5.22 (1H, t, J=7.3 Hz, ArCH₂CH=C), 5.06 (2H, t, J=7.0 Hz, 2×CH=C), 3.40 (2H, d, J=7.4 Hz, ArCH₂CH), 2.60 (3H, s, Ar—CH₃), 2.07 (2H, t, J=7.3 Hz, CH₂), 1.99 (4H, t, J=7.3 Hz, 2×CH₂), 1.92 (2H, t, J=7.5 Hz, CH₂), 1.79 (3H, s, CH₃), 1.64 (3H, s, CH₃), 1.58 (3H, s, CH₃), 1.56 (3H, s, CH₃). IR (KBr) 3256, 2967, 2913, 2853, 1613, 1452, 1424, 1373, 1281, 1229, 1163, 1109, 961, 905, 876, 786, 713, 633, 592, 569 cm⁻¹.

Scheme 6-2.

[Formula 6-2]

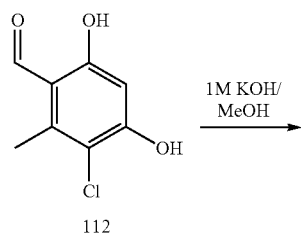

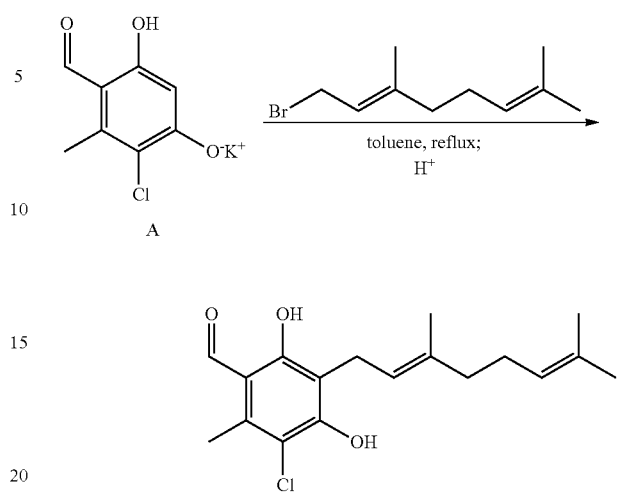

By applying the procedures described in literature (Tetrahedron, 1988, 44, 41-48), compound 112 (0.93 g, 5.0 mmol) was mixed with a 1 M KOH/MeOH solution (5 mL) and stirred for 12 hours. The resulting precipitates were washed with MeOH (50 mL), collected by filtration, and further azeotroped and dehydrated in toluene to quantitatively obtain compound A. Then, to a solution of geranyl bromide (43 mg, 0.2 mmol) in toluene (2 mL), compound A (72 mg, 0.32 mmol) was added and heated under reflux for 18 hours. After completion of the reaction, a 1 M aqueous HCl solution (5 mL) was added to separate and collect the organic layer, and the aqueous layer was extracted with EtOAc. The combined organic layers were washed with saturated aqueous sodium chloride and then dried over Na₂SO₄. After distilling off EtOAc, the resulting product was purified by silica gel column chromatography (hexane/AcOEt=20/1) to give known naturally occurring Colletochlorin B (44 mg, 68% yield).

7. Compounds 161, 157, 146 and 152

Scheme 7.

[Formula 7]

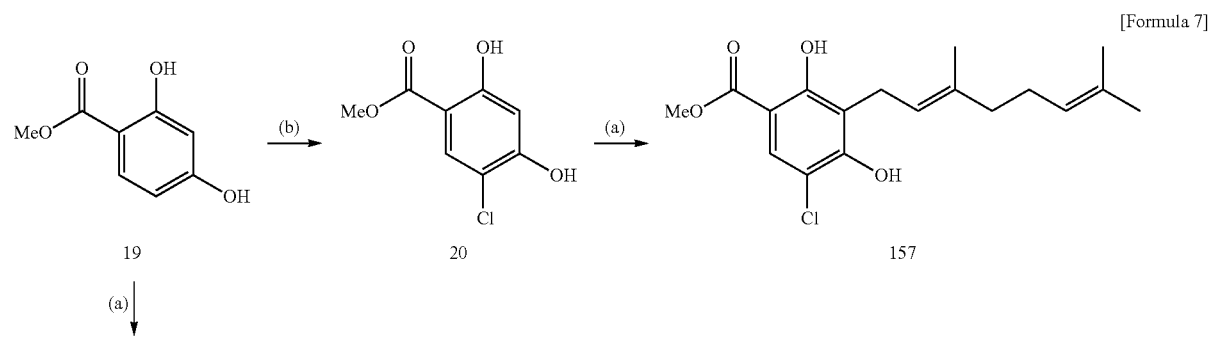

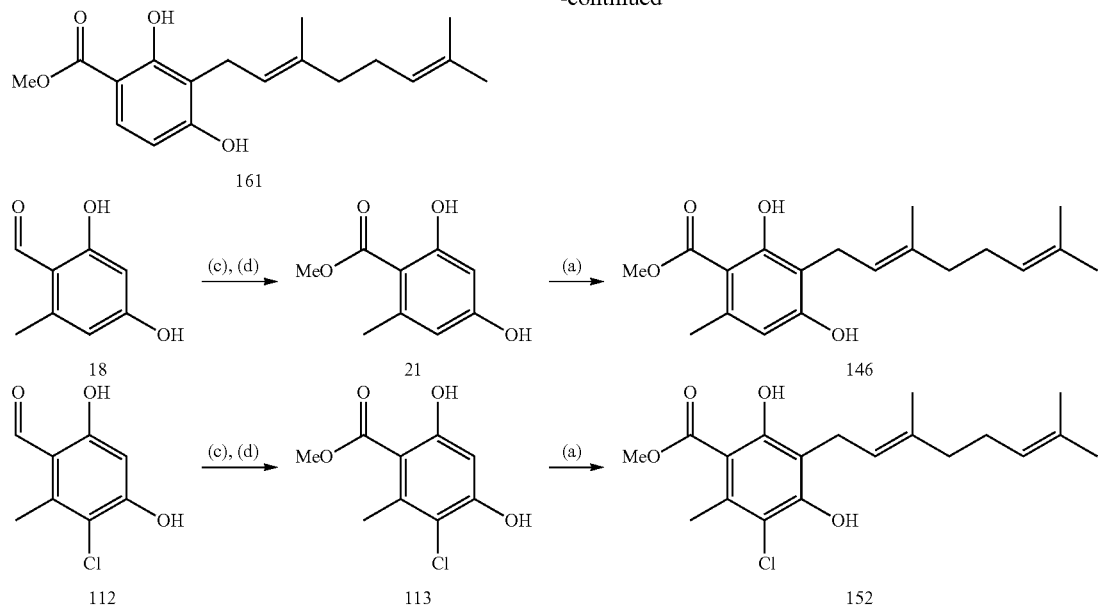

Reagents:
(a) Geranyl bromide, KOH, CaCl$_2$, MeOH
(b) NCS, AcOH
(c) NaClO$_2$, NaH$_2$PO$_4$, DMSO/H$_2$O
(d) MeOH, Ph$_3$P, DEAD, THF.

Methyl (E)-3-(3,7-dimethyl-2,6-octadienyl)-2,4-dihydroxybenzoate (compound 161)

Mp 62° C. $^1$H-NMR (400 MHz, CDCl$_3$) δ 11.31 (1H, s, Ar—OH), 7.63 (1H, d, J=8.6 Hz, Ar—H), 6.37 (1H, d, J=8.6 Hz, Ar—H), 5.93 (1H, s, Ar—OH), 5.27 (1H, t, J=7.0 Hz, ArCH$_2$CH=C), 5.05 {1H, m, CH=C(CH$_3$)$_2$}, 3.91 (1H, s, CO$_2$CH$_3$), 3.46 (2H, d, J=7.0 Hz, ArCH$_2$), 2.14-2.04 (4H, m, CH$_2$H$_2$), 1.82 (3H, s CH$_3$), 1.67 (3H, s CH$_3$), 1.59 (3H, s C H$_3$). IR (KBr) 3462, 2916, 1645, 1498, 1439, 1387, 1344, 1296, 1201, 1147, 1049, 783, 73, 1049, 783, 731, 631, 561 cm$^{-1}$. Anal. Found: C, 70.74; H, 7.70%. Calcd for C$_{18}$H$_{24}$O$_4$: C, 71.03; H, 7.95%.

Methyl 5-chloro-2,4-dihydroxybenzoate (compound 20)

39% yield. $^1$H-NMR (400 MHz, CDCl$_3$) δ 10.84 (1H, s, Ar—OH), 7.83 (1H, s, Ar—H), 6.62 (1H, s, Ar—OH), 5.92 (1H, br, Ar—OH), 3.93 (3H, s, CO$_2$CH$_3$).

Methyl (E)-5-chloro-3-(3,7-dimethyl-2,6-octadienyl)-2,4-dihydroxybenzoate (compound 157)

Mp 71° C. $^1$H-NMR (400 MHz, CDCl$_3$) δ 11.11 (1H, s, Ar—OH), 7.72 (1H, s, Ar—H, 6.10 (1H, s, Ar—OH), 5.23 (1H, t, J=7.2 Hz, ArCH$_2$CH=C), 5.06 {1H, m. C H=C(CH$_3$)$_2$}, 3.92 (3H, s, CO$_2$CH$_3$), 3.43 (2H, d, J=7.2 Hz, Ar—CH$_2$), 2.10-2.00 (2H, m, CH$_2$) 2.01-1.95 (2H, m, C H$_2$), 1.80 (3H, s, CH$_3$), 1.65 (3H, s, CH$_3$), 1.57 (3H, s, CH$_3$). HRMS (EI) Found: 338.1277. Calcd for C$_{18}$H$_{23}$O$_4$Cl: M$^+$, 338.1285.

Methyl 2,4-dihydroxy-6-methylbenzoate (compound 21)

This compound was prepared from the corresponding benzaldehyde (compound 18) through the steps of oxidation and esterification (52% from 18) (For details of the experimental operation, refer to compound 113 described below).
$^1$H NMR (400 MHz, CDCl$_3$) δ 11.78 (1H, s, Ar—OH), 6.28 (1H, d, J=2.6 Hz, Ar—H), 6.23 (1H, d, J=2.6 Hz, Ar—H), 5.25 (1H, br, Ar—OH), 3.93 (3H, s, CO$_2$CH$_3$), 2.49 (3H, s, Ar—CH$_3$).

Methyl (E)-3-(3,7-dimethyl-2,6-octadienyl)-2,4-dihydroxy-6-methylbenzoate (compound 146)

Mp 46-47° C. $^1$H-NMR (400 MHz, CDCl$_3$) δ 12.12 (1H, s, Ar—OH), 6.23 (1H, s, Ar—H), 5.84 (1H, s, Ar—OH), 5.23 (1H, t, J=7.1 Hz, ArCH$_2$CH=C), 5.06 {1H, m, C H=C(CH$_3$)}, 3.92 (3H, s, CO$_2$CH$_3$), 3.43 (2H, d, J=7.0 Hz, Ar—CH$_2$), 2.15-2.04 (4H, m, CH$_2$CH$_2$), 1.81 (3H, s, CH$_3$), 1.67 (3H, s, CH$_3$), 1.59 (3H, s, CH$_3$). IR (KBr) 3391, 2922, 2853, 1651, 1620, 1499, 1447, 1412, 1383, 1321, 1273, 1200, 1157, 1092, 1011, 984, 920, 878, 833, 812, 746, 718, 625, 604, 579 cm$^{-1}$.

Methyl 3-chloro-4,6-dihydroxy-2-methylbenzoate (113)

To a solution of compound 112 (0.505 g, 2.706 mmol) in DMSO (10 ml), H$_2$O (5 ml) was added and cooled to 0° C. This mixture was then mixed with NaH$_2$PO$_4$.2H$_2$O (1.113 g, 7.134 mmol) and, after 5 minutes, with NaClO$_2$ (79% purity, 0.719 g, 6.28 mmol), each being in solid state, and then stirred for 15 hours while gradually returning to room temperature. After the reaction mixture was diluted with EtOAc, sat. aq. NaHCO$_3$ was added to separate and collect the organic layer, to which sat. aq. NaHCO$_3$ was then added again for fractionation. The combined aqueous layers were acidified with 2 M aq. HCl and extracted three times with EtOAc. The combined organic layers were washed with sat. aq. NaCl and dried over Na$_2$SO$_4$. After the solvent was distilled off, the residue was loaded onto silica gel column chromatography (hexane:EtOAc=2:1→1:2) and then recrystallized from a mixed solvent of hexane:EtOAc=3:1 to give the corresponding carboxylic acid (0.410 g, 76%).

To a solution of Ph$_3$P (0.560 g, 2.14 mmol) in THF (4 ml), MeOH (0.085 ml, 2.1 mmol) was added at room temperature under an Ar atmosphere and cooled to 0° C. This mixture was mixed with DEAD (40% in toluene, 0.5 ml, 2.1 mmol) and stirred for 1 hour, and then mixed with the carboxylic acid (0.339 g, 1.67 mmol) in solid state and further stirred at 0° C. for 1.5 hours. After the reaction mixture was diluted with H$_2$O and EtOAc and stirred for 5 minutes, the organic layer was separated and collected, and the aqueous layer was extracted twice with EtOAc. The combined organic layers were washed twice with sat. aq. NaHCO$_3$ and once with sat. aq. NaCl, and then dried over Na$_2$SO$_4$. The solvent was distilled off, and the residue was loaded onto silica gel column chromatography (hexane:EtOAc=2:1) and then recrystallized from a mixed solvent of hexane:EtOAc=10:1 to give the desired product. In addition, the mother liquor was concentrated and then purified by silica gel column chromatography (hexane:EtOAc=7:1) to further give the desired product (combined yield, 0.286 g, 79%).

$^1$H-NMR (400 MHz, CDCl$_3$) δ 11.42 (1H, s, Ar—OH), 6.54 (1H, s, Ar—H), 6.06 (1H, s, Ar—OH), 3.95 (3H, s, CO$_2$CH$_3$), 2.63 (3H, s, Ar—H).

Methyl (E)-3-chloro-4,6-dihydroxy-5-(3,7-dimethyl-2,6-octadienyl)-2-methylbenzoate (compound 152)

$^1$H-NMR (500 MHz, CDCl$_3$) δ 11.65 (1H, s, Ar—OH), 6.20 (1H, s, Ar—OH), 5.23 (1H, t, J=7.1 Hz, ArCH$_2$CH=C), 5.06 {1H, t, J=6.9 Hz, CH=C(CH$_3$)$_2$}, 3.94 (3H, s, CO$_2$CH$_3$), 3.44 (2H, d, J=7.1 Hz, ArCH$_2$CH), 2.59 (3H, s, Ar—CH$_3$), 2.09-2.03 (2H, m, CH$_2$), 2.00-1.96 (2H, m, CH$_2$), 1.79 (3H, s, CH$_3$), 1.65 (3H, s, CH$_3$), 1.57 (3H, s, CH$_3$). IR (KBr) 3508, 2935, 1655, 1603, 1464, 1439, 1415, 1383, 1313, 1292, 1258, 1202, 1196, 1161, 1088, 978, 799, 700 cm$^{-1}$. HRMS (MI) Found: m/z, 338.1277. Calcd for C$_{11}$H$_{23}$O$_4$Cl: M$^+$, 338.1285.

8. Compounds 184, 177, 183, 173 and 282-12

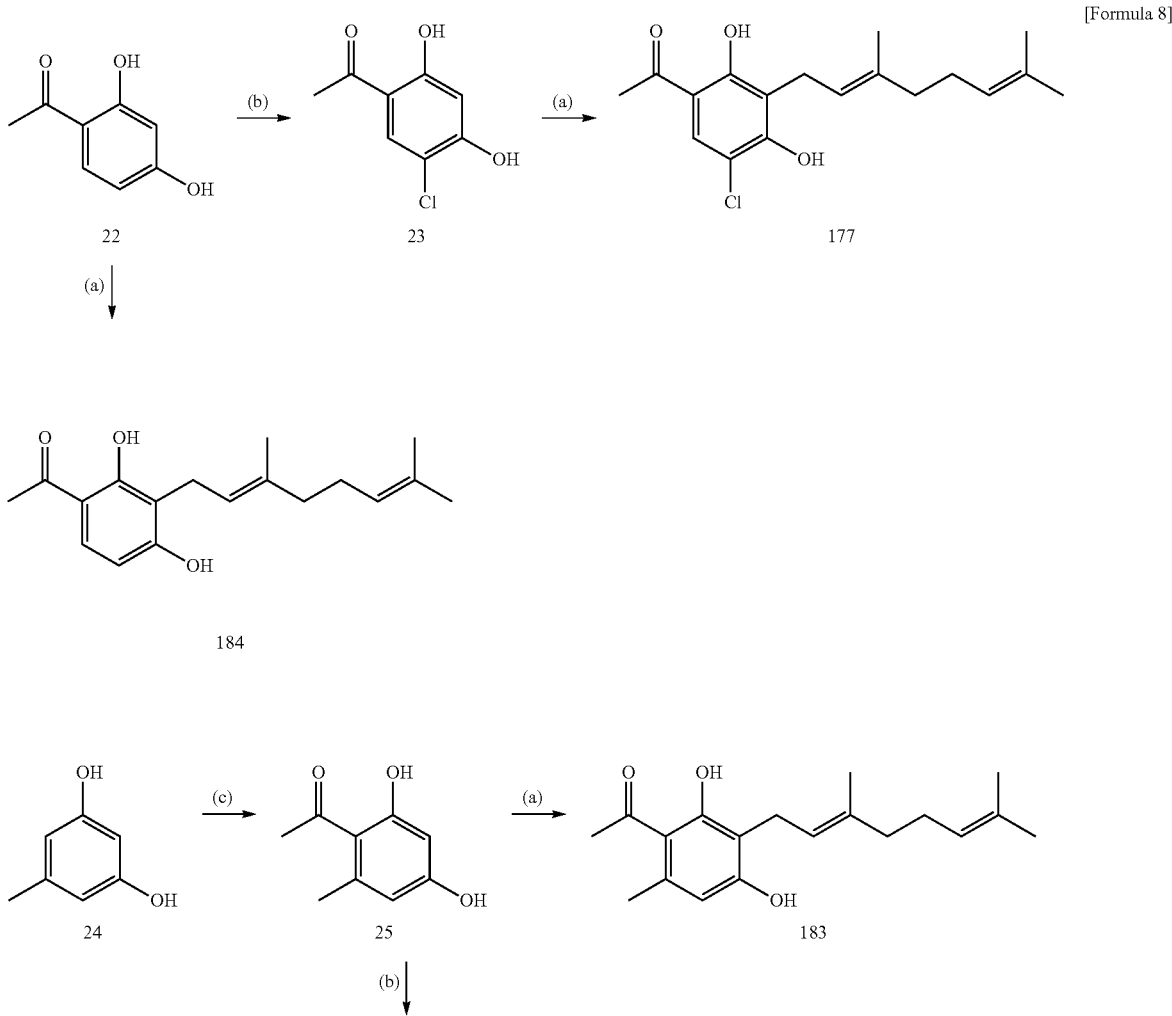

Scheme 8.

[Formula 8]

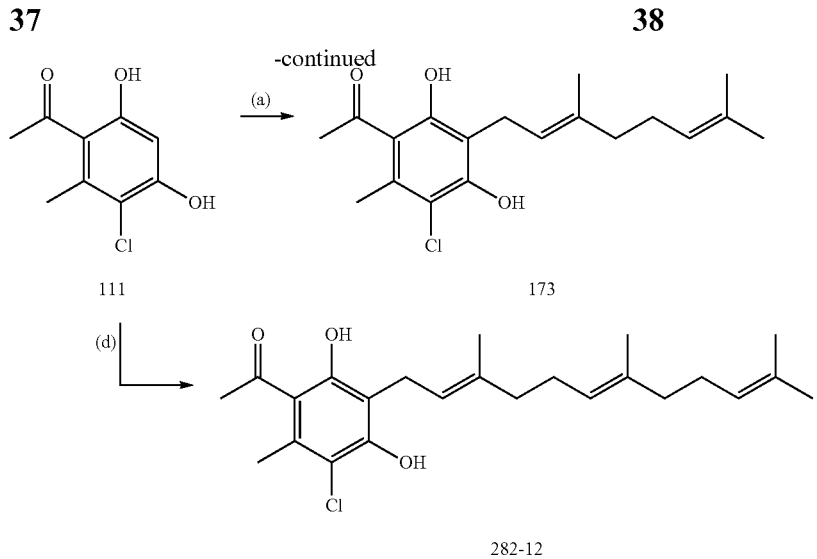

Reagents:
(a) Geranyl bromide, KOH, CaCl$_2$ 2H$_2$O, MeOH
(b) NCS, AcOH
(c) AcOH, BF$_3$—Et$_2$O
(d) Farnesyl bromide, KOH, CaCl$_2$ 2H$_2$O, MeOH

(E)-3-(3,7-Dimethyl-2,6-octadienyl)-2,4-dihydroxyacetophenone (compound 184)

Mp 134-135° C. $^1$H-NMR (400 MHz, CDCl$_3$) δ 13.13 (1H, s, Ar—OH), 7.54 (1H, d, J=8.8 Hz, Ar—H), 6.39 (1H, d, J=8.8 Hz, Ar—H), 6.11 (1H, s, Ar—OH), 5.27 (1H, t, J=7.0 Hz, ArCH$_2$CH=C), 5.05 {1H, m, CH$_2$CH=C(CH)$_2$}, 3.46 (2H, d, J=7.0 Hz, ArCH$_2$), 2.57 (3H, s, CH$_3$C=O), 2.15-2.05 (4H, m, CH$_2$CH$_2$), 1.82 (3H, s, CH$_3$), 1.68 (3H, s, CH$_3$), 1.59 (3 s CH$_3$). IR (KBr) 3161, 2964, 2916, 1624, 1589, 1499, 1456, 1379, 1317, 1279, 1223, 1163, 1055, 791, 721, 613, 567 cm$^{-1}$.

5-Chloro-2,4-dihydroxyacetophenone (compound 23)

66% yield. $^1$H-NMR (400 MHz, CDCl$_3$) δ 12.48 (1H, s, Ar—OH), 7.71 (1H, s, Ar—H), 6.60 (1H, s, Ar—H), 6.16 (1H, s, Ar—OH), 2.57 (3H, s, ArCOCH$_3$).

(E)-5-Chloro-3-(3,7-dimethyl-2,6-octadienyl)-2,4-dihydroxyacetophenone (compound 177)

Mp 109-110° C. $^1$H-NMR (500 MHz, CDCl$_3$) δ 12.83 (1H, s, Ar—OH), 7.60 (1H, s, Ar—H), 6.21 (1H, s, Ar—OH), 5.23 (1H, t, J=7.1 Hz, ArCH$_2$CH=C), 5.05 {1H, t, J=7.7 Hz, CH=C(CH$_3$)$_2$}, 3.43 (2H, d, J=7.1 Hz, ArCH$_2$), 2.56 (3H, s, CH$_3$C=O), 2.09-2.04 (2H, m, CH$_2$), 2.00-1.97 (2H, m, CH$_2$), 1.79 (3H, s, CH$_3$), 1.65 (3H, s, CH$_3$), 1.57 (3H, s, CH$_3$). IR (KBr) 3271, 2921, 1628, 1469, 1425, 1373, 1300, 1240, 1209, 1163, 1062, 907, 787 cm$^{-1}$. HRMS (MI) Found: m/z, 322.1353. Calcd for C$_{15}$H$_{23}$O$_3$Cl: M$^+$, 322.1336.

3-Chloro-4,6-dihydroxy-2-methylacetophenone (compound 111)

To a solution of orcinol (1.269 g, 10.22 mmol) in AcOH (4.0 ml, 70 mmol), BF$_3$.OEt$_2$ (2.6 ml, 21 mmol) was added at room temperature, followed by heating and stirring at 80° C. for 18 hours. After returning to room temperature, the reaction mixture was diluted with EtOAc and poured into H$_2$O. After the organic layer was separated and collected, the aqueous layer was extracted with EtOAc. The combined organic layers were washed three times with sat. aq. NaHCO$_3$ and once with sat. aq. NaCl, and then dried over Na$_2$SO$_4$. After the solvent was distilled off, the precipitated crude crystals were recrystallized from a mixed solvent of hexane:EtOAc=1:3 to give a C-acetylated product (compound 25). The mother liquor was concentrated and subjected to silica gel column chromatography (hexane:EtOAc=3:2) to collect only fractions containing compound 25, which were then purified by being recrystallized again from the same solvent (combined yield 65%).

$^1$H-NMR (400 MHz, CDCl$_3$) δ 13.44 (1H, s, Ar—OH), 6.26 (1H, d, J=2.6 Hz, Ar—H), 6.24 (1H, d, J=2.6 Hz Ar—H), 5.43 (1H, s, Ar—OH), 2.63 (3H, s, Ar—CH$_3$), 2.56 (3H, s, ArCOCH$_3$).

Compound 25 was chlorinated with NCS in AcOH to give the desired product (refer to the typical procedures, 65% yield).

$^1$H-NMR (400 MHz, CDCl$_3$) δ 12.37 (1H, s, Ar—OH), 6.52 (1H, s, Ar—H), 6.09 (1H, s, Ar—OH), 2.63 (6H, br, Ar—CH$_3$ & ArCOCH$_3$).

(E)-3-(3,7-Dimethyl-2,6-octadienyl)-2,4-dihydroxy-6-methylacetophenone (compound 183)

Mp 102° C. $^1$H-NMR (500 MHz, CDCl$_3$) δ 13.91 (1H, s, Ar—OH), 6.23 (1H, s, Ar—H), 5.98 (1H, s, Ar—OH), 5.27 (1H, t, J=6.8 Hz, ArCH$_2$CH=C), 5.05 {1H, t, J=6.2 Hz, CH=C(CH$_3$)$_2$}, 3.43 (2H, d, J=7.1 Hz, Ar—CH$_2$), 2.62 (3H, s, Ar—CH$_3$), 2.53 (3H, s, CH$_3$C=O), 2.14-2.04 (4H, m, CH$_2$CH$_2$), 1.84 (3H, s, CH$_3$), 1.68 (3H, s, CH$_3$), 1.59 (3H, s, CH$_3$). IR (KBr) 3175, 2964, 2922, 1568, 1439, 1362, 1258, 1223, 1171, 1094, 1011, 986, 829, 791, 608, 575 cm$^{-1}$. Anal. found: C, 75.22; H, 8.69%. Calcd. for C$_{19}$H$_{26}$O$_3$: C, 75.46; H, 8.67%.

(E)-3-Chloro-4,6-dihydroxy-5-(3,7-dimethyl-2,6-octadienyl)-2-methylacetophenone (compound 173)

Mp 57-58° C.; $^1$H-NMR (400 MHz, CDCl$_3$) δ 12.56 (1H, s, Ar—OH), 6.25 (1H, s, Ar—OH), 5.23 (1H, t, J=7.1 Hz,

ArCH$_2$CH=C), 5.06 {1H, t, J=6.7 Hz, CH=C(CH$_3$)$_2$}, 3.41 (2H, d, J=7.0 Hz, Ar—CH$_2$), 2.61 (3H, s, Ar—CH$_3$), 2.58 (3H, s, CH$_3$C=O), 2.10-2.03 (2H, m, CH$_2$), 2.01-1.95 (2H, m, CH$_2$), 1.79 (3H, s, CH$_3$), 1.65 (3H, s, CH$_3$), 1.57 (3H, s, CH$_3$). IR (KBr) 3460, 2922, 2866, 1595, 1468, 1421, 1381, 1360, 1275, 1236, 1209, 1175, 1094, 993, 916, 826, 785, 638, 621, 600 cm$^{-1}$. Anal. found: C, 67.80; H, 7.59%. Calcd. for C$_{19}$H$_{25}$ClO$_3$: C, 67.75; H, 7.48%. (Cl was impossible to measure because of too small amount of the sample).

(E,E)-3-Chloro-4,6-dihydroxy-5-(3,7,11-trimethyl-2,6,10-dodecatienyl)-2-methylacetophenone (compound 282-12)

Mp 92-93° C. $^1$H-NMR (400 MHz, CDCl$_3$) δ 12.55 (1H, s, Ar—OH), 6.23 (1H, s, Ar—OH), 5.23 (1H, t, J=7.2 Hz, ArCH$_2$CH=C), 5.06 (2H, t, J=6.6 Hz, 2×CH=C), 3.41 (2H, d, J=7.4 Hz, Ar—CH$_2$), 2.60 (3H, s, Ar—CH$_3$), 2.58 (3H, s, Ar—COCH$_3$), 2.07 (2H, t, J=7.3 Hz, CH$_2$), 2.01-1.96 (4H, m, 2×CH$_2$), 1.93 (2H, t, J=7.5 Hz, CH$_2$), 1.79 (3H, s, CH$_3$), 1.67 (3H, s, CH$_3$), 1.58 (3H, s, CH$_3$), 1.57 (3H, s, CH$_3$). IR (KBr) 3362, 2970, 2926, 2864, 1601, 1468, 1412, 1375, 1360, 1277, 1242, 1198, 1148, 1092, 1018, 991, 924, 887, 766, 617, 598, 556 cm$^{-1}$. Anal. Found: C, 70.90; H, 8.16; Cl, 8.77%. Calcd for C$_{24}$H$_{33}$ClO$_3$: C, 71.18; H, 8.21; Cl, 8.75%.

9. Compounds 200-11-OPiv, 215-11-OPiv, 200-12-OPiv, 215-12-OPiv, 200-13-OPiv, 215-13-OPiv, 200-12-OCO$^i$Pr, 215-12-OCO$^i$Pr, 215-13-OCO$^i$Pr, 215-12-OCOEt, 200-13-OCOEt and 215-13-OCOEt Scheme 9.

[Formula 9]

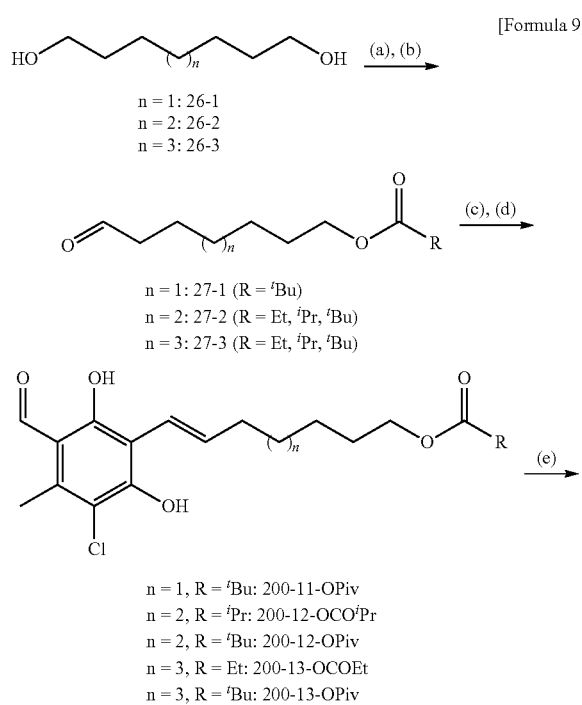

n = 1, R = $^t$Bu: 200-11-OPiv
n = 2, R = $^i$Pr: 200-12-OCO$^i$Pr
n = 2, R = $^t$Bu: 200-12-OPiv
n = 3, R = Et: 200-13-OCOEt
n = 3, R = $^t$Bu: 200-13-OPiv

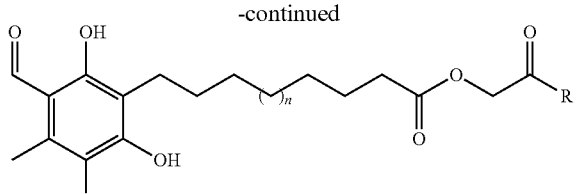

n = 1, R = $^t$Bu: 215-11-OPiv
n = 2, R = Et: 215-12-OCOEt
n = 2, R = $^i$Pr: 215-12-OCO$^i$Pr
n = 2, R = $^t$Bu: 215-12-OPiv
n = 3, R = Et: 215-13-OCOEt
n = 3, R = $^i$Pr: 215-13-OCO$^i$Pr
n = 3, R = $^t$Bu: 215-13-OPiv

Reagents and conditions:
(a) Coresponding acyl chloride, pyridine, CHCl$_3$
(b) Swern oxidation or TPAP, NMO, MS-4A, CHCl$_3$
(c) 112, KOH, CaCl$_2$ 2H$_2$O, MeOH
(d) H$_3$PO$_4$, AcOH, reflux
(e) H$_2$, Pd—C, EtOAc.

7-Oxoheptyl Pivalate (Compound 27-1, R=$^t$Bu)

To a solution of 1,7-heptanediol (compound 26-1, 0.28 ml, 2.0 mmol) in CH$_3$Cl (2 ml), Piv-Cl (0.12 ml, 1.0 mmol) and pyridine (0.03 ml, 0.4 mmol) were added at 0° C. and stirred for 1 day. After the reaction mixture was diluted with H$_2$O to separate and collect the organic layer, the aqueous layer was extracted with EtOAc. The combined organic layers were washed with sat. aq. NaCl and dried over Na$_2$SO$_4$. After the solvent was distilled off, the residue was purified by silica gel column chromatography (hexane:EtOAc=3:1) to give 7-hydroxyheptyl pivalate (147 mg, 68%).

To a solution of 7-hydroxyheptyl pivalate (552 mg, 2.55 mmol) in CH$_3$Cl (5.1 ml), NMO (597 mg, 5.11 mmol), MS-4A (1.290 g) and TPAP (44 mg, 0.13 mmol) were added at room temperature and stirred for 3 hours. After the reaction mixture was diluted with sat. aq. NH$_4$Cl to separate and collect the organic layer, the aqueous layer was extracted with CH$_3$Cl. The combined organic layers were extracted with CH$_3$Cl and dried over Na$_2$SO$_4$. After the solvent was distilled off, the residue was purified by silica gel column chromatography (hexane:EtOAc=7:1) to give the desired side chain precursor compound 27-1 (217 mg, 40%).

$^1$H-NMR (500 MHz, CDCl$_3$) δ 9.77 (1H, t, J=1.7 Hz, CHO), 4.05 (2H, t, J=6.5 Hz, CH$_2$OPiv), 2.44 (2H, dt, J=1.8, 7.3 Hz, CH$_2$CHO), 1.68-1.61 (4H, m, CH$_2$CH$_2$CHO & CH$_2$CH$_2$OPiv), 1.39-1.35 (4H, m, CH$_2$CH$_2$), 1.19 {9H, s, C(CH$_3$)$_3$}. IR (neat) 2941, 2860, 1728, 1477, 1286, 1159 cm$^{-1}$.

(E)-7-(3-Chloro-5-formyl-2,6-dihydroxy-4-methyl-phenyl)-6-heptenyl pivalate (compound 200-11-OPiv)

To a solution of the side chain precursor 27-1 (162 mg, 0.75 mmol) in MeOH (1.3 ml), compound 112 (118 mg, 0.63 mmol) and CaCl$_2$ 2H$_2$O (63 mg, 0.44 mmol) were added and cooled to 0° C. To this mixture, KOH (1.0 M in MeOH, 0.9 ml, 0.9 mmol) was added and stirred at the same temperature for 1 day. After addition of 1 M aq. HCl, the reaction mixture was extracted three times with EtOAc. The combined organic layers were washed with sat. aq. NaCl and dried over $Na_2SO_4$. After the solvent was distilled off, the residue was subjected to silica gel column chromatography (hexane:EtOAc=10:1) to give an aldol product (126 mg). The resulting product was used for the subsequent reaction without further purification.

Namely, the whole product was dissolved in AcOH (1.8 ml), and $H_3PO_4$ (85% purity, 0.2 ml) was added thereto at room temperature, followed by refluxing for 2 hours. After returning to room temperature, the reaction mixture was diluted with sat. aq. NaCl and extracted twice with EtOAc. The combined organic layers were dried over $Na_2SO_4$. After the solvent was distilled off, the residue was purified by silica gel column chromatography (hexane:EtOAc=10:1) to give the desired product (104 mg, 43% for 2 steps).

Mp 57-58° C. $^1$H-NMR (500 MHz, $CDCl_3$) δ 13.06 (1H, s, Ar—OH), 10.15 (1H, s, Ar—CHO), 6.66 (1H, dt, J=6.9, 16.3 Hz, ArCH=CH), 6.58 (1H, s, Ar—OH), 6.54 (1H, d, J=16.3 Hz, ArCH=CH), 4.06 (2H, t, J=6.7 Hz, CH$_2$OPiv), 2.62 (3H, s, Ar—CH$_3$), 2.28 (2H, q, J=7.1 Hz, CH=CHCH$_2$), 1.69-1.64 (2H, m, CH$_2$), 1.54-1.50 (2H, m, CH$_2$), 1.46-1.41 (2H, m, CH$_2$), 1.19 {9H, s, C(CH$_3$)$_3$}. IR (neat) 3387, 2930, 2885, 1726, 1634, 1462, 1426, 1375, 1285, 1256, 1161, 1028, 980, 816, 754 cm$^{-1}$. Anal. Found: C, 62.71; H, 7.05; Cl, 9.25%. Calcd for $C_{20}H_{27}O_5Cl$: C, 62.74; H, 7.11; Cl, 9.26%.

7-(3-Chloro-5-formyl-2,6-dihydroxy-4-methylphenyl)heptyl pivalate (compound 215-11-OPiv)

To a solution of 200-11-OPiv (70 mg, 0.18 mmol) in EtOH (2 ml), a catalytic amount of Pd—C was added at 0° C. and stirred for 80 minutes under a $H_2$ atmosphere. The reaction mixture was filtered through silica gel, and the filtrate was concentrated and then purified by PTLC (hexane:EtOAc=3:1) to give the desired product (34 mg, 49%).

Mp 63-64° C. $^1$H-NMR (500 MHz, $CDCl_3$) δ 12.65 (1H, s, Ar—OH), 10.14 (1H, s, Ar—CHO), 6.31 (1H, br, Ar—OH), 4.04 (2H, t, J=6.6 Hz, CH$_2$OPiv), 2.67 (2H, t, J=7.7 Hz, ArCH$_2$), 2.61 (3H, s, Ar—CH$_3$), 1.64-1.59 (2H, m, CH$_2$), 1.56-1.50 (2H, m, CH$_2$), 1.36 {6H, br, (CH$_2$)$_3$}, 1.19 {9H, s, C(CH$_3$)$_3$}. IR (KBr) 3435, 2920, 2848, 1730, 1637, 1458, 1425, 1366, 1277, 1161, 1048, 848, 800, 760 cm$^{-1}$. Anal. Found: C, 62.19; H, 7.57%. Calcd. for $C_{20}H_{29}O_5Cl$: C, 62.41; H, 7.59%.

Compounds differing in their side chain length and/or terminal acyl group were also synthesized in the same manner.

(E)-8-(3-Chloro-5-formyl-2,6-dihydroxy-4-methylphenyl)-7-octenyl pivalate (compound 200-12-OPiv)

Mp 57-58° C. $^1$H-NMR (400 MHz, $CDCl_3$) δ 13.07 (1H, s, Ar—OH), 10.15 (1H, s, Ar—CHO), 6.51-6.69 (2H, m, CH=CH), 4.06 (2H, t, J=7.0 Hz, CH$_2$OPiv), 2.62 (3H, s, Ar—CH$_3$), 2.27 (2H, q, J=6.6 Hz, CH=CHCH$_2$), 1.64-1.52 (4H, m, 2×CH$_2$), 1.39 (4H, br, 2×CH$_2$), 1.20 {9H, s, C(CH$_3$)$_3$}. IR (KBr) 3244, 2937, 1718, 1616, 1414, 1288, 1232, 978, 795, 596 cm$^{-1}$.

8-(3-Chloro-5-formyl-2,6-dihydroxy-4-methylphenyl)octyl pivalate (compound 215-12-OPiv)

Mp 70-71° C. $^1$H-NMR (400 MHz, $CDCl_3$) δ 12.66 (1H, s, Ar—OH), 10.15 (1H, s, Ar—CHO), 6.34 (1H, br, Ar—OH), 4.04 (2H, t, J≤6.4 Hz, CH$_2$OPiv), 2.66 (2H, t, J≤7.2 Hz, ArCH$_2$), 2.61 (3H, s, Ar—CH$_3$), 1.65-1.58 (2H, m, CH$_2$), 1.55-1.48 (2H, m, CH$_2$), 1.35 {8H, m, (CH$_2$)$_4$}, 1.20 {9H, s, C(CH$_3$)$_3$}. IR (KBr) 3350, 2930, 2858, 1724, 1612, 1421, 1362, 1248, 1159, 800, 714, 590 cm$^{-1}$. HRMS (EI) Found: 398.1890. Calcd. for $C_{21}H_{31}ClO_5$: 398.1860.

(E)-9-(3-Chloro-5-formyl-2,6-dihydroxy-4-methylphenyl)-8-nonenyl pivalate (compound 200-13-OPiv)

Mp 69-70° C. $^1$H-NMR (400 MHz, $CDCl_3$) δ 13.06 (1H, s, Ar—OH), 10.15 (1H, s, ArCHO), 6.65 (1H, dt, J=6.8, 16.0 Hz, ArCH=CH), 6.61 (1H, br, Ar—OH), 6.52 (1H, d, J=16.0 Hz, ArCH=CH), 4.05 (2H, t, J=6.8 Hz, CH$_2$OPiv), 2.62 (3H, s, Ar—CH$_3$), 2.27 (2H, q, J=6.8 Hz, CH=CH$_2$CH$_2$), 1.67-1.58 (2H, m, CH$_2$), 1.53-1.45 (2H, m, CH$_2$), 1.36 {6H, br, (CH$_2$)$_3$}, 1.20 {9H, s, C(CH$_3$)$_3$}. IR (KBr) 2943, 2860, 1724, 1628, 1460, 1391, 1377, 1286, 1161, 1028, 976, 941, 885, 808, 716, 590 cm$^{-1}$. HRMS (EI) Found: 410.1849. Calcd. for $C_{22}H_{31}ClO_5$: 410.1860.

9-(3-Chloro-5-formyl-2,6-dihydroxy-4-methylphenyl)nonyl pivalate (compound 215-13-OPiv)

Mp 62° C. $^1$H-NMR (400 MHz, $CDCl_3$) δ 12.66 (1H, s, Ar—OH), 10.14 (1H, s, Ar—CHO), 6.33 (1H, br, Ar—OH), 4.04 (2H, t, J=6.6 Hz, CH$_2$OPiv), 2.66 (2H, t, J=7.9 Hz, ArCH$_2$), 2.61 (3H, s, Ar—CH$_3$), 1.64-1.57 (2H, m, CH$_2$), 1.54-1.48 (2H, m, CH$_2$), 1.30 {10H, br, (CH$_2$)$_5$}, 1.19 {9H, s, C(CH$_3$)$_3$}. IR (KBr) 3377, 2916, 2853, 1732, 1614, 1481, 1421, 1366, 1283, 1240, 1145, 1126, 1032, 843, 785, 621, 586 cm$^{-1}$. HRMS (EI) Found: 412.2043. Calcd. for $C_{22}H_{33}ClO_5$: 412.2017.

(E)-8-(3-Chloro-5-formyl-2,6-dihydroxy-4-methylphenyl)-7-octenyl isobutylate (compound 200-12-OCO$^i$Pr)

Mp 73° C. $^1$H-NMR (400 MHz, $CDCl_3$) δ 13.06 (1H, s, Ar—OH), 10.15 (1H, s, Ar—CHO), 6.64 (1H, dt, J=6.8, 16.1 Hz, ArCH=CH), 6.60 (1H, br, Ar—OH), 6.53 (1H, d, J=16.1 Hz, ArCH=CH), 4.06 {2H, t, J=6.8 Hz, CH$_2$OC(O)$^i$Pr}, 2.62 (3H, s, Ar—CH$_3$), 2.58-2.51 {1H, m, CH(CH$_3$)$_2$}, 2.27 (2H, q, J=6.8 Hz, CH=CH$_2$CH$_2$), 1.68-1.60 (2H, m, CH$_2$), 1.53-1.47 (2H, m, CH$_2$), 1.42-1.35 {4H, m, (CH$_2$)$_2$}, 1.16 {6H, d, J=7.0 Hz, CH(CH$_3$)$_2$}. IR (KBr) 3206, 2972, 2928, 2855, 1732, 1618, 1456, 1414, 1283, 1204, 1163, 1132, 978, 793, 592 cm$^{-1}$. Anal. Found: C, 63.03; H, 7.16; Cl, 9.22%. Calcd. for $C_{20}H_{27}ClO_5$: C, 62.74; H, 7.11; Cl, 9.26%.

8-(3-Chloro-5-formyl-2,6-dihydroxy-4-methylphenyl)octyl isobutylate (compound 215-12-OCO$^i$Pr)

Mp 65° C. $^1$H-NMR (400 MHz, $CDCl_3$) δ 12.65 (1H, s, Ar—OH), 10.14 (1H, s, Ar—CHO), 6.33 (1H, br, Ar—OH), 4.05 {2H, t, J=6.8 Hz, CH$_2$OC(O)$^i$Pr}, 2.66 (2H, t, J=7.7 Hz, Ar—CH$_2$), 2.60 (3H, s, Ar—CH$_3$), 2.57-2.50 {1H, m, CH(CH$_3$)$_2$}, 1.65-1.58 (2H, m, CH$_2$), 1.54-1.48 (2H, m CH$_2$), 1.33 {8H, br, (CH$_2$)$_4$}, 1.16 {6H, d, J=7.0 Hz, CH(CH$_3$)$_2$}. IR (KBr) 3335, 2930, 2853, 2363, 1728, 1628, 1464, 1421, 1240, 1136, 791, 586. Anal. Found: C, 62.59; H, 7.62; Cl 9.01%. Calcd. for $C_{20}H_{29}ClO_5$: C, 62.41; H, 7.59; Cl, 9.21%.

9-(3-Chloro-5-formyl-2,6-dihydroxy-4-methylphenyl)nonyl isobutylate (compound 215-13-OCO$^i$Pr)

Mp 55-56° C. $^1$H-NMR (400 MHz, $CDCl_3$) δ 12.66 (1H, s, Ar—OH), 10.14 (1H, s, Ar—CHO), 6.33 (1H, s, Ar—O

H), 4.05 {2H, t, J=6.8 Hz, C$\underline{H}_2$OC(O)$^i$Pr}, 2.66 (2H, t, J=7.7 Hz, Ar—C$\underline{H}_2$), 2.61 (3H, s, Ar—C$\underline{H}_3$), 2.58-2.51 {1H, m, C$\underline{H}$(CH$_3$)$_2$}, 1.65-1.58 (2H, m, C$\underline{H}_2$), 1.54-1.48 (2H, m, C$\underline{H}_2$), 1.33 {10H, br, (C$\underline{H}_2$)$_5$}, 1.16 {6H, d, J=7.0 Hz, CH(C$\underline{H}_3$)$_2$}. IR (KBr) 3364, 2964, 2930, 2860, 1736, 1620, 1470, 1418, 1373, 1283, 1240, 1198, 1153, 1124, 787, 592 cm$^{-1}$. Anal. Found: C, 63.41; H, 7.82; Cl, 8.71%. Calcd for C$_{21}$H$_{31}$ClO$_5$: C, 63.23; H, 7.83; Cl, 8.89%.

8-(3-Chloro-5-formyl-2,6-dihydroxy-4-methylphenyl)octyl propionate (compound 215-12-OCOEt)

Mp 63-64° C. $^1$H-NMR (400 MHz, CDCl$_3$) δ 12.65 (1H, s, Ar—O$\underline{H}$), 10.15 (1H, s, Ar—C$\underline{H}$O), 6.33 (1H, br, Ar—O$\underline{H}$), 4.06 {2H, t, J=6.4 Hz, C$\underline{H}_2$OC(O)Et}, 2.67 (2H, t, J=7.7 Hz, Ar—C$\underline{H}_2$), 2.61 (3H, s, Ar—C$\underline{H}_3$), 2.32 {2H, q J=7.5 Hz, C(O)C$\underline{H}_2$CH$_3$}, 1.67-1.48 (4H, m, 2×C$\underline{H}_2$), 1.33 {8H, br, (C$\underline{H}_2$)$_4$}, 1.14 {3H, t, J=7.5 Hz, C(O)CH$_2$C$\underline{H}_3$}. IR (KBr) 3335, 2935, 2839, 1729, 1632, 1470, 1418, 1369, 1286, 1261, 1213, 1128, 1088, 812, 627, 590 cm$^{-1}$. HRMS (EI) Found: 370.1546. Calcd. for C$_{19}$H$_{27}$ClO$_5$: 370.1547.

(E)-9-(3-Chloro-5-formyl-2,6-dihydroxy-4-methylphenyl)-8-nonenyl propionate (compound 200-13-OCOEt)

Mp 72-73° C. $^1$H-NMR (400 MHz, CDCl$_3$) δ 13.05 (1H, s, Ar—O$\underline{H}$), 10.15 (1H, s, Ar—C$\underline{H}$O), 6.65 (1H, dt, J=6.8, 16.1 Hz, Ar—CH=C$\underline{H}_2$), 6.60 (1H, br, Ar—O$\underline{H}$), 6.53 (1H, d, J=16.1 Hz, ArC$\underline{H}$=CH$_2$), 4.07 {2H, t, J=6.8 Hz, C$\underline{H}_2$OC(O)Et}, 2.62 (3H, s, Ar—C$\underline{H}_3$), 2.32 {2H, q, J=7.5 Hz, C(O)C$\underline{H}_2$CH$_3$}, 2.27 (2H, q, J=6.8 Hz, CH=CH$_2$C$\underline{H}_2$), 1.66-1.58 (2H, m, C$\underline{H}_2$), 1.52-1.46 (2H, m, C$\underline{H}_2$), 1.36 {6H, br, (C$\underline{H}_2$)$_3$}, 1.14 (3H, t, J=7.5 Hz, CH$_2$C$\underline{H}_3$). IR (KBr) 3385, 2916, 2847, 1728, 1624, 1582, 1456, 1425, 1352, 1261, 1194, 1132, 1111, 1084, 964, 829, 791, 683, 592 cm$^{-1}$.

9-(3-Chloro-5-formyl-2,6-dihydroxy-4-methylphenyl)nonyl propionate (compound 215-13-OCOEt)

Mp 69-70° C. $^1$H-NMR (400 MHz, CDCl$_3$) δ 12.66 (1H, s, Ar—O$\underline{H}$), 10.14 (1H, s, Ar—C$\underline{H}$O), 6.33 (1H, s, Ar—O$\underline{H}$), 4.06 {2H, t, J=6.9 Hz, C$\underline{H}_2$OC(O)Et}, 2.66 (2H, t, J=7.7 Hz, Ar—C$\underline{H}_2$), 2.61 (3H, s, Ar—C$\underline{H}_3$), 2.31 {2H, q, J=7.7 Hz, C(O)C$\underline{H}_2$CH$_3$}, 1.67-1.48 (4H, m, 2×C$\underline{H}_2$), 1.30 {10H, br, (C$\underline{H}_2$)$_5$}, 1.14 {3H, t, J=7.7 Hz, C(O)CH$_2$C$\underline{H}_3$}. IR (KBr) 3352, 2926, 2853, 1742, 1614, 1421, 1369, 1285, 1238, 1184, 1124, 1082, 783, 627, 586 cm$^{-1}$. Anal. Found: C, 62.40; H, 7.45; Cl, 9.09%. Calcd for C$_{21}$H$_{29}$ClO$_5$: C, 62.41; H, 7.59; Cl, 9.21%.

10. Compounds 143-12-OPiv, 178-11-OPiv, 172-11-OPiv and 193-11-Opiv

Scheme 10.

[Formula 10]

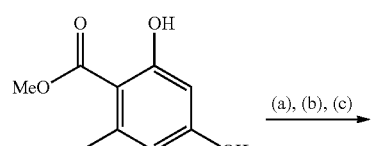

113

(a), (b), (c)

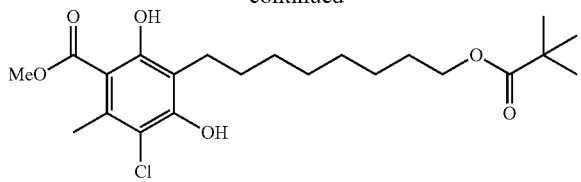

143-12-OPiv

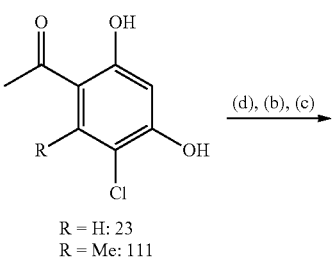

R = H: 23
R = Me: 111

(d), (b), (c)

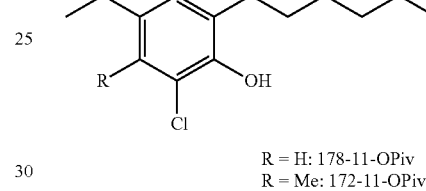

R = H: 178-11-OPiv
R = Me: 172-11-OPiv

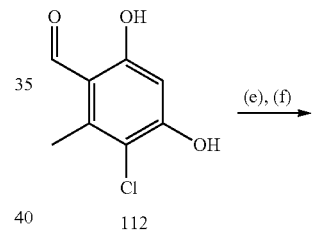

112

(e), (f)

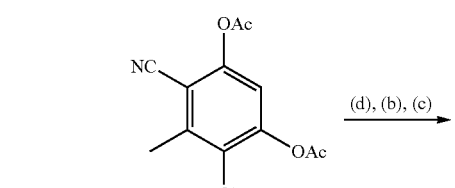

28

(d), (b), (c)

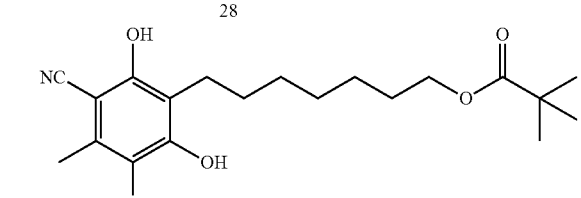

193-11-OPiv

Reagents and conditions:
(a) 27-2 (R = $^t$Bu), KOH, CaCl$_2$ 2H$_2$O, MeOH
(b) H$_3$PO$_4$, AcOH, reflux
(c) H$_2$, Pd—C, EtOAc
(d) 27-1 (R = $^t$Bu), KOH, CaCl$_2$ 2H$_2$O, MeOH
(e) NH$_2$OH·HCl, AcONa, AcOH
(f) Ac$_2$O, reflux

8-(3-Chloro-2,6-dihydroxy-5-methoxycarbonyl-4-methylphenyl)octyl pivalate (compound 143-12-OPiv)

In accordance with the same procedures as described in Scheme 9 above, the desired product was synthesized from the aromatic ring starting material in ester form (113).

$^1$H-NMR (400 MHz, CDCl$_3$) δ 11.63 (1H, s, Ar—O$\underline{H}$), 6.14 (1H, br, Ar—O$\underline{H}$), 4.04 (2H, t, J=6.6 Hz, C$\underline{H}_2$OPiv), 3.94 (3H, s, CO$_2$C$\underline{H}_3$), 2.68 (2H, t, J=7.7 Hz, ArC$\underline{H}_2$), 2.59 (3H, s, ArC$\underline{H}_3$), 1.65-1.49 (4H, m, ArCH$_2$C$\underline{H}_2$ & CH$_2$C$\underline{H}_2$OPiv), 1.33 (8H, br, (C$\underline{H}_2$)$_4$), 1.19 (9H, s, C(C$\underline{H}_3$)$_3$).

7-(3-Acetyl-5-chloro-2,6-dihydroxyphenyl)heptyl pivalate (compound 178-11-OPiv)

In accordance with the same procedures as described in Scheme 9 above, the desired product was synthesized from the aromatic ring starting material in ketone form (23).

Mp 48° C. $^1$H-NMR (400 MHz, CDCl$_3$) δ 12.78 (1H, s, Ar—O$\underline{H}$), 7.59 (1H, s, Ar—$\underline{H}$), 6.12 (1H, br, Ar—O$\underline{H}$), 4.04 (2H, t, J=6.6 Hz, C$\underline{H}_2$OPiv), 2.69 (2H, t, J=7.5 Hz, Ar—C$\underline{H}_2$), 2.55 (3H, s, C$\underline{H}_3$C=O), 1.66-1.58 (2H, m, C$\underline{H}_2$), 1.56-1.48 (2H, m, C$\underline{H}_2$), 1.36 {6H, br, (C$\underline{H}_2$)$_3$}, 1.19 {9H, s, C($\underline{H}_3$)$_3$}. IR (KBr) 3300, 2930, 2852, 1728, 1616, 1474, 1418, 1373, 1339, 1286, 1150, 1119, 1045, 968, 872, 787, 623, 586 cm$^{-1}$. HRMS (EI) Found: 384.1705. Calcd. for C$_{20}$H$_{29}$ClO$_5$: 384.1704.

7-(3-Acetyl-5-chloro-2,6-dihydroxy-4-methylphenyl)heptyl pivalate (compound 172-11-OPiv)

In accordance with the same procedures as described in Scheme 9 above, the desired product was synthesized from the aromatic ring starting material in ketone form (111).

$^1$H-NMR (400 MHz, CDCl$_3$) δ 12.64 (1H, s, Ar—O$\underline{H}$), 6.15 (1H, s, Ar—O$\underline{H}$), 4.04 (2H, t, J=6.6 Hz, C$\underline{H}_2$OPiv), 2.67 (2H, t, J=7.7 Hz, Ar—C$\underline{H}_2$), 2.61 (3H, s, Ar—C$\underline{H}_3$), 2.59 (3H, s, C$\underline{H}_3$C=O), 1.64-1.57 (2H, m, C$\underline{H}_2$), 1.55-1.48 (2H, m, C$\underline{H}_2$), 1.36 (6H, br, (C$\underline{H}_2$)$_3$), 1.19 (9H, s, C(C$\underline{H}_3$)$_3$). IR (KBr) 3412, 2943, 2866, 1720, 1607, 1464, 1416, 1366, 1273, 1161, 1115, 1074, 1036, 984, 860, 770, 596 cm$^{-1}$. HRMS (EI) Found: 398.1870. Calcd. for C$_{21}$H$_{31}$ClO$_5$: 398.1860.

4-Chloro-6-cyano-5-methylresorcinol diacetate (compound 28)

To a solution of AcONa (0.648 g, 7.90 mmol) in AcOH (10 ml), NH$_2$OH.HCl (0.589 g, 8.47 mmol) and compound 112 (1.308 g, 7.01 mmol) were added at room temperature and stirred for 7 hours. The reaction mixture was diluted with EtOAc and H$_2$O to separate and collect the organic layer, and the aqueous layer was then extracted with EtOAc. The combined organic layers were washed with sat. aq. NaHCO$_3$ and sat. aq. NaCl, and then dried over Na$_2$SO$_4$. The solvent was distilled off and the resulting corresponding oxime (1.400 g) was used in crude state for the subsequent reaction without purification.

Namely, the whole product was dissolved in Ac$_2$O (30 ml), and this solution was stirred at 130° C. for 12 hours. After returning to room temperature, the reaction mixture was diluted with Et$_2$O and H$_2$O to separate and collect the organic layer, and the aqueous layer was then extracted with Et$_2$O. The combined organic layers were washed twice with sat. aq. NaHCO$_3$ and once with sat. aq. NaCl, and then dried over Na$_2$SO$_4$. After the solvent was distilled off, the precipitated crude crystals were recrystallized from a mixed solvent of MeOH and H$_2$O (4:1) to give aromatic ring starting material compound 28. In addition, the mother liquor was concentrated, and the residue was purified by silica gel column chromatography (hexane:EtOAc=2:1) to also give compound 28 (1.388 g in total, 74% yield for 2 steps).

$^1$H-NMR (400 MHz, CDCl$_3$) δ 7.06 (1H, s, Ar—$\underline{H}$), 2.64 (3H, s, Ar—C$\underline{H}_3$), 2.39 (3H, s, OCOC$\underline{H}_3$), 2.37 (3H, s, OCOC$\underline{H}_3$). $^{13}$C-NMR (100 MHz, CDCl$_3$) 167.9, 167.5, 151.2, 150.7, 142.7, 125.7, 116.4, 113.6, 106.8, 20.8, 20.6, 19.4.

7-(3-Chloro-5-cyano-2,6-dihydroxy-4-methylphenyl)heptyl pivalate (compound 193-11-OPiv)

In accordance with the same procedures as described in Scheme 9 above, the desired product was synthesized from the aromatic ring starting material in nitrile form (28).

Mp 67-68° C. $^1$H-NMR (400 MHz, CDCl$_3$) δ 6.21 (1H, br, Ar—O$\underline{H}$), 6.17 (1H, s, Ar—O$\underline{H}$), 4.05 (2H, t, J=6.6 Hz, C$\underline{H}_2$OPiv), 2.66 (2H, t, J=7.7 Hz, ArC$\underline{H}_2$), 2.51 (3H, s, Ar—C$\underline{H}_3$), 1.66-1.58 (2H, m, C$\underline{H}_2$), 1.56-1.48 (2H, m, C$\underline{H}_2$), 1.35 {6H, br, (C$\underline{H}_2$)$_3$}, 1.20 {9H, s, C(C$\underline{H}_3$)$_3$}. $^{13}$C-NMR (100 MHz, CDCl$_3$) 178.8, 156.3, 154.1, 137.2, 115.8, 115.3, 113.4, 93.9, 64.4, 38.8, 29.3, 28.9, 28.6, 28.3, 27.2, 25.8, 23.7, 18.9. IR (KBr) 3383, 2926, 2853, 2232, 1715, 1593, 1468, 1416, 1366, 1325, 1286, 1244, 1171, 1119, 1057, 1036, 980, 847, 799, 690, 627, 590 cm$^{-1}$.

11. Compounds 215-11-OAc and 215-9-OH

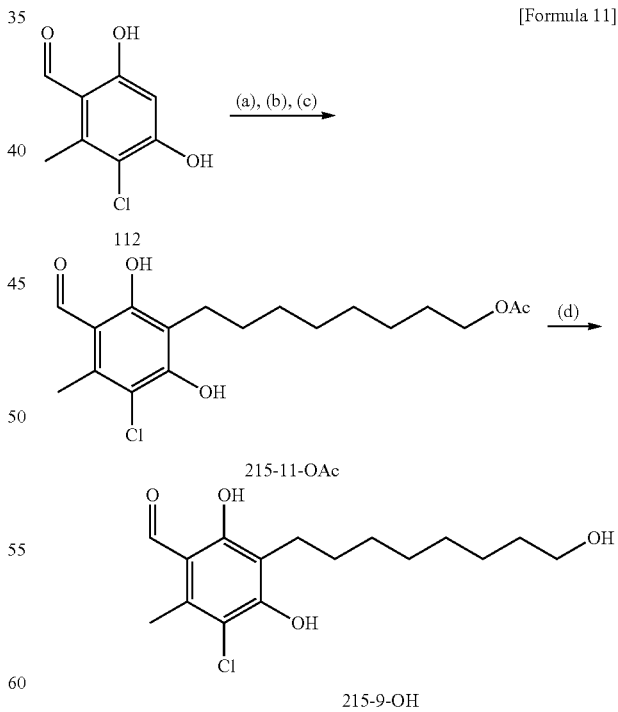

Scheme 11.

[Formula 11]

Reagents and conditions:
(a) 8, KOH, CaCl$_2$ 2H$_2$O, MeOH
(b) H$_3$PO$_4$, AcOH, reflux
(c) H$_2$, Pd—C, EtOAc
(d) NaOH, Acetone/H$_2$O

8-(3-Chloro-5-formyl-2,6-dihydroxy-4-methylphenyl)octyl acetate (compound 215-11-OAc)

When an aldol product, which had been prepared in the same manner as described above from aromatic ring starting material 112 and aldehyde 8, was refluxed in acetic acid in the presence of phosphoric acid, cleavage of the THP group and the subsequent acetylation occurred to give the desired product.

Mp. 68° C. $^1$H-NMR (400 MHz, CDCl$_3$) δ 12.65 (1H, s, Ar—O$\underline{H}$), 10.14 (1H, s, Ar—C$\underline{H}$O), 6.33 (1H, br, Ar—O$\underline{H}$), 4.05 (2H, t, J=6.8 Hz, C$\underline{H}_2$OPiv), 2.66 (2H, t, J=7.7 Hz, ArC$\underline{H}_2$), 2.61 (3H, s, Ar—C$\underline{H}_3$), 2.04 (3H, s, OC(O)C$\underline{H}_3$), 1.65-1.50 (4H, m, 2×C$\underline{H}_2$), 1.34 (8H, br, (C$\underline{H}_2$)$_4$). IR (KBr) 3321, 2930, 2853, 1728, 1624, 1464, 1258, 1128, 1051, 797, 596 cm$^{-1}$. HRMS (EI) Found: 356.1393. Calcd. for C$_{15}$H$_{25}$ClO$_5$: 356.1391.

5-Chloro-2,4-dihydroxy-3-(8-hydroxyoctyl)-6-methylbenzaldehyde (compound 215-9-OH)

The compound 215-11-OAc was hydrolyzed in the same manner as described above to give the desired product.

Mp 129-130° C. $^1$H-NMR (400 MHz, CDCl$_3$) δ 12.66 (1H, s, Ar—O$\underline{H}$), 10.14 (1H, s, Ar—C$\underline{H}$O), 6.33 (1H, s, Ar—O$\underline{H}$), 3.64 (2H, t, J=6.2 Hz, C$\underline{H}_2$OH), 2.67 (2H, t, J=7.3 Hz, Ar—C$\underline{H}_2$), 2.61 (3H, s, Ar—C$\underline{H}_3$), 1.64-1.47 (4H, m, C$\underline{H}_2$CH$_2$OH & ArCH$_2$C$\underline{H}_2$), 1.34 (8H, br, (C$\underline{H}_2$)$_4$). IR (KBr) 3539, 2924, 1627, 1421, 1296, 1257, 1132, 1016, 812 cm$^{-1}$. HRMS (EI) Found: 314.1265. Calcd. for C$_{16}$H$_{23}$ClO$_4$: 314.1285.

12. Compounds Ascofuranone, 214 (Acetyl AF), 209 (Demethyl AF), 249 and 250

Scheme 12.

[Formula 12]

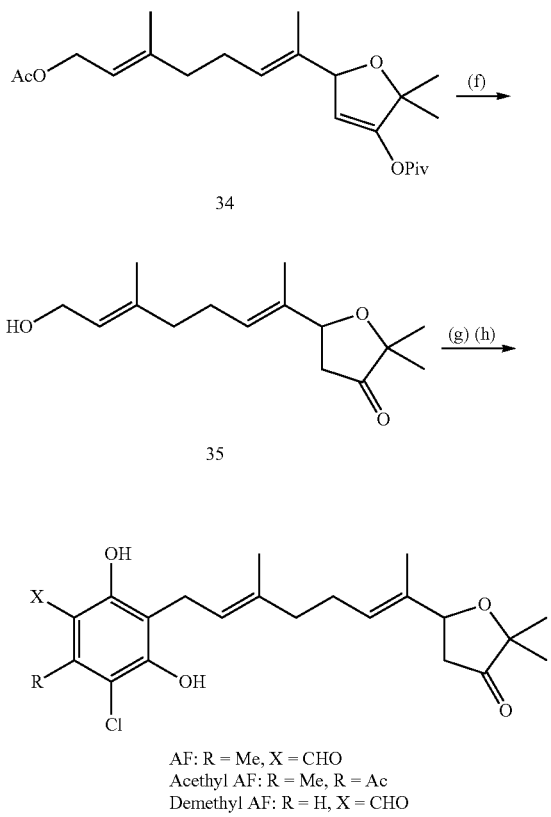

AF: R = Me, X = CHO
Acethyl AF: R = Me, R = Ac
Demethyl AF: R = H, X = CHO

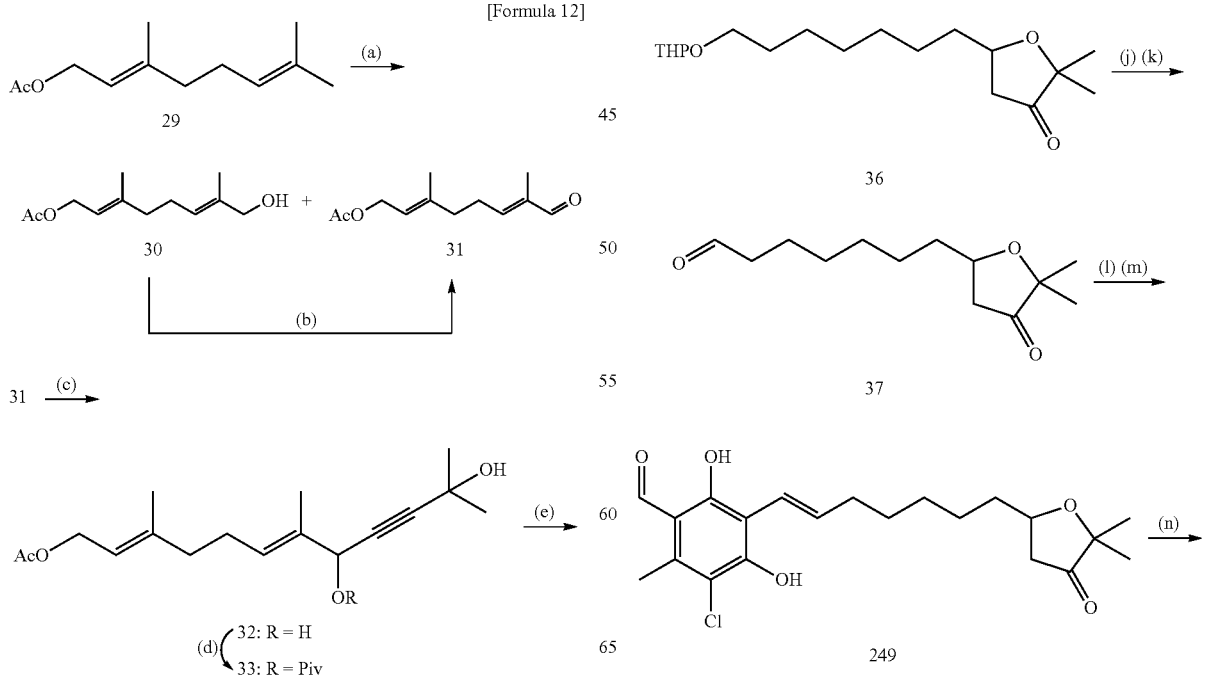

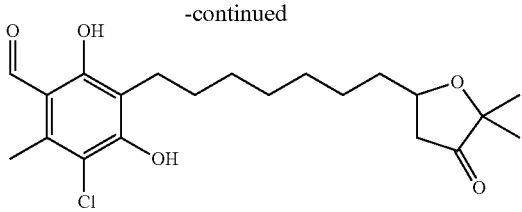

250

Reagents & conditions:
(a) SeO₂, EtOH
(b) MnO₂, Et₂O
(c) 2-Methyl-3-butyn-2-ol, ⁿBuLi, THF
(d) Piv—Cl, pyridine, DMAP, CHCl₃
(e) AgBF₄, toluene
(f) NaOMe, MeOH
(g) CBr₄, ⁿ(C₈H₁₇)₃P, Et₂O
(h) corresponding resorcinol derivatives, KOH, CaCl₂, MeOH
(i) Ac₂O, pyridine
(j) PPTS, EtOH
(k) Swern oxidation
(l) 112, KOH, CaCl₂, MeOH
(m) H₃PO₄, AcOH
(n) H₂, Pd—C, EtOAc.

dl-5-Chloro-2,4-dihydroxy-6-methyl-3-[(2E,6E)-3-methyl-7-(3,3-dimethyl-4-oxo-2-oxacyclopentyl)-2,6-octadienyl]benzaldehyde (Ascofuranone: AF)

To a solution of geranyl acetate (compound 29, 7.7 ml, 36 mmol) in EtOH (20 ml), SeO₂ (4.34 g, 37.9 mmol) was added at room temperature and refluxed for 1 hour. After returning to room temperature, the reaction mixture was filtered through celite. The filtrate was concentrated and then subjected to silica gel column chromatography (hexane:EtOAc=1:1) to collect fractions containing an alcohol (compound 30) and an aldehyde (compound 31). After the solvent was distilled off, the residue was dissolved in Et₂O (100 ml), to which MnO₂ (85% purity, 22.5 g, 220 mmol) was then added and stirred for 15 hours. After the reaction mixture was filtered through celite, the filtrate was washed with sat. aq. NaCl and dried over Na₂SO₄. After the solvent was distilled off, the residue was purified by silica gel column chromatography (hexane:EtOAc=4:1) to give the aldehyde (compound 31) (2.142 g, 28%).

To a solution of 2-methyl-3-buty2-ol (185 mg, 2.20 mmol) in THF (14 ml), BuLi (1.58 M in hexane, 2.7 ml, 4.3 mmol) was added at 20° C. under an Ar stream and stirred for 2 hours. After the reaction mixture was cooled to 50° C., 31 (505 mg, 2.40 mmol) in THF (18 ml) was added dropwise thereto. After stirring at the same temperature for 9 hours, sat. aq. NH₄Cl (5 ml) was added to stop the reaction. The reaction mixture was extracted with EtOAc, and the organic layer was washed with sat. aq. NaCl and dried over Na₂SO₄. After the solvent was distilled off, the residue was purified by silica gel column chromatography (hexane:EtOAc=2:1) to give a diol (compound 32) (479 mg, 68%).

$^1$H-NMR (400 MHz, CDCl₃) δ 5.54 (1H, t, J=7.0 Hz, AcOCH₂C$\underline{H}$=C), 5.33 {1H, t, J=7.1 Hz, C$\underline{H}$=C(CH₃)CH(OH)}, 4.76 {1H, d, J=5.1 Hz, CH=C(CH₃)C$\underline{H}$(OH)}, 4.59 (2H, d, J=7.0 Hz, AcOC$\underline{H}_2$CH=C), 2.20-2.16 (2H, m, C$\underline{H}_2$), 2.12-2.09 (2H, m, C$\underline{H}_2$), 2.06 (3H, s, C$\underline{H}_3$C=O), 1.97 {1H, d, J=5.1 Hz, CH=C(CH₃)CH(O$\underline{H}$)}, 1.74 (3H, s, C$\underline{H}_3$), 1.71 (3H, s, C$\underline{H}_3$), 1.61 {1H, s, C(O$\underline{H}$)(CH₃)₂}, 1.53 {6H, s, C(OH)(C$\underline{H}_3$)₂}. IR (neat) 3382, 2978, 2922, 1734, 1711, 1663, 1443, 1362, 1236, 1167, 1024, 951, 864, 712, 610, 554 cm⁻¹.

To a solution of compound 32 (1.058 g, 3.594 mmol) in CHCl₃ (2.8 ml), pyridine (1.06 ml, 13.1 mmol), DMAP (88 mg, 0.72 mmol) and Piv-Cl (0.97 ml, 7.9 mmol) were added at 0° C. under an Ar stream and stirred at the same temperature for 8 hours. The reaction mixture was diluted with H₂O to separate and collect the organic layer. The aqueous layer was extracted with EtOAc, and the combined organic layers were washed with sat. aq. NaCl and dried over Na₂SO₄. After the solvent was distilled off, the residue was purified by silica gel column chromatography (hexane:EtOAc=7:2) to give a pivalate (compound 33) (1.322 g, 97%).

$^1$H-NMR (400 MHz, CDCl₃) δ 5.77 (1H, s, C$\underline{H}$OPiv), 5.62 {1H, t, J=7.0 Hz, C$\underline{H}$=C(CH₃)CHOPiv}, 5.35 (1H, t, J=7.3 Hz, AcOCH₂C$\underline{H}$=C), 4.59 (2H, d, J=7.3 Hz, AcOC$\underline{H}_2$CH=C), 2.22-2.16 (2H, n, C$\underline{H}_2$), 2.12-2.08 (2H, m, C$\underline{H}_2$), 2.06 (3H, s, C$\underline{H}_3$C=O), 1.71 (3H, s, C$\underline{H}_3$), 1.69 (3H, s, C$\underline{H}_3$), 1.62 {1H, br, C(O$\underline{H}$)(CH₃)₂}, 1.51 {6H, s, C(OH)(C$\underline{H}_3$)₂}, 1.19 {9H, s, C(C$\underline{H}_3$)₃}. IR (neat) 3460, 2978, 2922, 2866, 1732, 1666, 1481, 1456, 1366, 1265, 1234, 1144, 1028, 955, 932, 864, 785, 708, 608, 561 cm⁻¹.

To a solution of compound 33 (937 mg, 2.48 mmol) in toluene (25 ml), AgBF₄ (38 mg, 0.20 mmol) was added at room temperature under an Ar stream and stirred at 80° C. for 4 hours under light-shielded conditions. After returning to room temperature, the reaction mixture was diluted with H₂O and extracted with CHCl₃. The combined organic layers were washed with sat. aq. NaCl and dried over Na₂SO₄. After the solvent was distilled off, the residue was purified by silica gel column chromatography (hexane:BuOAc=20:1) to give the corresponding cyclic product (compound 34) (589 mg, 63%).

$^1$H-NMR (400 MHz, CDCl₃) δ 5.58 (1H, d, J=1.5 Hz, CH=C$\underline{H}$OPiv), 5.47 (1H, t, J=6.8 Hz, CH₂CH₂C$\underline{H}$=C), 5.34 (1H, dt, J=1.1, 7.0 Hz. AcOCH₂C$\underline{H}$=C), 5.14 (1H, d, J=0.8 Hz, C$\underline{H}$=CHOPiv), 4.58 (2H, d, J=7.0 Hz, AcOC$\underline{H}_2$CH=C), 2.20-2.15 (2H, m, C$\underline{H}_2$), 2.10-2.05 (2H, m, C$\underline{H}_2$), 2.06 (3H, s, C$\underline{H}_3$C=O), 1.70 (3H, s, C$\underline{H}_3$), 1.60 (3H, s, C$\underline{H}_3$), 1.37 {3H, s, C(C$\underline{H}_3$)₂}, 1.33 {3H, s, C(C$\underline{H}_3$)₂}, 1.28 {9H, s, C(C$\underline{H}_3$)₃}. IR (neat) 2978, 2943, 2860, 1763, 1736, 1655, 1481, 1460, 1366, 1331, 1275, 1234, 1146, 1105, 1028, 955, 876, 837, 760, 604, 586 cm⁻¹.

To a solution of compound 34 (810 mg, 2.14 mmol) in MeOH (63 ml), NaOMe (1 M in MeOH, 0.63 ml, 0.63 mmol) was added at room temperature and stirred for 3 hours. The reaction mixture was diluted with H₂O and extracted with Et₂O. The combined organic layers were washed with sat. aq. NaCl and dried over Na₂SO₄. After the solvent was distilled off, the residue was purified by silica gel column chromatography (hexane:EtOAc=4:1) to give the corresponding primary alcohol (compound 35) (498 mg, 92%).

To a solution of known compound (H. Saimoto et al, *Bull. Chem. Soc. Jpn.*, 1999, 72, 279-284) 35 (448 mg, 1.78 mmol) in Et₂O (10 ml), CBr₄ (1.482 g, 4.469 mmol) and (ⁿC₈H₁₇)₃P (1.642 g, 4.430 mmol) were added at 0° C. under an Ar stream and stirred at the same temperature for 4 hours. After the solvent was distilled off, the residue was purified by silica gel column chromatography (hexane/EtOAc=20:1) to give the corresponding bromide (538 mg, 96%).

$^1$H-NMR (400 MHz, CDCl₃) δ 5.54 (2H, m, 2×C$\underline{H}$=C), 4.57 {1H, dd, J=6.4, 10.2 Hz, C(O)CH₂C$\underline{H}$}, 4.02 (2H, d, J=8.4 Hz, BrC$\underline{H}_2$CH=C), 2.53 {1H, dd, J=6.4, 18.2 Hz, C(O)C$\underline{H}_2$CH}, 2.45 {1H, dd, J=10.2, 18.2 Hz, C(O)C$\underline{H}_2$CH}, 2.24-2.17 (2H, m, C$\underline{H}_2$), 2.15-2.09 (2H, m, C$\underline{H}_2$), 1.74 (3H, s, CH₃), 1.67 (3H, s, CH₃), 1.31 {3H, s, C(CH₃)₂}, 1.24 {3H, s, C(CH₃)₂}. IR (neat) 2965, 2901, 2860, 1757, 1659, 1460, 1377, 1356, 1342, 1310, 1202, 1170, 1111, 1001, 856, 675 cm⁻¹.

To a solution of this bromide (136 mg, 0.431 mmol) in MeOH (0.5 ml), compound 112 (67 mg, 0.36 mmol) and CaCl₂·2H₂O (37 mg, 0.25 mmol) were added and cooled to 0° C. To this mixture, KOH (1 M in MeOH, 0.76 ml, 0.76 mmol) was added and stirred at the same temperature for 8 hours. The reaction mixture was diluted with sat. aq. NaCl and then extracted with EtOAc. After the combined organic layers were dried over Na₂SO₄, the solvent was distilled off and the residue was purified by PTLC (hexane:THF=5:1 for 1st run, hexane:EtOAc=5:1 for 2nd run) and recrystallization (hexane/EtOAc) to give the desired product dl-ascofuranone (52 mg, 34%).

Mp 88-90° C. ¹H-NMR (500 MHz, CDCl₃) δ 2.70 (1H, s, Ar—OH), 10.14 (1H, s, Ar—CHO), 6.43 (1H, s, Ar—OH), 5.51 (1H, t, J=6.9 Hz, CH=C), 5.21 (1H, d, J=7.1 Hz, ArCH₂CH=C), 4.52 {1H, dd, J=6.3, 10.1 Hz, C(O)CH₂CH}, 3.39 (2H, d, J=7.1 Hz, ArCH₂CH=C), 2.61 (3H, s, Ar—CH₃), 2.42 {1H, dd, J=6.3, 18.2 Hz, C(O)CH₂CH}, 2.35 {1H, dd, J=10.1, 18.2 Hz, C(O)CH₂CH}, 2.18-2.14 (2H, m, CH₂), 2.06-2.02 (2H, m, CH₂), 1.79 (3H, s, CH₃), 1.63 (3H, s, CH₃), 1.28 {3H, s, C(CH₃)₂}, 1.22 {3H, s, C(CH₃)₂}. IR (KBr) 3327, 2985, 2922, 2874, 1740, 1634, 1582, 1460, 1418, 1371, 1325, 1304, 1283, 1248, 1203, 1171, 1111, 1059, 1011, 907, 824, 712, 631, 592, 523 cm⁻¹.

5-Chloro-2,4-dihydroxy-6-methyl-3-[(2E,6E)-7-(5,5-dimethyl-4-oxotetrahydrofuran-2-yl)-3,7-dimethyl-2,6-heptadienyl]acetophenone (compound 214: Acetyl AF)

A bromide was prepared from the same known compound 35 as used above, and then reacted in the same manner with the aromatic ring starting material in ketone form (11) to give the desired product.

¹H-NMR (500 MHz, CDCl₃) δ 12.64 (1H, s, Ar—OH), 6.26 (1H, s, Ar—OH), 5.50 (1H, t, J=7.0 Hz, ArCH₂CH=C), 5.21 (1H, t, J=6.8 Hz, CH=C), 4.52 {1H, dd, J=6.4, 10.0 Hz, CHCH₂C=O}, 3.40 (2H, d, J=7.0 Hz, ArCH₂CH), 2.61 {3H, s, ArC(O)CH₃}, 2.59 (3H, s, ArCH₃), 2.40 (1H, dd, J=6.4, 18.3 Hz, CHCH₂C=O), 2.34 (1H, dd, J=10.0, 18.3 Hz, CHCH₂C=O), 2.19-2.13 (2H, m, CH₂), 2.07-2.01 (2H, m, CH₂), 1.79 (3H, s, CH₃), 1.62 (3H, s, CH₃), 1.28 (3H, s, CH₃), 1.22 (3H, s, CH₃).

5-Chloro-2,4-dihydroxy-3-[(2E,6E)-7-(5,5-dimethyl-4-oxotetrahydrofuran-2-yl)-3,7-dimethyl-2,6-heptadienyl]benzaldehyde (compound 209; Demethyl AF)

A bromide was prepared from the same known compound 35 as used above, and then reacted in the same manner with 5-chloro-2,4-dihydroxybenzaldehyde to give the desired product.

Mp 70-72° C. ¹H-NMR (400 MHz, CDCl₃) δ 11.54 (1H, s, Ar—OH), 9.67 (1H, s, CHO), 7.40 (1H, s, Ar—H), 6.39 (1H, s, Ar—OH), 5.51 (1H, t, J=6.8 Hz, CH₂CH₂CH=C), 5.22 (1H, t, J=7.1 Hz, ArCH₂CH=C), 4.53 {1H, dd, J=6.2, 9.9 Hz, C(O)CH₂CH}, 3.42 (2H, d, J=7.1 Hz, ArCH₂CH=C), 2.46 {1H, dd, J=6.2, 18.0 Hz, C(O)CH₂CH}, 2.38 {1H, dd, J=9.9, 18.0 Hz, C(O)CH₂CH}, 2.20-2.14 (2H, m, CH₂), 2.08-2.02 (2H, m, CH₂), 1.79 (3H, s, CH₃), 1.63 (3H, s, CH₃), 1.29 (3H, s, CH₃), 1.23 (3H, s, CH₃). IR (KBr) 3327, 2986, 2921, 2853, 1753, 1649, 1620, 1473, 1433, 137, 1331, 1290, 1252, 1205, 1167, 1111, 1084, 993, 916, 876, 820, 743, 610, 561, 523 cm⁻¹. HRMS (EI) Found: 406.1537. Calcd. for C₂₂H₂₇ClO₅: 406.1547.

3-Chloro-4,6-dihydroxy-2-methyl-5-[(E)-7-(5,5-dimethyl-4-oxo-tetrahydrofuran-2-yl)-1-heptenyl]benzaldehyde (compound 249)

Aldehyde 8 was converted into furanone 36 in the same manner as described in literature (H. Saimoto et al., *Bull. Chem. Soc. Jpn.*, 1995, 68, 2727-2734).

¹H-NMR (500 MHz, CDCl₃) δ 4.57 (1H, dd, J=2.8, 4.2 Hz, OCHO), 4.20-4.14 (1H, m, CH₂CHCH₂C=O), 3.89-3.85 (1H, m, CH₂O), 3.73 (1H, dt, J=6.9, 9.4 Hz, CH₂O), 3.52-3.48 (1H, m, CH₂O), 3.38 (1H, dt, J=6.7, 9.6 Hz, CH₂O), 2.55 (1H, dd, J=5.8, 18.1 Hz, CH₂C=O), 2.20 (1H, dd, J=10.1, 18.1 Hz, CH₂C=O), 1.86-1.80 (1H, m, CH₂CHO), 1.77-1.69 (2H, m), 1.64-1.51 (7H, m), 1.48-1.42 (1H, m), 1.35 (7H, br), 1.28 (3H, s, CH₃), 1.20 (3H, s, CH₃). IR (neat) 2922, 2854, 1757, 1462, 1443, 1369, 1350, 1177, 1119, 1070, 1032, 988, 905, 872, 814, 731 cm⁻¹.

To a solution of compound 36 (5.935 g, 19.00 mmol) in EtOH (100 ml), PPTS (1.933 g, 7.692 mmol) was added and stirred for 4 hours. After returning to room temperature, the reaction mixture was evaporated to distill off about half of the solvent, and then poured into saturated aqueous sodium chloride. This mixture was extracted twice with EtOAc, and the combined organic layers were dried over Na₂SO₄. After the solvent was distilled off, the residue was purified by silica gel column chromatography (hexane:EtOAc=4:1) to give the corresponding primary alcohol (4.007 g, 92%).

To a solution of oxalyl chloride (98% purity, 0.35 ml, 4.1 mmol) in CHCl₃ (5 ml), a solution of DMSO (0.57 ml, 8.0 mmol) in CHCl₃ (2.5 ml) was added dropwise at 60° C. After stirring at the same temperature for 50 minutes, a solution of the primary alcohol (235 mg, 1.03 mmol) in CHCl₃ (2 ml) was added and then further stirred for 2 hours. To this mixture, Et₃N (2.2 ml, 16 mmol) was added and further stirred for 40 minutes. After the reaction mixture was diluted with sat. aq. NH₄Cl to separate and collect the organic layer, the aqueous layer was extracted with CHCl₃. After the combined organic layers were dried over Na₂SO₄, the solvent was distilled off and the residue was purified by silica gel column chromatography (hexane:EtOAc=5:1) to give aldehyde 37 (203 mg, 87%).

¹H-NMR (500 MHz, CDCl₃) δ 9.60 (1H, t, J=1.7 Hz, CHO), 4.01 (1H, m, CH₂CHCO), 2.39 (1H, dd, J=5.7 Hz, 17.8 Hz, CH₂C=O), 2.27 (2H, dt, J=1.6 Hz, 7.4 Hz, CH₂CHO), 2.04 (1H, dd, J=10.1 Hz, 17.8 Hz, CH₂C=O), 1.62-1.52 (1H, m, CH₂CHCH₂C=O), 1.51-1.42 (3H, m), 1.35-1.26 (1H, m), 1.20 (5H, br), 1.09 (3H, s, CH₃), 1.03 (3H, s, CH₃). IR (neat) 2932, 2860, 2721, 1755, 1724, 1462, 1375, 1360, 1177, 1113, 1011, 83, 702, 534 cm⁻¹. HRMS (EI)) Found: 226.1569. Calcd. for C₁₃H₂₂O₃: M⁺ 226.1569.

In accordance with the same procedures as described above, an aldol product was prepared from compound 112 and compound 37, and this product was dehydrated in the presence of H₃PO₄ to give the desired product 249 (6% for 2 steps).

Mp 99-100° C. ¹H-NMR (500 MHz, CDCl₃) δ 13.07 (1H, s, Ar—OH), 10.15 (1H, s, Ar—CHO), 6.66 (1H, dt, J=6.9, 16.3 Hz, ArCH=CH), 6.59 (1H, s, Ar—OH), 6.53 (1H, d, J=16.3 Hz, ArCH=CH), 4.18 (1H, m, CHCH₂C=O), 2.62 (3H, s, Ar—CH₃), 2.57 (1H, dd, J=5.7, 17.9 Hz, CHCH₂C=O), 2.28 (2H, q, J=6.9 Hz, CH=CHCH₂), 2.21 (1H, dd, J=10.1, 17.9 Hz, CHCH₂C=O), 1.80-1.74 (1H, m, CH₂CHCH₂C=O), 1.66-1.60 (1H, m, CH₂CHCH₂C=O), 1.55-1.48 (2H, m, CH$_2$), 1.44-1.35 {4H, m, (CH$_2$)$_2$}, 1.27 (3H, s, CH$_3$), 1.20 (3H, s, CH$_3$). IR (neat) 3400, 2930, 2858, 1755, 1634, 1462, 1418, 1375, 1285, 1256, 1175, 1113, 978, 910, 733, 675, 592 cm$^{-1}$. HRMS (EI) Found: 394.1552. Calcd. for C$_{21}$H$_{70}$O$_5$Cl: M$^+$ 394.1547.

5-Chloro-2,4-dihydroxy-6-methyl-3-[7-(3,3-dimethyl-4-oxo-2-oxacyclopentyl)heptyl]benzaldehyde (compound 250)

In accordance with the same procedures as described above, compound 249 was subjected to catalytic reduction reaction to give the desired product (98% yield).

Mp 70-71° C. $^1$H-NMR (500 MHz, CDCl$_3$) δ12.66 (1H, s, Ar—OH), 10.14 (1H, s, Ar—CHO), 6.32 (1H, br, Ar—OH), 4.16 (1H, m, CHCH$_2$C=O), 2.66 (2H, t, J=7.7 Hz, ArCH$_2$), 2.61 (3H, s, Ar—CH$_3$), 2.55 (1H, dd, J=5.8, 18.1 Hz, CHCH$_2$C=O), 2.20 (1H, dd, J=10.1, 18.1 Hz, CHCH$_2$C=O), 1.78-1.71 (1H, m, CH$_2$CHCH$_2$C=O), 1.63-1.56 (2H, m, CH$_2$), 1.55-1.49 (2H, m, CH$_2$), 1.47-1.40 (1H, m, CH$_2$CHCH$_2$C=O), 1.34 {6H, m, (CH$_2$)$_3$}, 1.28 (3H, s, CH$_3$), 1.20 (3H, s, CH$_3$). HRMS (EI) Found: 396.1690. Calcd. for C$_{21}$H$_{29}$ClO$_5$: 396.1704.

13. Compounds 275-10-COOMe, 276-9, 277-11-OAc, 286-11-OAc, 277-9-OH and 286-9-OH Scheme 13.

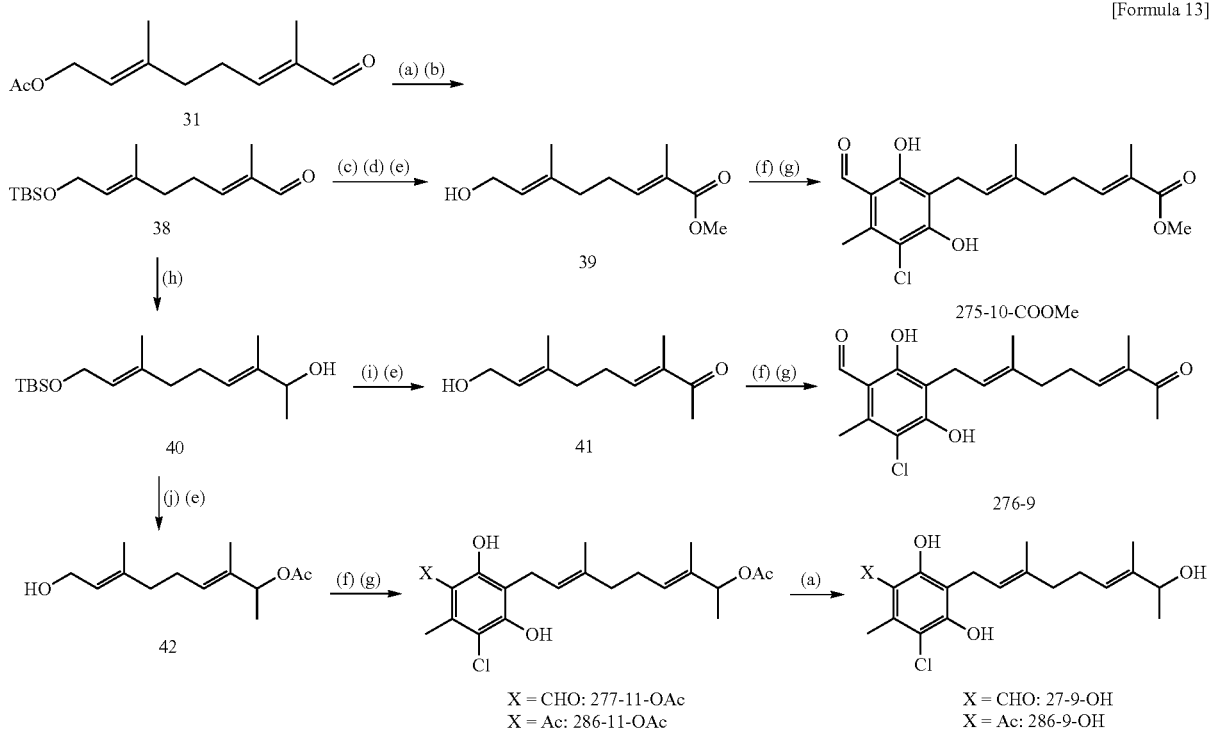

[Formula 13]

Reagents & conditions:
(a) K$_2$CO$_3$, MeOH
(b) TBS—Cl, Et$_3$N, DMAP, CHCl$_3$
(c) NaClO$_2$, 2-methyl-2-butene, NaH$_2$PO$_4$, $^t$BuOH/H$_2$O
(d) MeOH, Ph$_3$P, DEAD, THF
(e) TBAF, THF
(f) CBr$_4$, ($^n$C$_8$H$_{17}$)$_3$P, Et$_2$O
(g) 112, KOH, CaCl$_2$, MeOH
(h) MeLi, THF
(i) MnO$_2$, toluene
(j) Ac$_2$O, pyridine.

Methyl (2E,6E)-8-hydroxy-2,6-dimethylocta-2,6-dienoate (compound 39)

To a solution of aldehyde 31 (2.226 g, 10.59 mmol) in MeOH (50 ml), K$_2$CO$_3$ (0.802 g, 5.803 mmol) in crushed state was added at room temperature and stirred for 4 hours. The reaction mixture was diluted with H$_2$O and extracted twice with EtOAc and once with Et$_2$O. The combined organic layers were washed with sat. aq. NH$_4$Cl and sat. aq. NaCl, and then dried over Na$_2$SO$_4$. After the solvent was distilled off, the residue was purified by silica gel column chromatography (hexane:EtOAc=2:11:2) to give the corresponding primary alcohol (1.266 g, 71%).

To a solution of this primary alcohol (1.266 g, 7.525 mmol) in CHCl$_3$ (40 ml), Et$_3$N (3.1 ml, 22 mmol), DMAP (cat. amount) and TBS-Cl (50% in toluene, 8.0 ml, 23 mmol) were added at 0° C. and stirred at the same temperature for 2.5 hours. After the reaction mixture was diluted with sat. aq. NH$_4$Cl to separate and collect the organic layer, the aqueous layer was extracted once with EtOAc and twice with Et$_2$O.

The combined organic layers were washed with sat. aq. NaCl and dried over $Na_2SO_4$. After the solvent was distilled off, the residue was subjected to silica gel column chromatography (hexane:EtOAc=7:1) to give the corresponding silyl ether 38 (2.126 g, 100%).

$^1$H-NMR (400 MHz, $CDCl_3$) δ 9.37 (1H, s, C$\underline{H}$O), 6.46 (1H, t, J=7.1 Hz, C$\underline{H}$=CCHO), 5.34 (1H, t, J=6.2 Hz, TBSOCH$_2$C$\underline{H}$=C), 4.19 (2H, d, J=6.2 Hz, TBSOC$\underline{H}_2$CH), 2.47 (2H, q, J=7.3 Hz, C$\underline{H}_2$), 2.19 (2H, t, J=7.3 Hz, C$\underline{H}_2$), 1.74 (3H, s, C$\underline{H}_3$), 1.65 (3H, s, C$\underline{H}_3$), 0.89 (9H, s, C(C$\underline{H}_3$)$_3$), 0.06 (6H, s, Si(C$\underline{H}_3$)$_2$).

To a solution of silyl ether 38 (0.772 g, 2.733 mmol) in a mixture of $^t$BuOH (20 ml)/$H_2O$ (5 ml), $NaH_2PO_4 \cdot 2H_2O$ (1.067 g, 6.839 mmol) and 2-methyl-2-butene (3.0 ml, 28 mmol) were added at room temperature and cooled to 0° C. To this mixture, $NaClO_2$ (79% purity, 0.627 g, 5.48 mmol) was added and stirred for 15 hours while returning to room temperature. The reaction mixture was diluted with EtOAc and washed with sat. aq. NaCl, and the organic layer was dried over $Na_2SO_4$. After the solvent was distilled off, the residue was used directly for the subsequent reaction without purification. Namely, to a solution of $Ph_3P$ (0.868 g, 3.309 mmol) in THF (10 ml), MeOH (0.13 ml, 3.2 mmol) was added at room temperature and cooled to 0° C. After DEAD (40% in toluene, 1.35 ml, 2.96 mmol) was added dropwise and stirred for 30 minutes, a solution of the crude carboxylic acid (0.787 g) in THF (10 ml) was added dropwise and stirred for 4 hours while returning to room temperature. After the reaction mixture was diluted with $H_2O$ to separate and collect the organic layer, the aqueous layer was extracted with EtOAc. The combined organic layers were washed with sat. aq. NaCl and dried over $Na_2SO_4$. After the solvent was distilled off, the residue was purified by silica gel column chromatography (hexane:EtOAc=3:1) to give the corresponding methyl ester (0.535 g, 63% for 2 steps).

$^1$H-NMR (400 MHz, $CDCl_3$) δ 6.74 (1H, t, J=7.3 Hz, C$\underline{H}$=CCO$_2$Me), 5.33 (1H, t, J=6.2 Hz, TBSOCH$_2$C$\underline{H}$=C), 4.21 (2H, d, J=6.2 Hz, TBSOC$\underline{H}_2$CH), 3.73 (3H, s, CO$_2$C$\underline{H}_3$), 2.30 (2H, q, J=7.5 Hz, C$\underline{H}_2$), 2.13 (2H, t, J=7.5 Hz, C$\underline{H}_2$), 1.84 (3H, s, C$\underline{H}_3$), 1.64 (3H, s, C$\underline{H}_3$), 0.91 (9H, s, C(C$\underline{H}_3$)$_3$), 0.07 (6H, s, Si(C$\underline{H}_3$)$_2$).

The whole product (0.535 g, 1.712 mmol) was dissolved in THF (20 ml) and cooled to 0° C., followed by addition of TBAF (1.0 M in THE 2.0 ml, 2.0 mmol) and stirring for 15 hours while returning to room temperature. After the reaction mixture was diluted with $H_2O$ to separate and collect the organic layer, the aqueous layer was extracted twice with EtOAc. The combined organic layers were washed with sat. aq. NaCl and dried over $Na_2SO_4$. After the solvent was distilled off, the residue was purified by silica gel column chromatography (hexane:EtOAc=2:1) to give the desired side chain precursor 39 (0.245 g, 72%).

$^1$H-NMR (400 MHz, $CDCl_3$) δ 6.73 (1H, t, J=7.3 Hz, C$\underline{H}$=CCO$_2$Me), 5.44 (1H, t, J=7.0 Hz, HOCH$_2$C$\underline{H}$=C), 4.21 (2H, d, J=6.6 Hz, HOC$\underline{H}_2$CH), 3.73 (3H, s, CO$_2$C$\underline{H}_3$), 2.31 (2H, q, J=7.3 Hz, C$\underline{H}_2$), 2.15 (2H, t, J=7.7 Hz, C$\underline{H}_2$), 1.84 (3H, s, C$\underline{H}_3$), 1.69 (3H, s, C$\underline{H}_3$), 1.45 (1H, br, O$\underline{H}$).

Methyl (2E,6E)-8-(3-chloro-5-formyl-2,6-dihydroxy-4-methyl)phenyl-2,6-dimethyl-2,6-octa dienoate (compound 275-10-COOMe)

To a solution of primary alcohol 39 (0.245 g, 1.236 mmol) in $Et_2O$ (20 ml), $CBr_4$ (1.250 g, 3.769 mmol) and $(C_8H_{17})_3P$ (1.65 ml, 3.07 mmol) were added at 0° C. and stirred at 0° C. to 10° C. for 5 hours. After the solvent was distilled off, the residue was subjected to silica gel column chromatography (hexane:EtOAc=4:1) to give the corresponding bromide. The resulting product was used for the subsequent reaction without further purification.

Namely, to a solution of compound 112 (0.711 g, 3.810 mmol) in KOH (1.0 M in MeOH, 5.7 ml, 5.7 mmol), $CaCl_2 \cdot 2H_2O$ (0.419 g, 2.85 mmol) and the whole bromide obtained above dissolved in MeOH (8.5 ml) were added at 0° C. and stirred for 19 hours while returning to room temperature. After the reaction mixture was diluted with EtOAc and filtered through celite, the filtrate was washed with 0.1 M aq. KOH and sat. aq. NaCl, and then dried over $Na_2SO_4$. After the solvent was distilled off, the residue was subjected to silica gel column chromatography (hexane: EtOAc=3:1) and the precipitated crude crystals were then recrystallized from a mixed solvent of hexane:toluene=10:1 to give the desired product 275-10-COOMe (0.115 g, 25% yield from compound 39).

Mp 103-105° C. $^1$H-NMR (400 MHz, $CDCl_3$) δ 12.69 (1H, s, Ar—O$\underline{H}$), 10.14 (1H, s, C$\underline{H}$O), 6.71 (1H, t, J=7.4 Hz, C$\underline{H}$=C), 6.47 (1H, s, Ar—O$\underline{H}$), 5.24 (1H, t, J=7.0 Hz, C$\underline{H}$=C), 3.71 (3H, s, COOC$\underline{H}_3$), 3.39 (2H, d, J=7.0 Hz, Ar—C$\underline{H}_2$), 2.60 (3H, s, Ar—C$\underline{H}_3$), 2.29-2.23 (2H, m, C$\underline{H}_2$), 2.11-2.08 (2H, m, C$\underline{H}_2$), 1.80 (3H, s, C$\underline{H}_3$), 1.79 (3H, s, C$\underline{H}_3$). IR (KBr) 3369, 2957, 2908, 1715, 1624, 1526, 1456, 1433, 1377, 1279, 1240, 1212, 1161, 1128, 962, 907, 808, 787, 712, 627, 596, 569, 527 cm$^{-1}$.

(3E,7E)-9-Hydroxy-3,7-dimethylnona-3,7-diene-2-one (compound 41)

To a solution of aldehyde 38 (1.600 g, 5.664 mmol) in THF (50 ml), MeLi (1.0 M in $Et_2O$, 11.5 ml, 11.5 mmol) was added at 85° C. and stirred for 2 hours while elevating the temperature to 50° C. To this mixture, $H_2O$ was added to stop the reaction. After the organic layer was separated and collected, the aqueous layer was extracted with $Et_2O$. The combined organic layers were washed with sat. aq. NaCl and dried over $Na_2SO_4$. After the solvent was distilled off, the residue was purified by silica gel column chromatography (hexane:EtOAc=4:1) to give the corresponding secondary alcohol 40 (1.212 g, 72%).

To a solution of this secondary alcohol (0.570 g, 1.91 mmol) in toluene (40 ml), $MnO_2$ (85% purity, 2.05 g, 20.0 mmol) was added and stirred vigorously for 18 hours. $MnO_2$ (2.60 g, 25.4 mmol) was further added and stirring was continued for an additional 1 day. After the reaction mixture was filtered through silica gel and the filtrate was concentrated, the residue was purified by silica gel column chromatography (hexane:EtOAc=8:1) to give the corresponding ketone. Moreover, 96 mg of the starting material was collected and oxidized again with $MnO_2$ (1.20 g, 11.7 mmol) in toluene (10 ml), followed by the same purification procedures to give the ketone (0.444 g, 87% yield).

The whole product (0.444 g, 1.497 mmol) was dissolved in THF (20 ml) and cooled to 0° C., followed by addition of TBAF (1.0 M in THF, 1.8 ml, 1.8 mmol) and stirring for 2.5 hours while returning to room temperature. After the reaction mixture was diluted with $H_2O$ to separate and collect the organic layer, the aqueous layer was extracted twice with EtOAc. The combined organic layers were washed with saturated aqueous sodium chloride and dried over $Na_2SO_4$. After the solvent was distilled off, the residue was purified by silica gel column chromatography (hexane:EtOAc=2: 1→1:1) to give the desired product 41 (0.222 g, 81%).

$^1$H-NMR (400 MHz, $CDCl_3$) δ 6.61 {1H, t, J=6.4 Hz, C$\underline{H}$=C(CH$_3$)C=O}, 5.45 (1H, t, J=7.0 Hz, HOCH$_2$C$\underline{H}$=C), 4.21 (2H, d, J=7.0 Hz, HOCH₂CH), 2.38 (2H, q, J=7.3 Hz, CH₂), 2.30 (3H, s, COCH₃), 2.19 (2H, t, J=7.7 Hz, CH₂), 1.77 (3H, s, CH₃), 1.71 (3H, s, CH₃).

(2E,6E)-3-Chloro-4,6-dihydroxy-2-methyl-5-(2E, 6E)-3,7-dimethyl)-(3,7-dimethyl-8-oxo-26-nonadienyl)benzaldehyde (compound 276-9)

In accordance with the same procedures as described above, the desired product was obtained from alcohol 41.

Mp 119-120° C. ¹H-NMR (400 MHz, CDCl₃) δ 12.69 (1H, s, Ar—OH), 10.14 (1H, s, CHO), 6.54 (1H, t, J=7.2 Hz, CH=C), 6.39 (1H, s, Ar—OH), 5.26 (1H, t, J=7.3 Hz, CH=C), 3.40 (2H, d, J=7.3 Hz, Ar—CH₂), 2.61 (3H, s, Ar—CH₃), 2.34 (2H, m, CH₂), 2.19 {3H, s, C(O)CH₃}, 2.14 (2H, m, CH₂), 1.81 (3H, s, CH₃), 1.72 (3H, s, CH₃). IR (KBr) 3356, 2920, 2840, 1663, 1620, 1520, 1460, 1425, 1366, 1279, 1236, 1196, 1161, 1111, 962, 903, 812, 787, 708, 631, 592, 569, 527 cm⁻¹. Anal. Found: C, 65.05; H, 6.61; Cl, 10.11%. Calcd for C₁₉H₂₃ClO₄: C, 64.91; H, 6.52; Cl, 10.09%.

(3E,7E)-9-Hydroxy-3,7-dimethylnona-3,7-dien-2-yl acetate (compound 42)

To a solution of secondary alcohol 40 (0.682 g, 2.28 mmol) in pyridine (12 ml), Ac₂O (6 ml) was added at room temperature and stirred for 2.5 hours. The reaction mixture was poured into H₂O and extracted twice with Et₂O and once with EtOAc. The combined organic layers were washed with 1 M aq. HCl and sat. aq. NaCl, and then dried over Na₂SO₄. After the solvent was distilled off, the residue was purified by silica gel column chromatography (hexane:EtOAc=4:1) to give the corresponding acetate (0.585 g, 75%).

¹H-NMR (400 MHz, CDCl₃) δ 5.42 (1H, t, J=7.0 Hz, CH=C(CH₃)CHOAc), 5.30 (1H, t, J=6.2 Hz, TBSOCH₂CH=C), 5.24 (1H, q, J=6.6 Hz, CH=C(CH₃)CHOAc), 4.18 (2H, d, J=6.2 Hz, TBSOCH₂CH), 2.13 (2H, q, J=6.6 Hz, CH₂), 2.03 (3H, s, COCH₃), 2.03 (2H, t, J=7.3 Hz, CH₂), 1.62 (6H, s, 2×CH₃), 1.28 (3H, d, J=6.6 Hz, CH(OAc)CH₃), 0.90 (9H, s, C(CH₃)₃), 0.07 (6H, s, Si(CH₃)₂).

The whole product (0.585 g, 1.718 mmol) was dissolved in THF (20 ml) and cooled to 0° C., followed by addition of TBAF (1.0 M in THF, 2.0 ml, 2.0 mmol) and stirring for 17 hours while returning to room temperature. After the reaction mixture was diluted with H₂O to separate and collect the organic layer, the aqueous layer was extracted twice with EtOAc. The combined organic layers were washed with saturated aqueous sodium chloride and dried over Na₂SO₄. After the solvent was distilled off, the residue was purified by silica gel column chromatography (hexane:EtOAc=2:1) to give the desired product 42 (0.340 g, 87%).

¹H-NMR (400 MHz, CDCl₃) δ 5.39 (2H, m, 2×CH=C), 5.22 (1H, q, J=6.6 Hz, CHOAc), 4.21 (2H, d, J=6.2 Hz, HOCH₂CH), 2.19-2.13 (2H, m, CH₂), 2.09-2.05 (2H, m, CH₂), 2.03 (3H, s, COCH₃), 1.66 (3H, s, CH₃), 1.61 (3H, s, CH₃), 1.28 (3H, d, J=6.6 Hz, CHCOCH₃).

(3E,7E)-9-(3-Chloro-5-formyl-2,6-dihydroxy-4-methyl)phenyl-3,7-dimethyl-3,7-nonadien-2-yl acetate (compound 277-11-OAc)

In accordance with the same procedures as described above, the desired product was obtained from alcohol 42.

Mp 101-102° C. ¹H-NMR (400 MHz, CDCl₃) δ 12.69 (1H, s, Ar—OH), 10.14 (1H, s, CHO), 6.56 (1H, s, Ar—OH), 5.36 (1H, t, J=7.3 Hz, CH=C), 5.20 {2H, m, CH(OAc)CH₃ & CH=C}, 3.39 (2H, d, J=7.3 Hz, Ar—CH₂), 2.61 (3H, s, Ar—CH₃), 2.10 (2H, m, CH₂), 2.02 {3H, s, OC(O)CH₃}, 2.03-2.00 (2H, m, CH₂), 1.77 (3H, s, CH₃), 1.58 (3H, s, CH₃), 1.22 {3H, d, J=6.6 Hz, CH(OAc)CH₃}. IR (KBr) 3356, 2986, 2916, 1711, 1624, 1456, 1422, 1377, 1283, 1254, 1157, 1115, 1080, 1024, 959, 910, 841, 808, 708, 631, 583, 544, 523 cm⁻¹. Anal. Found: C, 63.85; H, 6.91; Cl, 8.95%. Calcd for C₂₁H₂₇ClO₅: C, 63.87; H, 6.89; Cl, 8.98%.

(3E,7E)-9-(5-Acetyl-3-chloro-2,6-dihydroxy-4-methyl)phenyl-3,7-dimethyl-3,7-nonadien-2-yl acetate (compound 286-11-OAc)

Mp 89-91° C. ¹H-NMR (400 MHz, CDCl₃) δ 12.57 (1H, s, Ar—OH), 6.35 (1H, s, Ar—OH) 5.37 (2H, t, J=6.8 Hz, CH=C), 5.24-5.17 (2H, m, CH=C & CHOAc), 3.40 (2H, d, J=6.84 Hz, ArCH₂), 2.61 (3H, s, ArCH₃), 2.58 (3H, s, ArCOCH₃), 2.07-2.04 (2H, m, CH₂), 2.03-1.99 (2H, s, CH₂), 2.02 (3H, s, COCH₃), 1.78 (3H, s, CH₃), 1.58 (3H, s, CH₃), 1.22 (3H, d, J=6.4 Hz, CHOAc). IR (KBr) 3354, 2978, 2920, 1717, 1611, 1589, 1414, 1379, 1362, 1279, 1258, 1155, 1140, 1096, 1024, 953, 922, 891, 866, 845, 870, 642, 619 cm⁻¹.

3-Chloro-4,6-dihydroxy-2-methyl-5-(2E,6E)-(8-hydroxy-3,7-dimethyl-2,6-nonadien yl)benzaldehyde (compound 277-9-OH)

To a solution of the compound 277-11-OAc (73 mg, 0.185 mmol) in MeOH (10 ml). K₂CO₃ (45 mg, 0.33 mmol) was added at room temperature and stirred for 19 hours. After the reaction mixture was diluted with sat. aq. NH₄Cl and EtOAc to separate and collect the organic layer, the aqueous layer was extracted twice with EtOAc. The combined organic layers were washed with sat. aq. NaCl and dried over Na₂SO₄. After the solvent was distilled off, the residue was purified by silica gel column chromatography (toluene:EtOAc=10:1) to give the desired product (11 mg, 17%).

Mp 105-107° C. ¹H-NMR (400 MHz, CDCl₃) δ 12.71 (1H, s, Ar—OH), 10.14 (1H, s, CHO), 6.61 (1H, s, Ar—OH), 5.32 (1H, t, J=6.6 Hz, CH=C), 5.21 (1H, t, J=7.0 Hz, CH=C), 4.17 (1H, m, CHOH), 3.40 (2H, d, J=7.0 Hz, Ar—CH₂), 2.60 (3H, s, Ar—CH₃), 2.16-2.08 (2H, m, CH₂), 2.07-2.03 (2H, m, CH₂), 1.78 (3H, s, CH₃), 1.59 (3H, s, CH₃), 1.48 (1H, br, OH), 1.20 {3H, d, J=6.2 Hz, CH(OH)CH₃}. IR (KBr) 3341, 2970, 2916, 1616, 1456, 1421, 1377, 1279, 1234, 1165, 1111, 1080, 966, 907, 865, 785, 716, 635, 579 cm⁻¹.

(2E,6E)-3-Chloro-4,6-dihydroxy-2-methyl-5-(8-hydroxy-3,7-dimethyl-2, 6-nonadienyl)acetophenone (compound 286-9-OH)

¹H-NMR (400 MHz, CDCl₃) δ 12.58 (1H, s, Ar—OH), 6.40 (1H, s, Ar—OH), 5.31 (H, t, J=6.9 Hz, CH=C), 5.22 (H, t, J=7.0 Hz, CH=C), 4.17 (1H, m, CHOH), 3.41 (2H, d, J=7.0 Hz, Ar—CH₂), 2.61 (3H, s, Ar—CH₃), 2.58 (3H, s, CH₃C=O), 2.17-2.08 (2H, m, CH₂), 2.07-2.02 (2H, m, CH₂), 1.78 (3H, s, CH₃), 1.59 (3H, s, CH₃), 1.49 (1H, br, OH), 1.20 {3H, d, J=6.6 Hz, CH(OH)CH₃}. IR (KBr) 3345, 2972, 2920, 1596, 1410, 1377, 1361, 1287, 1261, 1209, 1159, 1099, 1078, 1049, 986, 949, 922, 885, 862, 843, 772, 604 cm⁻¹.

14. Compounds 273-12 and 271-12

Scheme 14.

[Formula 14]

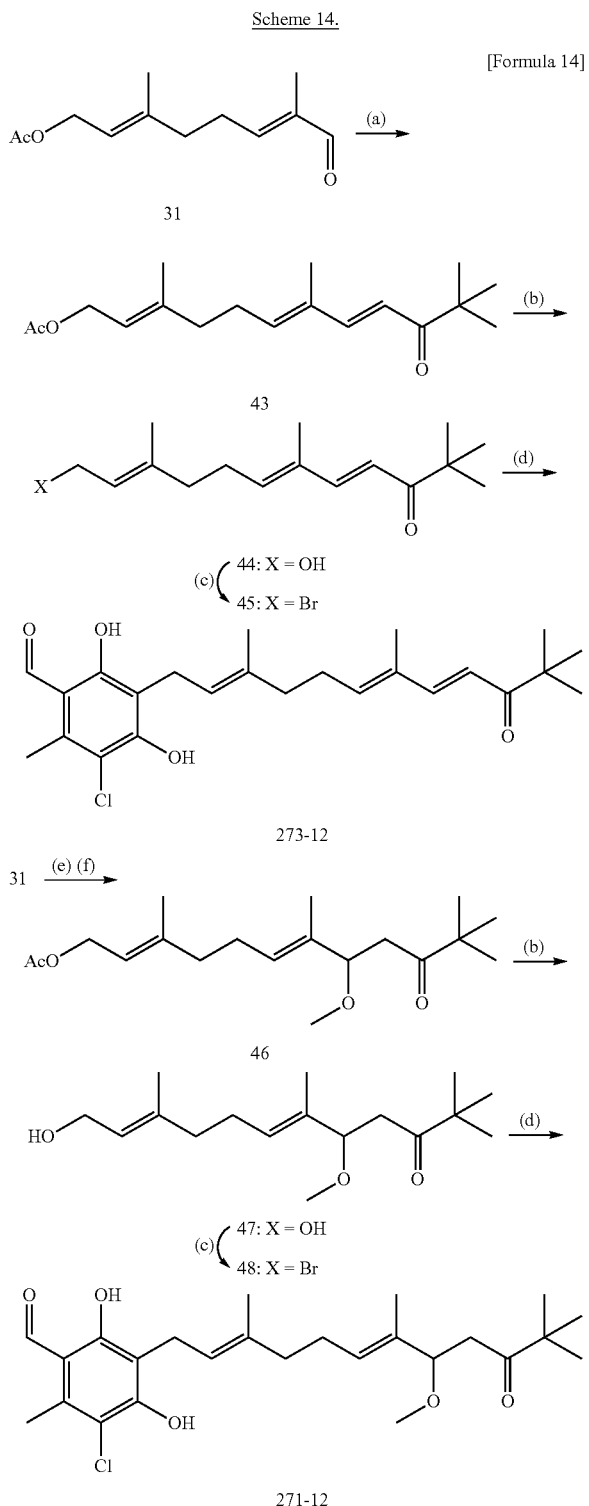

Reagents & conditions:
(a) pinacolone, HMDS, ⁿBuLi, THF, rt
(b) (NH$_2$)$_2$C=NH HCl, NaOMe, MeOH/CHCl$_3$
(c) CBr$_4$, (ⁿC$_8$H$_{17}$)$_3$P, Et$_2$O
(d) 112, KOH, CaCl$_2$, MeOH
(e) pinacolone, HMDS, ⁿBuLi, THF, -50+
(f) MeI, Ag$_2$O, CH$_3$CN.

3-Chloro-4,6-dihydroxy-2-methyl-5-[(2E,6E,8E)-3,7,11,11-tetramethyl-10-oxo-2,6,8-dodecatrienyl] benzaldehyde (compound 273-12)

To a solution of HMDS (0.8 ml, 3.8 mmol) in THF (20 ml), BuLi (1.58 M in hexane, 2.4 ml, 3.8 mmol) was added dropwise at 50° C. and stirred for 10 minutes. To this mixture, pinacolone (0.44 ml, 3.5 mmol) was added and stirred for 2 hours while elevating the temperature to 20° C. After the reaction mixture was cooled to −80° C., a solution of compound 31 (0.625 g, 3.184 mmol) in THF (5 ml) was added dropwise thereto and stirred at the same temperature for 1 hour and then stirred for 15 hours while returning to room temperature. After the reaction mixture was diluted with H$_2$O to separate and collect the organic layer, the aqueous layer was extracted twice with Et$_2$O. The combined organic layers were washed with sat. aq. NaCl and dried over Na$_2$SO$_4$. After the solvent was distilled off, the residue was purified by silica gel column chromatography (hexane:EtOAc=7:1) to give the corresponding α,β-unsaturated ketone (compound 43) (0.333 g, 36%).

$^1$H-NMR (400 MHz, CDCl$_3$) δ 7.31 (1H, d, J=15.4 Hz, CH=CHC=O), 6.47 (1H, d, J=15.4 Hz, CH=CHC=O), 5.92 (1H, t, J=7.0 Hz, AcOCH$_2$CH=C), 5.36 (1H, t, J=6.6 Hz, CH=C(CH$_3$)CH=CH), 4.59 (2H, d, J=7.0 Hz, AcOCH$_2$CH=C), 2.38-2.32 (2H, m, CH$_2$), 2.17-2.13 (2H, m, CH$_2$), 2.06 (3H, s, CH$_3$C=O), 1.81 (3H, s, CH$_3$), 1.68 (3H, s, CH$_3$), 1.18 (9H, s, C(CH$_3$)$_3$).

To a solution of compound 43 (0.333 g, 1.14 mmol) in a mixture of MeOH (18 ml)/CHCl$_3$ (2 ml), guanidine hydrochloride (0.120 g, 1.26 mmol) and NaOMe (0.015 g, 0.28 mmol) were added at room temperature and stirred for 6 hours. After the solvent was distilled off, the residue was extracted with EtOAc. This organic layer was washed with sat. aq. NaCl and then dried over Na$_2$SO$_4$. The solvent was distilled off and the residue was purified by silica gel column chromatography (hexane:EtOAc=7:1) to give the corresponding primary alcohol 44 (0.218 g, 76%).

$^1$H-NMR (400 MHz, CDCl$_3$) δ 7.31 (1H, d, J=15.4 Hz, CH=CHC=O), 6.47 (1H, d, J=15.4 Hz, CH=CHC=O), 5.93 (1H, t, J=7.3 Hz, HOCH$_2$CH=C), 5.43 (1H, t, J=6.8 Hz, CH=C(CH$_3$)CH=CH), 4.16 (2H, d, J=7.0 Hz, HOCH$_2$CH=C), 2.38-2.32 (2H, m, CH$_2$), 2.15-2.11 (2H, m, CH$_2$), 1.81 (3H, s, CH$_3$), 1.69 (3H, s, CH$_3$), 1.18 (9H, s, C(CH$_3$)$_3$).

To a solution of compound 44 (0.218 g, 0.871 mmol) in CHCl$_3$ (10 ml), CBr$_4$ (0.647 mmol, 1.95 mmol) and (C$_8$H$_{17}$)$_3$P (0.86 ml, 1.93 mmol) were added at 0° C. and stirred for 2 hours. After the solvent was distilled off, the residue was subjected to silica gel column chromatography (hexane:EtOAc=2:1) to give a bromide (compound 45).

The whole product was dissolved in MeOH (2.1 ml) and added at 0° C. to a solution of compound 112 (0.190 g, 1.02 mmol) in KOH (1 M in MeOH, 1.4 ml, 1.4 mmol). CaCl$_2$.2H$_2$O (0.107 g, 0.73 mmol) was further added and the mixture was stirred for 20 hours while returning to room temperature. After the reaction mixture was filtered, the filtrate was diluted with EtOAc and washed with 0.1 M aq. KOH and sat. aq. NaCl, and then dried over Na$_2$SO$_4$. After the solvent was distilled off, the residue was subjected to silica gel column chromatography (hexane:EtOAc=3:1). The solvent was distilled off and the resulting crude crystals were purified by recrystallization (hexane:EtOAc=10:1) to give the desired product. The mother liquor was concentrated, and the residue was purified by silica gel column chromatography (hexane:EtOAc=3:1) to further give the desired product (70 mg in total, 19% from compound 44).

Mp. 108-110° C. $^1$H-NMR (400 MHz, CDCl$_3$) δ 12.69 (1H, s, Ar—OH), 10.14 (1H, s, CHO), 7.23 {1H, d, J=15.4 Hz, CH=CHC(O)}, 6.43 (1H, d, J=15.4 Hz, CH=C HC(O)), 6.40 (1H, s, Ar—OH), 5.37 (1H, t, J=7.0 Hz, CH=C), 5.21 (1H, t, J=6.6 Hz, CH=C), 3.39 (2H, d, J=7.0 Hz, Ar—CH$_2$), 2.61 (3H, s, Ar—CH$_3$), 2.30 (2H, m, CH$_2$), 2.08 (2H, m, CH$_2$), 1.79 (3H, s, CH$_3$), 1.77 (3H, s, CH$_3$), 1.17 (9H, s, C(CH$_3$)$_3$). IR (KBr) 3194, 2964, 2916, 1672, 1599, 1460, 1421, 1394, 1369, 1275, 1236, 1205, 1165, 1115, 1074, 980, 910, 806, 764, 715, 631, 586 cm$^{-1}$.

3-Chloro-4,6-dihydroxy-2-methyl-5-(2E,6E)-(8-methoxy-3,7,11,11-tetramethyl-10-oxo-2,6-dodecadienyl)benzaldehyde (compound 271-12)

To a solution of HMDS (1.6 ml, 7.6 mmol) in THF (25 ml), BuLi (1.58 M in hexane, 5.0 ml, 7.9 mmol) was added dropwise at −50° C. and stirred for 15 minutes. To this mixture, pinacolone (0.96 ml, 7.7 mmol) was added and stirred for 1 hour while elevating the temperature to −20° C. After the reaction mixture was cooled to −80° C., a solution of compound 31 (1.069 g, 5.084 mmol) in THF (10 ml) was added dropwise thereto and stirred for 6 hours while elevating the temperature to −50° C. After the reaction mixture was diluted with H$_2$O to separate and collect the organic layer, the aqueous layer was extracted twice with EtOAc. The combined organic layers were washed with saturated aqueous sodium chloride and dried over Na$_2$SO$_4$. After the solvent was distilled off, the residue was purified by silica gel column chromatography (hexane:EtOAc=3:1) to give the corresponding aldol product (1.047 g, 66%).

$^1$H-NMR (400 MHz, CDCl$_3$) δ 5.44 (1H, t, J=6.4 Hz, AcOCH$_2$CH=C), 5.34 (1H, t, J=7.1 Hz, CH=C(CH$_3$)CH(OH)), 4.59 (2H, d, J=7.3 Hz, AcOCH$_2$CH=C), 4.42 (1H, t, J=5.9 Hz, CH(OH)), 3.22 (1H, br, CH(OH)), 2.68 (2H, d, J=6.0 Hz, CH$_2$CO), 2.18-2.12 (2H, m, CH$_2$), 2.11-2.07 (2H, m, CH$_2$), 2.06 (3H, s, CH$_3$C=O), 1.71 (3H, s, CH$_3$), 1.64 (3H, s, CH$_3$), 1.15 (9H, s, C(CH$_3$)$_3$).

To a solution of the resulting aldol adduct (0.504 g, 1.624 mmol) in MeCN (5 ml), MeI (1.5 ml, 24 mmol) and Ag$_2$O (0.609 g, 2.63 mmol) were added at room temperature under an Ar atmosphere and refluxed for 1 day. After returning to room temperature, the reaction mixture was diluted with EtOAc and then filtered. The filtrate was washed with water, and the organic layer was dried over Na$_2$SO$_4$. After the solvent was distilled off, the residue was purified by silica gel column chromatography (hexane:EtOAc=4:1) to give the corresponding methyl ether 46 (0.258 g, 49%).

$^1$H-NMR (400 MHz, CDCl$_3$) δ 5.33 (1H, t, J=6.3 Hz, CH=C), 5.29 (1H, t, J=7.0 Hz, CH=C), 4.51 (2H, d, J=7.3 Hz, AcOCH$_2$CH=C), 3.97 (1H, dd, J=4.4, 8.0 Hz, CHOCH$_3$), 3.07 (3H, s, OCH$_3$), 2.80 (1H, d, J=8.0, 16.9 Hz, CH$_2$C=O), 2.33 (1H, d, J=4.4, 16.9 Hz, CH$_2$C=O), 2.16-2.01 (4H, m, CH$_2$CH$_2$), 1.99 (3H, s, CH$_3$C=O), 1.63 (3H, s, CH$_3$), 1.48 (3H, s, CH$_3$), 1.05 (9H, s, C(CH$_3$)$_3$).

It should be noted that retro-aldol occurred as a side reaction and thereby aldehyde 31 was collected.

To a solution of compound 46 (0.306 g, 0.943 mmol) in MeOH (4.5 ml)/CHCl$_3$ (0.5 ml), a guanidine solution (which was prepared from a solution of guanidine hydrochloride (0.103 g, 1.08 mmol) in MeOH (9.0 ml) by addition of CHCl$_3$ (1.0 ml) and NaOMe (12 mg, 0.23 mmol) and then stirring for 10 minutes) was added dropwise at room temperature under an Ar stream and stirred for 6 hours. After the solvent was distilled off, the residue was diluted with EtOAc and washed with saturated aqueous sodium chloride, and then dried over Na$_2$SO$_4$. After the solvent was distilled off the residue was subjected to silica gel column chromatography (hexane:EtOAc=2:1) to give a mixture (213 mg) of primary alcohol 47 and compound 44 free from the methoxy group, which was used for the subsequent reaction without further purification.

Namely, the whole mixture was dissolved in Et$_2$O (20 ml) and cooled to 0° C., followed by addition of CBr$_4$ (563 mg, 1.70 mmol) and (C$_8$H$_{17}$)$_3$P (0.75 ml, 1.7 mmol) and stirring at the same temperature for 2 hours. The reaction mixture was diluted with H$_1$O and then extracted twice with Et$_2$O. The combined organic layers were washed with saturated aqueous sodium chloride and dried over Na$_2$SO$_4$. The residue was subjected to silica gel column chromatography (hexane:EtOAc=2:1) to give a fraction containing bromides (compound 48 and compound 45).

Compound 112 (387 mg, 2.07 mmol) was mixed with KOH (1.0 M in MeOH, 3.2 ml, 3.2 mmol) and cooled to −10° C. To this mixture, CaCl$_2$ 2H$_2$O (221 mg, 1.50 mmol) and a solution of the above bromide mixture in MeOH (5 ml) were added and stirred at the same temperature for 1 day. After the reaction mixture was diluted with EtOAc and 0.1 M aq. KOH to separate and collect the organic layer, the aqueous layer was extracted with EtOAc. The combined organic layers were washed with saturated aqueous sodium chloride and dried over Na$_2$SO$_4$. After the solvent was distilled off, the residue was purified by silica gel column chromatography (hexane/EtOAc=4:1) and PTLC (hexane/EtOAc=7:1) to give the desired product (compound 271-12) and a by-product (compound 273-12) in amounts of 10 mg (2% from compound 46) and 12 mg (3% from compound 46), respectively.

$^1$H-NMR (400 MHz, CDCl$_3$) δ 12.69 (1H, s, Ar—OH), 10.14 (1H, s, CHO), 6.56 (1H, s, Ar—OH), 5.37 (1H, t, J=6.6 Hz, CH=C), 5.23 (1H, t, J=7.0 Hz, CH=C), 3.99 (1H, dd, J=4.4, 8.1 Hz, C(O)CH$_2$CHOMe), 3.39 (2H, d, J=7.0 Hz, Ar—CH$_2$), 3.08 (3H, s, OCH$_3$), 2.85 (1H, dd, J=4.4, 16.6 Hz, C(O)CH$_2$CHOMe), 2.61 (3H, s, Ar—CH$_3$), 2.39 (1H, dd, J=8.1, 16.6 Hz, C(O)CH$_2$CHOMe), 2.19-2.08 (2H, m, CH$_2$), 2.05-2.01 (2H, m, CH$_2$), 1.78 (3H, s, CH$_3$), 1.52 (3H, s, CH$_3$), 1.11 (9H, s, C(CH$_3$)$_3$).

15. Compounds 234-12-OPiv, 175-12-OPiv and 235-12-Opiv

Scheme 15.

[Formula 15]

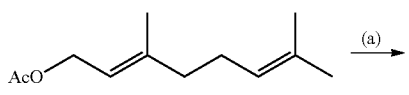

29

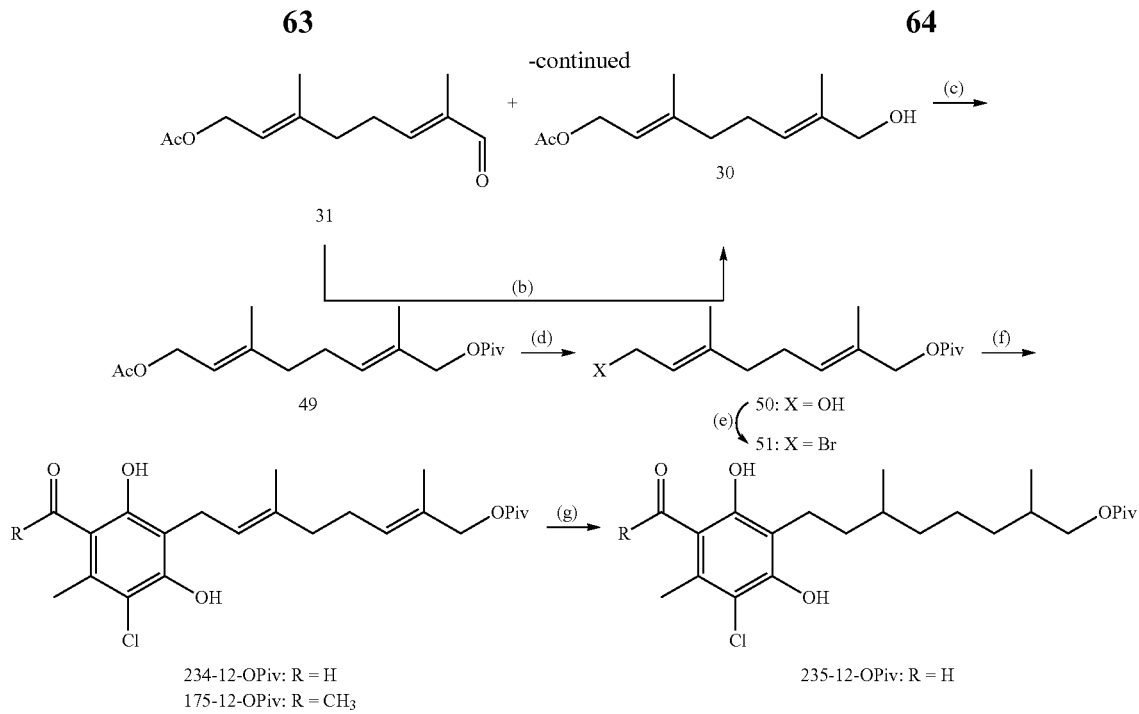

234-12-OPiv: R = H
175-12-OPiv: R = CH$_3$

Reagents & conditions:
(a) SeO$_2$, EtOH
(b) NaBH$_4$, EtOH
(c) Piv—Cl, Et$_3$N, DMAP, CH$_3$Cl
(d) (NH$_2$)$_2$C=NH HCl, NaOMe, MeOH/CHCl$_3$
(e) CBr$_4$, ($^n$C$_8$H$_{17}$)$_3$P, Et$_2$O
(f) 112 or 111, KOH, CaCl$_2$, MeOH
(g) H$_2$, Pd—C, EtOAc (2E,6E)-8-(3-Chloro-5-formyl-2,6-dihydroxy-4-methylphenyl)-2,6-dimethyl-2,6-octadienyl pivalate (compound 234-12-OPiv)

To a solution of geranyl acetate (compound 29, 1.0 ml, 4.7 mmol) in EtOH (20 ml). SeO$_2$ (602 mg, 5.43 mmol) was added at room temperature and refluxed for 1 hour. After returning to room temperature, the reaction mixture was filtered through celite. The filtrate was concentrated and mixed with EtOH (20 ml), followed by cooling to 0° C. To this mixture, NaBH$_4$ (58 mg, 1.5 mmol) was added and stirred for 1 hour. After addition of 2 M aq. HCl (2 ml), the reaction mixture was stirred for 5 minutes and then poured into H$_2$O (30 ml). After extraction with EtOAc, the combined organic layers were washed with sat. aq. NaCl and dried over Na$_2$SO$_4$. After the solvent was distilled off, the residue was subjected to silica gel column chromatography (hexane:EtOAc=2:1) to give a primary alcohol (compound 30) as a crude product (1.517 g).

To this crude product, CHCl$_3$ (10 ml) was added and cooled to 0° C., followed by addition of Et$_3$N (0.5 ml, 3.6 mmol), DMAP (18 mg, 0.15 mmol) and Piv-Cl (0.46 ml, 3.8 mmol) in this order. The mixture was stirred for 16 hours while returning to room temperature. After addition of H$_2$O (20 ml), the reaction mixture was extracted with EtOAc, and the combined organic layers were washed sequentially with sat. aq. NH$_4$Cl, sat. aq. NaHCO$_3$ and sat. aq. NaCl, and then dried over Na$_2$SO$_4$. After the solvent was distilled off, the residue was purified by silica gel column chromatography (hexane:EtOAc=4:1) to give diester 49 (389 mg, 28% for 2 steps).

$^1$H-NMR (400 MHz, CDCl$_3$) δ 5.41 (1H, t, J=7.0 Hz, CH=C), 5.35 (1H, t, J=7.1 Hz, CH=C), 4.59 (2H, d, J=7.0 Hz, AcOCH$_2$), 4.44 (2H, s, CH$_2$OPiv), 2.21-2.15 (2H, m, CH$_2$), 2.11-2.07 (2H, m, CH$_2$), 1.71 (3H s, CH$_3$), 1.64 (3H, s, CH$_3$), 1.20 (9H, s, C(CH$_3$)$_3$).

To a solution of diester 49 (411 mg, 1.39 mmol) in a mixture of MeOH (4.5 ml)/CHCl$_3$ (0.5 ml), a guanidine solution (which was prepared from a solution of guanidine hydrochloride (0.146 g, 1.528 mmol) in MeOH (13.5 ml) by addition of CHCl$_3$ (1.5 ml) and NaOMe (17 mg, 0.32 mmol) and then stirring for 10 minutes) was added dropwise at room temperature under an Ar stream and stirred for 3 hours. After the solvent was distilled off, the residue was diluted with EtOAc and washed sequentially with saturated aqueous NH$_4$Cl and saturated aqueous sodium chloride, and then dried over Na$_2$SO$_4$. After the solvent was distilled off, the residue was purified by silica gel column chromatography (hexane:EtOAc=3:12:1) to give primary alcohol 50 (316 mg, 90%).

$^1$H-NMR (400 MHz, CDCl$_3$) δ 5.47-5.34 (2H, m, 2×CH=C), 4.44 (2H, s, CH$_2$OPiv), 4.15 (2H, d, J=6.6 Hz, CH$_2$OH), 2.23-2.13 (2H, m, CH$_2$), 2.11-2.03 (2H, m, CH$_2$), 1.67 (3H, s, CH$_3$), 1.64 (3H, s, CH$_3$), 1.42 (1H, br, CH$_2$OH), 1.21 (9H, s, C(CH$_3$)$_3$).

To a solution of primary alcohol 50 (316 mg, 1.24 mmol) in Et$_2$O (10 ml), CBr$_4$ (856 mg, 2.58 mmol) and (C$_8$H$_{17}$)$_3$P (1.1 ml, 2.5 mmol) were added at 0° C. under an Ar stream and stirred at the same temperature for 40 minutes. After the solvent was distilled off, the residue was subjected to silica gel column chromatography (hexane:EtOAc=10:1) to give bromide 51.

Compound 112 (928 mg, 4.97 mmol) was mixed with KOH (0.99 M in MeOH, 7.0 ml, 6.9 mmol) and cooled to 0° C. To this mixture. CaCl$_2$ 2H$_2$O (506 mg, 3.44 mmol) in crushed state and a solution of compound 51 (crude, 1.055 g) in MeOH (10 ml) were added and stirred at −5° C. for 18 hours. After the solvent was distilled off, the residue was diluted with EtOAc (30 ml) and 0.1 M aq. KOH (30 ml), and then filtered through celite. The filtrate was extracted with EtOAc (220 ml), and the combined organic layers were washed with saturated aqueous sodium chloride (20 ml) and dried over Na$_2$SO$_4$. After the solvent was distilled off, the residue was purified by silica gel column chromatography (hexane/EtOAc=5:1) and the resulting solids were further purified by recrystallization (hexane) to give the desired product 234-12-OPiv (213 mg, 41%).

Mp 60° C. $^1$H-NMR (400 MHz, CDCl$_3$) δ 12.70 (1H, s, Ar—OH), 10.14 (1H, s, Ar—CHO), 6.54 (1H, s, Ar—OH), 5.38 (1H, t, J=6.8 Hz, CH=C), 5.22 (1H, t, J=6.8 Hz, CH=C), 4.40 (2H, s, CH$_2$OPiv), 3.39 (2H, d, J=6.8 Hz, Ar—CH$_2$), 2.60 (3H, s, Ar—CH$_3$), 2.16-2.11 (2H, m, CH$_2$), 2.04-2.00 (2H, m, CH$_2$), 1.78 (3H, s, CH$_3$), 1.61 3H, s, CH$_3$), 1.20 {9H, s, C(CH$_3$)$_3$}. $^{13}$C-NMR (100 MHz, CDCl$_3$) δ193.3, 178.4, 162.2, 156.4, 137.7, 136.2, 130.3, 128.4, 121.2, 114.4, 113.6, 113.3, 69.9, 39.1, 38.9, 27.2, 26.1, 22.0, 16.1, 14.4, 13.8. IR (KBr) 3244, 2978, 2922, 1728, 1616, 1485, 1450, 1421, 1369, 1279, 1234, 1157, 1105, 1032, 959, 910, 876, 770, 718, 635, 604, 575, 536 cm$^{-1}$. Anal. Found: C, 65.07; H, 7.32; Cl, 8.44%. Calcd for C$_{23}$H$_{31}$ClO$_5$: C, 65.32; H, 7.39; Cl, 8.38%.

(2E,6E)-8-(5-Acetyl-3-chloro-2,6-dihydroxy-4-methylphenyl)-2,6-dimethyl-2,6-octa dienyl pivalate (compound 175-12-OPiv)

Compound 111 was used as an aromatic ring starting material and synthesis was conducted in the same manner to give the desired product.

$^1$H-NMR (400 MHz, CDCl$_3$) δ 12.62 (1H, s, Ar—OH), 6.31 (1H, s, Ar—OH), 5.38 (1H, t, J=6.8 Hz, CH=C), 5.23 (1H, t, J=6.2 Hz, CH=C), 4.39 (2H, s, CH$_2$OPiv), 3.40 (2H, d, J=7.3 Hz, Ar—CH$_2$), 2.61 (3H, s, Ar—CH$_3$), 2.59 (3H, s, CH$_3$C=O), 2.17-2.10 (2H, m, CH$_2$), 2.06-1.98 (2H, m, CH$_2$), 1.79 (3H, s, CH$_3$), 1.60 (3H, s, CH$_3$), 1.19 {9H, s, C(CH$_3$)$_3$}. IR (KBr) 3412, 2978, 2922, 1728, 1610, 1464, 1416, 1360, 1279, 1157, 1094, 1036, 984, 951, 841, 768, 600 cm$^{-1}$. HRMS (EI) Found: 436.2024. Calcd. for C$_{24}$H$_{33}$ClO$_5$: 436.2017.

8-(3-Chloro-5-formyl-2,6-dihydroxy-4-methylphenyl)-2,6-dimethyloctyl pivalate (compound 235-12-OPiv)

The compound 234-12-OPiv was reduced in the same manner as used in Scheme 1 to give the desired product.

$^1$H-NMR (400 MHz, CDCl$_3$) δ 12.61 (1H, s, Ar—OH), 10.10 (1H, s, Ar—CHO), 6.50 (1H, d, J=12.1 Hz, Ar—OH), 3.98-3.93 (1H, m, CH$_2$OPiv), 3.87-3.82 (1H, m, CH$_2$OPiv), 2.66-2.59 (2H, m, Ar—CH$_2$), 2.56 (3H, s, Ar—CH$_2$), 1.80-1.70 (2H, m, CH$_2$), 1.53-1.41 (2H, m), 1.36-1.27 (4H, br, CH$_2$CH$_2$), 1.23-1.17 (2H, m), 1.17 {9H, s, C(CH$_3$)$_3$}, 0.91 (3H, d, J=7.0 Hz, CH(CH$_3$), 0.90 (3H, d, J=7.0 Hz, CHCH$_3$). $^{13}$C-NMR (100 MHz, CDCl$_3$) δ 193.19, 178.75, 162.31, 156.22, 137.20, 115.6, 113.45, 113.86, 69.18, 38.83, 36.79, 35.21, 33.74, 32.77, 32.61, 27.19, 23.89, 20.43, 19.61, 16.99, 14.39. IR (neat) 3395, 2961, 2932, 2872, 1724, 1717, 1634, 1462, 1422, 1375, 1290, 1248, 1167, 1034, 980, 800, 710, 592 cm$^{-1}$. HRMS (EI) Found: 426.2144. Calcd. for C$_{23}$H$_{35}$ClO$_5$: 426.2173.

16. Compounds 264-11-OPiv and 265-11-Opiv

Scheme 16.

[Formula 16]

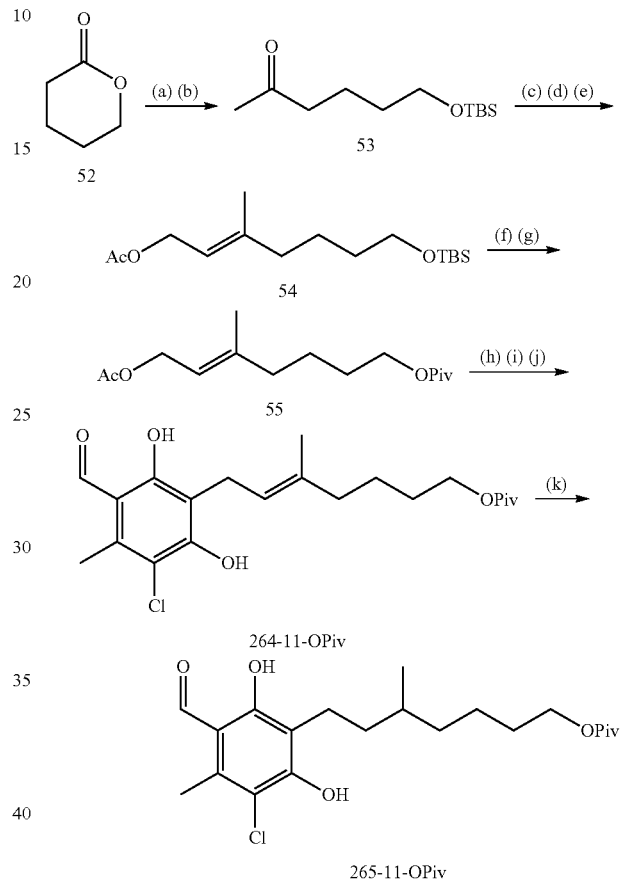

Reagennts & conditions:
(a) MeLi, THF
(b) TBS—Cl, Et$_3$N, DMAP, CHCl$_3$
(c) (EtO)$_2$P(O)CH$_2$CO$_2$Et, NaH, THF
(d) DIBAL, toluene
(e) Ac$_2$O, pyridine
(f) TBAF, THF
(g) Piv—Cl, Et$_3$N, DMAP, CHCl$_3$
(h) (NH$_2$)$_2$C=NH HCl, NaOMe, MeOH/CHCl$_3$
(i) CBr$_4$, Ph$_3$P, CHCl$_3$
(j) 112, KOH, CaCl$_2$, MeOH
(k) H$_2$, Pd—C, EtOAc (5E)-7-(3-Chloro-5-formyl-2,6-dihydroxy-4-methylphenyl)-5-methyl-5-heptenyl pivalate (compound 264-1-OPiv)

To a solution of 8-valerolactone (compound 52, 3.0 ml, 32 mmol) in THF (50 ml), MeLi (1.04 M in Et$_2$O, 33 ml, 34 mmol) was added dropwise at −80° C. under an Ar atmosphere and stirred for 4 hours while elevating the temperature to −65° C. The reaction was stopped by addition of H$_2$O, followed by stirring at room temperature for 5 minutes. The organic layer was then separated and collected, and the aqueous layer was extracted twice with EtOAc. The combined organic layers were washed with saturated aqueous sodium chloride and dried over $Na_2SO_4$. After the solvent was distilled off, the residue was purified by silica gel column chromatography (EtOAc) to give 7-hydroxy-2-hexanone (2.545 g, 68%).

To a solution of this ketone (2.545 g, 21.91 mmol) in $CHCl_3$ (70 ml), $Et_3N$ (6.1 ml, 44 mmol), DMAP (cat. amount) and TBS-Cl (50% in toluene, 4.5 ml, 27 mmol) were added at 0° C. and stirred for 13 hours while returning to room temperature. The reaction mixture was diluted with $H_2O$ and stirred for 5 minutes. The organic layer was then separated and collected, and the aqueous layer was extracted twice with EtOAc. The combined organic layers were washed with saturated aqueous $NH_4Cl$ and saturated aqueous sodium chloride, and then dried over $Na_2SO_4$. After the solvent was distilled off, the residue was purified by silica gel column chromatography (hexane:EtOAc=5:1) to give the corresponding silyl ether 53 (4.385 g, 87%).

$^1$H-NMR (400 MHz, $CDCl_3$) δ 3.57 (2H, t, J=6.6 Hz, C$\underline{H}_2$OTBS), 2.41 (2H, t, J=7.3 Hz, C(O)C$\underline{H}_2$CH$_2$), 2.09 (3H, s, C$\underline{H}_3$C=O), 1.62-1.55 (2H, m, C$\underline{H}_2$), 1.51-1.43 (2H, m, C$\underline{H}_2$), 0.85 (9H, s, C(C$\underline{H}_3$)$_3$), 0.01 (6H, s, Si(C$\underline{H}_3$)$_2$).

To a suspension of NaH (60% in oil, 146 mg, 3.65 mmol) in THF (20 ml), triethyl phosphonoacetate (0.7 ml, 3.2 mmol) was added at 0° C. under an Ar atmosphere and stirred for 1.5 hours while returning to room temperature. The mixture was cooled to −65° C., and a solution of compound 53 (676 mg, 2.93 mmol) in THF (10 ml) was added dropwise thereto and stirred for 16 hours while returning to room temperature. The reaction was stopped by addition of $H_2O$, followed by stirring for 5 minutes. The organic layer was then separated and collected, and the aqueous layer was extracted twice with $Et_2O$. The combined organic layers were washed with saturated aqueous $NH_4Cl$ and dried over $Na_2SO_4$. After the solvent was distilled off, the residue was purified by silica gel column chromatography (hexane:EtOAc=10:1) to give the corresponding unsaturated ester as an (E)-isomer and as a mixture of (E)- and (Z)-isomers (total 0.336 g, 38%6).

(E)-isomer: $^1$H-NMR (400 MHz, $CDCl_3$) δ 5.66 (1H, d, J=1.1 Hz, C=C$\underline{H}$CO$_2$Et), 4.14 (2H, q, J=7.3 Hz, CO$_2$C$\underline{H}_2$CH$_3$), 3.61 (2H, t, J=5.9 Hz, C$\underline{H}_2$OTBS), 2.17-2.13 (2H, m, CH=C(CH$_3$)C$\underline{H}_2$), 2.15 (3H, d, J=1.1 Hz, CH=C(C$\underline{H}_3$)CH$_2$), 1.55-1.51 (4H, m, (C$\underline{H}_2$)$_2$), 1.28 (3H, t, J=7.3 Hz, CO$_2$CH$_2$C$\underline{H}_3$), 0.89 (9H, s, C(C$\underline{H}_3$)$_3$), 0.05 (6H, s, Si(C$\underline{H}_3$)$_2$).

To a solution of the (E)-isomer of the unsaturated ester (1.441 g, 4.795 mmol) in toluene (50 ml), DIBAL (1.0 M in hexane, 25 ml, 25 mmol) was added dropwise at −80° C. under an Ar atmosphere and stirred at −65° C. for 2.5 hours. To the reaction mixture, EtOAc was added slowly and then $H_2O$ and 2 M aq. HCl were further added, followed by stirring for 15 minutes while returning to room temperature. After this mixture was filtered through celite, the organic layer of the filtrate was separated and collected, and the aqueous layer was further extracted twice with EtOAc. The combined organic layers were washed with sat. aq. $NaHCO_3$ and sat. aq. NaCl, and then dried over $Na_2SO_4$. After the solvent was distilled off, the residue was loaded onto silica gel column chromatography (hexane:EtOAc=1:1) to give the corresponding allyl alcohol (1.458 g) as a crude product.

The whole product was dissolved in pyridine (12 ml), and $Ac_2O$ (6 ml) was added thereto at room temperature and stirred for 5 hours. The reaction mixture was diluted with EtOAc, to which $H_2O$ and 2 M aq. HCl were then added and stirred for 5 minutes. After the organic layer was separated and collected, the aqueous layer was extracted twice with EtOAc, and the combined organic layers were washed with sat. aq. $NaHCO_3$ and sat. aq. NaCl, and then dried over $Na_2SO_4$. After the solvent was distilled off, the residue was purified by silica gel column chromatography (hexane:EtOAc=7:1) to give the corresponding acetate 54 (1.259 g, 87% for 2 steps).

$^1$H-NMR (400 MHz, $CDCl_1$) δ 5.34 (1H, dt, J=1.1, 7.0 Hz, C=C$\underline{H}$), 4.57 (2H, d, J=7.0 Hz, C$\underline{H}_2$OAc), 3.61 (2H, t, J=6.0 Hz, C$\underline{H}_2$OTBS), 2.13-2.05 (5H, m, C$\underline{H}_3$OC=O & CH=C(CH$_3$)C$\underline{H}_2$), 1.69 (3H, s, CH=C(C$\underline{H}_3$)CH$_2$), 1.53-1.43 (4H, m, C$\underline{H}_2$C$\underline{H}_2$), 0.89 (9H, s, C(C$\underline{H}_3$)$_3$), 0.05 (6H, s, Si(C$\underline{H}_3$)$_2$).

To a solution of compound 54 (1.26 g, 4.19 mmol) in THF (30 ml), TBAF (1.0 M in THF, 5.0 ml, 5.0 mmol) was added at 0° C. and stirred for 6 hours while returning to room temperature. After TBAF (0.5 ml, 0.5 mmol) were further added and stirred for 2 hours, the reaction mixture was diluted with $H_2O$ to stop the reaction. This mixture was extracted with EtOAc, and the combined organic layers were washed with sat. aq. $NaHCO_3$ and sat. aq. NaCl, and then dried over $Na_2SO_4$. After the solvent was distilled off, the residue was purified by silica gel column chromatography (hexane:EtOAc=2:1→1:1) to give the corresponding primary alcohol (0.741 g, 95%).

$^1$H-NMR (400 MHz, $CDCl_3$) δ 5.35 (1H, dt, J=1.1, 7.0 Hz, C=C$\underline{H}$), 4.58 (2H, d, J=7.0 Hz, C$\underline{H}_2$OAc), 3.65 (2H, t, J=6.2 Hz, C$\underline{H}_2$OH), 2.08-2.05 (5H, m, C$\underline{H}_3$OC=O & CH=C(CH$_3$)C$\underline{H}_2$), 1.70 (3H, s, CH=C(C$\underline{H}_3$)CH$_2$), 1.59-1.46 (4H, m, C$\underline{H}_2$C$\underline{H}_2$).

To a solution of this primary alcohol (0.741 g, 3.98 mmol) in $CHCl_3$ (30 ml), $Et_3N$ (0.65 ml, 4.7 mmol), DMAP (cat. amount) and Piv-Cl (0.55 ml, 4.5 mmol) were added at 0° C. and stirred at room temperature for 16 hours. After the reaction mixture was diluted with $H_2O$ and stirred for 5 minutes, the organic layer was separated and collected, and the aqueous layer was extracted twice with EtOAc. The combined organic layers were washed with saturated aqueous $NaHCO_3$ and saturated aqueous sodium chloride, and then dried over $Na_2SO_4$. After the solvent was distilled off, the residue was purified by silica gel column chromatography (hexane:EtOAc=5:11:1) to give pivalate 55 (0.471 g, 44%).

$^1$H-NMR (400 MHz, $CDCl_3$) δ 5.35 (1H, t, J=7.1 Hz, C=C$\underline{H}$), 4.58 (2H, d, J=7.0 Hz, C$\underline{H}_2$OAc), 4.06 (2H, t, J=6.4 Hz, C$\underline{H}_2$OPiv), 2.09-2.03 (5H, m, C$\underline{H}_3$OC=O & CH=C(CH$_3$)C$\underline{H}_2$), 1.69 (3H, s, CH=C(C$\underline{H}_3$)CH$_2$), 1.63-1.57 (2H, m, C$\underline{H}_2$), 1.53-1.46 (2H, m, C$\underline{H}_2$), 1.20 (9H, s, C(C$\underline{H}_3$)$_3$).

It should be noted that the unreacted starting material was collected (0.392 g, 53%).

To a mixed solvent of MeOH (13.5 ml) and $CHCl_3$ (1.5 ml), guanidine hydrochloride (0.184 g, 1.926 mmol) and NaOMe (0.024 g, 0.44 mmol) were added at room temperature under an Ar atmosphere and stirred for 10 minutes. This solution was added dropwise to a solution of compound 55 (0.471 g, 1.74 mmol) in a mixture of MeOH (4.5 ml) and $CHCl_3$ (0.5 ml), followed by stirring at room temperature for 5 hours. After the solvent was distilled off, the residue was diluted with EtOAc and $H_2O$ to separate and collect the organic layer. The aqueous layer was further extracted with EtOAc, and the combined organic layers were washed with sat. aq. $NaHCO_3$ and sat. aq. NaCl, and then dried over $Na_2SO_4$. After the solvent was distilled off, the residue was purified by silica gel column chromatography (hexane:EtOAc=2:1) to give the corresponding allyl alcohol (0.376 g, 95%).

¹H NMR (400 MHz, CDCl₃) δ 5.42 (1H, ddt, J=1.5, 2.6, 7.0 Hz, C═CH), 4.16 (2H, d, J=6.6 Hz, CH₂OH), 4.06 (2H, t, J=6.2 Hz, CH₂OPiv), 2.05 (2H, t, J=7.3 Hz, CH═C(CH₃)CH₂), 1.67 (3H, s, CH═C(CH₃)CH₂), 1.63-1.58 (2H, m, CH₂), 1.53-1.46 (2H, m, CH₂), 1.28 (1H, br, OH), 1.19 (9H, s, C(CH₃)₃).

To a solution of this allyl alcohol (0.376 g, 1.65 mmol) in CHCl₃ (20 ml), Ph₃P (0.952 g, 3.63 mmol) and CBr₄ (1.205 g, 3.633 mmol) were added at 0° C. and stirred for 1 hour. After the solvent was distilled off, the residue was subjected to silica gel column chromatography (hexane:EtOAc=2:1) to give the corresponding bromide. The resulting product was used for the subsequent reaction without further purification.

Namely, to a solution of compound 112 (1.358 g, 7.278 mmol) in MeOH (10 ml), KOH (1.0 M in MeOH, 11.0 ml, 11.0 mmol) was added and cooled to 0° C. To this mixture, the bromide (crude, 0.736 g) in MeOH (10 ml) and CaCl₂.2H₂O (0.749 g, 5.09 mmol) were added and stirred at room temperature for 1 day. After the reaction mixture was filtered through celite, the filtrate was concentrated and the residue was diluted with EtOAc and 0.1 M aq. KOH. The organic layer was separated and collected, and the aqueous layer was extracted twice with Et₂O and once with EtOAc. The combined organic layers were washed with sat. aq. NaCl and dried over Na₂SO₄. After the solvent was distilled off, the residue was purified by silica gel column chromatography (hexane:EtOAc=4:1) and further recrystallized twice from hexane to give the desired product (0.188 g, 28%).

Mp 74-75° C. ¹H-NMR (400 MHz, CDCl₃) δ 12.69 (1H, s, Ar—OH), 10.14 (1H, s, Ar—CHO), 6.42 (1H, s, Ar—OH), 5.22 (1H, dt, J=1.5, 7.3 Hz, CH═C), 4.03 (2H t, J=6.4 Hz, CH₂OPiv), 3.40 (2H, d, J=7.3 Hz, Ar—CH₂), 2.61 (3H, s, Ar—CH₃), 2.00 (2H, t, J=7.5 Hz, CH═C(CH₃)CH₂), 1.77 (3H, s, CH═C(CH₃)CH₂), 1.58-1.53 (2H, m, CH₂), 1.49-1.43 (2H, m, CH₂), 1.18 (9H, s, C(CH₃)₃). IR (KBr) 3188, 2964, 2874, 1728, 1607, 1477, 1456, 1421, 1377, 1283, 1231, 1161, 1111, 1031, 910, 868, 770, 712, 631, 592 cm⁻¹. Anal. Found: C, 63.53; H, 7.41; Cl, 8.72%. Calcd for C₂₁H₂₉ClO₅: C, 63.55; H, 7.36; Cl, 8.93%.

It should be noted that the aqueous layer was acidified with 2 M hydrochloric acid and then extracted with EtOAc to thereby collect the unreacted compound 112.

7-(3-Chloro-2,6-dihydroxy-5-formyl-4-methylphenyl)-5-methylheptyl pivalate (compound 265-11-OPiv)

To a solution of the compound 264-11-OPiv (0.130 g, 0.328 mmol) in EtOAc (10 ml), Pd—C (cat. amount) was added at 0° C. and stirred for 5 hours under a H₂ atmosphere. After Pd—C was filtered off, the solvent was distilled off and the residue was purified by silica gel column chromatography (hexane:EtOAc=7:1) to give the desired product (0.108 g, 83%).

¹H-NMR (400 MHz, CDCl₃) δ 12.65 (1H, s, Ar—OH), 10.14 (1H, s, Ar—CHO), 6.35 (1H, br, Ar—OH), 4.05 (2H, t, J=6.6 Hz, CH₂OPiv), 2.70-2.63 (2H, m, Ar—CH₂), 2.60 (3H, s, Ar—CH₃), 1.64-1.57 (2H, m, CH₂), 1.55-1.30 (5H, m, CHCH₃ & CH₂CH₂), 1.23-1.17 (2H, m, CH₂), 1.19 (9H, s, C(CH₃)₃), 0.95 (3H, d, J=6.2 Hz, CH(CH₃)CH₂). IR (KBr) 3391, 2957, 2874, 1720, 1628, 1481, 1468, 1421, 1373, 1292, 1248, 1165, 1126, 1094, 1036, 972, 937, 802, 708, 631, 590, 523 cm⁻¹. HRMS (EI) Found: 398.1865. Calcd. for C₂₁H₃₁ClO₅: 398.1860.

17. Compounds 264-8, 265-8, (Z)-264-8, 268-8, 270-8 and 269-8

Scheme 17.

[Formula 17]

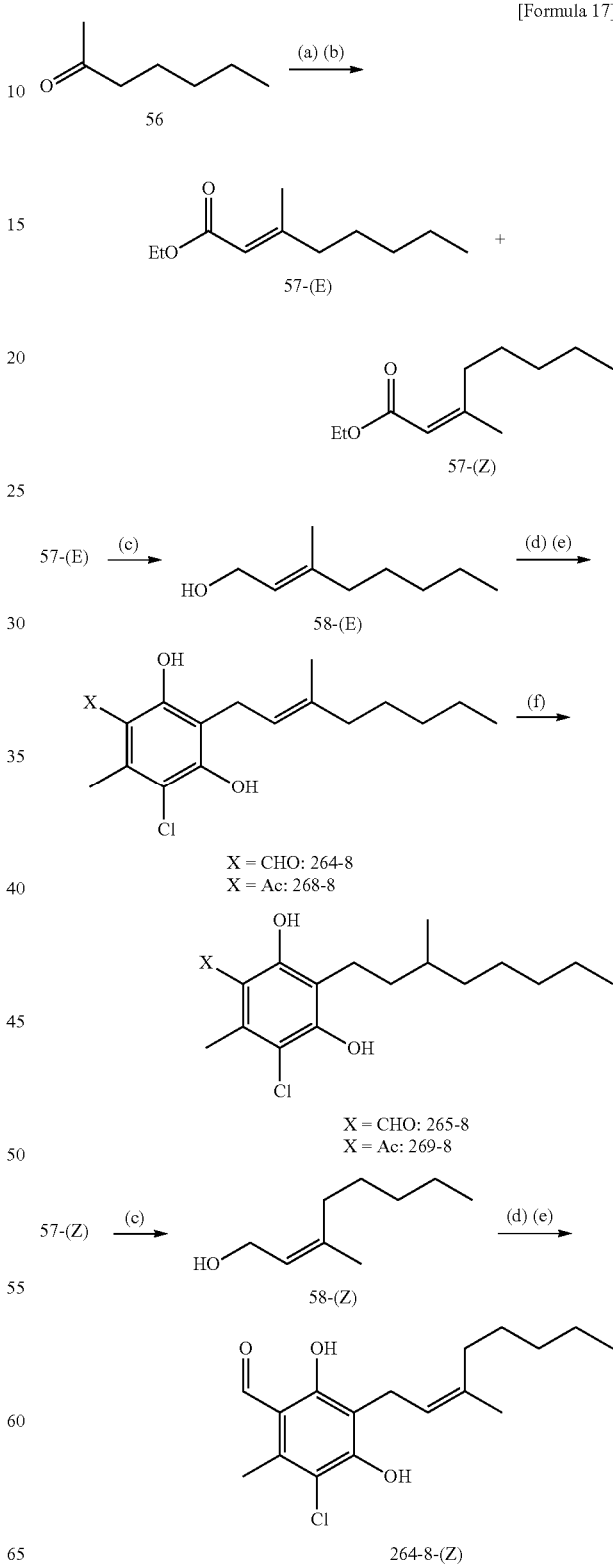

-continued

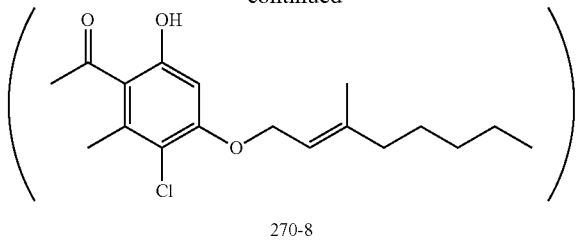
270-8

Reagents & conditions:
(a) (EtO)₂P(O)CH₂CO₂Et, NAH, THF
(b) Silica gel column chlomatography
(c) DIBAL, toluene
(d) CBr₄, Ph₃P, CHCl₃
(e) 112 or 111, KOH, CaCl₂, MeOH
(f) H₂, Pd—C, EtOAc

(E)-3-Chloro-4,6-dihydroxy-2-methyl-5-(3-methyl-2-octenyl)benzaldehyde (compound 264-8)

To a suspension of NaH (60% in oil, 0.511 g, 12.8 mmol) in THF (20 ml), triethyl phosphonoacetate (2.4 ml, 11 mmol) was added at 0° C. and stirred for 1.5 hours while returning to room temperature. This mixture was cooled to −65° C. and 2-heptanone (compound 56, 1.3 ml, 9.3 mmol) was then added dropwise thereto and stirred for 1 day while returning to room temperature. The reaction was quenched by addition of H₂O, followed by stirring for 5 minutes. The organic layer was then separated and collected, and the aqueous layer was extracted once with Et₂O and once with EtOAc. The combined organic layers were washed with sat. aq. NH₄Cl and sat. aq. NaCl, and then dried over Na₂SO₄. After the solvent was distilled off, the residue was purified by silica gel column chromatography (hexane:EtOAc=30:1) to give unsaturated ester 57 as an (E)-isomer, a (Z)-isomer and a mixture thereof (total 1.102 g, 64%).

(E)-isomer: ¹H NMR (400 MHz, CDCl₃) δ 5.66 (1H, dd, J=1.6, 2.4 Hz, C═C$\underline{H}$CO₂Et), 4.14 (2H, q, J=7.0 Hz, CO₂C$\underline{H}_2$CH₃), 2.15-2.10 (5H, m, CH═C(C$\underline{H}_3$)C$\underline{H}_2$), 1.51-1.43 (2H, m, CH₂CH₂CH₂C$\underline{H}_2$CH₃), 1.33-1.23 (7H, m, CO₂CH₂C$\underline{H}_3$ & CH₂C$\underline{H}_2$C$\underline{H}_2$CH₂CH₃), 0.89 {3H, t, J=7.0 Hz, (CH₂)₄C$\underline{H}_3$}. (Z)-isomer: ¹H NMR (400 MHz, CDCl₃) δ 5.64 (1H, d, J=1.4 Hz, C═C$\underline{H}$CO₂Et), 4.14 (2H, q, J=7.3 Hz, CO₂C$\underline{H}_2$CH₃), 2.61 (2H, t, J=7.8 Hz, CH═C(C$\underline{H}_3$)C$\underline{H}_2$), 1.88 (3H, d, J=1.4 Hz, CH═C(C$\underline{H}_3$)CH₂), 1.50-1.42 {2H, m, CH₂CH₂CH$\underline{H}_2$H₂CH₃}, 1.34-1.23 (7H, m, CO₂CH₂C$\underline{H}_3$ & CH₂C$\underline{H}_2$C$\underline{H}_2$CH₂CH₃), 0.89 (3H, t, J=7.3 Hz, (CH₂)₄C$\underline{H}_3$).

To a solution of compound (E)-57 (1.030 g, 5.589 mmol) in toluene (70 ml), DIBAL (1.0 M in hexane, 30 ml, 30 mmol) was added dropwise at −85° C. under an Ar atmosphere and stirred at −65° C. for 2 hours. To the reaction mixture, 1 M aq. HCl was added slowly and stirred for 10 minutes while returning to room temperature. The organic layer was then separated and collected, followed by extraction twice with EtOAc. The combined organic layers were washed with sat. aq. NaCl and dried over Na₂SO₄. After the solvent was distilled off, the residue was purified by silica gel column chromatography (hexane:EtOAc=1:1) to give allyl alcohol (E)-58 (0.738 g, 64%).

¹H-NMR (400 MHz, CDCl₃) δ 5.40 (1H, dt, J=1.1, 7.0 Hz, C$\underline{H}$═C), 4.15 (2H, d, J=7.0 Hz, C$\underline{H}_2$OH), 2.01 (2H, t, J=7.7 Hz, CH═C(CH₃)C$\underline{H}_2$), 1.67 {3H, s, CH═C(C$\underline{H}_3$)CH₂}, 1.45-1.38 (2H, m, CH₂CH₂CH₂C$\underline{H}_2$CH₃), 1.36-1.21 (5H, m, CH₂OH & CH₂C$\underline{H}_2$C$\underline{H}_2$CH₂CH₃), 0.89 (3H, t, J=7.0 Hz, (CH₂)₄C$\underline{H}$3).

To a solution of allyl alcohol (E)-58 (0.738 g, 5.19 mmol) in CHCl₃ (30 ml), Ph₃P (3.067 g, 11.69 mmol) and CBr₄ (3.788 g, 11.42 mmol) were added at 0° C. and stirred for 1 hour. The reaction mixture was diluted with H₂O to separate and collect the organic layer, followed by extraction twice with EtOAc. The combined organic layers were washed with saturated aqueous sodium chloride and dried over Na₂SO₄. After the solvent was distilled off, the residue was purified by silica gel column chromatography (hexane:EtOAc=4:1) to give the corresponding bromide (1.20 g). The resulting product was used for the subsequent reaction without further purification.

Namely, to a solution of compound 112 (2.121 g, 11.37 mmol) in MeOH (4.0 ml), KOH (0.99 M in MeOH, 16.0 ml, 15.8 mmol) was added and cooled to 0° C. To this mixture, CaCl₂·2H₂O (1.176 g, 7.999 mmol) and a solution of the bromide (crude, 1.20 g) in MeOH (10 ml) were added and stirred at room temperature for 15 hours. After the reaction mixture was filtered through celite, the filtrate was concentrated and the residue was diluted with EtOAc and then poured into 0.1 M aq. KOH. The organic layer was separated and collected, and the aqueous layer was extracted with Et₂O and EtOAc. The combined organic layers were washed with saturated aqueous sodium chloride and dried over Na₂SO₄. After the solvent was distilled off, the residue was purified by silica gel column chromatography (hexane:EtOAc=2:1) and further recrystallized twice from a mixed solvent of hexane and CHCl₃ (5:1) to give the desired product 264-8 (0.371 g, 23%).

Mp 99-101° C. ¹H-NMR (400 MHz, CDCl₃) δ 12.70 (1H, s, Ar—O$\underline{H}$), 10.14 (1H, s, Ar—C$\underline{H}$O), 6.42 (1H, s, Ar—O$\underline{H}$), 5.21 (1H, tq, J=1.1, 7.0 Hz, C$\underline{H}$═C), 3.40 (2H, d, J=7.0 Hz, Ar—C$\underline{H}_2$), 2.60 (3H, s, Ar—C$\underline{H}_3$), 1.96 {2H, t, J=7.5 Hz, CH═C(CH₃)C$\underline{H}_2$}, 1.78 {3H, s, CH═C(C$\underline{H}_3$)CH₂}, 1.41-1.34 {2H, m, CH₂(CH₂)₂C$\underline{H}_2$CH₃}, 1.31-1.18 {4H, m, CH₂(C$\underline{H}_2$)₂CH₂CH₃}, 0.86 {3H, t, J=7.1 Hz, CH₂(CH₂)₃C$\underline{H}_3$}. IR (KBr) 3341, 2922, 2860, 1620, 1525, 1464, 1421, 1373, 1330, 1279, 1234, 1165, 1111, 955, 907, 876, 787, 715, 625, 592, 561 cm⁻¹. Anal. Found: C, 65.43; H, 7.44; Cl, 11.43%. Calcd for C₁₇H₂₃ClO₃: C, 65.69; H, 7.46; Cl, 11.41%.

It should be noted that the aqueous layer was acidified with 2 M aq. HCl and then extracted with EtOAc to thereby collect the unreacted compound 112.

3-Chloro-4,6-dihydroxy-2-methyl-5-(3-methyloctyl)benzaldehyde (compound 265-8)

To a solution of the compound 264-8 (0.185 g, 0.595 mmol) in EtOH (10 ml), Pd—C (cat. amount) was added at 0° C. and stirred under a H₂ atmosphere at 0° C. for 2 hours and at room temperature for 3 hours. After Pd—C was filtered off, the solvent was distilled off and the residue was purified by silica gel column chromatography (hexane:EtOAc=12:1) and further recrystallized twice from hexane to give the desired product 265-8 (0.071 g, 38%).

Mp 65-67° C. ¹H-NMR (400 MHz, CDCl₃) δ 12.65 (1H, s, Ar—O$\underline{H}$), 10.14 (1H, s, Ar—C$\underline{H}$O), 6.30 (1H, s, Ar—O$\underline{H}$), 2.69-2.64 (2H, m, Ar—C$\underline{H}_2$), 2.60 (3H, s, Ar—C$\underline{H}_3$), 1.53-1.41 (2H, m, CH₂), 1.38-1.20 {8H, m, (CH₂)₄}, 1.19-1.10 (1H, m, C$\underline{H}$CH₃), 0.95 {3H, d, J=6.6 Hz, CH(C$\underline{H}_3$)CH₂}, 0.88 {3H, t, J=7.0 Hz, CH₂(CH₂)₃C$\underline{H}_3$}IR (KBr) 3258, 2922, 2860, 1603, 1464, 1418, 1373, 1290, 1240, 1128, 924, 799, 764, 708, 631, 592, 530 cm⁻¹. HRMS (EI) Found: 312.1479. Calcd for C₁₇H₂₅ClO₃: 312.1492.

(Z)-3-Chloro-4,6-dihydroxy-2-methyl-5-(3-methyl-2-octenyl)benzaldehyde (compound (Z)-264-8)

The desired product was obtained in the same manner, starting from compound (2)-57.

Mp 157-158° C. $^1$H-NMR (400 MHz, CDCl$_3$) δ 12.69 (1H, s, Ar—O$\underline{H}$), 10.14 (1H, s, Ar—C$\underline{H}$O), 6.42 (1H, br, Ar—O$\underline{H}$), 5.23 (1H, t, J=7.3 Hz, C$\underline{H}$=C), 3.40 (2H, d, J=7.3 Hz, Ar—C$\underline{H}_2$), 2.60 (3H, s, Ar—C$\underline{H}_3$), 2.21 (2H, t, J=7.5 Hz, CH=C(CH$_3$)C$\underline{H}_2$), 1.68 (3H, s, CH=C(C$\underline{H}_3$)CH$_2$), 1.47-1.39 (2H, m, CH$_2$(CH$_2$)$_2$C$\underline{H}_2$CH$_3$), 1.37-1.30 (4H, m, CH$_2$(C$\underline{H}_2$)$_2$CH$_2$CH$_3$), 0.91 (3H, t, J=6.8 Hz, CH$_2$(CH$_2$)$_3$C$\underline{H}_3$). IR (KBr) 3279, 2964, 2916, 2860, 1616, 1516, 1452, 1421, 1373, 1334, 1279, 1231, 1192, 1157, 1109, 959, 899, 868, 787, 718, 621, 592, 527 cm$^{-1}$. HRMS (EI) Found: 310.1337. Calcd for C$_{17}$H$_{23}$ClO$_3$: 310.1336.

(E/Z)-3-Chloro-4,6-dihydroxy-2-methyl-5-(3-methyl-2-octenyl)acetophenone (compound 268-8)

The desired product was obtained in the same manner, starting from the alcohol (compound 58, as an (E)/(Z) mixture).

(E):(Z)=5:1. Mp 42-46° C. $^1$H NMR (400 MHz, CDCl$_3$) δ 12.55 {1/6H, s, Ar—O$\underline{H}$, (Z)}, 12.53 {5/6H, s, Ar—O$\underline{H}$, (E)}, 6.25 (1H, s, Ar—O$\underline{H}$), 5.21 (1H, t, J=6.8 Hz, C$\underline{H}$=C), 3.41 (2H, d, 6.8 Hz, Ar—C$\underline{H}_2$), 2.60 (3H, s, Ar—C$\underline{H}_3$), 2.58 (3H, s, C$\underline{H}_3$C=O), 2.21 {1/3H, t, J=7.5 Hz, CH=C(CH$_3$)C$\underline{H}_2$, (Z)}, 1.96 {5/3H, t, J=7.7 Hz, CH=C(CH$_3$)C$\underline{H}_2$, (E)}, 1.77 {5/2H, s, CH=C(C$\underline{H}_3$)CH$_2$, (E)}, 1.68 {2/2H, s, CH=C(C$\underline{H}_3$)CH$_2$, (Z)}, 1.41-1.18 {6H, m, CH$_2$(C$\underline{H}_2$)$_3$CH$_3$}, 0.91 (1/2H, t, J=7.0 Hz, CH$_2$(CH$_2$)$_3$C$\underline{H}_3$, (Z)), 0.86 {5/2H, t, J=7.1 Hz, CH$_2$(CH$_2$)$_3$C$\underline{H}_3$, (E)}.

(E)-3-Chloro-6-hydroxy-2-methyl-(3-methyl-2-octenoxy)acetophenone (compound 270-8)

This compound was obtained as a by-product of the compound 268-8.

$^1$H-NMR (400 MHz, CDCl$_3$) δ 12.65 (1H, s, Ar—O$\underline{H}$), 6.38 (1H, s, Ar—$\underline{H}$), 5.46 (1H, t, J=6.2 Hz, C$\underline{H}$=C), 4.63 (2H, d, J=6.2 Hz, ArOC$\underline{H}_2$), 2.61 (3H, s, Ar—C$\underline{H}_3$), 2.57 (3H, s, C$\underline{H}_3$C=O), 2.06 {2H, t, J=7.5 Hz, CH=C(CH$_3$)C$\underline{H}_2$}, 1.73 {3H, s, CH=C(C$\underline{H}_3$)CH$_2$}, 1.43 {2H, m, (CH$_2$)$_3$C$\underline{H}_2$CH$_3$}, 1.34-1.23 {4H, m, CH$_2$(C$\underline{H}_2$)$_2$CH$_2$CH$_3$}, 0.88 {3H, t, J=7.0 Hz, CH$_2$(CH$_2$)$_3$C$\underline{H}_3$}. IR (KBr) 2978, 2916, 1607, 1460, 1408, 1360, 1273, 1249, 1202, 1094, 1040, 1011, 824, 752, 638, 625 cm$^{-1}$.

3-Chloro-4,6-dihydroxy-2-methyl-5-(3-methyloctyl)acetophenone (compound 269-8)

$^1$H NMR (400 MHz, CDCl$_3$) δ 12.53 (1H, s, Ar—O$\underline{H}$), 6.08 (1H, s, Ar—O$\underline{H}$), 2.64-2.56 (2H, m, Ar—C$\underline{H}_2$), 2.53 (3H, s, Ar—C$\underline{H}_3$), 2.51 (3H, s, C$\underline{H}_3$C=O), 1.48-1.35 (2H, m, C$\underline{H}_2$), 1.33-1.13 {8H, m, (C$\underline{H}_2$)$_4$}, 1.12-1.03 (1H, m, C$\underline{H}$CH$_3$), 0.87 {3H, d, J=6.8 Hz, CH(C$\underline{H}_3$)CH$_2$}, 0.81 {3H, t, J=7.0 Hz, CH$_2$(CH$_2$)$_3$C$\underline{H}_3$}, $^{13}$C-NMR (100 MHz, CDCl$_3$) δ 204.58, 160.76, 153.88, 134.47, 117.14, 116.16, 113.86, 36.81, 35.57, 33.08, 32.85, 32.27, 26.64, 22.72, 21.25, 20.76, 19.61, 14.23. IR (KBr) 3391, 2922, 2860, 1610, 1468, 1404, 1356, 1269, 1192, 1119, 1092, 997, 951, 868, 785, 742, 603 cm$^{-1}$. HRMS (EI) Found: 326.1659. Calcd. for C$_{18}$H$_{27}$ClO$_3$: 326.1649.

18. Compound 206-12-Opiv

Scheme 18.

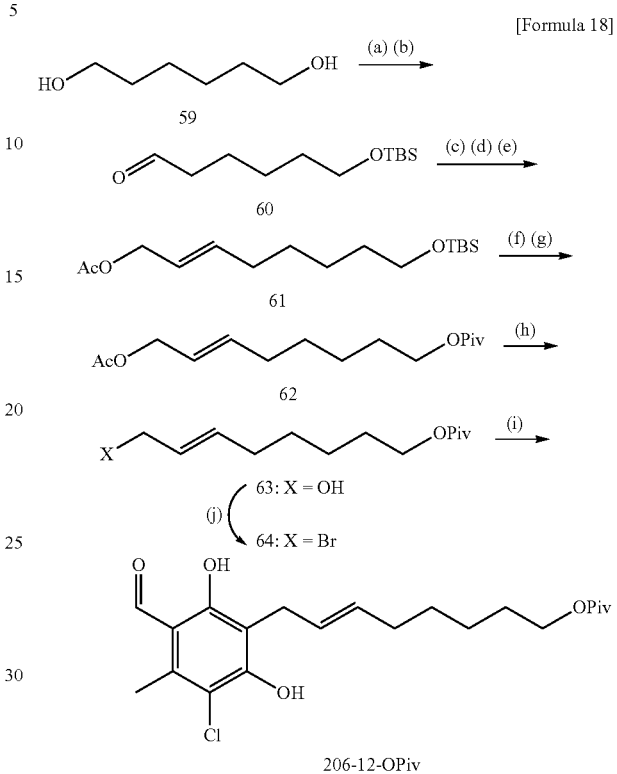

[Formula 18]

206-12-OPiv

Reagents & conditions:
(a) TBS—Cl, imidazole, DMAP, DMF
(b) Swern Oxidation
(c) (EtO)$_2$P(O)CH$_2$CO$_2$Et, MeLi, THF
(d) DIBAL, toluene
(e) Ac$_2$O, pyridine
(f) TBAF, THF
(g) Piv—Cl, Et$_3$N, DMAP, CHCl$_3$
(h) (NH$_2$)$_2$C=NH HCl, NaOMe, MeOH/CHCl$_3$
(i) CBr$_4$, Ph$_3$P, CHCl$_3$
(j) 112, KOH, CaCl$_2$, MeOH.

(E)-8-(3-Chloro-5-formyl-2,6-dihydroxy-4-methylphenyl)-6-octenyl pivalate (compound 206-12-OPiv)

To a solution of 1,6-hexanediol (compound 59, 3.369 g, 28.51 mmol) in DMF (30 ml), imidazole (1.724 g, 25.32 mmol), DMAP (cat. amount) and TBS-Cl (50% in toluene, 3.50 ml, 10.1 mmol) were added at 0° C. and stirred for 15 hours while returning to room temperature. After the reaction mixture was diluted with H$_2$O to separate and collect the organic layer, the aqueous layer was extracted twice with Et$_2$O. The combined organic layers were washed with sat. aq. NaHCO$_3$ and sat. aq. NaCl, and then dried over Na$_2$SO$_4$. After the solvent was distilled off, the residue was purified by silica gel column chromatography (hexane:EtOAc=3:1) to give the corresponding silyl ether (1.671 g, 71%).

$^1$H-NMR (400 MHz, CDCl$_3$) δ 3.66-3.59 (4H, m, C$\underline{H}_2$OH & C$\underline{H}_2$OTBS), 1.60-1.51 (4H, m, C$\underline{H}_2$CH$_2$OH & C$\underline{H}_2$CH$_2$OTBS), 1.43-1.36 (5H, m, C$\underline{H}_2$C$\underline{H}_2$ & O$\underline{H}$), 0.89 {9H, s, C(C$\underline{H}_3$)$_3$}, 0.05 {6H, s, Si(C$\underline{H}_3$)$_2$}.

To a solution of oxalyl chloride (1.25 ml, 14.6 mmol) in CHCl$_3$ (50 ml). DMSO (2.2 ml, 31 mmol) was added dropwise at −60° C. and stirred for 10 minutes. To this mixture, a solution of the above alcohol (1.671 g, 7.189 mmol) in CHCl₃ (15 ml) was added dropwise and stirred at the same temperature for 2 hours. Et₃N (6.0 ml, 43 mmol) was further added dropwise and stirred at the same temperature for 1 hour, followed addition of H₂O to stop the reaction. After the organic layer was separated and collected, the aqueous layer was extracted twice with Et₂O, and the combined organic layers were washed with sat. aq. NH₄Cl and sat. aq. NaCl, and then dried over Na₂SO₄. After the solvent was distilled off, the residue was purified by silica gel column chromatography (hexane:EtOAc=4:1) to give aldehyde 60 (1.400 g, 85%).

To a solution of ethyl diethylphosphonoacetate (1.8 ml, 9.1 mmol) in THF (50 ml), MeLi (1.60 M in Et₂O, 6.5 ml, 10.4 mmol) was added dropwise at −15° C. and stirred for 1 hour while returning to room temperature. The mixture was cooled again to −15° C., and a solution of compound 60 (1.460 g, 6.336 mmol) in THF (10 ml) was added dropwise thereto and then stirred for 20 hours while returning to room temperature. After the reaction mixture was diluted with H₂O to separate and collect the organic layer, the aqueous layer was extracted twice with EtOAc. The combined organic layers were washed with sat. aq. NaHCO₃ and sat. aq. NaCl, and then dried over Na₂SO₄. After the solvent was distilled off, the residue was purified by silica gel column chromatography (hexane:EtOAc=15:1) to give the corresponding unsaturated ester (1.305 g, 69%).

To a solution of this unsaturated ester (1.305 g, 4.343 mmol) in toluene (50 ml), DIBAL (1.0 M in hexane, 22 ml, 22 mmol) was added dropwise at −80° C. and stirred for 3 hours while elevating the temperature to −65° C. After the reaction mixture was diluted with H₂O to separate and collect the organic layer, the aqueous layer was extracted with Et₂O. The combined organic layers were washed with 2 M aq. HCl and sat. aq. NaCl, and then dried over Na₂SO₄. After the solvent was distilled off, the residue was subjected to silica gel column chromatography (hexane:EtOAc=3:1) to give the corresponding allyl alcohol. The resulting product was used for the subsequent reaction without further purification.

Namely, the whole allyl alcohol thus obtained was dissolved in pyridine (10 ml), and Ac₂O (5 ml) was added thereto at room temperature and stirred for 16 hours. The reaction mixture was diluted with EtOAc and then poured into H₂O. After the organic layer was separated and collected, the aqueous layer was extracted with EtOAc, and the combined organic layers were washed twice with 2 M aq. HCl and once with each of sat. aq. NaCO₃ and sat. aq. NaCl, and then dried over Na₂SO₄. After the solvent was distilled off, the residue was purified by silica gel column chromatography (hexane:EtOAc=7:1) to give acetate 61 (1.178 g, 90% for 2 steps).

¹H-NMR (400 MHz, CDCl₃) δ 5.77 (1H, dt, J=6.6, 15.4 Hz, AcOCH₂CH<u>C</u>=H), 5.56 (1H, dt, J=6.6, 15.4 Hz, AcOCH₂CH=C<u>H</u>, 4.50 (2H, d, J=6.2 Hz, AcOC<u>H</u>₂CH=CH), 3.60 (2H, t, J=6.6 Hz, C<u>H</u>₂OTBS), 2.06 (5H, br, C<u>H</u>₃C=O & CH=CHC<u>H</u>₂), 1.55-1.48 (2H, m, C<u>H</u>₂CH₂OTBS), 1.44-1.30 (4H, m, 2×C<u>H</u>₂), 0.89 {9H, s, C(C<u>H</u>₃)₃}, 0.05 {6H, s, Si(C<u>H</u>₃)₂}.

To a solution of compound 61 (1.178 g, 3.919 mmol) in THF (15 ml), TBAF (1.0 M in THF, 4.2 ml, 4.2 mmol) was added at room temperature and stirred for 18 hours. After the reaction mixture was diluted with H₂O to separate and collect the organic layer, the aqueous layer was extracted twice with EtOAc. The combined organic layers were washed with sat. aq. NaCl and dried over Na₂SO₄. After the solvent was distilled off, the residue was purified by silica gel column chromatography (hexane:EtOAc=3:1→1:1) to give the corresponding primary alcohol (0.640 g, 88%).

To a solution of this primary alcohol (0.640 g, 3.436 mmol) in CH₃Cl (15 ml), Et₃N (0.55 mil, 3.9 mmol), Piv-Cl (0.50 ml, 4.1 mmol) and DMAP (cat. amount) were added at 0° C. and stirred for 20 hours while returning to room temperature. After the reaction mixture was diluted with H₂O to separate and collect the organic layer, the aqueous layer was extracted twice with EtOAc. The combined organic layers were washed with sat. aq. NaCl and dried over Na₂SO₄. After the solvent was distilled off, the residue was purified by silica gel column chromatography (hexane:EtOAc=5:1) to give the corresponding pivalate (compound 62) (0.359 g, 39%).

To a mixed solvent of MeOH (13.5 ml) and CHCl₃ (1.5 ml), guanidine hydrochloride (0.151 g, 1.58 mmol) and NaOMe (19 mg, 0.35 mmol) were added at room temperature under an Ar atmosphere and stirred for 10 minutes. This solution was added dropwise to a solution of the pivalate (0.359 g, 1.33 mmol) in a mixture of MeOH (4.5 ml) and CHCl₃ (0.5 ml), followed by stirring at room temperature for 5 hours. After the solvent was distilled off, the residue was diluted with EtOAc and H₂O to separate and collect the organic layer. The aqueous layer was further extracted with EtOAc, and the combined organic layers were washed with sat. aq. NaCl and dried over Na₂SO₄. After the solvent was distilled off, the residue was purified by silica gel column chromatography (hexane:EtOAc=2:1) to give the corresponding allyl alcohol 63 (0.294 g, 97%).

To a solution of this allyl alcohol 63 (0.294 g, 1.288 mmol) in CHCl₃ (20 ml), Ph₃P (0.756 g, 2.88 mmol) and CBr₄ (0.965 g, 2.91 mmol) were added at 0° C. and stirred at the same temperature for 1.5 hours. After the solvent was distilled off, the residue was subjected to silica gel column chromatography (hexane:EtOAc=2:1) to give the corresponding bromide 64. The resulting product was used for the subsequent reaction without further purification.

Namely, to a solution of compound 112 (0.419 g, 2.25 mmol) in MeOH (3.0 ml), KOH (1.0 M in MeOH, 3.5 ml, 3.5 mmol) was added and cooled to 0° C. To this mixture, a solution of the above bromide (crude 64) in MeOH (3.0 ml) and CaCl₂ 2H₂O (0.294 g, 2.00 mmol) were added and stirred for 18 hours while returning to room temperature. The reaction mixture was diluted with Et₂O to separate and collect the organic layer, and the aqueous layer was then extracted once with each of Et₂O and EtOAc. The combined organic layers were washed with 0.1 M aq. KOH and sat. aq. NaCl, and then dried over Na₂SO₄. After the solvent was distilled off, the residue was purified by silica gel column chromatography (hexane:EtOAc=4:1) and then further purified by recrystallization from hexane to give the desired product 206-12-OPiv (35 mg, 7% for 2 steps).

Mp 89-90° C. ¹H-NMR (400 MHz, CDCl₃) δ 12.68 (1H, s, Ar—O<u>H</u>), 10.15 (1H, s, C<u>H</u>O), 6.38 (1H, br, Ar—O<u>H</u>), 5.54-5.51 (2H, m, C<u>H</u>=CH), 4.02 (2H, t, J=6.6 Hz, C<u>H</u>₂OPiv), 3.38 (2H, d, J=4.0 Hz, ArC<u>H</u>₃CH=CH), 2.61 (3H, s, Ar—C<u>H</u>₃), 2.03-1.95 (2H, m, C<u>H</u>₂), 1.63-1.57 (2H, m, C<u>H</u>₂), 1.40-1.29 {4H, m, (C<u>H</u>₂)₂}, 1.18 {9H, s, C(C<u>H</u>₃) <u>H</u>₃}. IR (KBr), 3300, 2970, 2916, 1724, 1620, 1481, 1452, 1429, 1286, 1248, 1223, 1175, 1123, 980, 895, 787, 592 cm⁻¹. HRMS (EI) Found: 396.1684. Calcd. for C₂₁H₂₉ClO₅: 396.1704.

19. Compounds 278-8 and 279-8

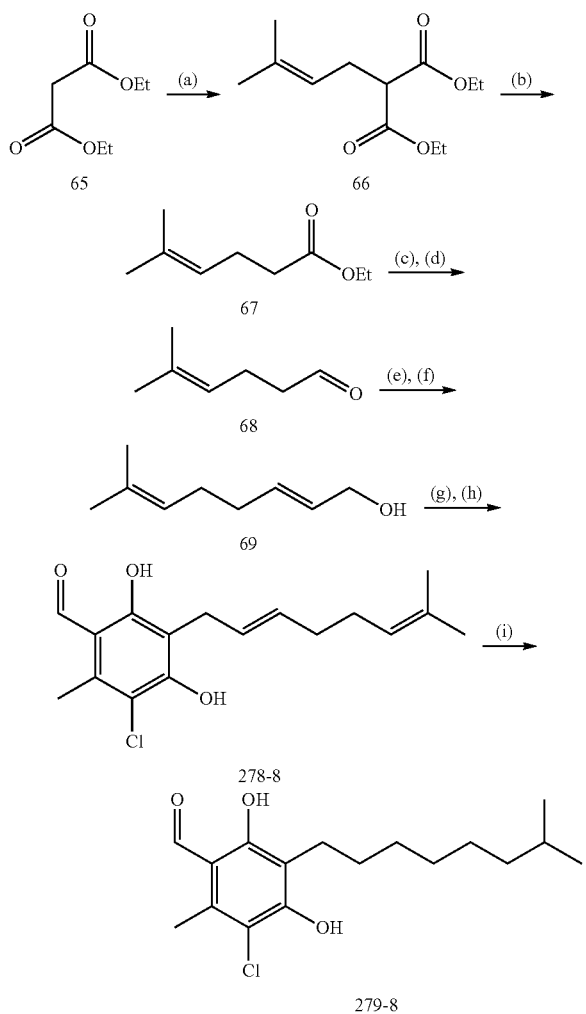

Reagents & conditions:
(a) Prenyl bromide, NaH, toluene
(b) DMSO, NaCl, H₂O
(c) LAH, THF
(d) Swern ox.
(e) (EtO)₂P(O)CH₂CO₂Et, NaH, THF
(f) DIBAL, toluene
(g) CBr₄, (ⁿC₈H₁₇)₃P, Et₂O
(h) 112, KOH, CaCl₂, MeOH,
(i) H₂, Pd—C, EtOAc.

(E)-3-Chloro-4,6-dihydroxy-2-methyl-5-(7-methyl-2,6-octadienyl)-benzaldehyde (compound 278-8)

Diethyl malonate 65 was prenylated in a standard manner (Tetrahedron, 2003, 59, 2991-2998) to give compound 66 (84% yield). Subsequently, a solution of compound 66 (10.00 g, 43.8 mmol) in DMSO (60 ml) was added to a mixture of NaCl (4.10 g, 70.1 mmol) and water (3.5 ml), and then stirred at 150° C. for 18 hours. After cooling to room temperature, the reaction mixture was extracted with ethyl acetate and dried over Na₂SO₄. After concentration under reduced pressure, the resulting crude product was subjected to silica gel column chromatography (hexane:EtOAc=20:1) to give the corresponding monoester 67 (5.69 g, 83% yield).

A solution of this monoester 67 (2.30 g, 14.7 mmol) in THF (30 ml) was added at 0° C. to a suspension of lithium aluminum hydride (528 mg, 12.8 mmol) in THF (30 ml), followed by stirring for 10 minutes. After addition of ice (30 g) and 1 M hydrochloric acid (30 ml), the reaction mixture was extracted with ethyl acetate and dried over Na₂SO₄, followed by concentration under reduced pressure to give an alcohol form (1.39 g, 83% yield). This alcohol form was converted into the corresponding aldehyde 68 through the same oxidation procedure as used in Scheme 18(b) (51% yield).

Aldehyde 68 was converted into alcohol 69 whose carbon chain was extended by two carbons in the same manner as used in Scheme 18(c) and (d) (54% yield for 2 steps).

Alcohol 69 was further converted into the corresponding bromide in the same manner as used in Scheme 13(f) and (g), and then reacted with compound 112 to give the desired product 278-8 (20% yield for 2 steps).

Mp 131-132° C. ¹H-NMR (400 MHz, CDCl₃) δ 12.69 (1H, s, Ar—OH), 10.15 (1H, s, Ar—CHO), 6.37 (1H, s, Ar—OH), 5.55 (2H, m, CH=CH), 5.08 {1H, t, J=1.3 Hz, CH=C(CH₃)₂}, 3.38 (2H, d, J=3.7 Hz, Ar—CH₂), 2.61 (3H, s, Ar—CH₃), 2.01 (4H, br, CH₂CH₂), 1.66 (3H, s, CH₃), 1.57 (3H, s, CH₃). IR (KBr) 3433, 2908, 1624, 1425, 1219, 1111, 781, 529. HRMS (EI) Found: 308.1169. Calcd. for C₁₇H₂₁ClO₃: 308.1179.

3-Chloro-4,6-dihydroxy-2-methyl-5-(7-methyloctyl) benzaldehyde (compound 279-8)

Reduction of the compound 278-8 was accomplished in the same manner as used in Scheme 17(f), i.e., synthesis of 265-8 to give compound 279-8 (97% yield).

Mp 93-94° C. ¹H-NMR (400 MHz, CDCl₃) δ 12.65 (1H, s, Ar—OH), 10.14 (1H, s, Ar—CHO), 6.30 (1H, s, Ar—OH), 2.66 (2H, d, J=7.6 Hz, Ar—CH₂), 2.61 (3H, s, Ar—CH₃), 1.60-1.46 {3H, m, CH(CH₃)₂ & CH₂}, 1.40-1.23 {6H, m, (CH₂)₃}, 1.18-1.11 (2H, m, CH₂), 0.85 {6H, d, J=6.8 Hz, CH(CH₃)₂}. IR (KBr) 3260, 2916, 2847, 1607, 1470, 1421, 1248, 1132, 871, 762, 710, 596, 529 cm⁻¹. HRMS (EI) Found: 312.1484. Calcd. for C₁₇H₂₅ClO₃: 312.1492.

20. Compounds 278-12-OPiv and 279-12-Opiv

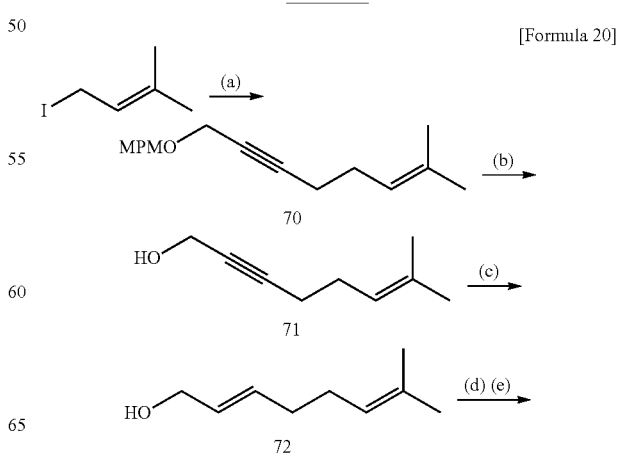

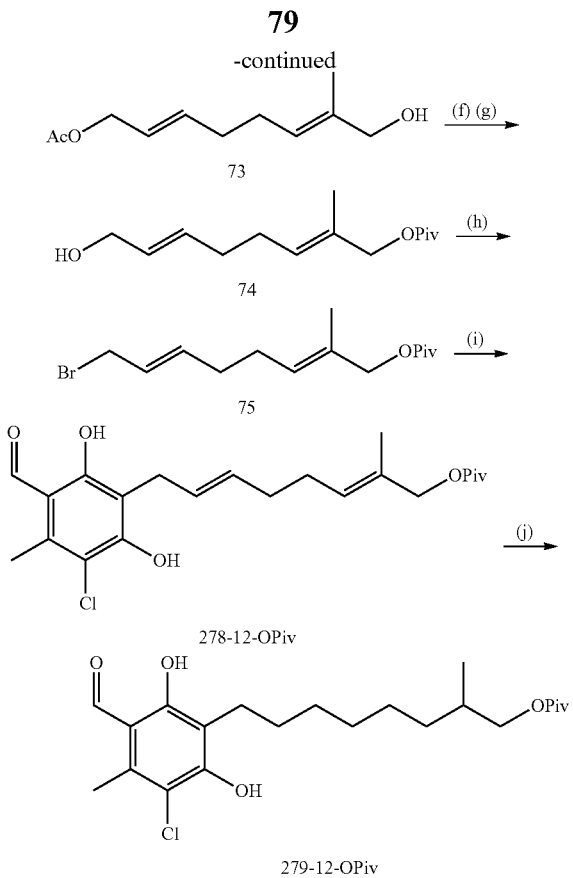

(a) MPM—OCH₂CCH, BuLi, THF/DMPU;
(b) DDQ, CHCl₃/H₂O;
(c) RedAl, THF;
(d) Ac₂O, Et₃N, DMAP;
(e) SeO₂, TBHP, 4-hydroxybenzoic acid, CHCl₃;
(f) pivaloyl chloride, pyridine, DMAP, CHCl₃;
(g) HN=C(NH₂)₂ HCl, NaOMe, MeOH/CHCl₃;
(h) CBr₄, (octyl)₃P, Et₂O;
(i) 112, KOH/CaCl₂, MeOH;
(j) H₂, Pd/C, EtOAc.

(2E,6E)-8-(3-Chloro-5-formyl-2,6-dihydroxy-4-methylphenyl)-2-methyl-2,6-octadienyl pivalate (compound 278-12-OPiv)

A solution of prenyl iodide (obtained from cyclohexyl methyl ketone as described in literature (Synthesis, 1979, 37-38.), 220 mg, 1.05 mmol) in DMPU (1.5 ml) was added at −20° C. to a reaction mixture containing a solution of 3-(4-methoxybenzyloxy)-1-propyne (282 mg, 1.50 mmol) in THF (1 ml) and a solution of butyllithium in hexane (2.00 mmol, 1.2 ml), which had been mixed at −20° C. and stirred for 2 hours. This mixture was warmed to room temperature while stirring for 12 hours. The mixture was extracted with ethyl acetate, worked up and then purified by silica gel column chromatography (hexane:EtOAc=25:1) to give MPM ether product 70 (203 mg, 40% yield). This product was converted into 71 by being treated with 2,3-dichloro-5,6-dicyanobenzoquinone in a standard manner (*J. Am. Chem. Soc.*, 2002, 13670-13671) to remove the protecting group for alcohol, followed by reduction with Red-Al (*Org. Lett.*, 2004, 1785-1787) to give (E)-7-methylocta-2,6-dien-1-ol (72) (88% yield for 2 steps).

To a solution of alcohol 72 (855 mg, 6.10 mmol) in chloroform (20 ml), triethylamine (1.86 g, 18.3 mmol), acetic anhydride (1.57 g, 15.2 mmol) and dimethylaminopyridine (80 mg, 0.61 mmol) were added and stirred at room temperature for 16 hours. The reaction mixture was worked up by extraction and then purified by silica gel column chromatography (hexane:EtOAc=9:1) to give an ester in which the hydroxyl group was acetylated (1082 mg, 97% yield). The resulting ester was oxidized by the selenium dioxide-catalyzed method (*Tetrahedron Lett.*, 2001, 42, 2205-2208) to give compound 73 (44% yield).

Then, compound 73 was converted into a diester (91% yield) in the same manner as used for synthesis in Scheme 15(c). Among the two ester linkages, the acetic acid ester was hydrolyzed in the same manner as used for synthesis in Scheme 15(d) to give the desired monoester 74 (86% yield).

This monoester 74 was converted into bromide 75 in the same manner as used for synthesis in Scheme 15(e), and then reacted with aromatic ring moiety 112 in the same manner as used for synthesis in Scheme 15(f) to give compound 278-12-OPiv (25% yield for 2 steps).

Mp 90-91° C. ¹H-NMR (400 MHz, CDCl₃) δ 12.69 (1H, s, Ar—OH), 10.15 (1H, s, Ar—CHO), 6.44 (1H, s, Ar—OH), 5.55-5.51 (2H, m, CH=CH), 5.40 (1H, m, CH=C(CH₃)CH₂OPiv), 4.42 (2H, s, CH₂OPiv), 3.37 (2H, d, J=4.8 Hz, Ar—CH₂), 2.61 (3H, s, Ar—CH₃), 2.09-2.04 (4H, m, CH₂CH₂), 1.60 (3H, s, CH₃), 1.21 (9H, s, C(CH₃)₃). IR (KBr) 3293, 2972, 1724, 1622, 1622, 1425, 1283, 1227, 1167, 1117, 976, 893, 781, 592 cm⁻¹.

8-(3-Chloro-5-formyl-2,6-dihydroxy-4-methylphenyl)-2-methyloctyl pivalate (compound 279-12-OPiv)

In the same manner as used for synthesis in Scheme 15(g), the compound 278-12-OPiv was reduced to give compound 279-12-OPiv (84% yield).

¹H-NMR (400 MHz, CDCl₃) δ 12.66 (1H, s, Ar—OH), 10.14 (1H, s, Ar—CHO), 6.36 (1H, br, Ar—OH), 3.94 (1H, dd, J=5.8, 10.6 Hz, CH₂OPiv) 3.82 (1H, dd, J=6.6, 10.6 Hz, CH₂OPiv) 2.66 (2H, t, J=7.9 Hz, Ar—CH₂), 2.61 (3H, s, Ar—CH₃), 1.82-1.72 (1H, m, CH), 1.60-1.49 (4H, m, 2×CH₂), 1.40-1.28 {6H, br, (CH₂)₃}, 1.20 {9H, s, C(CH₃)₃}, 0.91 (3H, d, J=6.6 Hz, CH₃). IR (KBr) 3393, 2961, 2930, 2857, 1724, 1717, 1630, 1460, 1422, 1375, 1288, 1248, 1165, 1128, 1034, 982, 806, 772, 710, 590 cm⁻¹. HRMS (EI) calcd. for C₂₂H₃₃ClO₅ (m/z) 412.2017. found 412.2025.

21. Compounds 287-12-OPiv and 287-12-OCOⁱPr

Scheme 21

[Formula 21]

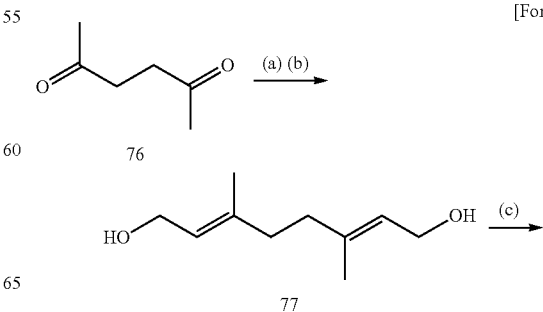

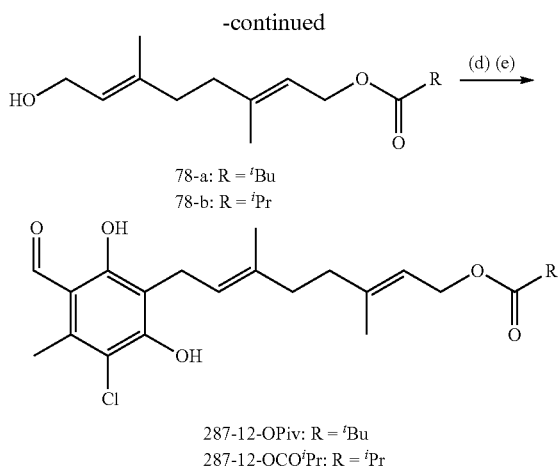

78-a: R = $^t$Bu
78-b: R = $^i$Pr 287-12-OPiv: R = $^t$Bu
287-12-OCO$^i$Pr: R = $^i$Pr

Reagents & conditions:
(a) (EtO)$_2$P(O)CH$_2$CO$_2$Et, NaH, THF
(b) DIBAL, toluene
(c) corresponding acylchloride, Et$_3$N, DMAP, CHCl$_3$
(d) CBr$_4$, ($^n$C$_6$H$_{17}$)$_3$P, Et$_2$O
(e) 112, KOH, CaCl$_2$, MeOH.

(2E,6E)-8-(3-Chloro-5-formyl-2,6-dihydroxy-4-methylphenyl)-3,6-dimethyl-2,6-octadienyl pivalate (compound 287-12-OPiv)

To a suspension of NaH (60% in oil, 0.820 g, 20.5 mmol) in THF (30 ml), triethyl phosphonoacetate (3.6 ml, 18 mmol) was added at 0° C. and stirred for 30 minutes while returning to room temperature. The reaction mixture was cooled again to 0° C., and acetonylacetone (compound 76, 1.0 ml, 8.2 mmol) was added dropwise thereto and stirred for 15 hours while returning to room temperature. The reaction was quenched by addition of H$_2$O, followed stirring for 5 minutes. The organic layer was then separated and collected, and the aqueous layer was extracted twice with EtOAc. The combined organic layers were washed with sat. aq. NaCl and dried over Na$_2$SO$_4$. After the solvent was distilled off, the residue was subjected to silica gel column chromatography (hexane:EtOAc=10:1) to fractionate the corresponding diester into an (E,E)-isomer, an (E,Z)-isomer, a (Z,Z)-isomer and a mixture thereof.

(E,E)-isomer; 0.513 g (25% yield). $^1$H NMR (400 MHz, CDCl$_3$) δ 5.67 (2H, s, 2×C=C$\underline{H}$CO$_2$Et), 4.15 (4H, q, J=7.1 Hz, 2×CO$_2$C$\underline{H}_2$CH$_3$), 2.31 (4H, s, C$\underline{H}_2$C$\underline{H}_2$), 2.17 (6H, s, 2×CH=CC$\underline{H}_3$), 1.28 (6H, t, J=7.1 Hz, ×CO$_2$C$\underline{H}_2$CH$_3$).

To a solution of this diester (0.513 g, 2.017 mmol) in toluene (20 ml), DIBAL (1.0 M in hexane, 12 ml, 12 mmol) was added dropwise at −70° C. and stirred at the same temperature for 3 hours. To the reaction mixture, H$_2$O was added slowly and then 2 M aq. HCl was further added, followed by stirring for 10 minutes while returning to room temperature. After the organic layer was separated and collected, the aqueous layer was extracted twice with EtOAc. The combined organic layers were washed with sat. aq. NaHCO$_3$ and sat. aq. NaCl, and then dried over Na$_2$SO$_4$. After the solvent was distilled off, the precipitated crude crystals were recrystallized from toluene to give a diol (compound 77) (0.320 g, 93%).

To a solution of compound 77 (0.320 g, 1.88 mol) in CHCl$_3$ (20 ml), Et$_3$N (0.26 ml, 1.9 mmol), DMAP (cat. amount) and Piv-Cl (0.14 ml, 1.1 mmol) were added at 0° C. and stirred for 12 hours while returning to room temperature. The reaction mixture was diluted with sat. aq. NaCl to separate and collect the organic layer, and the aqueous layer was then extracted twice with EtOAc. The combined organic layers were dried over Na$_2$SO$_4$. After the solvent was distilled off, the residue was purified by silica gel column chromatography (hexane:EtOAc=2:1) to give the corresponding pivalate (compound 78-a) (0.163 g, 58%). It should be noted that the unreacted starting material was collected.

$^1$H NMR (400 MHz, CDCl$_3$) δ 5.41 (1H, t, J=7.0 Hz, C=C$\underline{H}$CH$_2$OPiv), 5.30 (1H, t, J=7.0 Hz, C=C$\underline{H}$CH$_2$OH), 4.56 (2H, d, J=7.0 Hz, C$\underline{H}_2$OPiv), 4.14 (2H, d, J=7.0 Hz, C$\underline{H}_2$OH), 2.15 (4H, s, C$\underline{H}_2$CH$_2$), 1.71 (3H, s, C$\underline{H}_3$), 1.67 (3H, s, C$\underline{H}_3$), 1.23 (1H, s, O$\underline{H}$), 1.19 {9H, s, C(C$\underline{H}_3$)$_3$}.

To compound 78-a (0.184 g, 0.723 mmol) in Et$_2$O (15 ml), ($^n$C$_8$H$_{17}$)$_3$P (1.1 ml, 2.5 mmol) and CBr$_4$ (0.853 g, 2.57 mmol) were added at 0° C. and stirred for 2 hours. The reaction mixture was poured into sat. aq. NaCl to separate and collect the organic layer, and the aqueous layer was then extracted with EtOAc. The combined organic layers were dried over Na$_2$SO$_4$. After the solvent was distilled off, the residue was subjected to silica gel column chromatography (hexane:EtOAc=7:1) to give the corresponding bromide. The resulting product was used for the subsequent reaction without further purification.

Namely, to a solution of compound 112 (0.413 g, 2.213 mmol) in KOH (1.0 M in MeOH, 3.3 ml, 3.3 mmol), CaCl$_2$·2H$_2$O (0.251 g, 1.71 mmol) and a solution of the above crude bromide (whole) in MeOH (4 ml) were added at 0° C. and stirred for 14 hours while returning to room temperature. The reaction mixture was diluted with EtOAc and filtered through celite. The filtrate was then poured into 0.1 M aq. KOH. After the organic layer was separated and collected, the aqueous layer was extracted twice with EtOAc, and the combined organic layers were washed with sat. aq. NaCl and dried over Na$_2$SO$_4$. After the solvent was distilled off, the residue was purified by silica gel column chromatography (hexane:EtOAc=4:1) and further recrystallized from hexane to give the desired product 287-12-OPiv (65 mg, 21% for 2 steps from compound 78-a).

Mp 78-79° C. $^1$H-NMR (400 MHz, CDCl$_3$) δ 12.69 (1H, s, Ar—O$\underline{H}$), 10.14 (1H, s, Ar—C$\underline{H}$O), 6.48 (1H, s, Ar—O$\underline{H}$), 5.28 (1H, t, J=7.0 Hz, C=C$\underline{H}$CH$_2$OPiv), 5.22 (1H, t, J=7.1 Hz, ArCH$_2$C$\underline{H}$=C), 4.52 (2H, d, J=7.0 Hz, C=CHC$\underline{H}_2$OPiv), 3.39 (2H, d, J=7.0 Hz, ArC$\underline{H}_2$CH=C), 2.61 (3H, s, Ar—C$\underline{H}_3$), 2.10 (4H, br, C$\underline{H}_2$C$\underline{H}_2$), 1.78 (3H, s, C$\underline{H}_3$), 1.66 (3H, s, C$\underline{H}_3$), 1.19 {9H, s, C(C$\underline{H}_3$)$_3$}. IR (KBr) 3356, 2970, 2932, 1728, 1620, 1526, 1479, 1460, 1424, 1373, 1281, 1231, 1207, 1153, 1113, 1033, 964, 903, 868, 789, 594, 581 cm$^{-1}$.

It should be noted that the aqueous layer was acidified with 2 M aq. HCl and then extracted with EtOAc to thereby collect the unreacted compound 112.

(2E,6E)-8-(3-Chloro-5-formyl-2,6-dihydroxy-4-methylphenyl)-3,6-dimethyl-2,6-octa dienyl isobutylate (compound 287-12-OCO$^i$Pr)

Mp 62-63° C. $^1$H-NMR (400 MHz, CDCl$_3$) δ 12.69 (1H, s, Ar—O$\underline{H}$), 10.14 (1H, s, Ar—C$\underline{H}$O), 6.48 (1H, s, Ar—O$\underline{H}$), 5.28 (1H, t, J=6.8 Hz, C=C$\underline{H}$CH$_2$O), 5.22 (1H, t, J=7.3 Hz, ArCH$_2$C$\underline{H}$=C), 4.53 (2H, d, J=6.8 Hz, C=CHC$\underline{H}_2$O), 3.39 (2H, d, J=7.3 Hz, ArC$\underline{H}_2$CH=C), 2.61 (3H, s, Ar—C$\underline{H}_3$), 2.57-2.50 {1H, m, C$\underline{H}$(CH$_3$)$_2$}, 2.10 (4H, br, C$\underline{H}_2$C$\underline{H}_2$), 1.78 (3H, s, C$\underline{H}_3$), 1.66 (3H, s, C$\underline{H}_3$), 1.16 {6H, d, J=7.3 Hz, CH(C$\underline{H}_3$)$_2$}. IR (KBr) 3273, 2974, 2934, 1732, 1620, 1526, 1470, 1452, 1425, 1376, 1283, 1256, 1231, 1209, 1153, 1109, 1065, 961, 889, 791, 716, 629, 586 cm$^{-1}$.

22. Compounds 284-8 and 285-8

23. Compounds 288-12-Piv and 215-12-Piv

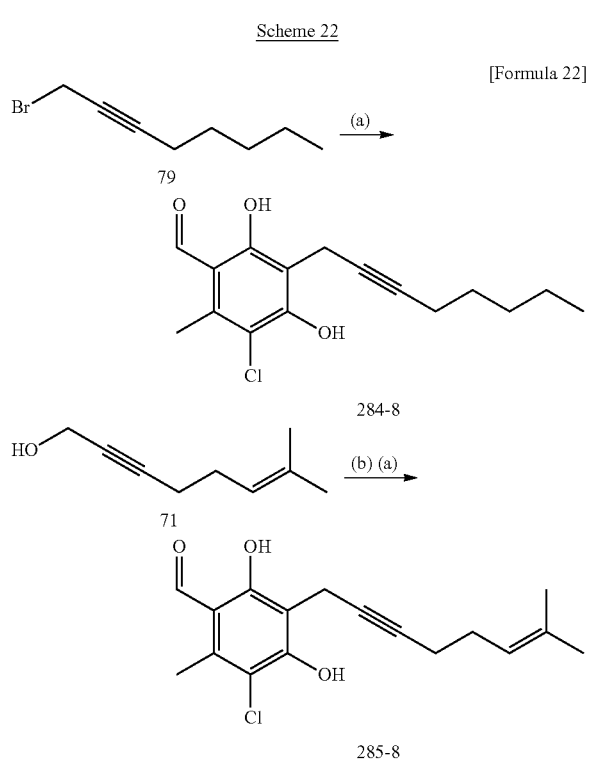

Scheme 22 [Formula 22]

284-8

285-8

(a) 112, KOH, MgCl$_2$, MeOH;
(b) CBr$_4$, (octyl)$_3$P, Et$_2$O.

3-Chloro-4,6-dihydroxy-5-(2-octynyl)-2-methylbenzaldehyde (compound 284-8)

Aromatic ring moiety 112 and commercially available 1-bromo-2-octyne (compound 79) were used as starting materials and reacted by the same operation as used for synthesis in Scheme 15(f) using magnesium chloride as an additive to give the desired product 284-8 (21% yield).

Mp 135-136° C. $^1$H-NMR (400 MHz, CDCl$_3$) δ 12.81 (1H, s, Ar—OH), 10.15 (1H, s, Ar—CHO), 7.03 (1H, s, Ar—OH), 3.59 (2H, d, J=2.6 Hz, Ar—CH$_2$), 2.62 (3H, s, Ar—CH$_3$), 2.16-2.13 (2H, m, CCCH$_2$), 1.49 (2H, m, CH$_2$), 1.35-1.25 (4H, m, CH$_2$CH$_2$), 0.88 (3H, t, J=7.0 Hz, CH$_2$CH$_3$). IR (KBr) 3200, 2963, 2930, 1610, 1460, 1425, 1285, 1227, 1194, 1132, 1119, 887, 759, 713, 637, 584, 536 cm$^{-1}$.

3-Chloro-4,6-dihydroxy-2-methyl-5-(7-methyl-6-octen-2-ynyl)benzaldehyde (compound 285-8)

Alcohol 71 synthesized in Scheme 20 above was used as a starting material for side chain synthesis, and the same operations as used in Scheme 20(h) and (i) were repeated to synthesize the desired product 285-8.

Mp 138° C. $^1$H-NMR (400 MHz; CDCl$_3$) δ 12.81 (1H, s, Ar—OH), 10.15 (1H, s, Ar—CHO), 7.04 (1H, s, Ar—OH), 5.12 {1H, m, CH=C(CH$_3$)$_2$}, 3.59 (2H, s, Ar—CH$_2$), 2.62 (3H, s, Ar—CH$_3$), 2.16 (4H, br, CH$_2$CH$_2$), 1.68 (3H, s, CH$_3$), 1.59 (3H, s, CH$_3$). IR (KBr) 3198, 2967, 2924, 1618, 1452, 1429, 1285, 1229, 1186, 1113, 893, 791, 588, 538 cm$^{-1}$. HRMS (EI) calcd. for C$_{17}$H$_{19}$ClO$_3$ (m/z) 306.1023. found 306.1049.

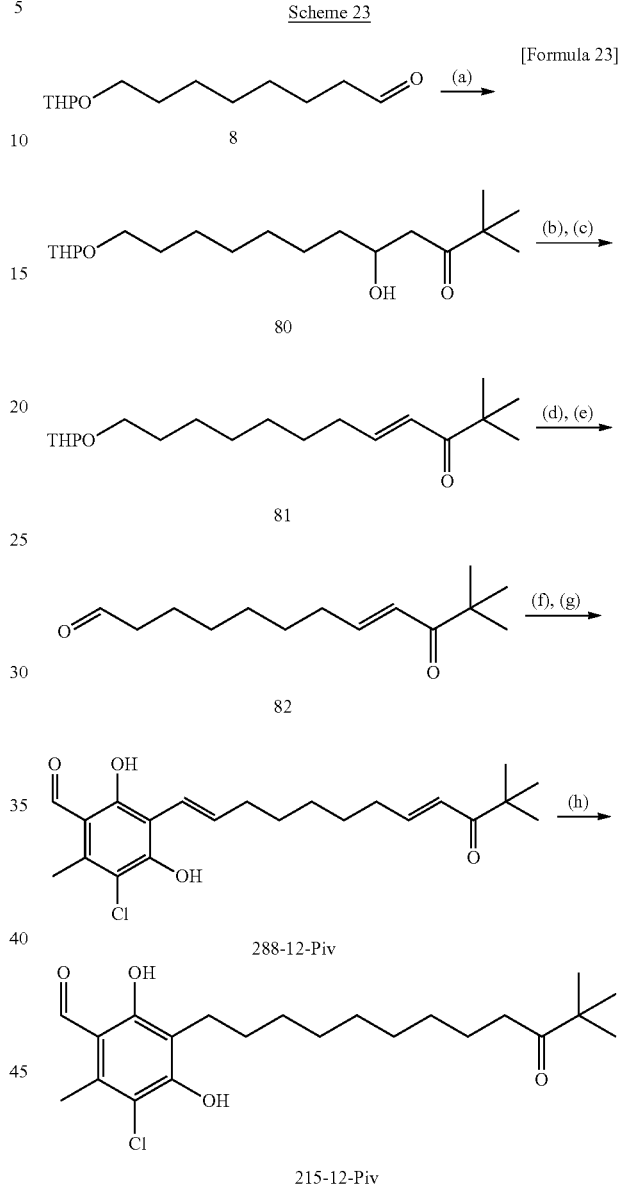

Scheme 23 [Formula 23]

288-12-Piv 215-12-Piv

Reagents & conditions:
(a) pinacolon, LHMDS, THF
(b) Ac$_2$O, DMAP, pyrindine
(c) DBU, CHCl$_3$
(d) PPTS, EtOH
(e) Swernoxidation
(f) 112, KOH, CaCl$_2$ 2H$_2$O, MeOH
(g) H$_3$PO$_4$, AcOH
(h) H$_2$, Pd—C, EtOAc

3-Chloro-4,6-dihydroxy-5-((E,E)-11,11-dimethyl-10-oxo-2,8-dodecadienyl)-2-methylbenzaldehyde (compound 288-12-Piv)

In the manner known from literature (K. Mori and S. Takechi, *Tetrahedron,* 1985, 41, 3049-3062), aldehyde 8 and 3,3-dimethyl-2-butanone were reacted to give adduct 80 (59% yield).

Then, the secondary hydroxyl group was acetylated in the same manner as used in Scheme 20(e) and then treated with DBU to give compound 81 (98% yield for 2 steps).

Then, the primary hydroxyl group was deprotected in the same manner as used in Scheme 2(d), and then the primary hydroxyl group was oxidized in the same manner as used in Scheme 1(d) to give aldehyde 82 (91% yield for 2 steps).

Subsequently, the side chain was introduced into aromatic ring starting material 112 in the same manner as used in Scheme 1(e) and (f) to give the desired product 288-12-Piv (36% yield for 2 steps).

$^1$H-NMR (400 MHz, CDCl$_3$) δ 13.06 (1H, s, Ar—O$\underline{H}$), 10.15 (1H, s, Ar—C$\underline{H}$O), 6.95 (1H, dt, J=15.0, 7.3 Hz), 6.68 (1H, s, Ar—O$\underline{H}$), 6.64 (1H, dt, J=16.1, 6.8 Hz), 6.52 (1H, d, J=16.1 Hz), 6.50 (1H, d, J=15.0 Hz), 2.62 (3H, s, Ar—C$\underline{H}_3$), 2.19-2.30 (4H, m, allylic C$\underline{H}_2$), 1.60-1.35 (6H, m, —(C$\underline{H}_2$)$_3$—), 1.15 (9H, s, C(C$\underline{H}_3$)$_3$).

3-Chloro-4,6-dihydroxy-5-(11,11-dimethyl-10-oxododecyl)-2-methylbenzaldehyde (compound 215-12-Piv)

The compound 288-12-Piv was reduced in the same manner as used in Scheme 1(g) to give the desired product 215-12-Piv (79% yield).

$^1$H-NMR (400 MHz, CDCl$_3$) δ12.65 (1H, s, Ar—O$\underline{H}$), 10.14 (1H, s, Ar—C$\underline{H}$O), 6.40 (1H, br s, Ar—O$\underline{H}$), 2.71-2.57 (6H, m+s (δ2.60)), 2.49-2.35 (1H, m), 1.61-1.20 (14H, —(C$\underline{H}_2$)$_7$—), 1.13 (9H, s, C(C$\underline{H}_3$)$_3$).

24. Compounds 289-12-OPiv and 290-12-Opiv.

Scheme 24

[Formula 24]

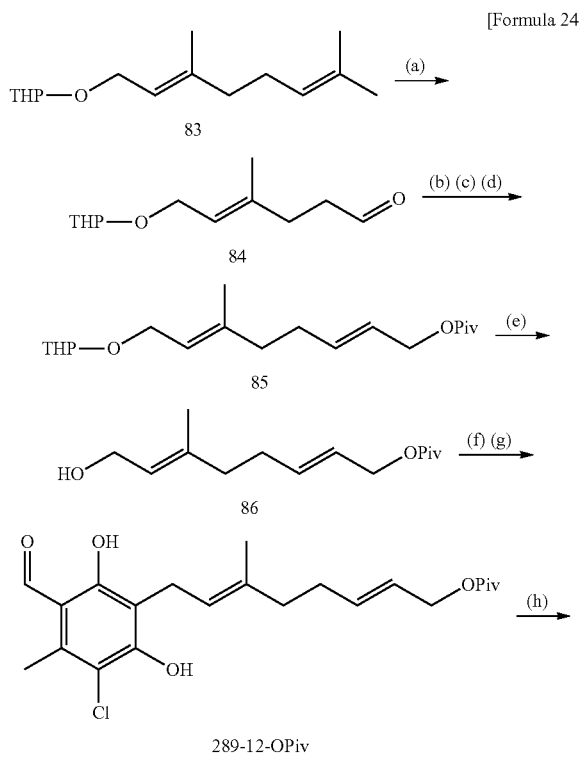

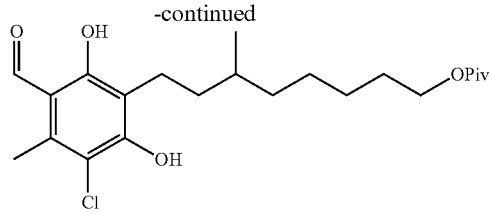

290-12-OPiv (a) O$_3$, Ph$_3$P, CHCl$_3$;
(b) (EtO)$_2$P(O)CH$_2$CO$_2$Et, NaH, THF;
(c) DIBAL, toluene;
(d) Pivaloyl chloride, pyridine, CHCl$_3$;
(e) PPTS, EtOH;
(f) CBr$_4$, (octyl)$_3$P, Et$_2$O;
(g) 112, KOH/CaCl$_2$, MeOH;
(h) H$_2$, Pd/C, EtOAc.

(2E,6E)-8-(3-Chloro-5-formyl-2,6-dihydroxy-4-methylphenyl)-6-methyl-2,6-octadienyl pivalate (compound 289-12-OPiv)

THP ether 83 known from literature (*Tetrahedron Lett.*, 2001, 42, 2205-2208) (5.56 g, 21.2 mmol) was dissolved in CH$_2$Cl$_2$ (115 ml), and pyridine (5.1 ml, 63.6 mmol) was added thereto and cooled to −80° C. This solution was vigorously stirred with ozone bubbling for 5 hours. After the reactor was purged with argon, Ph$_3$P (16.603 g, 63.6 mmol, 3.0 eq.) was added thereto and stirred for 12 hours while returning to room temperature. The residue obtained upon work-up was purified by silica gel column chromatography (hexane:EtOAc=10:1) to give aldehyde 84 (1.96 g, 44% yield).

This aldehyde 84 was converted into pivalic acid ester 85 by procedures (b) and (c) (the same procedures as used for synthesis in Scheme 18(c) and (d) above) and the subsequent procedure (d) (the same procedure as used for synthesis in Scheme 15(c) above) (87% yield for 3 steps).

Then, pivalic acid ester 85 was deprotected by procedure (e) (the same procedure as used for synthesis in Scheme 2(d) above) to give alcohol 86 (95% yield). Alcohol 86 was converted into the desired product 289-12-OPiv by procedures (f) and (g) (the same procedures as used for synthesis in Scheme 15(e) and (f) above) (25% yield for 2 steps).

$^1$H-NMR (400 MHz, CDCl$_3$) δ 12.70 (1H, s, Ar—O$\underline{H}$), 10.14 (1H, s, Ar—C$\underline{H}$O), 6.46 (1H, s, Ar—O$\underline{H}$), 5.69 (1H, dt, J=6.0, 15.4 Hz, C$\underline{H}$=C), 5.22 (1H, dt, J=5.8, 15.4 Hz, C$\underline{H}$=C), 5.22 (1H, t, J=7.0 Hz, ArCH$_2$C$\underline{H}$=C), 4.46 (2H, d, J=5.9 Hz, C$\underline{H}_2$OPiv), 3.39 (2H, d, J=7.3 Hz, Ar—C$\underline{H}_2$), 2.61 (3H, s, Ar—C$\underline{H}_3$), 2.18-2.12 (2H, m, C$\underline{H}_2$), 2.07-2.03 (2H, m, C$\underline{H}_2$), 1.78 (3H, s, C$\underline{H}_3$), 1.56 (3H, s, C$\underline{H}_3$), 1.19 {9H, s, C(C$\underline{H}_3$)$_3$}. IR (KBr) 3273, 2974, 2932, 1728, 1618, 1479, 1452, 1424, 1281, 1229, 1159, 1107, 963, 905, 783, 714, 592, 538 cm$^{-1}$.

8-(3-Chloro-5-formyl-2,6-dihydroxy-4-methylphenyl)-6-methyloctyl pivalate (compound 290-12-OPiv)

289-12-OPiv was reduced by procedure (h) (the same procedure as used for synthesis in Scheme 15(g) above) to give the desired product 290-12-OPiv (63% yield).

$^1$H-NMR (400 MHz, CDCl$_3$) δ 12.65 (1H, s, Ar—O$\underline{H}$), 10.14 (1H, s, Ar—C$\underline{H}$O), 6.38 (1H, s, Ar—O$\underline{H}$), 4.05 (2H, t, J=6.6 Hz, C$\underline{H}_2$OPiv), 2.67-2.63 (2H, m, Ar—C$\underline{H}_2$), 2.61 (3H, s, Ar—C$\underline{H}_3$), 1.64-1.61 (2H, m, C$\underline{H}_2$), 1.55-1.30 (7H, m, C<u>H</u>CH₃ & C<u>H</u>₂CH₂), 1.23-1.17 (2H, m, C<u>H</u>₂), 1.19 {9H, s, C(C<u>H</u>₃)₃}, 0.95 {3H, d, J=6.6 Hz, CH(C<u>H</u>₃)CH₂}. IR (KBr) 3380, 2932, 2868, 1717, 1630, 1460, 142, 1375, 1327, 1290, 1248, 1163, 1126, 802, 709, 629, 592 cm⁻¹. HRMS (EI) calcd. for $C_{22}H_{33}ClO_5$ (m/z) 412.2017. found 412.2041.

25. Compound 231-9-OMe

Scheme 25

[Formula 25]

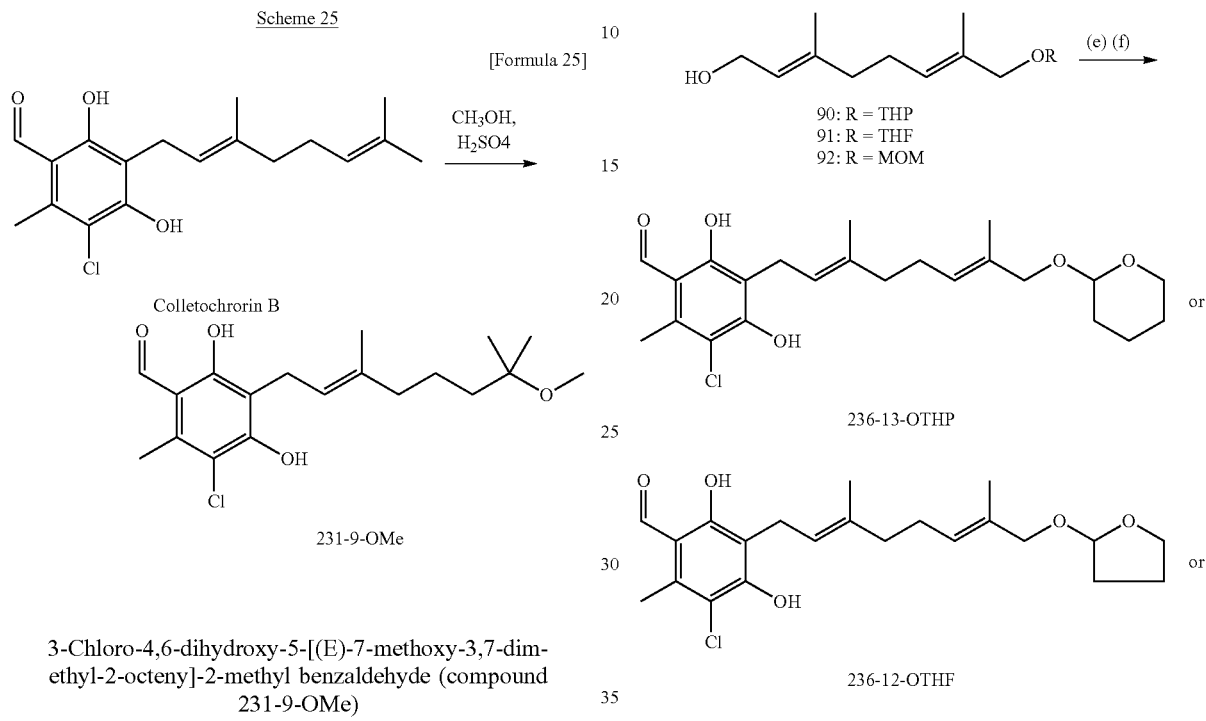

231-9-OMe

3-Chloro-4,6-dihydroxy-5-[(E)-7-methoxy-3,7-dimethyl-2-octeny]-2-methyl benzaldehyde (compound 231-9-OMe)

To a solution of 216 synthesized in Scheme 6 above (Colletochlorin B, 74 mg, 0.23 mmol) in methanol (5 ml), concentrated sulfuric acid (23 mg, 0.23 mmol) was added. After stirring at 30° C. for 15 hours, the reaction mixture was neutralized with saturated aqueous sodium bicarbonate, extracted with ethyl acetate and then worked up to give a crude product (109 mg), which was then purified by preparative TLC (hexane:EtOAc=3/1) to give the desired product 231-9-OMe (39 mg, 48% yield).

¹H-NMR (400 MHz, CDCl₃) δ 1.11 (s, 6H, C(OCH₃)(C<u>H</u>₃)₂) 1.34-1.43 (m, 4H, —CH=C(CH₃)CH₂C<u>H</u>₂C<u>H</u>₂—), 1.78 (s, 3H, —CH=C(C<u>H</u>₃)—), 1.91-2.00 (m, 2H, —CH=C(CH₃)C<u>H</u>₂—), 2.60 (s, 3H, Ar—C<u>H</u>₃), 3.14 (s, 3H, C(OC<u>H</u>₃)(CH₃)₂), 3.40 (d, J=7.0 Hz, 2H, Ar—C<u>H</u>₂CH=C(CH₃)—), 5.22 (t, J=7.0 Hz, 1H, ArCH₂C<u>H</u>=C(CH₃)—), 6.39 (br s, 1H, Ar—O<u>H</u>), 10.14 (s, 1H, Ar—C<u>H</u>O), 12.69 (s, 1H, Ar—O<u>H</u>).

26. Compounds 236-13-OTHP, 236-9-OH, 236-12-OTHF 236-12-OMOM, 274-9 and 281-12

Scheme 26

[Formula 26]

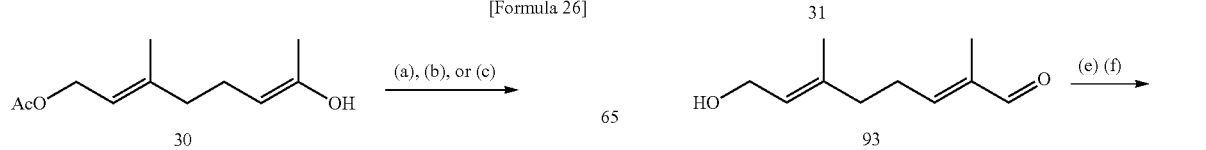

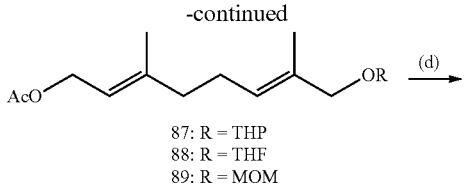

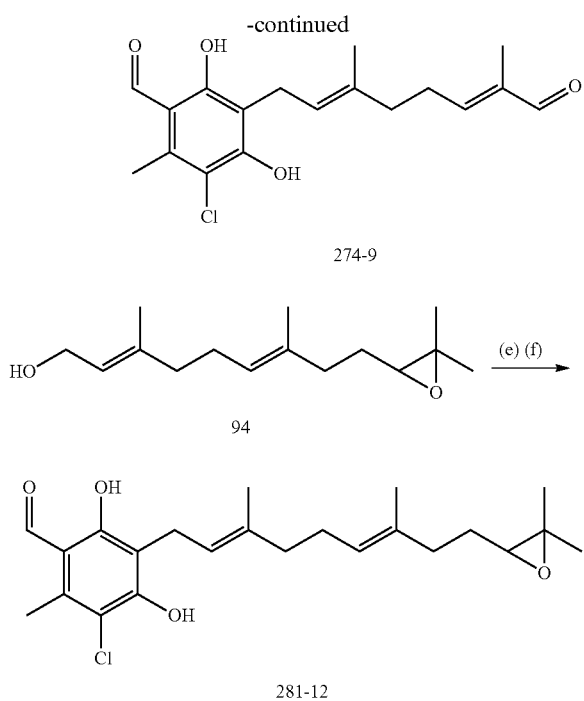

(a) DMP, PPTS, CHCl₃;
(b) DHF, PPTS, CHCl₃;
(c) MOM—Cl, (i-Pr)₂NEt;
(d) K₂CO₃, MeOH, H₂O;
(e) CBr₄, (octyl)₃P, Et₂O;
(f) 112, KOH/CaCl₂, MeOH;
(g) PPTS, MeOH.

3-Chloro-5-(2E,6E)-3,7-dimethyl-8-(tetrahydropyran-2-yloxy)-2,6-octadienyl-4,6-dihydroxy-2-methylbenzaldehyde (compound 236-13-OTHP)

By standard procedure (a) (the same procedure as used in Scheme 2(a) above), alcohol 30 known from literature (*J. Braz. Chem. Soc.* 2003, 14, 975-981) was converted into compound 87 whose alcohol moiety was protected (96% yield). To a solution of this compound 87 (1.32 g, 4.46 mmol) in MeOH (8 ml), H₂O (10 ml) and K₂CO₃ (1.24 g, 8.92 mmol) were added and stirred for 16 hours. The crude product obtained upon work-up by ether extraction was purified by column chromatography (n-hexane/EtOAc=1/1) to give alcohol 90 (664 mg, 60% yield).

Alcohol 90 was converted into the desired product 236-13-OTHP by procedures (e) and (f) (the same procedures as used for synthesis in Scheme 15(e) and (f) above) (30% yield for 2 steps).

Mp 44-45° C. H-NMR (400 MHz, CDCl₃) δ 12.70 (1H, s, Ar—O$\underline{H}$), 10.14 (1H, s, Ar—C$\underline{H}$O), 6.66 (1H, s, Ar—O$\underline{H}$), 5.37 (1H, t, J=6.8 Hz, CH₂C$\underline{H}$=C), 5.22 (1H, t, J=7.1 Hz, CH₂C$\underline{H}$=C), 4.61 (1H, t, J=3.5 Hz, THP(2)-$\underline{H}$), 4.05 (1H, d, J=11.9 Hz, C(CH₃)C$\underline{H}$₂O), 3.83-3.90 (1H, m, THP(6)-$\underline{H}$), 3.83 (1H, d, J=11.9 Hz, C(CH₃)C$\underline{H}$₂O), 3.48-3.54 (1H, m, THP(6)-$\underline{H}$), 3.37-3.41 (2H, m, Ar—C$\underline{H}$₂), 2.61 (3H, s, Ar—C$\underline{H}$₃), 2.0-2.2 (4H, m, C(CH₃)C$\underline{H}$₂C$\underline{H}$₂CH=C), 1.6-1.9 (12H, m+s (δ1.77, C$\underline{H}$₃)+s (δ1.62, C$\underline{H}$₃), THP(3,4,5)-$\underline{H}$₂). IR (KBr) 3200-3500, 1613, 1424, 1281, 1250, 1233, 1111 cm⁻¹. Calcd for C₂₃H₃₁ClO₅: C, 65.32; H, 7.39; Cl, 8.38%. Found: C, 65.18; H, 7.36; Cl, 8.41%.

3-Chloro-4,6-dihydroxy-5-(2E,6E)-8-hydroxy-3,7-dimethyl-2,6-octadienyl-2-methylbenzaldehyde (compound 236-9-OH)

The compound 236-13-OTHP obtained above was treated to remove THP by procedure (g) (the same procedure as used in Scheme 2(d) above) to give the desired product 236-9-OH (90% yield).

Mp 99.0-99.7° C. H-NMR (400 MHz, CDCl₃) δ 12.72 (1H, s, Ar—O$\underline{H}$), 10.14 (1H, s, Ar—C$\underline{H}$O), 5.34 (1H, t, J=6.6 Hz, CH₂C$\underline{H}$=C), 5.22 (1H, t, J=6.9 Hz, CH₂C$\underline{H}$=C), 3.97 (2H, d, J=6.9 Hz, Ar—C$\underline{H}$₂), 2.61 (3H, s, Ar—C$\underline{H}$₃), 2.0-2.2 (4H, m, C(CH₃)C$\underline{H}$₂C$\underline{H}$₂CH=C), 1.78 (3H, s, C$\underline{H}$₃), 1.64 (3H, s, C$\underline{H}$₃). HRMS (DART) calcd for C₁₈H₂₂ClO₃ (M-OH) 321.1257. found 321.1235.

3-Chloro-5-(2E,6E)-3,7-dimethyl-8-(tetrahydrofuran-2-yloxy)-2,6-octadienyl-4,6-dihydroxy-2-methylbenzaldehyde (compound 236-12-OTHF)

The above alcohol 30 was treated by standard procedure (b) (the same procedure as used in Scheme 2(a) above, except that dihydropyran (DHP) was replaced with dihydrofuran (DHF)) to modify the alcohol moiety with THF to thereby give compound 88 (97% yield). Subsequently, the above procedure (d) was repeated to convert this compound into similar alcohol 91 (60% yield). Then, the procedures (e) and (f) (the same procedures as used for synthesis in Scheme 15(e) and (f) above) were repeated to give the desired product 236-12-OTHF (13% yield for 2 steps).

Mp 35-36° C. ¹H-NMR (400 MHz, CDCl₃) δ 12.70 (1H, s, Ar—O$\underline{H}$), 10.14 (1H, s, Ar—C$\underline{H}$O), 6.71 (1H, s, Ar—O$\underline{H}$), 5.36 (1H, t, J=7.0 Hz, CH₂C$\underline{H}$=C), 5.22 (1H, t, J=7.0 Hz, CH₂C$\underline{H}$=C), 5.11 (1H, dd, J=2.6, 4.0 Hz, THF(2)-$\underline{H}$), 3.98 (1H, d, J=11.7 Hz, C(CH₃)C$\underline{H}$₂O), 3.85-3.94 (2H, m, THF(5)-$\underline{H}$₂), 3.81 (1H, d, J=11.7 Hz, C(CH₃)C$\underline{H}$₂O), 3.34-3.44 (2H, m, Ar—C$\underline{H}$₂), 2.61 (3H, s, Ar—C$\underline{H}$₃), 1.8-2.2 (8H, m, C(CH₃)C$\underline{H}$₂C$\underline{H}$₂CH=C and THF(3,4)-$\underline{H}$₂), 1.77 (s, C$\underline{H}$₃), 1.60 (s, C$\underline{H}$₃). IR (KBr) 3150-3350, 1613, 1422, 1283, 1250, 1234, 1109, 1024 cm⁻¹. HRMS (DART) calcd for C₂₂H₃₀ClO₅(MH⁺) 409.1782. found: 409.1758.

3-Chloro-5-(2E,6E)-3,7-dimethyl-8-(methoxymethoxy)-2,6-octadienyl)-4,6-dihydroxy-2-methylbenzaldehyde (236-12-OMOM)

The above alcohol 30 was methoxymethylated by standard procedure (c) (*J. Am. Chem. Soc.* 1977, 99, 1275-1276) to give compound 89 (71% yield). Subsequently, the above procedure (d) was repeated to convert this compound into alcohol 92 (80% yield). Then, 92 was treated by the procedures (e) and (f) (the same procedures as used for synthesis in Scheme 15(e) and (f) above) to give the desired product 236-12-OMOM (12% yield for 2 steps).

Mp 49-50° C. ¹H-NMR (400 MHz, CDCl₃) δ 12.70 (1H, s, Ar—O$\underline{H}$), 10.14 (1H, s, Ar—C$\underline{H}$O), 6.65 (1H, s, Ar—O$\underline{H}$), 5.37 (1H, t, J=6.4 Hz, CH₂C$\underline{H}$=C), 5.24 (1H, t, J=6.4 Hz, CH₂C$\underline{H}$=C), 4.59 (2H, s, OC$\underline{H}$₂O), 3.89 (2H, s, C(CH₃)C$\underline{H}$₂O), 3.39 (2H, d, J=6.4 Hz, Ar—C$\underline{H}$₂), 3.38 (3H, s, OC$\underline{H}$₃), 2.61 (3H, s, Ar—C$\underline{H}$₃), 2.11-2.17 (2H, m, C(CH₃)C$\underline{H}$₂C$\underline{H}$₂CH=C), 2.01-2.06 (2H, m, C(CH₃)C$\underline{H}$₂C$\underline{H}$₂CH=C), 1.77 (s, C$\underline{H}$₃), 1.63 (s, C$\underline{H}$₃). IR (KBr) 3200-3400, 1631, 1422, 1288, 1254, 1022, 903 cm⁻¹. Calcd for C₂₀H₂₇ClO₅: C, 62.74; H, 7.11; Cl, 9.26%. Found: C, 62.64; H, 7.09; Cl, 9.22%.

3-Chloro-5-[(2E,6E)-3,7-dimethyl-8-oxo-2,6-octadienyl]-4,6-dihydroxy-2-methylbenzaldehyde (compound 274-9)

Aldehyde 31 known from literature (*Tetrahedron* 1974, 30, 715-718) was deacetylated by the above procedure (d) to give compound 93 (90% yield). Then, 93 was treated by the procedures (e) and (f) (the same procedures as used for synthesis in Scheme 15(e) and (f) above) to give the desired product 274-9 (27% yield for 2 steps).

Mp 111.2-111.4° C. $^1$H-NMR (400 MHz, CDCl$_3$) δ 12.70 (1H, s, Ar—O$\underline{H}$), 10.15 (1H, s, Ar—C$\underline{H}$O), 9.31 (1H, s, C(CH$_3$)—C$\underline{H}$O), 6.41 (1H, t, J=7.4 Hz, CH$_2$C$\underline{H}$=C), 6.35 (1H, s, Ar—O$\underline{H}$), 5.26 (1H, t, J=6.8 Hz, CH$_2$C$\underline{H}$=C), 3.40 (2H, d, J=7.4 Hz, Ar—C$\underline{H}_2$), 2.61 (3H, s, Ar—C$\underline{H}_3$), 2.4-2.5 (2H, m, C(CH$_3$)CH$_2$C$\underline{H}_2$CH=C), 2.1-2.2 (2H, m, C(CH$_3$)CH$_2$C$\underline{H}_2$CH=C), 1.81 (3H, s, C$\underline{H}_3$), 1.70 (3H, s, C$\underline{H}_3$). MS (EI) m/z 338 (5, M+2), 336 (13, M$^+$).

3-Chloro-5-(2E,6E)-3,7-dimethyl-9-(3,3-dimethyloxiran-2-yl)-2,6-nonadienyl)-4,6-dihydroxy-2-methylbenzaldehyde (compound 281-12)

Alcohol 94 known from literature (*Org. Lett.* 2006, 8, 5649-5652) was used and treated by the procedures (e) and (f) (the same procedures as used for synthesis in Scheme 15(e) and (f) above) to give the desired product 281-12 (4% yield for 2 steps).

Mp 36-37° C. $^1$H-NMR (400 MHz, CDCl$_3$) δ 12.70 (1H, s, Ar—O$\underline{H}$), 10.14 (1H, s, Ar—C$\underline{H}$O), 6.57 (1H, s, Ar—O$\underline{H}$), 5.21 (1H, t, J=7.1 Hz, CH$_2$C$\underline{H}$=C), 5.11 (1H, t, J=6.2 Hz, CH$_2$C$\underline{H}$=C), 3.39 (2H, d, J=7.1 Hz, Ar—C$\underline{H}_2$), 2.69 (1H, t, J=6.2 Hz, oxiran(2)-$\underline{H}$), 2.61 (3H, s, Ar—C$\underline{H}_3$), 1.96-2.12 (6H, m, C(CH$_3$)C$\underline{H}_2$C$\underline{H}_2$CH=C(CH$_3$)C$\underline{H}_2$), 1.78 (s, C$\underline{H}_3$), 1.56-1.64 (5H, m+s (δ 1.59), nonadienyl(9)-$\underline{H}_2$ and C$\underline{H}_3$), 1.30 (s, C$\underline{H}_3$), 1.25 (s, C$\underline{H}_3$). IR (KBr) 3300-3500, 1614, 1418, 1281, 1250, 1233, 1109 cm$^{-1}$.

27. Compound 509-11

Scheme 27

[Formula 27]

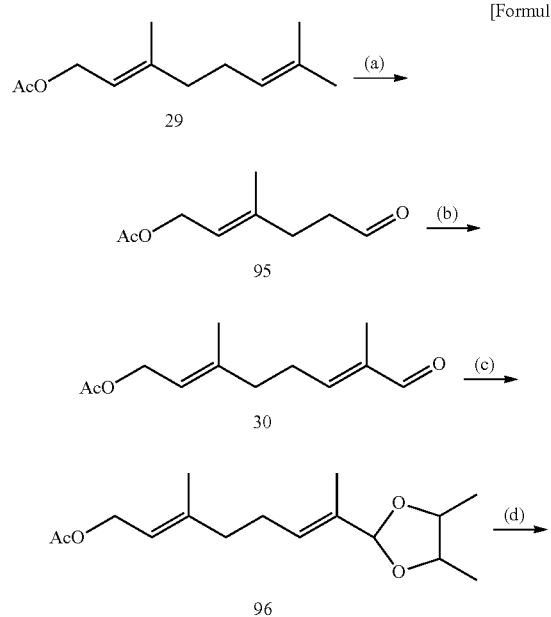

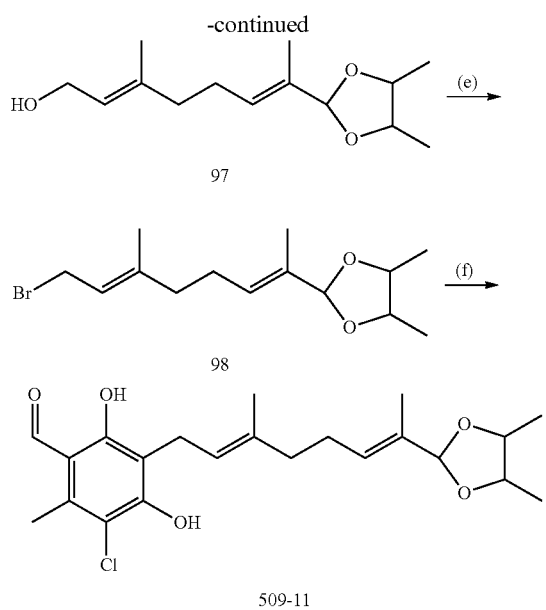

(a) O$_3$, Ph$_3$P, CH$_2$Cl$_2$;
(b) Ph$_2$P=C(CH$_3$)C=O, toluene;
(c) 2,3-dimethylbutane, PPTS;
(d) K$_2$CO$_3$, MeOH, H$_2$O;
(e) n-BuLi, LiBr, p-TsOH;
(f) 112, KOH/CaCl$_2$, MeOH.

3-Chloro-5-((2E,6E)-7-(4,5-dimethyl-1,3-dioxolan-2-yl)-3-methyl-2,6-octadienyl)-4,6-dihydroxy-2-methylbenzaldehyde (compound 509-11)

Aldehyde 95 known from literature (*J. Am. Chem. Soc.* 2005, 127, 7014-7024), which can be obtained from commercially available 29 by procedure (a), was converted into 30 whose carbon chain was extended by procedure (b) (*Org. Lett.* 2007, 9, 1461-1464) (55% yield for 2 steps).

Then, in accordance with standard procedure (c) (also described in *J. Am. Chem. Soc.* 2005, 127, 7014-7024), compound 30 was acetalized with 2,3-butanediol to give compound 96. Subsequently, the resulting compound was deacetylated by procedure (d) (the same procedure as used in Scheme 26(d) above) to give alcohol 97 (56% yield for 2 steps).

Alcohol 97 was converted into bromide 98 by procedure (e) (the procedure described in the above literature with modifications: *Tetrahedron* 1984, 40, 2711-2720) and then treated by procedure (f) (the same procedure as used for synthesis in Scheme 15(f) above) to give the desired product 509-11 (18% yield for 2 steps).

Mp. 91.5-92.3° C. $^1$H-NMR (400 MHz, CDCl$_3$) δ 12.70 (1H, s, Ar—O$\underline{H}$), 10.14 (1H, s, C$\underline{H}$O), 6.67 (1H, s, Ar—O$\underline{H}$), 5.54 (1H, t, J=7.3 Hz, C$\underline{H}$=C), 5.23 (1H, s, dioxolan(2)-$\underline{H}$), 5.19 (1H, t, J=7.2 Hz, C$\underline{H}$=C), 3.51-3.71 (2H, m, dioxolan(4,5)-$\underline{H}$), 3.33-3.44 (2H, m, Ar—C$\underline{H}_2$), 2.60 (3H, s, Ar—C$\underline{H}_3$), 2.14-2.20 (2H, m, C$\underline{H}_2$), 2.01-2.07 (2H, m, C$\underline{H}_2$), 1.76 (3H, s, C$\underline{H}_3$), 1.61 (3H, s, C$\underline{H}_3$), 1.31-1.33 (3H, m, C$\underline{H}_3$), 1.25-1.27 (3H, m, C$\underline{H}_3$). IR (KBr) 3100-3400, 1618, 1424, 1279, 1250, 1231, 1109, 1086, 667 cm$^{-1}$. HRMS (DART) calcd for C$_{22}$H$_{30}$ClO$_5$ (MH$^+$) 409.1782. found 409.1757.

28. Compound 503-12-OPiv

Scheme 28

[Formula 28]

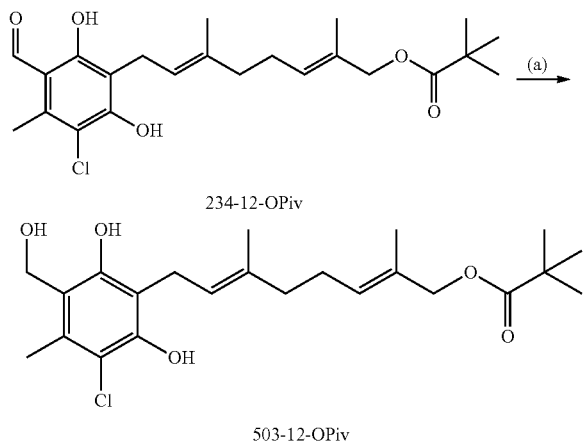

(a) NaBH₄, EtOH.

(2E,6E)-8-(3-Chloro-2,6-dihydroxy-5-hydroxymethyl-4-methylphenyl)-2,6-dimethyl-2,6-octadienyl pivalate (compound 503-12-OPiv)

234-12-OPiv obtained in Scheme 15 above was treated by procedure (a) (the same procedure as used for synthesis in Scheme 15(b) above) to give the desired product 503-12-OPiv (40% yield).

$^1$H-NMR (400 MHz, CDCl$_3$) δ 7.54 (1H, s, Ar—O$\underline{H}$), 5.72 (1H, s, Ar—O$\underline{H}$), 5.34 (1H, t, J=7.0 Hz, CH$_2$C$\underline{H}$=C), 5.23 (1H, t, J=7.0 Hz, ArCH$_2$C$\underline{H}$=C), 4.86 (2H, s, ArC$\underline{H}_2$OH), 4.32 (2H, s, C$\underline{H}_2$OPiv), 3.41 (2H, d, J=7.0 Hz, ArC$\underline{H}_2$), 2.74 (1H, br s, ArCH$_2$O$\underline{H}$), 2.31 (3H, s, ArC$\underline{H}_3$), 2.12-2.18 (2H, m, C$\underline{H}_2$), 2.03-2.08 (2H, m, C$\underline{H}_2$), 1.79 (3H, s, C$\underline{H}_3$), 1.57 (3H, s, C$\underline{H}_3$), 1.19 (9H, s, C(C$\underline{H}_3$)$_3$); IR (KBr) 3300-3500, 1715, 1614, 1456, 1285, 1231, 1159, 1096 cm$^{-1}$. HRMS (DART) calcd for C$_{23}$H$_{32}$ClO$_5$ (M-H) 423.1938. found 423.1912.

24. Compounds 289-12-OPiv and 290-12-Opiv

Scheme 29

[Formula 29]

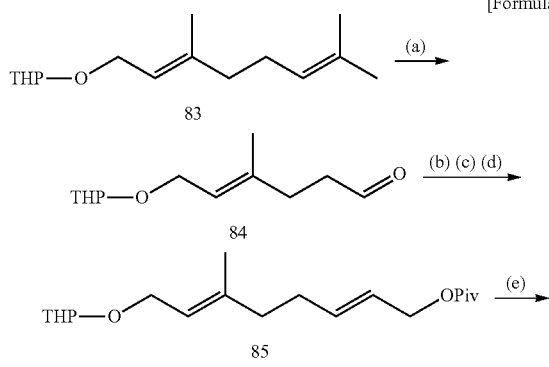

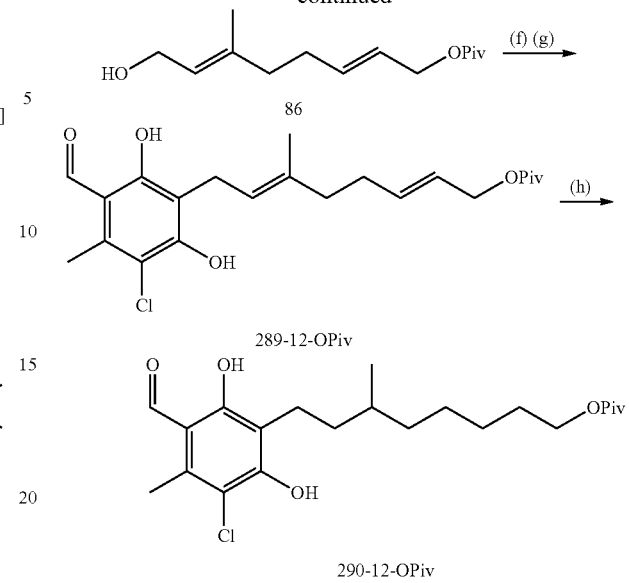

(a) O$_3$, Ph$_3$P, CHCl$_3$;
(b) (EtO)$_2$P(O)CH$_2$CO$_2$Et, NaH, THF;
(c) DIBAL, toluene;
(d) Pivaloyl chloride, pyridine, CHCl$_3$;
(e) PPTS, EtOH;
(f) CBr$_4$, (octyl)$_3$P, Et$_2$O;
(g) 112, KOH/CaCl$_2$, MeOH;
(h) H$_2$, Pd/C, EtOAc.

(2E,6E)-8-(3-Chloro-5-formyl-2,6-dihydroxy-4-methylphenyl)-6-methyl-2,6-octadienyl pivalate (compound 289-12-OPiv)

THP ether 83 known from literature (*Tetrahedron Lett.*, 2001, 42, 2205-2208) (5.56 g, 21.2 mmol) was dissolved in CH$_2$Cl$_2$ (115 ml), and pyridine (5.1 ml, 63.6 mmol) was added thereto and cooled to -80° C. This solution was vigorously stirred with ozone bubbling for 5 hours. After the reactor was purged with argon, Ph$_3$P (16.603 g, 63.6 mmol, 3.0 eq.) was added thereto and stirred for 12 hours while returning to room temperature. The residue obtained upon work-up was purified by silica gel column chromatography (hexane:EtOAc=10:1) to give aldehyde 84 (1.96 g, 44% yield).

This 84 was converted into pivalic acid ester 85 by procedures (b) and (c) (the same procedures as used for synthesis in Scheme 18(c) and (d) above) and the subsequent procedure (d) (the same procedure as used for synthesis in Scheme 15(c) above) (87% yield for 3 steps).

Then, 85 was deprotected by procedure (e) (the same procedure as used for synthesis in Scheme 2(d) above) to give 86 (95% yield). Alcohol 86 was converted into the desired product 289-12-OPiv by procedures (f) and (g) (the same procedures as used for synthesis in Scheme 15(e) and (f) above) (25% yield for 2 steps).

$^1$H-NMR (400 MHz, CDCl$_3$) δ 12.70 (1H, s, Ar—O$\underline{H}$), 10.14 (1H, s, Ar—C$\underline{H}$O), 6.46 (1H, s, Ar—O$\underline{H}$), 5.69 (1H, dt, J=6.0, 15.4 Hz, C$\underline{H}$=C), 5.22 (1H, dt, J=5.8, 15.4 Hz, C$\underline{H}$=C), 5.22 (1H, t, J=7.0 Hz, ArCH$_2$C$\underline{H}$=C), 4.46 (2H, d, J=5.9 Hz, CH$_2$OPiv), 3.39 (2H, d, J=7.3 Hz, Ar—C$\underline{H}_2$), 2.61 (3H, s, Ar—C$\underline{H}_3$), 2.18-2.12 (2H, m, C$\underline{H}_2$), 2.07-2.03 (2H, m, C$\underline{H}_2$), 1.78 (3H, s, C$\underline{H}_3$), 1.56 (3H, s, C$\underline{H}_3$), 1.19 {9H, s, C(CH₃)₃}. IR (KBr) 3273, 2974, 2932, 1728, 1618, 1479, 1452, 1424, 1281, 1229, 1159, 1107, 963, 905, 783, 714, 592, 538 cm⁻¹.

8-(3-Chloro-5-formyl-2,6-dihydroxy-4-methylphenyl)-6-methyloctyl pivalate (compound 290-12-OPiv)

289-12-OPiv was reduced by procedure (h) (the same procedure as used for synthesis in Scheme 15(g) above) to give the desired product 290-12-OPiv (63% yield).

¹H-NMR (400 MHz, CDCl₃) δ 12.65 (1H, s, Ar—OH), 10.14 (1H, s, Ar—CHO), 6.38 (1H, s, Ar—OH), 4.05 (2H, t, J=6.6 Hz, CH₂OPiv), 2.67-2.63 (2H, m, Ar—CH₂), 2.61 (3H, s, Ar—CH₃), 1.64-1.61 (2H, m, CH₂), 1.55-1.30 (7H, m, CHCH₃ & CH₂CH₂), 1.23-1.17 (2H, m, CH₂), 1.19 {9H, s, C(CH₃)₃}, 0.95 {3H, d, J=6.6 Hz, CH(CH₃)CH₂}. IR (KBr) 3380, 2932, 2868, 1717, 1630, 1460, 142, 1375, 1327, 1290, 1248, 1163, 1126, 802, 709, 629, 592 cm⁻¹. HRMS (EI) calcd. for C₂₂H₃₃ClO₅ (m/z) 412.2017. found 412.2041.

25. Compound 231-9-Ome

Scheme 30

[Formula 30]

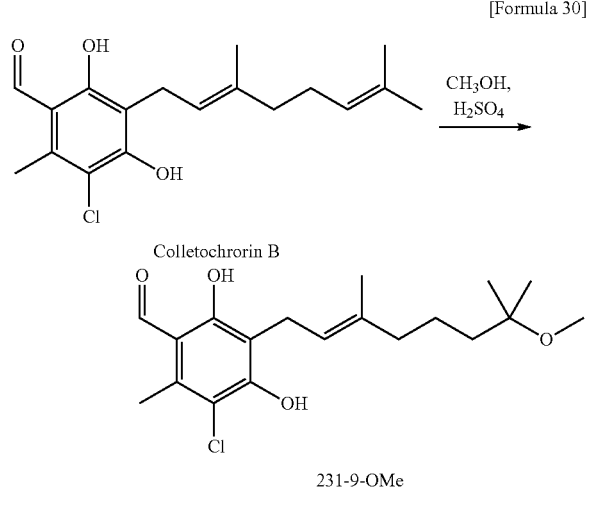

3-Chloro-4,6-dihydroxy-5-[(E)-7-methoxy-3,7-dimethyl-2-octenyl]-2-methyl benzaldehyde (compound 231-9-OMe)

To a solution of compound 216 synthesized in Scheme 6 above (Colletochlorin B, 74 mg, 0.23 mmol) in methanol (5 ml), concentrated sulfuric acid (23 mg, 0.23 mmol) was added. After stirring at 30° C. for 15 hours, the reaction mixture was neutralized with saturated aqueous sodium bicarbonate, extracted with ethyl acetate and then worked up to give a crude product (109 mg), which was then purified by preparative TLC (hexane:EtOAc=3/1) to give the desired product 231-9-OMe (39 mg, 48% yield).

¹H-NMR (400 MHz, CDCl₃) δ 1.11 (s, 6H, C(OCH₃)(CH₃)₂), 1.34-1.43 (m, 4H, —CH═C(CH₃)CH₂CH₂CH₂—), 1.78 (s, 3H, —CH═C(CH₃)—), 1.91-2.00 (m, 2H, —CH═C(CH₃)CH₂—), 2.60 (s, 3H, Ar—CH₃), 3.14 (s, 3H, C(OCH₃)(CH₃)₂), 3.40 (d, J=7.0 Hz, 2H, Ar—CH₂CH═C(CH₃)—), 5.22 (t, J=7.0 Hz, 1H, ArCH₂CH═C(CH₃)—), 6.39 (br s, 1H, Ar—OH), 10.14 (s, 1H, Ar—CHO), 12.69 (s, 1H, Ar—OH).

26. Compounds 236-13-OTHP, 236-9-OH, 236-12-OTHF, 236-12-OMOM, 274-9

Scheme 31

[Formula 31]

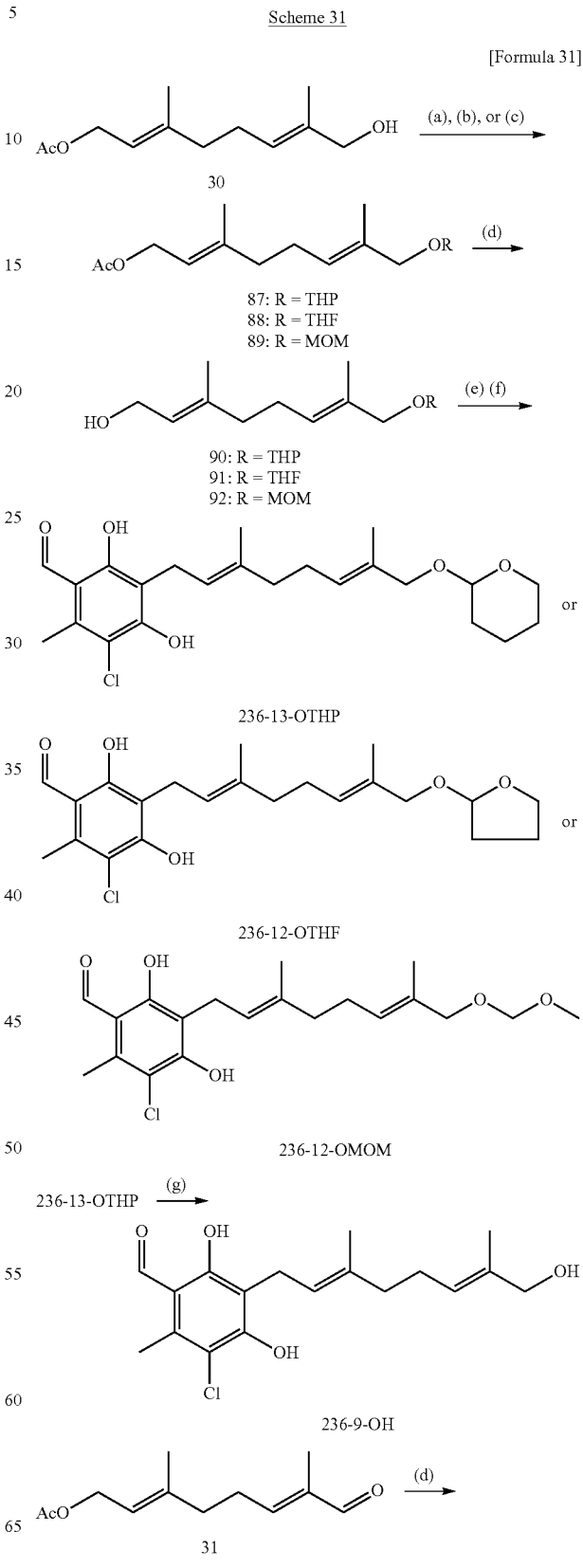

-continued

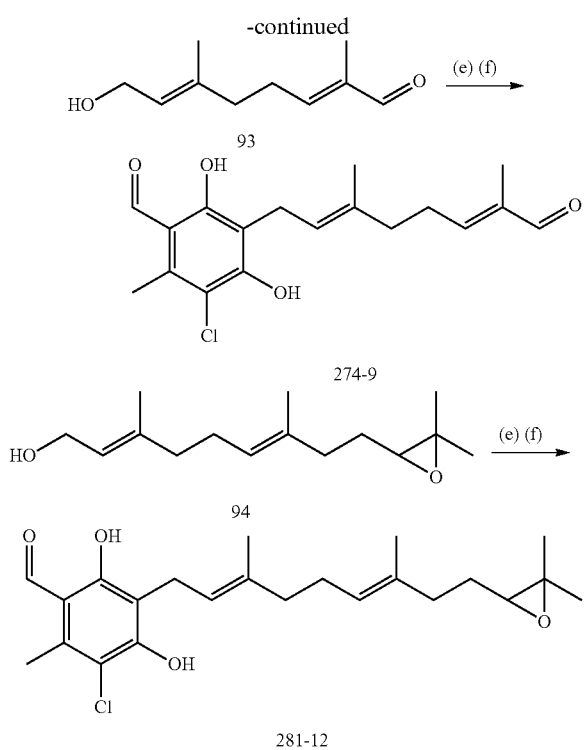

(a) DMP, PPTS, CHCl₃;
(b) DHF, PPTS, CHCl₃;
(c) MOM—Cl, (i-Pr)₂NEt;
(d) K₂CO₃, MeOH, H₂O;
(e) CBr₄, (octyl)₃P, Et₂O;
(f) 112, KOH/CaCl₂, MeOH;
(g) PPTS, MeOH.

3-Chloro-5-(2E,6E)-3,7-dimethyl-8-(tetrahydropyran-2-yloxy)-2,6-octadienyl-4,6-dihydroxy-2-methylbenzaldehyde (compound 236-13-OTHP)

By standard procedure (a) (the same procedure as used in Scheme 2(a) above), alcohol 30 known from literature (*J. Braz. Chem. Soc.* 2003, 14, 975-981) was converted into compound 87 whose alcohol moiety was protected (96% yield). To a solution of this compound 87 (1.32 g, 4.46 mmol) in MeOH (8 ml), H₂O (10 ml) and K₂CO₃ (1.24 g, 8.92 mmol) were added and stirred for 16 hours. The crude product obtained upon work-up by ether extraction was purified by column chromatography (n-hexane/EtOAc=1/1) to give alcohol 90 (664 mg, 60% yield).

Alcohol 90 was converted into the desired product 236-13-OTHP by procedures (e) and (f) (the same procedures as used for synthesis in Scheme 15(e) and (1) above) (30% yield for 2 steps).

Mp 44-45° C. ¹H-NMR (400 MHz, CDCl₃) δ 12.70 (1H, s, Ar—OH), 10.14 (1H, s, Ar—CHO), 6.66 (1H, s, Ar—OH), 5.37 (1H, t, J=6.8 Hz, CH₂CH=C), 5.22 (1H, t, J=7.1 Hz, CH₂CH=C), 4.61 (1H, t, J=3.5 Hz, THP(2)-H), 4.05 (1H, d, J=11.9 Hz, C(CH₃)CH₂O), 3.83-3.90 (1H, m, THP(6)-H), 3.83 (1H, d, J=11.9 Hz, C(CH₃)CH₂O), 3.48-3.54 (1H, m, THP(6)-H), 3.37-3.41 (2H, m, Ar—CH₂), 2.61 (3H, s, Ar—CH₃), 2.0-2.2 (4H, m, C(CH₃)CH₂CH₂CH=C), 1.6-1.9 (12H, m+s (δ1.77, CH₃)+s (1.62, CH₃), THP(3,4,5)-H₂). IR (KBr) 3200-3500, 1613, 1424, 1281, 1250, 1233, 1111 cm⁻¹. Calcd for C₂₃H₃₁ClO₅: C, 65.32; H, 7.39; Cl, 8.38%. Found: C, 65.18; H, 7.36; Cl, 8.41%.

3-Chloro-4,6-dihydroxy-5-(2E,6E)-8-hydroxy-3,7-dimethyl-2,6-octadienyl-2-methylbenzaldehyde (compound 236-9-OH)

236-13-OTHP obtained above was treated to remove THP by procedure (g) (the same procedure as used in Scheme 2(d) above) to give the desired product 236-9-OH (90% yield).

Mp 99.0-99.7° C. H-NMR (400 MHz, CDCl₃) δ 12.72 (1H, s, Ar—OH), 10.14 (1H, s, Ar—CHO), 5.34 (1H t, J=6.6 Hz, CH₂CH=C), 5.22 (1H, t, J=6.9 Hz, CH₂CH=C), 3.97 (2H, d, J=6.9 Hz, Ar—CH₂), 2.61 (3H, s, Ar—CH₃), 2.0-2.2 (4H, m, C(CH₃)CH₂CH₂CH=C), 1.78 (3H, s, CH₃), 1.64 (3H, s, CH₃). HRMS (DART) calcd for C₁₈H₂₂ClO₃ (M-OH) 321.1257, found 321.1235.

3-Chloro-5-(2E,6E)-3,7-dimethyl-8-(tetrahydrofuran-2-yloxy)-2,6-octadienyl-4,6-dihydroxy-2-methylbenzaldehyde (compound 236-12-OTHF)

The above alcohol 30 was treated by standard procedure (b) (the same procedure as used in Scheme 2(a) above, except that dihydropyran (DHP) was replaced with dihydrofuran (DHF)) to modify the alcohol moiety with THF to thereby give compound 88 (97% yield). Subsequently, the above procedure (d) was repeated to convert this compound into similar alcohol 91 (60% yield). Then, the procedures (e) and (f) (the same procedures as used for synthesis in Scheme 15(e) and (f) above) were repeated to give the desired product 236-12-OTHF (13% yield for 2 steps).

Mp 35-36° C. ¹H-NMR (400 MHz, CDCl₃) δ 12.70 (1H, s, Ar—OH), 10.14 (1H, s, Ar—CHO), 6.71 (1H, s, Ar—OH), 5.36 (1H, t, J=7.0 Hz, CH₂CH=C), 5.22 (1H, t, J=7.0 Hz, CH₂CH=C), 5.11 (1H, dd, J=2.6, 4.0 Hz, THF(2)-H), 3.98 (1H, d, J=11.7 Hz, C(CH₃)CH₂O), 3.85-3.94 (2H, m, THF(5)-H₂), 3.81 (1H, d, J=11.7 Hz, C(CH₃)CH₂O), 3.34-3.44 (2H, m, Ar—CH₂), 2.61 (3H, s, Ar—CH₃), 1.8-2.2 (8H, m, C(CH₃)CH₂CH₂CH=C and THF(3,4)-H₂), 1.77 (s, CH₃), 1.60 (s, CH₃). IR (KBr) 3150-3350, 1613, 1422, 1283, 1250, 1234, 1109, 1024 cm⁻¹. HRMS (DART) calcd for C₂₂H₃₀ClO₅ (MH⁺) 409.1782, found: 409.1758.

3-Chloro-5-(2E,6E)-3,7-dimethyl-8-(methoxymethoxy)-2,6-octadienyl-4,6-dihydroxy-2-methylbenzaldehyde (compound 236-12-OMOM)

The above alcohol 30 was methoxymethylated by standard procedure (c) (*J. Am. Chem. Soc.* 1977, 99, 1275-1276) to give compound 89 (71% yield). Subsequently, the above procedure (d) was repeated to convert this compound into alcohol 92 (80% yield). Then, 92 was treated by the procedures (e) and (f) (the same procedures as used for synthesis in Scheme 15(e) and (f) above) to give the desired product 236-12-OMOM (12% yield for 2 steps).

Mp 49-50° C. ¹H-NMR (400 MHz, CDCl₃) δ 12.70 (1H, s, Ar—OH), 10.14 (1H, s, Ar—CHO), 6.65 (1H, s, Ar—OH), 5.37 (1H, t, J=6.4 Hz, CH₂CH=C), 5.24 (1H, t, J=6.4 Hz, CH₂CH=C), 4.59 (2H, s, OCH₂O), 3.89 (2H, s, C(CH₃)CH₂O), 3.39 (2H, d, J=6.4 Hz, Ar—CH₂), 3.38 (3H, s, OCH₃), 2.61 (3H, s, Ar—CH₂), 2.11-2.17 (2H, m, C(CH₃)CH₂CH₂CH=C), 2.01-2.06 (2H, m, C(CH₃)CH₂CH₂CH=C) 1.77 (s, CH₃), 1.63 (s, H₃). IR (KBr) 3200-3400, 1631, 1422, 1288, 1254, 1022, 903 cm⁻¹. Calcd for C₂₀H₂₇ClO₅: C, 62.74; H, 7.11; Cl, 9.26%. Found: C, 62.64; H, 7.09; Cl, 9.22%.

3-Chloro-5-(2E,6E)-3,7-dimethyl-8-oxo-2,6-octadienyl-4,6-dihydroxy-2-methylbenzaldehyde (compound 274-9)

Aldehyde 31 known from literature (*Tetrahedron* 1974, 30, 715-718) was deacetylated by the above procedure (d) to give compound 93 (90% yield). Then, 93 was treated by the procedures (e) and (f) (the same procedures as used for synthesis in Scheme 15(e) and (f) above) to give the desired product 274-9 (27% yield for 2 steps).

Mp 111.2-111.4° C. $^1$H-NMR (400 MHz, CDCl$_3$) δ 12.70 (1H, s, Ar—OH), 10.15 (1H, s, Ar—CHO), 9.31 (1H, s, C(CH$_3$)—CHO), 6.41 (1H t, J=7.4 Hz, CH$_2$CH═C), 6.35 (1H, s, Ar—OH), 5.26 (1H, J=6.8 Hz, CH$_2$CH═C), 3.40 (2H, d, J=7.4 Hz, Ar—CH$_2$), 2.61 (3H, s, Ar—CH$_3$), 2.4-2.5 (2H, m, C(CH$_3$)CH$_2$CH$_2$CH═C), 2.1-2.2 (2H, m, C(CH$_3$)CH$_2$CH$_2$CH═C), 1.81 (3H, s, CH$_3$), 1.70 (3H, s, CH$_3$). MS (EI) m/z 338 (5, M+2), 336 (13, M$^+$).

3-Chloro-5-(2E,6E)-3,7-dimethyl-9-(3,3-dimethyloxiran-2-yl)-2,6-nonadienyl-4,6-dihydroxy-2-methylbenzaldehyde (compound 281-12)

Alcohol 94 known from literature (*Org. Lett.* 2006, 8, 5649-5652) was used and treated by the procedures (e) and (f) (the same procedures as used for synthesis in Scheme 15(e) and (f) above) to give the desired product 281-12 (4% yield for 2 steps).

Mp 36-37° C. $^1$H-NMR (400 MHz, CDCl$_3$) δ 12.70 (1H, s, Ar—OH), 10.14 (1H, s, Ar—CHO), 6.57 (1H, s, Ar—OH), 5.21 (1H, t, J=7.1 Hz, CH$_2$CH═C), 5.11 (1H, t, J=6.2 Hz, CH$_2$CH═C), 3.39 (2H, d, J=7.1 Hz, Ar—CH$_2$), 2.69 (1H, t, J=6.2 Hz, oxiran(2)-H), 2.61 (3H, s, Ar—CH$_3$), 1.96-2.12 (6H, m, C(CH$_3$)CH$_2$CH$_2$CH═C(CH$_3$)CH$_2$), 1.78 (s, CH$_3$), 1.56-1.64 (5H, m+s (δ 1.59), nonadienyl(9)-H$_2$ and CH$_3$), 1.30 (s, CH$_3$), 1.25 (s, CH$_3$). IR (KBr) 3300-3500, 1614, 1418, 1281, 1250, 1233, 1109 cm$^{-1}$.

EXAMPLES

The DHOD inhibitor of the present invention will be further described in more detail by way of the following illustrative examples. It should be noted that the present invention is not limited in any way by these examples.

Example 1

Measurement of DHOD Inhibitory Activity

The compounds of the present invention were used and measured for their DHOD inhibitory activity at concentrations of 200 nM and 1000 nM.

Assay buffer (100 mM HEPES pH 8.0, 150 mM NaCl, 5% glycerol, 0.05% Triton X-100, 200 μM dihydroorotate, 120 μM DCIP, 11 μM decylubiquinone) (190 μl) and a DMSO solution of each inhibitor (5 pd) were added, and a 8 g/ml human DHOD solution (5 μl) was added thereto to initiate the enzyme reaction (final concentration of human DHOD: 0.2 μg/ml (4 nM)). Reduction of DCIP was measured at 600 nm over 20 minutes. Based on a change in absorbance at 600 nm between 0 minutes and 20 minutes, each compound was measured for its human DHOD inhibition rate at concentrations of 200 nM and 1000 nM by using the value obtained in the presence of the DMSO solution alone as a control in the end point assay. Moreover, the concentration (nM) required to inhibit 50% of human DHOD activity was determined as IC50 (50% inhibitory concentration). The results obtained are shown in Table 1.

TABLE 1

| Compound | DHOD inhibition rate (%) 200 nM | DHOD inhibition rate (%) 100 nM | IC50 (nM) |
|---|---|---|---|
| Ascofuranone (control) | 73 | 95 | 38 ± 12 |
| 07-11-116-4 | 57 | 87 | 146 ± 19 |
| 200-12-OCOiPr | 51 | 85 | 326 ± 41 |
| 231-9-OMe | 75 | 98 | 67 ± 7 |
| 234-12-OPiv | 72 | 102 | 98 ± 5 |
| 236-12-OTHF | 86 | 97 | 33 ± 3 |
| 236-9-OH | 82 | 103 | 44 ± 5 |
| 264-11-OPiv | 58 | 94 | 123 ± 18 |
| 264-8 | 74 | 90 | 71 ± 2 |
| 271-12 | 76 | 95 | 60 ± 21 |
| 274-9 | 90 | 98 | 31 ± 3 |
| 275-10-COOMe | 100 | 100 | 4.2 ± 0.4 |
| 276-9 | 87 | 96 | 24 ± 3 |
| 277-11-OAc | 97 | 103 | 6.5 ± 0.2 |
| 277-9-OH | 75 | 107 | 64 ± 11 |
| 280-12 | 104 | 94 | 6.0 ± 0.5 |
| 281-12 | 79 | 100 | 50 ± 5 |
| 287-12-OCOiPr | 101 | 109 | 21.5 ± 0.3 |
| 287-12-OPiv | 82 | 104 | 67 ± 3 |
| CC-B | 69 | 100 | 1052 ± 214 |

Example 2

Anticancer Effect

Conventional anticancer agents are designed to directly act on the process of cell division, but they have been significantly disadvantageous in developing serious side effects due to their low specificity to tumor cells and strong cytotoxicity on normal cells. After that, molecular targeted drugs have appeared, which are designed to target molecules involved in the growth, invasion and metastasis of tumor cells and thereby allow not only suppression of tumor cell growth and tumor cell progression, but also suppression of tumor metastasis.

For these reasons, screening was conducted by cancer cell growth inhibition test using a panel of 39 types of human cancer cell lines (JFCR39) and by cancer cell informatics based on information analysis (Kong D., T. Yamori; Bioorganic & Med. Chem., 20, 1947-51, 2012). The concentration (μM) required to inhibit 50% of human cancer cell growth was determined as GI50 (50% inhibitory concentration).

The results obtained are shown in Table 2.

Inhibitory Effects on Various Human Cancer Cells

TABLE 2

| | | GI50 (μM) | | | | | |
|---|---|---|---|---|---|---|---|
| | | Ascofuranone | 287-12-OCOiPr | 280-12 | 277-11-Oac | 277-9-OH | 275-10-COOMe |
| Br (Breast) | HBC-4 | 9.1 | 9.4 | 2.2 | 5.0 | 37.0 | 5.6 |
| | BSY-1 | 16.0 | 16.0 | 13.0 | 20.0 | 59.0 | 27.0 |
| | HBC-5 | 28.0 | 18.0 | 16.0 | 25.0 | 61.0 | 28.0 |
| | MCF-7 | 9.0 | 6.7 | 1.3 | 4.9 | 36.0 | 7.3 |
| | MDA-MB-231 | 7.4 | 10.0 | 2.8 | 11.0 | 36.0 | 14.0 |

TABLE 2-continued

| | | GI50 (μM) | | | | | |
|---|---|---|---|---|---|---|---|
| | | Ascofuranone | 287-12-OCOiPr | 280-12 | 277-11-Oac | 277-9-OH | 275-10-COOMe |
| CNS | U251 | 1.5 | 4.9 | 0.43 | 1.5 | 5.1 | 0.97 |
| (Central Nervous | SF-268 | 7.0 | 9.5 | 0.93 | 5.0 | 12.0 | 8.1 |
| Systems) | SF-295 | 5.3 | 16.0 | 1.3 | 8.0 | 16.0 | 11.0 |
| | SF-539 | 1.7 | 2.2 | 0.24 | 0.27 | 5.3 | 0.54 |
| | SNB-75 | 23.0 | 28.0 | 0.70 | 22.0 | 59.0 | 9.7 |
| | SNB-78 | 23.0 | 28.0 | 16.0 | 21.0 | 43.0 | 8.8 |
| Co | HCC2998 | 17.0 | 15.0 | 12.0 | 13.0 | 43.0 | 17.0 |
| (Colon) | KM-12 | 9.3 | 10.0 | 2.0 | 5.7 | 32.0 | 6.4 |
| | HT-29 | 6.6 | 5.8 | 1.1 | 3.2 | 39.0 | 6.5 |
| | HCT-15 | 1.3 | 1.9 | 0.043 | 0.58 | 6.2 | 0.83 |
| | HCT-116 | 5.1 | 4.6 | 0.46 | 1.5 | 14.0 | 2.5 |
| Lu | NCI-H23 | 15.0 | 13.0 | 2.8 | 15.0 | 39.0 | 7.8 |
| (Lung) | NCI-H226 | 15.0 | 8.0 | 10.0 | 11.0 | 24.0 | 13.0 |
| | NCI-H522 | 8.4 | 4.2 | 1.2 | 4.9 | 22.0 | 5.3 |
| | NCI-H460 | 2.0 | 4.5 | 0.21 | 0.94 | 12.0 | 4.3 |
| | A549 | 7.6 | 7.1 | 0.77 | 3.3 | 37.0 | 4.7 |
| | DMS273 | 5.9 | 3.6 | 0.45 | 0.91 | 18.0 | 3.0 |
| | DMS114 | 19.0 | 12.0 | 2.5 | 14.0 | 35.0 | 15.0 |
| Me (Melanoma) | L0X-IMVI | 2.8 | 3.4 | 0.61 | 1.5 | 13.0 | 2.1 |
| Ov | OVCAR-3 | 8.0 | 7.1 | 1.9 | 13.0 | 27.0 | 5.3 |
| (Ovarian) | OVCAR-4 | 5.9 | 19.0 | 13.0 | 27.0 | 39.0 | 11.0 |
| | OVCAR-5 | 7.6 | 22.0 | 6.6 | 18.0 | 58.0 | 12.0 |
| | OVCAR-8 | 9.5 | 9.1 | 0.97 | 8.8 | 25.0 | 4.4 |
| | SK-OV-3 | 13.0 | 49.0 | 37.0 | 12.0 | 27.0 | 11.0 |
| Re | RXF-631L | 12.0 | 16.0 | 11.0 | 7.5 | 45.0 | 8.4 |
| (Renal) | ACHN | 10.0 | 16.0 | 0.79 | 9.9 | 22.0 | 9.9 |
| St | St-4 | 14.0 | 17.0 | 1.1 | 13.0 | 44.0 | 7.5 |
| (Stomac) | MKN1 | 14.0 | 12.0 | 8.2 | 16.0 | 44.0 | 14.0 |
| | MKN7 | 15.0 | 16.0 | 2.1 | 16.0 | 36.0 | 13.0 |
| | MKN28 | 9.7 | 10.0 | 1.3 | 11.0 | 36.0 | 12.0 |
| | MKN45 | 10.0 | 24.0 | 6.4 | 20.0 | 65.0 | 14.0 |
| | MKN74 | 13.0 | 14.0 | 1.3 | 11.0 | 26.0 | 14.0 |
| xPg | DU-145 | 11.0 | 23.0 | 0.26 | 14.0 | 25.0 | 10.0 |
| (Prostate) | PC-3 | 13.0 | 13.0 | 1.2 | 15.0 | 22.0 | 22.0 |
| IC50 (nM) | HsDHOD | 38.0 | 21.5 | 6.0 | 6.5 | 64.0 | 4.2 |

Example 3

Anticancer Effect Under Hypoxic and Subnutritional Conditions

Until now, various studies have been attempted to overcome cancers. As a result, outcomes of early cancer treatment have been dramatically improved. However, treatment of progressive cancers is still difficult, and hence cancers hold the top spot among causes of death in Japanese patients. This is because areas having internal environments including hypoxia and subnutrition (hypoxic areas) are found widely in progressive solid cancers due to perfusion insufficiency induced by incomplete vascular construction. Namely, many anticancer agents used for clinical purposes have been found to clearly reduce their anticancer effect under hypoxic and subnutritional conditions (Lue J. et. al.; Cancer Sci., 95, 6.547-552, 2004). In such areas, drugs are difficult to reach, a new character is acquired to avoid cell death, and cell division is less active. Due to these features, progressive solid cancers are considered to be resistant to conventional chemotherapies.

For these reasons, cells of colorectal and pancreatic cancers, each being regarded as intractable, were used to test the inhibitory effect of compounds under hypoxic and subnutritional conditions. Moreover, the same test was also performed on normal skin cells.

Figure 2:
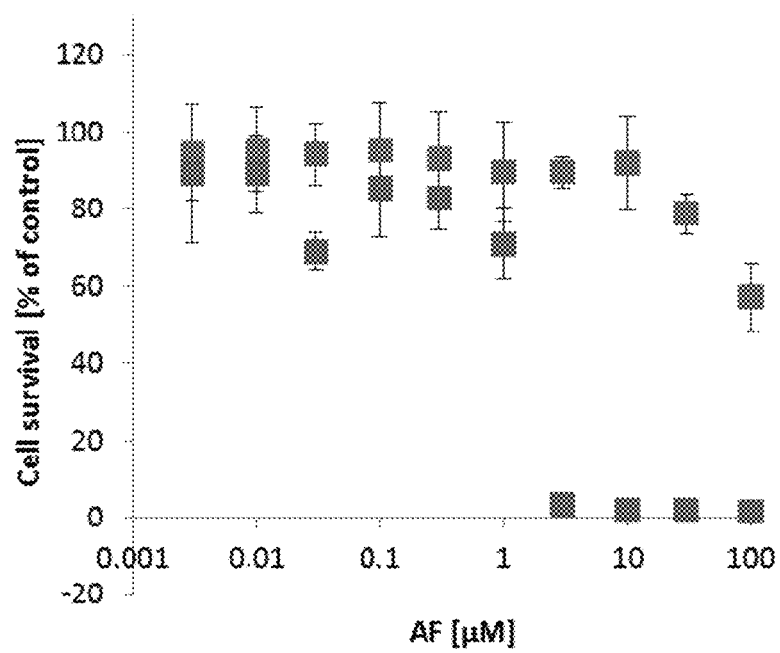
FIG. 2 shows a graph indicating the growth inhibitory effect on pancreatic cancer cells (Panc-1 cells) provided by the compounds of the present invention.
Figure 3:
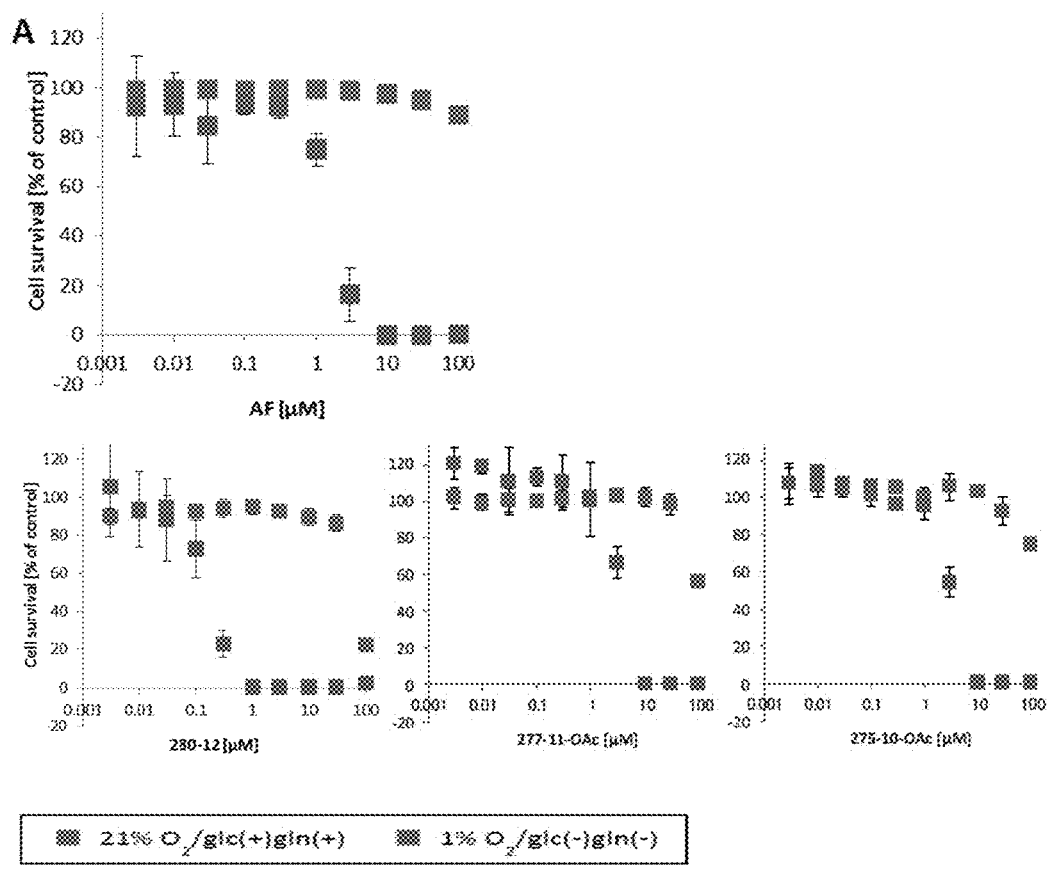
FIG. 3 shows graphs indicating the growth inhibitory effect on normal skin cells (HDF cells) provided by the compounds of the present invention.

The cells used were two types of cancer cells, i.e., DLD-1 cells (human colorectal cancer cells) and Panc-1 cells (human pancreatic cells), as well as HDF cells (human dermal fibroblast cells). Culture conditions were set as follows: 21% oxygen with glucose and glutamic acid (10% FBS) for the control group, and 1% oxygen without glucose and glutamic acid (10% FBS) for the hypoxic and subnutritional group. The results obtained are shown in Tables 3, 4 and 5, as well as FIGS. 1, 2 and 3.

Inhibitory Effect on DLD-1 Cells

TABLE 3

| | | $IC_{50}$ | | | | |
|---|---|---|---|---|---|---|
| | | DLD-1 [μM] | | | | bovine |
| compound | time [hours] | 21% $O_2$ glc(+)gln(+) | 1% $O_2$ glc(-)gln(-) | Selectivity | HsDHOD [nM] | complex II-III [nM] |
| 280-12 | 24 | 76 | 0.069 | 1100 | 6.0 | 260 |
| | 48 | 37 | 0.025 | 1480 | | |
| 277-11-OAc | 24 | >100 | 1.9 | >53 | 6.5 | 4500 |
| | 48 | >100 | 0.92 | >109 | | |

TABLE 3-continued

| | | IC$_{50}$ | | | | |
|---|---|---|---|---|---|---|
| | | DLD-1 [μM] | | | | bovine |
| compound | time [hours] | 21% O$_2$ glc(+)gln(+) | 1% O$_2$ glc(−)gln(−) | Selectivity | HsDHOD [nM] | complex II-III [nM] |
| 275-10-COOMe | 24 | >100 | 1.7 | >59 | 4.2 | 1900 |
| | 48 | >100 | 0.64 | >156 | | |

Selectivity = 21% glc(+)gln(+) IC$_{50}$/1% glc(−)gln(−) IC$_{50}$

Inhibitory Effect on Panc-1 Cells

TABLE 4

| | IC$_{50}$ [μM] | | |
|---|---|---|---|
| | 21% O$_2$ glc(+)gln(+) | 1% O$_2$ glc(−)gln(−) | Selectivity |
| AF | >100 | 1.4 | >71 |

Selectivity = 21% glc(+)gln(+) IC$_{50}$/1% glc(−)gln(−) IC$_{50}$

Inhibitory Effect on HDF Cells

TABLE 5

| | IC$_{50}$ [μM] | | |
|---|---|---|---|
| compound | 21% O$_2$ glc(+)gln(+) | 1% O$_2$ glc(−)gln(−) | Selectivity |
| AF | >100 | 1.6 | >63 |
| 280-12 | 60 | 0.17 | 353 |
| 277-11-OAc | >100 | 4.0 | >25 |
| 275-10-COOMe | >100 | 3.1 | >32 |

Selectivity = 21% glc(+)gln(+) IC$_{50}$/1% glc(−)gln(−) IC$_{50}$

The above results indicated that ascofuranone and derivatives thereof showed an inhibitory effect specifically and even at low concentration against human cultured cells under hypoxic and subnutritional environment.

One or two or more of the compounds of the present invention can be used to prepare a pharmaceutical composition comprising one or more pharmaceutically acceptable carriers. Such a pharmaceutical composition can be administered in any dosage form as appropriate for the intended route of administration. The route of administration may be either parenteral or oral. For example, formulation examples as shown below can be presented.

Formulation Examples (a) Tablet 1 (Amount Per Tablet)

| The compound(s) of the present invention | 100 mg |
|---|---|
| Lactose | 182.75 mg |
| Croscarmellose sodium | 12 mg |
| Corn starch paste (5% w/v paste) | 2.25 mg |
| Magnesium stearate | 3 mg |

(b) Tablet 2 (Amount Per Tablet)

| The compound(s) of the present invention | 50 mg |
|---|---|
| Lactose | 223.75 mg |
| Croscarmellose sodium | 6 mg |
| Corn starch | 15 mg |
| Polyvinylpyrrolidone | 2.25 mg |
| Magnesium stearate | 3 mg |

(c) Tablet 3 (Amount Per Tablet)

| The compound(s) of the present invention | 1 mg |
|---|---|
| Lactose | 93.25 mg |
| Croscarmellose sodium | 4 mg |
| Corn starch paste (5% w/v paste) | 0.75 mg |
| Magnesium stearate | 1 mg |

(d) Capsule (Amount Per Capsule)

| The compound(s) of the present invention | 10 mg |
|---|---|
| Lactose | 488.5 mg |
| Magnesium stearate | 1.5 mg |

(e) Injection 1 (Amount Per Ml)

| The compound(s) of the present invention | 1% w/v |
|---|---|
| Sodium phosphate | 3.6% w/v |
| 0.1M Aqueous sodium hydroxide | 15% v/v |
| Injectable water | balanced to 100% |

(f) Injection 2 (Amount Per Ml)

| The compound(s) of the present invention | 0.1% w/v |
|---|---|
| Sodium phosphate | 2.26% w/v |
| Citric acid | 0.38% w/v |
| Polyethylene glycol 400 | 3.5% w/v |
| Injectable water | balanced to 100%. |

The above formulations can be obtained by prior art techniques well known in the pharmaceutical industry. Tablets 1 to 3 can be enteric-coated, e.g., by using shellac, cellulose acetate, monophthalic acid ester, phenyl salicylate, polyvinylpyrrolidone, keratin or the like. Likewise, the capsules can also be designed to be soluble in the intestinal tract by using enteric capsules (e.g., glutoid capsules).

INDUSTRIAL APPLICABILITY

Because of having high DHOD inhibitory activity, the above dihydroxybenzene derivatives represented by formula (I) are extremely useful as DHOD inhibitors for use in therapeutic agents for various DHOD-related diseases, such as various types of cancers, rheumatism, graft rejection in organ transplantation, diabetes, virus-induced diseases and H. pylori-induced diseases. Moreover, the dihydroxyben-

The invention claimed is:

1. A method for suppressing immune system, or treating a rheumatism, a cancer, a graft rejection in organ transplantation, or a *H. pylori* infection, wherein the method comprises administering to a subject in need thereof an effective amount of a dihydroorotic acid dehydrogenase inhibitor,
wherein the dihydroorotic acid dehydrogenase inhibitor comprises, as an active ingredient(s), one or two or more of compounds represented by formula (I):

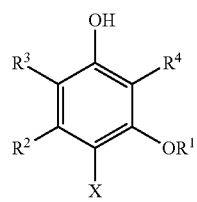

(I)

(wherein
X represents a halogen atom,
$R^1$ represents a hydrogen atom,
$R^2$ represents a $C_{1-7}$ alkyl group,
$R^3$ represents —CHO, and
$R^4$ represents —$CH_2$—CH=C($CH_3$)—$R^0$ (wherein $R^0$ represents a $C_{1-12}$ alkyl group which may have a substituent on the terminal carbon and/or on a non-terminal carbon, a $C_{2-12}$ alkenyl group which may have a substituent on the terminal carbon and/or on a non-terminal carbon, or a $C_{2-12}$ alkynyl group which may have a substituent on the terminal carbon and/or on a non-terminal carbon), or —CH=CH—$(CH_2)_6$—O—CO—CH($CH_3)_2$),
wherein the substituent for the $C_{1-12}$ alkyl group, the $C_{2-12}$ alkenyl group, and the $C_{2-12}$ alkynyl group is selected from the group consisting of —COOH, —COORa, where Ra represents a $C_{1-7}$ alkyl group, —CHO, —COOCH$_2$CH(OH)CH$_2$OH, —COO—CH$_2$—Rb, where Rb represents a group obtained by removing one of the hydrogen atoms on the carbons of an aromatic hydrocarbon, —O—CO-Rc, where Rc represents a $C_{1-7}$ alkyl group, —OH, —O-Rd, where Rd represents a $C_{1-7}$ alkyl group, —O—CH$_2$—O—CH$_3$, —CH(OCH$_3$)—CH$_2$—CO—C(CH$_3$)$_3$, —CO—CH$_3$, —CO—C(CH$_3$)$_3$, -HET, where HET represents a group obtained by removing one hydrogen atom from the carbon or nitrogen atom(s) of pyridine, furan, thiophene, pyran, pyranone, imidazole, 1,3-dioxolane, oxirane, or 3,3-dimethyloxirane, and —O-HET,
optical isomers thereof and pharmaceutically acceptable salts thereof, as well as a pharmaceutically acceptable carrier.

2. The method according to claim 1,
wherein
X represents a chlorine atom,
$R^2$ represents a methyl group, and
$R^4$ represents —$CH_2$—CH=C($CH_3$)—$R^0$ (wherein R represents a $C_{1-12}$ alkyl group which may have a substituent on the terminal carbon and/or on a non-terminal carbon, or a $C_{2-12}$ alkenyl group which may have a substituent on the terminal carbon and/or on a non-terminal carbon), provided that when $R^0$ has a substituent, the substituent is selected from the group consisting of —O—CO—C(CH$_3$)$_3$, —O—CO—CH(CH$_3$)$_2$, —C(CH$_3$)$_2$—O—CH$_3$, —O—(2-furyl), —OH, —CH(OCH$_3$)—CH$_2$—CO—C(CH$_3$)$_3$, —CHO, —CO—O—CH$_3$, —CO—CH$_3$, —O—CO—CH$_3$ and —CO—C(CH$_3$)$_3$.

3. The method according to claim 1, wherein the compounds represented by formula (I) are selected from the group consisting of:

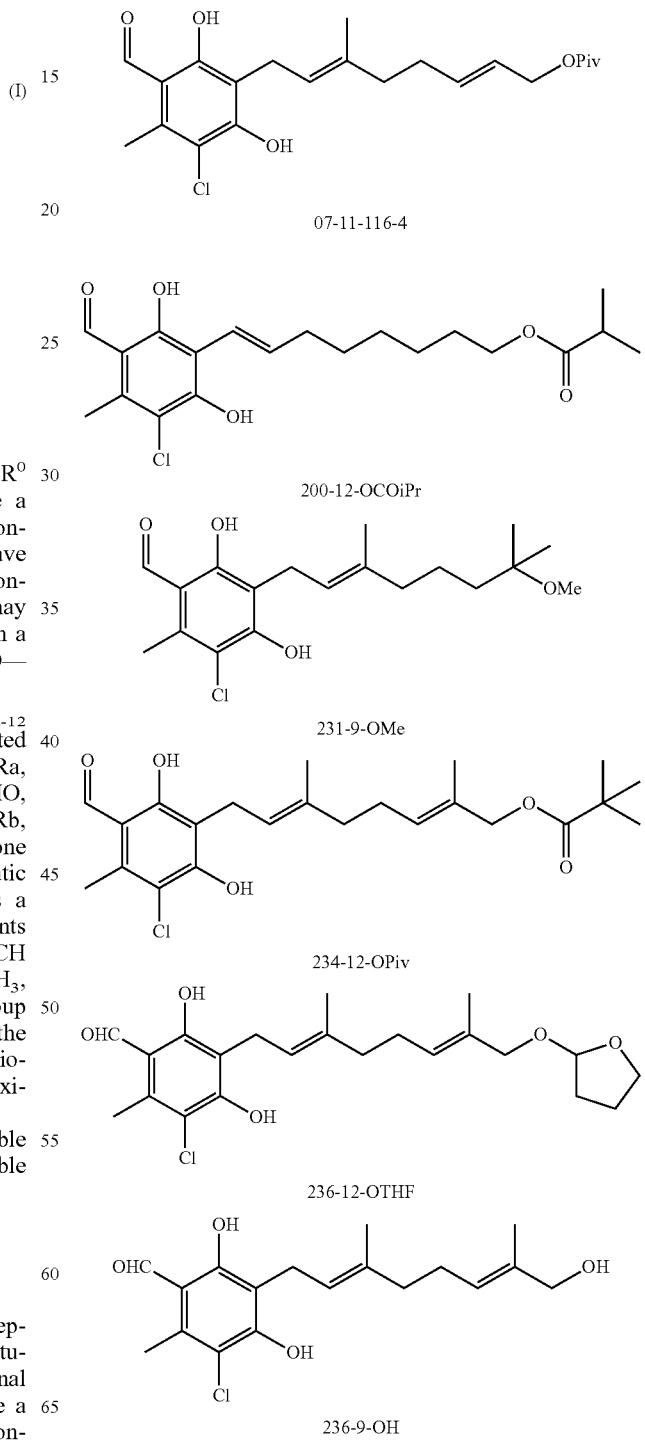

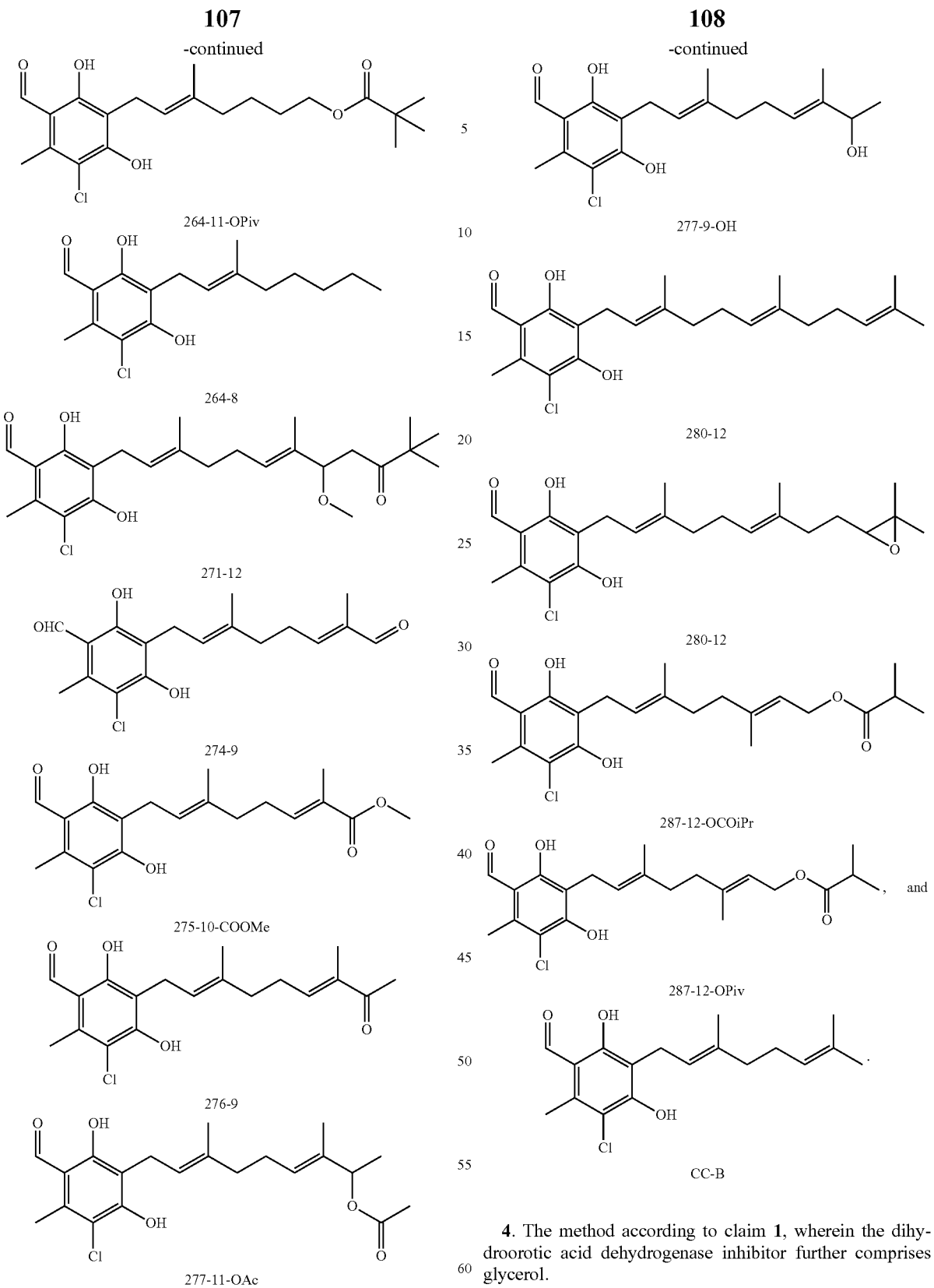
4. The method according to claim 1, wherein the dihydroorotic acid dehydrogenase inhibitor further comprises glycerol.
* * * * *